US012005073B2

(12) United States Patent
Anderson et al.

(10) Patent No.: US 12,005,073 B2
(45) Date of Patent: Jun. 11, 2024

(54) METHODS FOR MODULATING REGULATORY T CELLS, REGULATORY B CELLS, AND IMMUNE RESPONSES USING MODULATORS OF THE APRIL-TACI INTERACTION

(71) Applicant: Dana-Farber Cancer Institute, Inc., Boston, MA (US)

(72) Inventors: Kenneth C. Anderson, Wellesley, MA (US); Yu-Tzu Tai, Newton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 284 days.

(21) Appl. No.: 16/612,938

(22) PCT Filed: Jun. 20, 2018

(86) PCT No.: PCT/US2018/038490
§ 371 (c)(1),
(2) Date: Nov. 12, 2019

(87) PCT Pub. No.: WO2018/236995
PCT Pub. Date: Dec. 27, 2018

(65) Prior Publication Data

US 2021/0113605 A1 Apr. 22, 2021

Related U.S. Application Data

(60) Provisional application No. 62/677,265, filed on May 29, 2018, provisional application No. 62/573,264, filed on Oct. 17, 2017, provisional application No. 62/522,167, filed on Jun. 20, 2017.

(51) Int. Cl.

| | |
|---|---|
| ***A61K 31/7105*** | (2006.01) |
| ***A61K 45/06*** | (2006.01) |
| ***A61K 47/68*** | (2017.01) |
| ***C07K 16/28*** | (2006.01) |
| ***C12N 15/113*** | (2010.01) |

(52) U.S. Cl.
CPC ...... *A61K 31/7105* (2013.01); *A61K 47/6803* (2017.08); *C07K 16/2875* (2013.01); *C12N 15/113* (2013.01); *A61K 45/06* (2013.01); *C07K 2317/24* (2013.01); *C07K 2319/30* (2013.01); *C12N 2310/11* (2013.01); *C12N 2310/141* (2013.01); *C12N 2310/20* (2017.05)

(58) Field of Classification Search
CPC .... A61K 39/39; A61K 45/06; A61K 47/6803; A61K 2039/505; C07K 2317/76; C07K 2319/30; C12N 15/113; C12N 2310/11
USPC ............ 530/300, 350; 435/6.1, 91.1, 901.31, 435/455, 458; 514/44 A, 44 R; 536/23.1, 536/24.5
See application file for complete search history.

(56) References Cited

U.S. PATENT DOCUMENTS

2021/0113605 A1 4/2021 Anderson et al.

FOREIGN PATENT DOCUMENTS

| | | | | |
|---|---|---|---|---|
| CN | 102585016 A | 7/2012 | | |
| WO | WO-2001/087979 A2 | 11/2001 | | |
| WO | WO-0244321 A2 * | 6/2002 | ......... | A01K 67/0336 |
| WO | WO-2008/154814 A1 | 12/2008 | | |
| WO | WO-2010/075249 A2 | 7/2010 | | |
| WO | WO-2011/047121 A1 | 4/2011 | | |
| WO | WO-2011047121 A1 * | 4/2011 | ......... | C07K 16/2875 |
| WO | WO-2016/110587 A1 | 7/2016 | | |
| WO | WO-2016110587 A1 * | 7/2016 | ......... | A61K 39/3955 |
| WO | WO-2018/236995 A2 | 12/2018 | | |

OTHER PUBLICATIONS

Holen et al (Nucleic Acids Res., vol. 30, No. 8, 1757-1766 (2002)) (Year: 2002).*
Makarova et al, Nature Reviews, vol. 18, pp. 67-83 (2019) (Year: 2019).*
Koonin et al, Current Opinion in Microbiology, vol. 37, pp. 67-78 (2017) (Year: 2017).*
Dulos et al (No. 653: Myeloma: Therapy, Excluding Transplantation: Bion-1301: A novel Fully Blocking APRIL Antibody for the Treatment of Multiple Myeloma (2016)). (Year: 2016).*
Yu et al (Nature Immunology, vol. 1, No. 3, pp. 252-256 (2000)). (Year: 2000).*
Hartung et al., "Atacicept: targeting B cells in multiple sclerosis," Therapeutic advances in neurological disorders, 3(4):205-216 (2010).
International Search Report and Written Opinion for International Application No. PCT/US18/38490 dated Dec. 11, 2018.
Tang et al., "Agonist-mediated activation of STING induces apoptosis in malignant B cells," Cancer research, 76(8):2137-2152 (2016).
Dulos et al., "Bion-1301: A Novel Fully Blocking APRIL Antibody for the Treatment of Multiple Myeloma," Blood, 128(22): 2112 (2016).
Dulos et al., "Development of a first in class APRIL Fully Blocking Antibody BION-1301 for the Treatment of Multiple Myeloma," Blood: 1 page (2017).
Extended European Search Report and EP Application No. 18820336.8 dated Mar. 25, 2021.
Khan et al., "PD-L1hi B cells are critical regulators of humoral immunity", Nature communications 6(1): 5997 (2015).

* cited by examiner

*Primary Examiner* — Jane J Zara
(74) *Attorney, Agent, or Firm* — Foley Hoag LLP

(57) ABSTRACT

The present invention is based, in part, on methods for modulating regulatory T cells, regulatory B cells, and immune responses using modulators of the APRIL-TACI interaction.

20 Claims, 44 Drawing Sheets

Specification includes a Sequence Listing.

NT: wild type/parental H929
KD: BCMA-knockout H929

NT: wild type/parental H929
KD: BCMA-knockout H929

MM Patients
N=17 (33-41,45-51,53)

METHODS FOR MODULATING REGULATORY T CELLS, REGULATORY B CELLS, AND IMMUNE RESPONSES USING MODULATORS OF THE APRIL-TACI INTERACTION

CROSS-REFERENCE TO RELATED APPLICATIONS

This application is the U.S. national phase of International Patent Application No. PCT/US2018/038490, filed on 20 Jun. 2018, which claims the benefit of priority to U.S. Provisional Application Ser. No. 62/522,167, filed on 20 Jun. 2017; U.S. Provisional Application Ser. No. 62/573,264, filed on 17 Oct. 2017; and U.S. Provisional Application Ser. No. 62/677,265, filed on 29 May 2018; the entire contents of each of said applications are incorporated herein in their entirety by this reference.

STATEMENT OF RIGHTS

This invention was made with government support under grant number P50 CA100707 and R01 CA050947 awarded by The National Institutes of Health. The government has certain rights in the present invention.

BACKGROUND OF THE INVENTION

Multiple myeloma (MM) development and progression is associated with evolving genetic aberrations and alterations in the bone marrow (BM) microenvironment which promote malignant plasma cell (PC) growth while suppressing host immunity. Indeed, MM is characterized by recurrent infections due to immune deficiency, as well as bone lesions due to hyperactive osteoclasts (OCs). Moreover, the suppressive immune microenvironment underlies drug resistance and disease relapse. To date, however, the regulatory mechanisms of MM-related immune cell dysfunction have not been fully characterized.

Regulatory T cells (Tregs), traditionally defined as CD4+CD25+Foxp3+, are essential components of immune surveillance to maintain immune homeostasis and self-tolerance (Sakaguchi et al. (2008) *Cell* 133:775-787). Tregs are broadly divided by lineage into thymic-derived naturally occurring Tregs (nTregs) from CD4+CD8+ T-cells, and peripheral Tregs induced from naïve CD4+ T cells (iTregs; Knutson et al. (2007) *Cancer Immunol. Immunother.* 56:271-285). The latter are generated via cell-cell contact and/or cytokine-dependent mechanisms, i.e., TGF-β, IL-10, to prevent cellular and humoral immune responses (Campbell et al. (2001) *J Immunol.* 167:553-561). The function of nTregs and iTregs are quite similar, and it is difficult to distinguish them. Recently, Tregs have been associated with long-lived PCs in the BM, further suggesting their role in controlling homeostasis of PC populations (Zaretsky et al. (2017) *Cell Rep.* 18:1906-1916).

Increasing evidence indicates that the expansion of Tregs contributes to impaired anti-tumor immune responses resulting in immune escape and progression of solid and blood cancers, including MM (Fridman et al. (2012) *Nat. Rev. Cancer* 12:298-306; Tanaka et al. (2017) *Cell Res.* 27:109-118; Nishikawa et al. (2014) *Curr. Opin. Immunol.* 27:1-7; Kiniwa et al. (2007) *Clin. Cancer Res.* 13:6947-6958; Beyer et al. (2006) *Blood* 107:3940-3949; Feyler et al. (2009) *Br. J Haematol.* 144:686-695; Raja et al. (2012) *PloS One* 7:e47077; Feng et al. (2017) *Clin. Cancer Res.* 23:4290-4300). Tumor cells can positively interact with Tregs to inhibit tumor-specific CD8+ and CD4+T effector cell function and exhaust effector cells in the tumor microenvironment (Marabelle et al. (2013) *J. Clin. Invest.* 123:2447-2463; Bulliard et al. (2014) *Immunol. Cell Biol.* 92:475-480; Paiva et al. (2016) *Blood* 127:1151-1162; Arce Vargas et al. (2017) *Immunity* 46:577-586). In MM patients, the proportion of circulating functional Tregs in T cells were increased, which correlated with disease burden and higher risk of progression (Beyer et al. (2006) *Blood* 107:3940-3949; Feyler et al. (2009) *Br. J. Haematol.* 144:686-695; Raja et al. (2012) *PloS One* 7:e47077; Feng et al. (2017) *Clin. Cancer Res.* 23:4290-4300; Giannopoulos et al. (2012) *Br. J Cancer* 106:546-552; Raja et al. (2012) *PloS One* 7:e49446). Elevated Treg levels or numbers in MM patients can be derived from naïve CD4 T cells by stimulation with tumor cells and tumor bystander cells (Feng et al. (2017) *Clin. Cancer Res.* 23:4290-4300; Whiteside et al. (2012) *Expert Opin. Biol. Ther.* 12:1383-1397; Adeegbe et al. (2013) *Front. Immunol.* 4:190; Frassanito et al. (2015) *Eur. J Haematol.* 95:65-74). As shown in ex vivo co-cultures, MM cells significantly induce generation of iTreg from Tcons (Feng et al. (2017) *Clin. Cancer Res.* 23:4290-4300; Frassanito et al. (2015) *Eur. J Haematol.* 95:65-74; Feyler et al. (2012) *PloS One* 7:e35981). CD38-expressing Tregs (both nTregs and iTregs) have been identified and characterized as immune modulators in MM patients (Feng et al. (2017) *Clin. Cancer Res.* 23:4290-4300; Krejcik et al. (2016) *Blood* 128:384-394; Tai et al. (2016) *Blood* 128:318-319). Importantly, therapeutic CD38 targeting monoclonal antibodies (mAbs) deplete CD38-expressing Tregs and stimulate T and NK effector cell function (Feng et al. (2017) *Clin. Cancer Res.* 23:4290-4300; Tai et al. (2017) *Oncotarget* 8:112166-112167; Krejcik et al. (2016) *Blood* 128:384-394). Overexpressed Foxp3 and CTLA-4 in BM samples further supports a local accumulation of immunosuppressive Tregs in the MM microenvironment (Braga et al. (2014) *Cancer Immunol. Immunother.* 63:1189-1197). Finally, MM cells directly drive Tregs via a positive feedback loop in a transplantation mouse model to promote disease progression and inferior outcome (Kawano et al. (2018) *J Clin. Invest.* DOI:10.1172/JCI88169).

A proliferation-inducing ligand (APRIL), a critical PC growth and survival factor, binds with high affinity to B cell maturation antigen (BCMA), the most specific MM antigen expressed at high levels in malignant PCs of all MM patients (Carpenter et al. (2013) *Clin. Cancer Res.* 19:2048-2060; Tai et al. (2014) *Blood* 123:3128-3138). Most recently, targeting BCMA by novel immunotherapies has achieved impressive clinical responses in relapsed and refractory MM (Carpenter et al. (2013) *Clin. Cancer Res.* 19:2048-2060; Tai et al. (2014) *Blood* 123:3128-3138; Tai et al. (2015) *Immunotherapy* 7:1187-1199; Ali et al. (2016) *Blood* 128:1688-1700; Mikkilineni et al. (2017) *Blood* 130:2594-2602). Constitutive in vivo activation of APRIL/BCMA signaling promotes MM cell progression and induction of immune inhibitory factors in MM cells (Tai et al. (2016) *Blood* 127:3225-3236). In addition, MM cell growth is significantly reduced in APRIL-deficient SCID mice, indicating that APRIL by itself can induce in vivo MM progression (Matthes et al. (2015) *Leukemia* 29:1901-1908). Myeloma-supporting OCs produce APRIL (Moreaux et al. (2005) *Blood* 106:1021-1030; Tucci et al. (2011) *Exp. Hematol.* 39:773-783; Yaccoby et al. (2008) *Leukemia* 22:406-413; Abe et al. (2006) *Leukemia* 20:1313-1315) and PD-L1 (An et al. (2016) *Blood* 128:1590-1603) in the BM, and OCs further block autologous T cell proliferation via immune checkpoint molecules including PD-L1 (An et al. (2016)

*Blood* 128:1590-1603). However, it is not yet known whether Tregs mediate OC-induced immunosuppression and whether APRIL regulates these processes.

APRIL also binds to transmembrane activator and calcium modulator and cyclophilin ligand interactor (TACI; Marsters et al. (2000) *Current Biol.* 10:785-788), which is expressed at lower levels and reduced frequency in patient MM cells when compared with BCMA (Moreaux et al. (2005) *Blood* 106:1021-1030; Tai et al. (2006) *Cancer Res.* 66:6675-6682). Unlike BCMA that is only important in long-lived and malignant PCs but not normal B cells, TACI can negatively or positively regulate B cell responses (Yan et al. (2001) *Nat. Immunol.* 2:638-643; Castigli et al. (2005) *J. Exp. Med.* 201:35-39; Sakurai et al. (2007) *Blood* 109: 2961-2967; Tsuji et al. (2011) *Blood* 118:5832-5839; Garcia-Carmona et al. (2015) *Blood* 125:1749-1758). Results from TACI and APRIL knockout mice indicate their roles in serum IgA production (Yan et al. (2001) *Nat. Immunol.* 2:638-643; von Bulow et al. (2001) *Immunity* 14:573-582; Castigli et al. (2004) *Proc. Natl. Acad. Sci. U.S.A.* 101:3903-3908; Planelles et al. (2004) *Cancer Cell* 6:399-408), and TACI requires heparan sulfate proteoglycans (i.e., CD138) for APRIL-induced IgA production (Sakurai et al. (2007) *Blood* 109:2961-2967; Guadagnoli et al. (2011) *Blood* 117: 6856-6865). However, it is unclear whether APRIL directly acts on immune regulatory T- and B-linage cells through TACI to downregulate effector T cells in MM.

Thus, regulatory T cells (Tregs), such as $CD4^{+}CD25^{high}FoxP3^{high}$ T cells, are important regulators of immune responses because they inhibit immune effector cells (Feng et al. (2017) *Clin. Cancer Res.* DOI:10.1158/1078-0432.CCR-16-3192; Hori et al. (2003) *Science* 299: 1057-1061; Fontenot et al. (2003) *Nat. Immunol.* 4:330-336; Vignali et al. (2008) *Nat. Rev. Immunol.* 8:523-532; Josefowicz et al. (2012) *Annu. Rev. Immunol.* 30:531-564; Shevach and Thornton (2014) *Immunol. Rev.* 259:88-102; Smigiel et al. (2014) *Immunol. Rev.* 259:40-59). Similarly, regulatory B cells (Bregs), such as $CD19^{+}CD24^{high}CD38^{high}$ B cells, are important regulators of immune responses because they also inhibit immune effector cells. In particular, Bregs suppress immune responses chiefly through the production of anti-inflammatory cytokine interleukin 10 (IL-10) and also modulate CD4+ T-cell activation and differentiation (Zhang et al. (2017) *Blood Cancer J.* 24:e547; Rosser et al. (2015) *Immunity* 42:607-612). Since Tregs and Bregs are involved in many diseases, such as autoimmunity, cancer, and infections, modulating the number and/or inhibitory immune activity of Tregs and/or Bregs is desired (Rosenblum et al. (2012) *Science Transl. Med.* 4:125sr121; Chapman and Chi (2014) *Immunother.* 6:1295-1311; Bluestone et al. (2015) *J. Clin. Invest.* 125:220-2260). However, it has been a challenge in the field to selectively modulate the number and/or inhibitory immune activity of Tregs and/or Bregs because the genes and pathways expressed by these cells and related to cell growth, survival, and/or inhibitory immune activity are generally shared with those of other immunomodulatory cells, such as effector T cells. Thus, a great need in the art exists to identify and target genes and pathways selectively expressed by Tregs and/or Bregs that regulate their cell growth, survival, and/or inhibitory immune activity that allow for selective modification of these properties among Tregs and/or Bregs.

Accordingly, a great need in the art exists to understand the mechanism of immune regulation in tumor environment, and to identify and target genes in this pathway that are useful for the prevention and treatment of cancer. In addition, there exists a great need in the art to understand, identify, and target the pathways selectively expressed by Tregs and/or Bregs that regulate their cell growth, survival, and/or inhibitory immune activity that allow for selective modification of these properties among Tregs and/or Bregs.

SUMMARY OF THE INVENTION

The present invention is based, at least in part, on the discovery that APRIL promotes immunosuppression in cancer cells via its interaction with TAC. For Example, APRIL signaling via TACI significantly upregulates proliferation, survival, and immune inhibitory function of both Tregs and Bregs. Furthermore, targeting APRIL, alone and together with PD1/PD-L1 blockade, decreases OC-induced immune suppression in the tumor microenvironment. These findings provide the framework for targeting APRIL and/or APRIL-TACI interaction to overcome immunosuppression, enhance cytotoxicity of cancer cells, and improve patient outcome.

The present invention is also based, at least in part, on the discovery that TACI, one of two receptors of the APRIL ligand, is significantly expressed by regulatory T cells (Tregs), such as $CD4^{+}CD25^{high}FoxP3^{high}$ Tregs, whereas conventional T cells (Tcons), such as CD4+CD25− T cells, do not appreciably express TAC. The other receptor of the APRIL ligand, which is known as BCMA, is not expressed by Tregs or Tcons. Similarly, it is believed that regulatory B cells (Bregs) also express TAC. Since the binding of APRIL to immune cells expressing TACI is believed to lead to up-regulation of growth and survival genes and TACI is selectively expressed by Tregs/Bregs, it is believed that APRIL preferentially activates TACI in Tregs/Bregs as opposed to Tcons to selectively up-regulation of growth and survival genes in Tregs/Bregs to thereby increase Tregs/Bregs number and/or inhibitor immune activity than Tcons leading to enhanced inhibitory immune function. Thus, modulating the APRIL/TACI interaction on Tregs/Bregs is believed to allow for the selective modification (e.g., enhanced or decreased) or Tregs/Bregs number and/or their inhibitor immune activity based on the direction of the APRIL/TACI interaction modulation (e.g., enhancing or decreasing, respectively).

In one aspect, a method of selectively modifying the number and/or inhibitory immune activity of regulatory T cells (Tregs) and/or regulatory B cells (Bregs) in a subject, comprising administering to the subject a therapeutically effective amount of at least one agent that modulates the interaction of TACI receptor protein expressed by the Tregs and/or Bregs with APRIL ligand such that the number and/or inhibitory immune activity of the Tregs and/or Bregs is selectively modified, is provided.

Numerous embodiments are further provided that can be applied to any aspect of the present invention and/or combined with any other embodiment described herein. For example, in one embodiment, the agent downregulates the interaction between the TACI receptor protein expressed by the Tregs and/or Bregs with APRIL ligand such that the number of the Tregs and/or Bregs is decreased and/or the inhibitory immune activity of the Tregs and/or Bregs is decreased, optionally wherein the expression of IL10, PD-L1, and/or one or more growth or survival genes (e.g., MCL1, Bcl-2, Bcl-xL, CCND1, CCND2, and/or BIRC3) is decreased. In another embodiment, the agent is a small molecule inhibitor, CRISPR guide RNA (gRNA), RNA interfering agent, antisense oligonucleotide, peptide or peptidomimetic inhibitor, aptamer, or antibody. In still another embodiment, the RNA interfering agent is a small interfering RNA (siRNA), CRISPR RNA (crRNA), a small hairpin RNA (shRNA), a microRNA (miRNA), or a piwi-interacting RNA (piRNA). In yet another embodiment, the RNA interfering agent is a CRISPR guide RNA (gRNA). In another embodiment, the agent comprises a blocking antibody, or an antigen binding fragment thereof, which specifically binds to the TACI receptor or the APRIL ligand. In still another embodiment, the antibody, or antigen binding fragment thereof, is murine, chimeric, humanized, composite, or human. In yet another embodiment, the antibody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In another embodiment, the antibody, or antigen binding fragment thereof, is conjugated to a cytotoxic agent. In still another embodiment, the cytotoxic agent is selected from the group consisting of a chemotherapeutic agent, a biologic agent, a toxin, and a radioactive isotope. In yet another embodiment, the method further comprises administering to the subject an inhibitor of the STING pathway. In another embodiment, the agent upregulates the interaction between the TACI receptor protein expressed by the Tregs and/or Bregs with APRIL ligand such that the number of the Tregs and/or Bregs is increased and/or the inhibitory immune activity of the Tregs and/or Bregs is increased, optionally wherein the expression of IL10, PD-L1, and/or one or more growth or survival genes (e.g., MCL1, Bcl-2, Bcl-xL, CCND1, CCND2, and/or BIRC3) is increased. In still another embodiment, the agent is a nucleic acid molecule encoding APRIL ligand polypeptide or fragment thereof, an APRIL polypeptide or fragment thereof, an activating antibody, or an antigen binding fragment thereof, which specifically binds to the TACI receptor or the APRIL ligand; or an antibody that specifically binds to both the TACI receptor and the APRIL ligand. In yet another embodiment, the antibody, or antigen binding fragment thereof, is murine, chimeric, humanized, composite, or human. In another embodiment, the antibody, or antigen binding fragment thereof, is detectably labeled, comprises an effector domain, comprises an Fe domain, and/or is selected from the group consisting of Fv, Fav, F(ab')2, Fab', dsFv, scFv, sc(Fv)2, and diabodies fragments. In still another embodiment, the APRIL ligand polypeptide or fragment thereof is a fusion protein. In yet another embodiment, the APRIL ligand polypeptide or fragment thereof is fused to an Fe domain. In another embodiment, the method further comprises administering to the subject an activator of the STING pathway (e.g., a STING agonist). In still another embodiment, the method further comprises administering to the subject at least one immunotherapy. In yet another embodiment, the immunotherapy is selected from the group consisting of a cell-based immunotherapy, a cancer vaccine, a virus, an immune checkpoint inhibitor, and an immunomodulatory cytokine. In another embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM4-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, IDO1, IDO2, and A2aR. In still another embodiment, the agent, either alone or in combination with the inhibitor or the activator of the STING pathway and/or the immunotherapy, i) does not significantly modulate the number and/or immune activity of the Tcons and/or ii) modulates immunomodulatory cytokine production in the Tregs and/or Bregs. In yet another embodiment, the subject has a cancer and the agent, either alone or in combination with the inhibitor or the activator of the STING pathway and/or the immunotherapy, reduces the number of proliferating cells in the cancer and/or reduces the volume or size of a tumor comprising the cancer cells, optionally determining responsiveness to the agent that modulates the TACI receptor protein expressed by the Tregs and/or Bregs with APRIL ligand measured by at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In another embodiment, the method further comprises administering to the subject at least one additional therapeutic agent or regimen for treating the cancer. In still another embodiment, the agent, the inhibitor or the activator of the STING pathway immunotherapy, and/or at least one additional therapeutic agent is non-systemically administered to a microenvironment containing Tregs and/or Bregs.

In another aspect, a method of selectively modifying the number and/or inhibitory immune activity of Tregs and/or Bregs comprising contacting the Tregs and/or Bregs with at least one agent that modulates the interaction of TACI receptor protein expressed by the Tregs and/or Bregs with APRIL ligand such that the number and/or inhibitory immune activity of the Tregs and/or Bregs is selectively modified, is provided.

As described above, numerous embodiments are further provided that can be applied to any aspect of the present invention and/or combined with any other embodiment described herein. For example, in one embodiment, the agent downregulates the interaction between the TACI receptor protein expressed by the Tregs and/or Bregs with APRIL ligand such that the number of the Tregs and/or Bregs is decreased and/or the inhibitory immune activity of the Tregs and/or Bregs is decreased, optionally wherein the expression of IL10, PD-L1, and/or one or more growth or survival genes (e.g., MCL1, Bcl-2, Bcl-xL, CCND1, CCND2, and/or BIRC3) is decreased. In another embodiment, the agent is a small molecule inhibitor, CRISPR guide RNA (gRNA), RNA interfering agent, antisense oligonucleotide, peptide or peptidomimetic inhibitor, aptamer, or antibody. In still another embodiment, the RNA interfering agent is a small interfering RNA (siRNA), CRISPR RNA (crRNA), a small hairpin RNA (shRNA), a microRNA (miRNA), or a piwi-interacting RNA (piRNA). In yet another embodiment, the RNA interfering agent is a CRISPR guide RNA (gRNA). In another embodiment, the agent comprises a blocking antibody, or an antigen binding fragment thereof, which specifically binds to the TACI receptor or the APRIL ligand. In still another embodiment, the antibody, or antigen binding fragment thereof, is murine, chimeric, humanized, composite, or human. In yet another embodiment, the antibody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In another embodiment, the antibody, or antigen binding fragment thereof, is conjugated to a cytotoxic agent. In still another embodiment, the cytotoxic agent is selected from the group consisting of a chemotherapeutic agent, a biologic agent, a toxin, and a radioactive isotope. In yet another embodiment, the method further comprises administering to the subject an inhibitor of the STING pathway. In another embodiment, the agent upregulates the interaction between the TACI receptor protein expressed by the Tregs and/or Bregs with APRIL ligand such that the number of the Tregs and/or Bregs is increased and/or the inhibitory immune activity of the Tregs and/or Bregs is increased, optionally wherein the expression of IL10, PD-L1, and/or one or more growth or survival genes (e.g., MCL1, Bcl-2, Bcl-xL, CCND1, CCND2, and/or BIRC3) is increased. In still another embodiment, the agent is a nucleic acid molecule encoding APRIL ligand polypeptide or fragment thereof; an APRIL polypeptide or fragment thereof, an activating antibody, or an antigen binding fragment thereof, which specifically binds to the TACI receptor or the APRIL ligand; or an antibody that specifically binds to both the TACI receptor and the APRIL ligand. In yet another embodiment, the antibody, or antigen binding fragment thereof, is murine, chimeric, humanized, composite, or human. In another embodiment, the antibody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In still another embodiment, the APRIL ligand polypeptide or fragment thereof is a fusion protein. In yet another embodiment, the APRIL ligand polypeptide or fragment thereof is fused to an Fc domain. In another embodiment, the method further comprises administering to the subject an activator of the STING pathway (e.g., a STING agonist). In still another embodiment, the method further comprises contacting the Tregs and/or Bregs with at least one immunotherapy. In yet another embodiment, the immunotherapy is selected from the group consisting of a cell-based immunotherapy, a cancer vaccine, a virus, an immune checkpoint inhibitor, and an immunomodulatory cytokine. In another embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, IDO1, IDO2, and A2aR. In still another embodiment, the agent, either alone or in combination with the inhibitor or the activator of the STING pathway and/or the immunotherapy, contacts the Tregs and/or Bregs in the presence of Tcons and i) does not significantly modulate the number and/or immune activity of the Tcons and/or ii) modulates immunomodulatory cytokine production in the Tregs and/or Bregs. In yet another embodiment, the agent, either alone or in combination with the inhibitor or the activator of the STING pathway and/or the immunotherapy, contacts the Tregs and/or Bregs in the presence of Tcons and cancer cells, and the agent, either alone or in combination with the immunotherapy, reduces the number of proliferating cells in the cancer and/or reduces the volume or size of a tumor comprising the cancer cells. In another embodiment, the method further comprises contacting the cancer cells with at least one additional cancer therapeutic agent or regimen. In still another embodiment, the agent, the inhibitor or the activator of the STING pathway, or immunotherapy, and/or at least one additional therapeutic agent contacts the Tregs, Bregs, Tcons, and/or cancer cells in vitro or ex vivo.

In still another aspect, a cell-based assay for screening for agents that selectively modifies the number and/or inhibitory immune activity of Tregs and/or Bregs comprising contacting Tregs and/or Bregs with a test agent, and determining the ability of the test agent to modulate the interaction of TACI receptor protein expressed by the Tregs and/or Bregs with APRIL ligand, wherein a test agent that modulates the interaction of TACI receptor protein expressed by the Tregs and/or Bregs with APRIL ligand selectively modifies the number and/or inhibitory immune activity of the Tregs and/or Bregs, is provided.

As described above, numerous embodiments are further provided that can be applied to any aspect of the present invention and/or combined with any other embodiment described herein. For example, in one embodiment, the step of contacting occurs in vivo, ex vivo, or in vitro. In another embodiment, Tregs and/or Bregs are contacted with an inhibitor or an activator of the STING pathway. In still another embodiment, the activator of the STING pathway is a STING agonist. In yet another embodiment, Tregs and/or Bregs are contacted with at least one immunotherapy. In another embodiment, the immunotherapy is selected from the group consisting of a cell-based immunotherapy, a cancer vaccine, a virus, an immune checkpoint inhibitor, and an immunomodulatory cytokine. In still another embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM4-4, LAG-3, GITR, 4-IBB, OX-40, BTLA, SIRPalpha (CD47), CD48, 2B4 (CD244), B7.1, B7.2, LT-2, ILT-4, TIGIT, HHLA2, butyrophilins, IDO1, IDO2, and A2aR. In yet another embodiment, Tregs and/or Bregs are contacted with a test agent, either alone or in combination with the inhibitor or the activator of the STING pathway and/or the immunotherapy, in the presence of Tcons and i) a lack of significant modulation in the number and/or immune activity of the Tcons and/or ii) modulation of immunomodulatory cytokine production in the Tregs and/or Bregs, is determined. In another embodiment, Tregs and/or Bregs are contacted with a test agent, either alone or in combination with the inhibitor or the activator of the STING pathway, or the immunotherapy, in the presence of Tcons and cancer cells and a reduction in the number of proliferating cancer cells and/or a reduction in the volume or size of a tumor comprising the cancer cells, is determined. In still another embodiment, cancer cells are further contacted with at least one additional cancer therapeutic agent or regimen.

In another embodiment, the Tregs comprise CD4+CD25+, CD4+FOXP3+, and/or CD4+CD25+FOXP3+ Tregs, such as CD4+CD25$^{high}$FOXP3+ Tregs. In another embodiment, the Tregs comprise CD8+CD25+FOXP3+ Tregs. In still another embodiment, the Bregs comprise CD19+CD24+CD38+ Bregs, such as CD19+CD24$^{high}$CD38$^{high}$ Bregs. In yet another embodiment, the Tcons comprise CD4+CD25− Tcons. In another embodiment, the subject has a condition that would benefit from upregulation of an immune response. In still another embodiment, the subject has a condition selected from the group consisting of a cancer, a viral infection, a bacterial infection, a protozoal infection, a helminth infection, asthma associated with impaired airway tolerance, and an immunosuppressive disease. In yet another embodiment, the subject has a cancer or the cell population comprises cancer cells. In another embodiment, the cancer is multiple myeloma. In still another embodiment, the cancer is an animal model of the cancer, optionally wherein the animal model is a mouse model. In yet another embodiment, the subject is a mammal. In another embodiment, the mammal is a mouse or a human. In still another embodiment, the mammal is a human.

Figure 1:
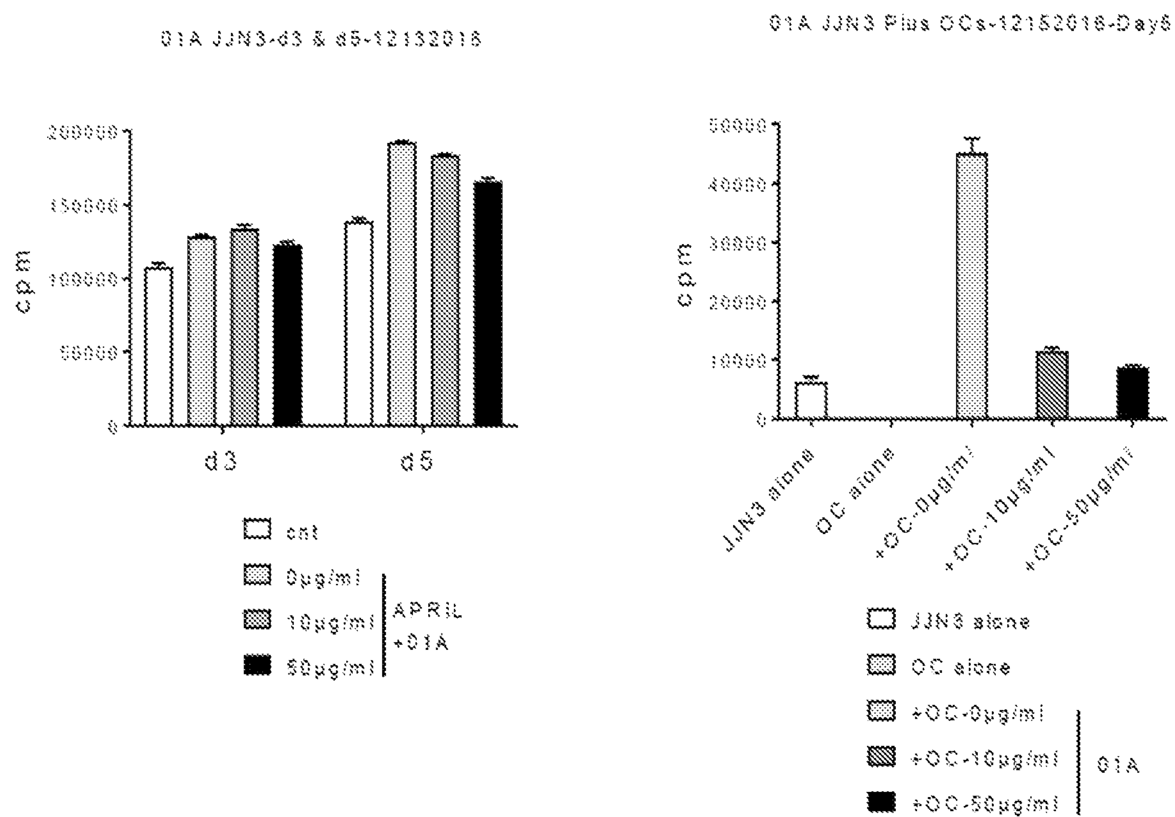
FIG. 1 shows that the anti-APRIL blocking antibody, 01A, obtained from Aduro Biotech blocks APRIL- and OC-induced multiple myeloma (MM) cell growth.
Figure 2:
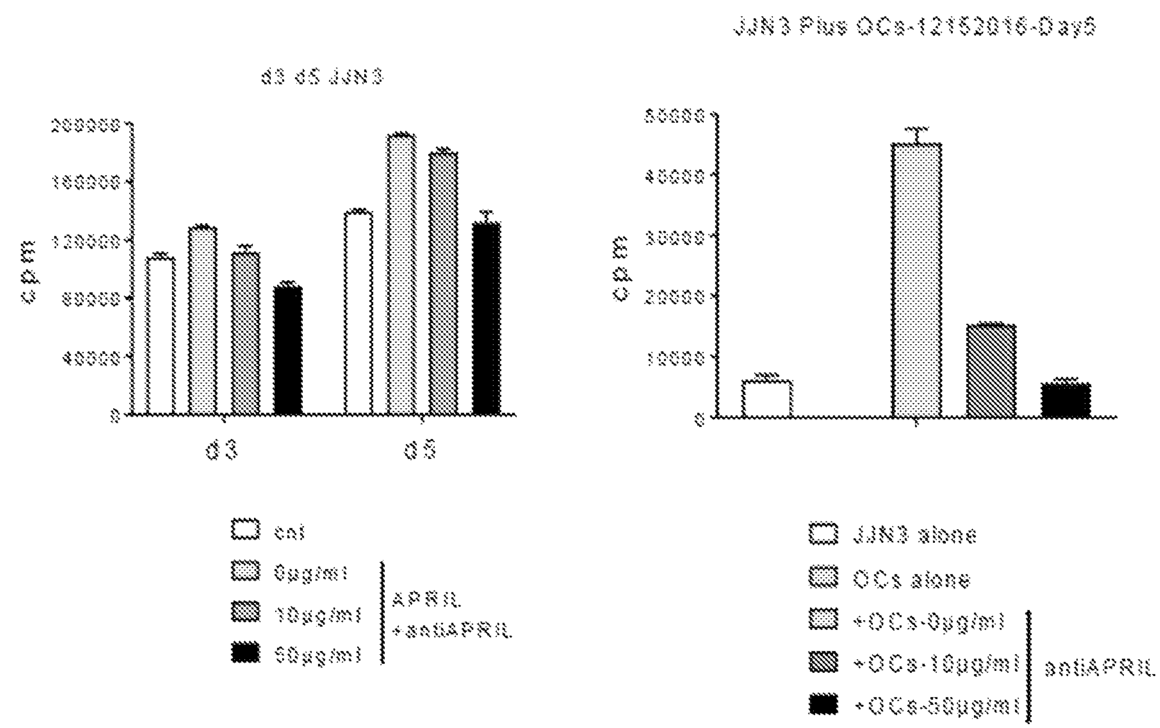
FIG. 2 shows that anti-APRIL monoclonal antibody blocks APRIL- and OC-induced MM cell growth in a dose-dependent manner.
Figure 3:
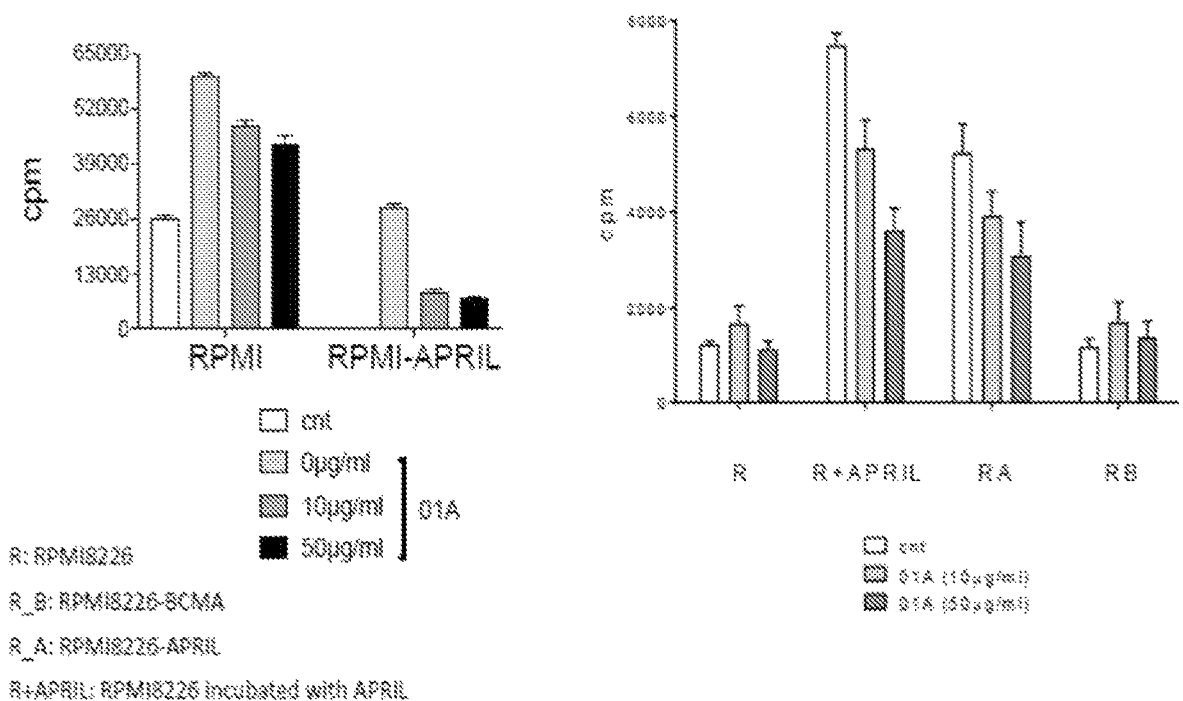
FIG. 3 shows that the anti-APRIL antibody, 01A, potently inhibits growth of APRIL-expressing MM cells when compared with blockage of APRIL-induced cell proliferation in parental RPMI8226 cells. APRIL and anti-APRIL are from Adipogen.
Figure 4:
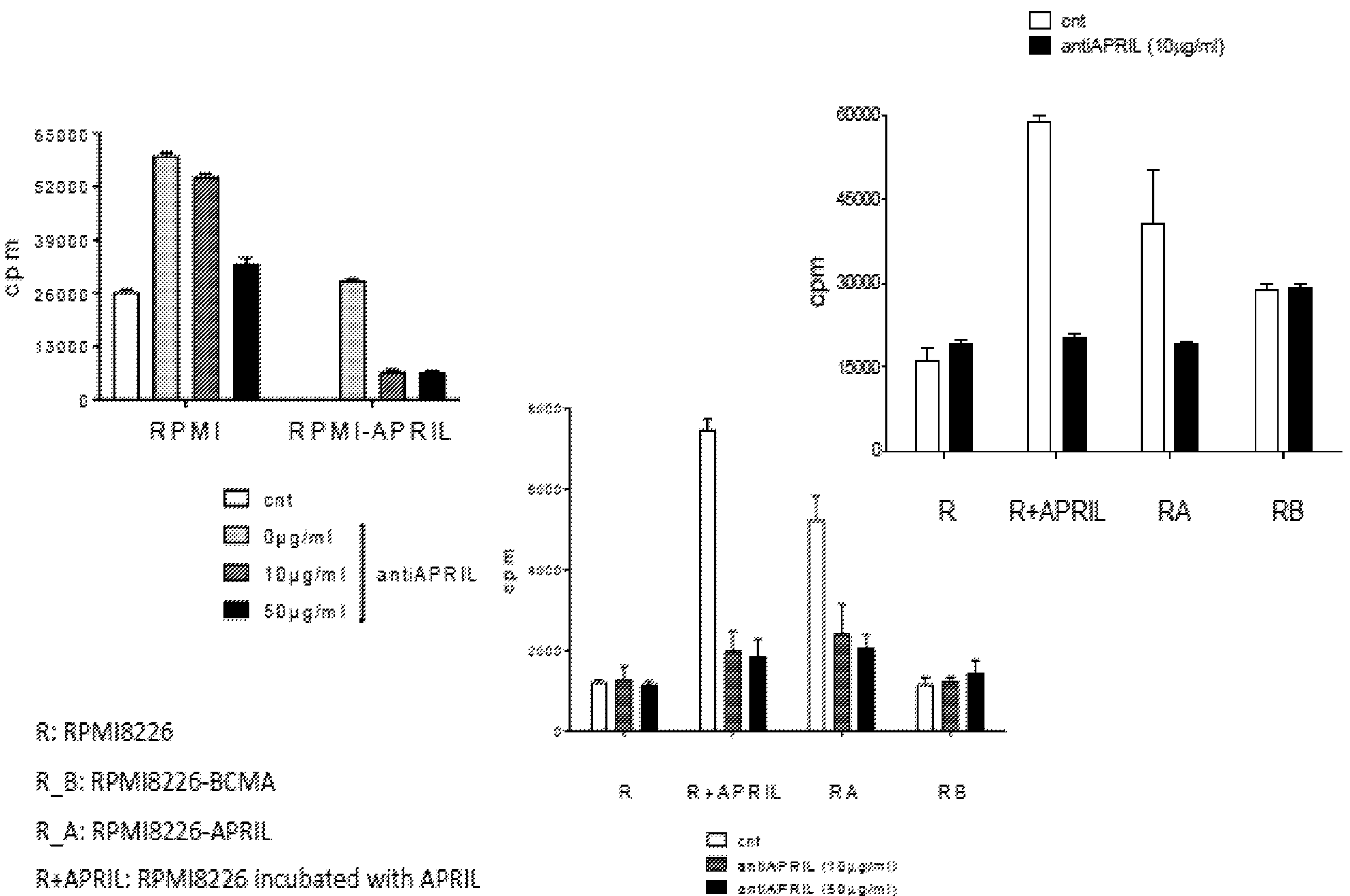
FIG. 4 shows that anti-APRIL mAb potently inhibits APRIL-expressing MM cell growth.
Figure 5:
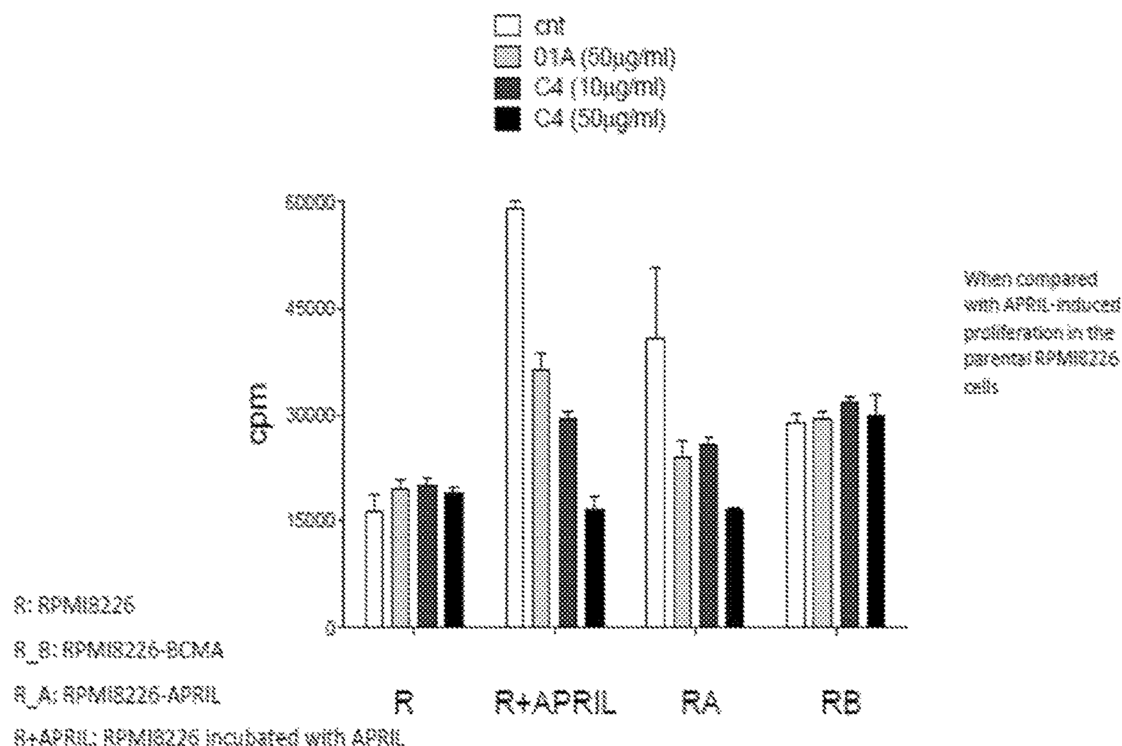
FIG. 5 shows that anti-APRIL blocking antibody, C4, blocks proliferation of APRIL-expressing MM cells more potently than 01A.
Figure 6:
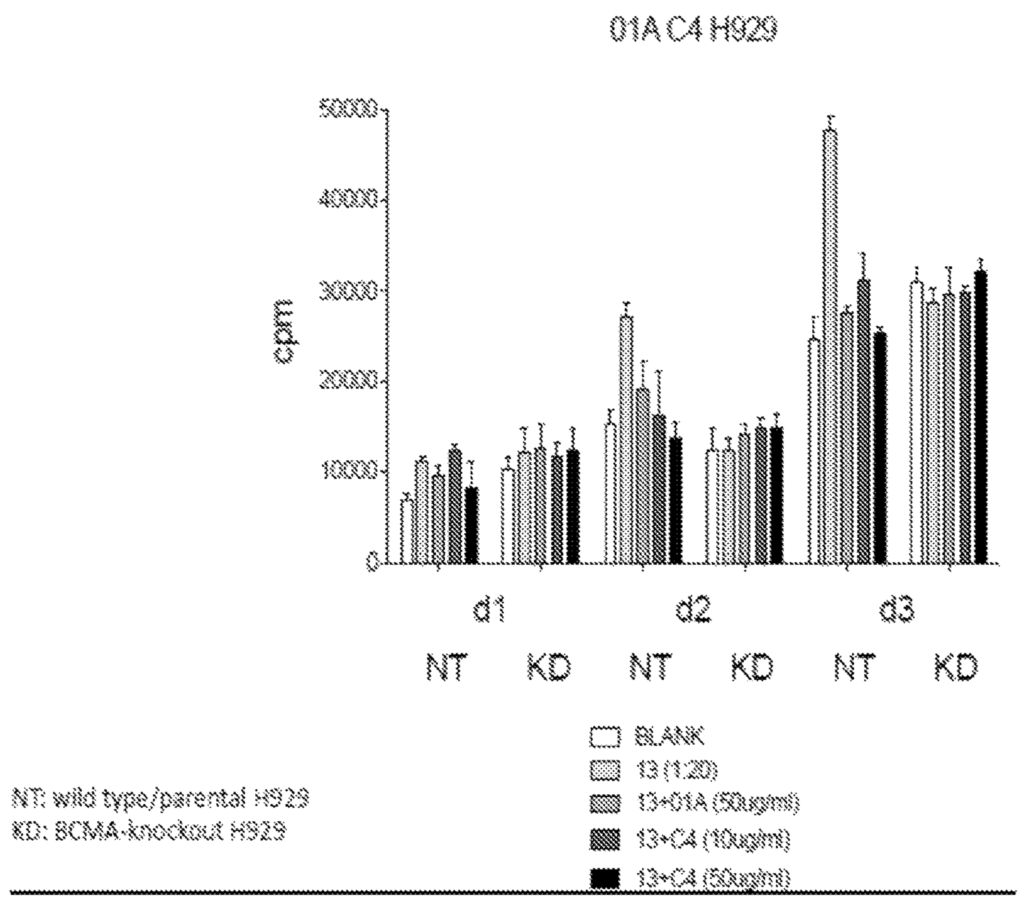
FIG. 6 shows that anti-APRIL blocking antibody, C4, selectively inhibits APRIL-induced MM cell growth more potently than 01A.
Figure 7:
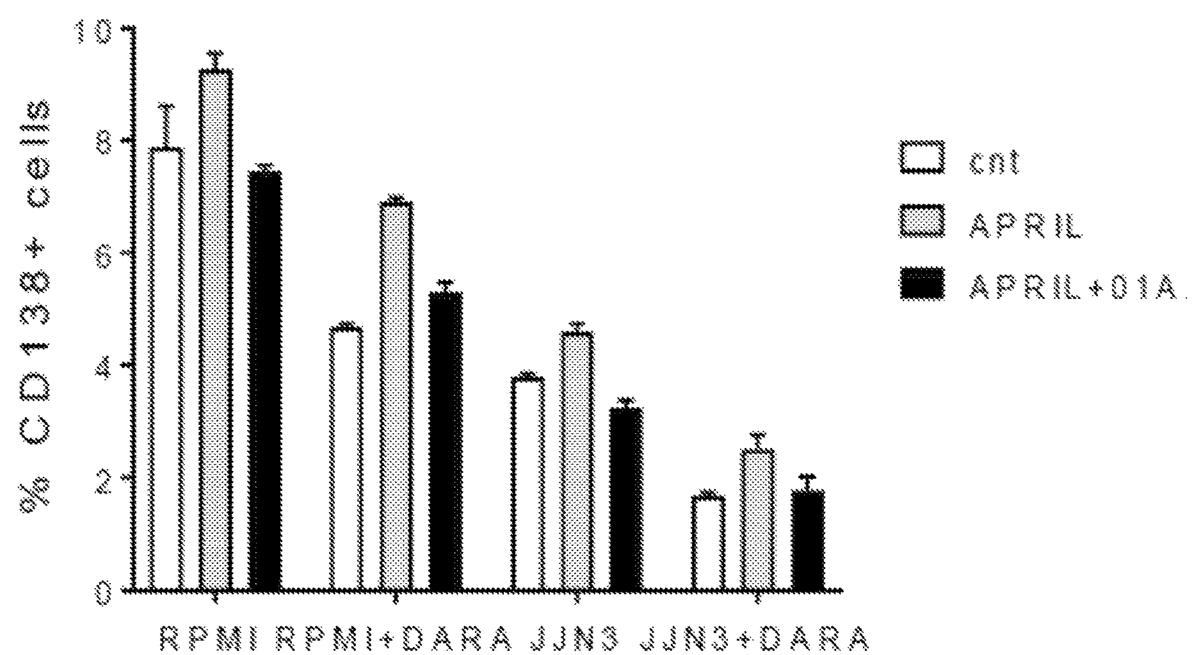
FIG. 7 shows that pre-incubation of APRIL in MM cells protects MM cell lysis by daratumumab (Dara), thereby indicating therapeutic combination of anti-APRIL agent with Dara.
Figure 8:
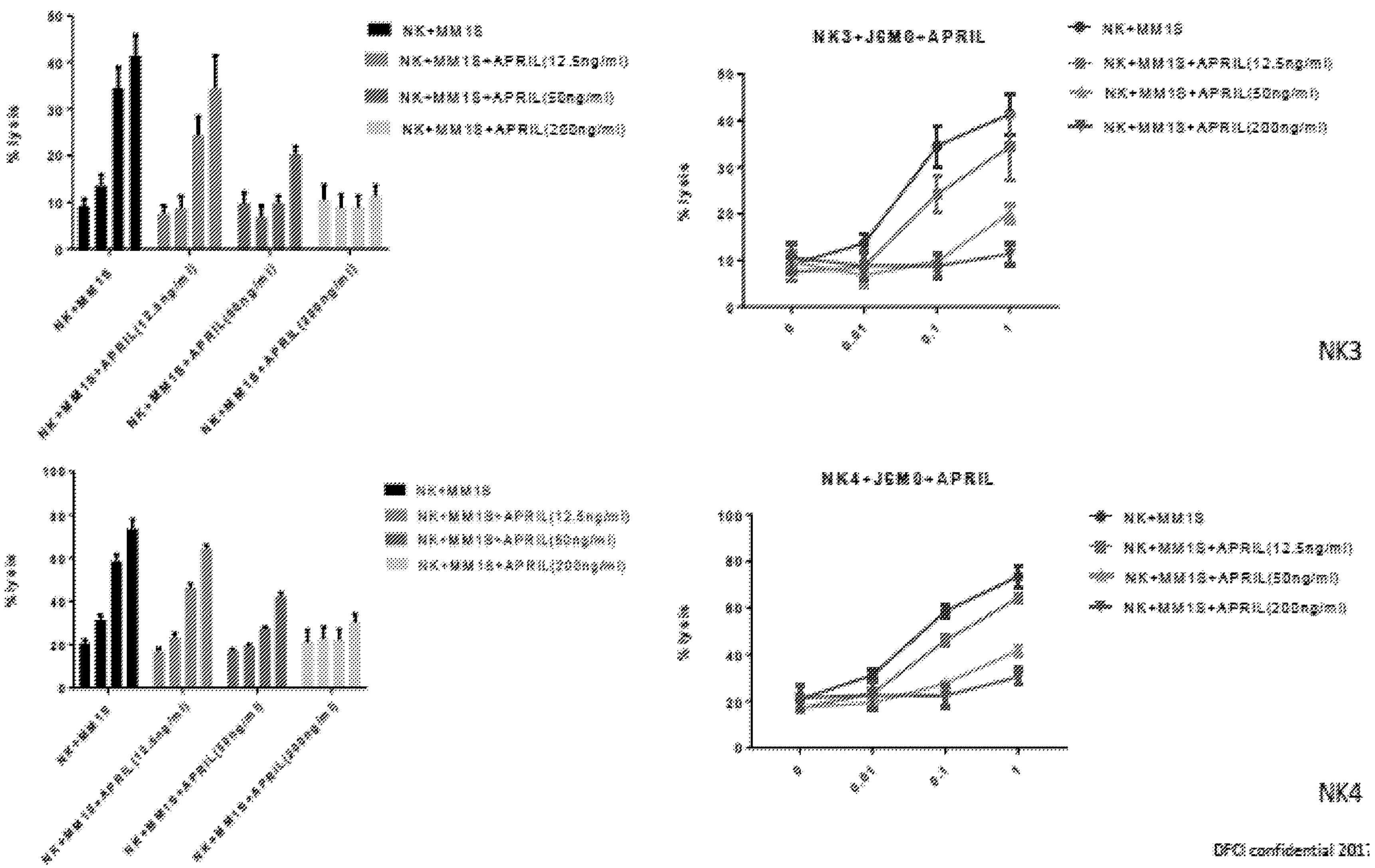
FIG. 8 shows that APRIL prevents J6M0-induced MM1S cell lysis in a dose-dependent manner, thereby indicating therapeutic combination of anti-APRIL agent with BCMA-related immunotherapy. J6M0 is a BCMA-specific anti-TNFRSF17 antibody.
Figure 9:
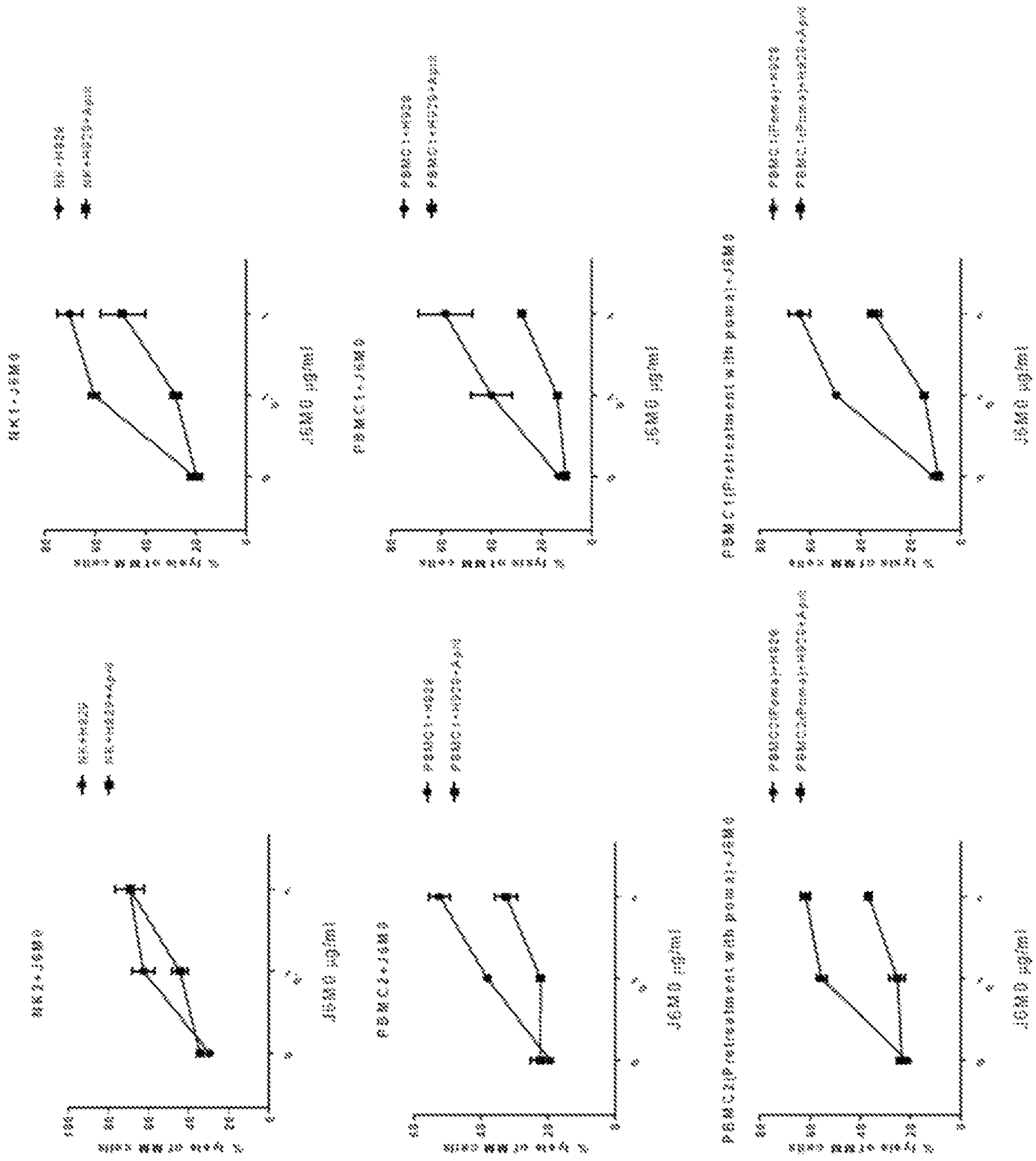
FIG. 9 further shows that APRIL prevents J6M0-induced MM1S cell lysis in a dose-dependent manner, thereby indicating therapeutic combination of anti-APRIL agent with BCMA-related immunotherapy.
Figure 10:
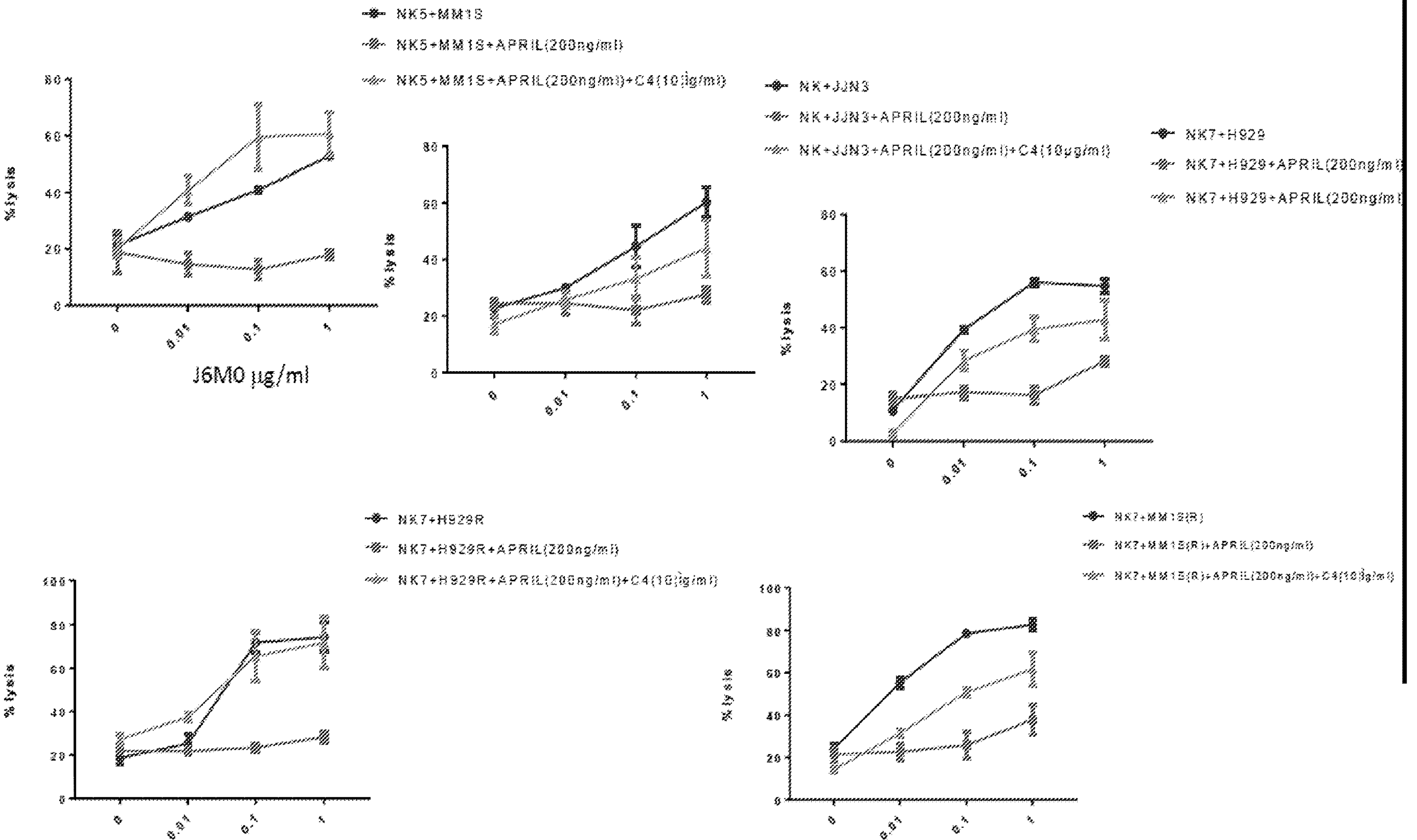
FIG. 10 shows that C4 (01A) overcomes APRIL-blocked J6M0-induced lysis of MM cells sensitive and resistant to current anti-MM treatment such as lenalidomide/pomalidomide.
Figure 11:
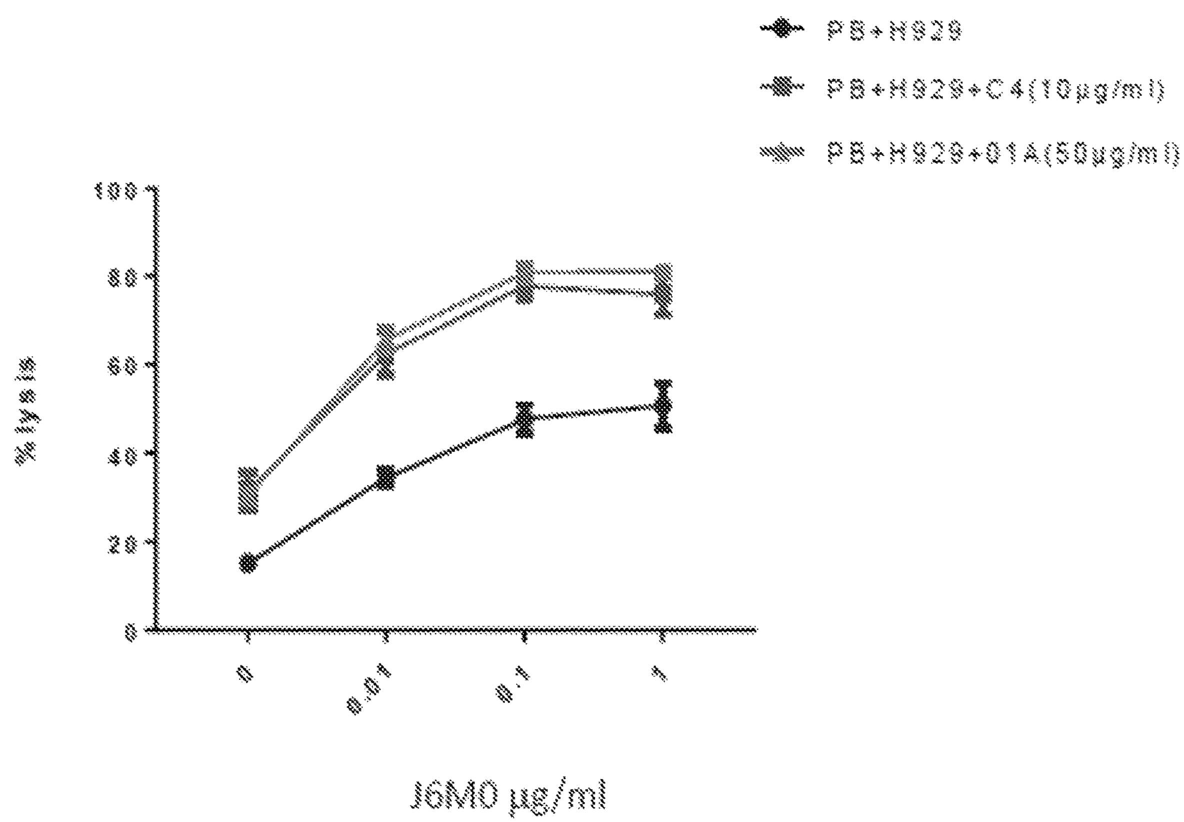
FIG. 11 shows that J6M-induced ADCC using C4/01A-pre-treated PBMC effector cells.
Figure 12:
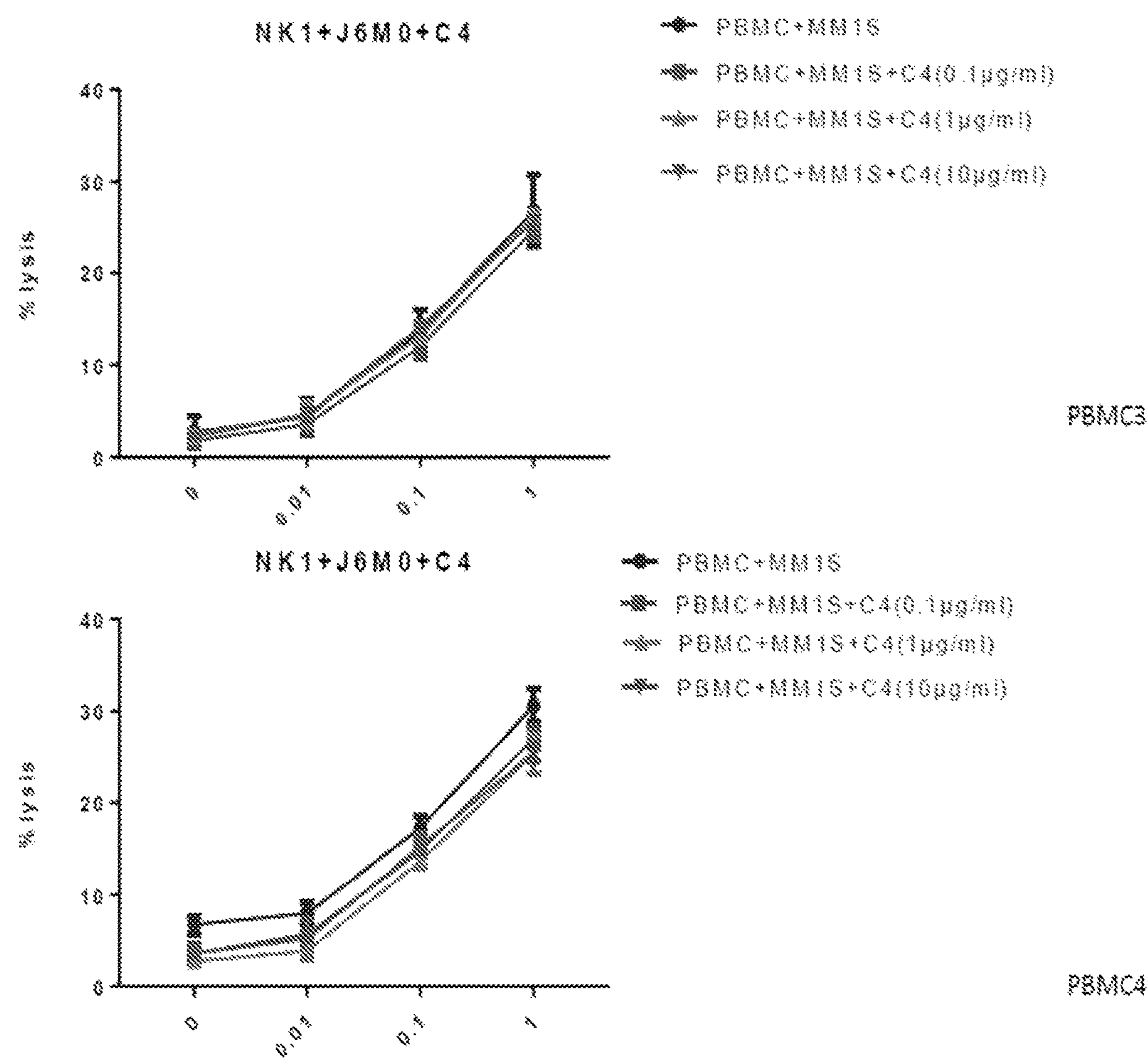
FIG. 12 shows that C4 did not alter anti-BCMA mAb-induced MM cell lysis when added during ADCC assays.

Note that for every figure containing a histogram, the bars from left to right for each discreet measurement correspond to the figure boxes from top to bottom in the figure legend as indicated.

DETAILED DESCRIPTION OF THE INVENTION

Regulatory T and B cells negatively inhibit immune responses and are useful targets for modulating immune responses. However, it has been challenging to identify genes and pathways that are selectively expressed by immune cell populations and modify such genes and pathways in order to selectively modulate immune cell numbers and/or immune activity of subsets of immune cell populations. It has been determined herein that TACI, a receptor for APRIL ligand, is significantly expressed on Tregs, such as CD4+CD25+FoxP3+ Tregs, and $CD4^{+}CD25^{high}FoxP3^{high}$ Tregs, when compared with conventional T cells (Tcons), such as $CD4^{+}CD25^{-}$ T cells. It has also been determined herein that TACI is significantly expressed on CD8+CD25+ FoxP3+ Tregs. It is also believed that Bregs selectively express TACI like Tregs. Since the binding of APRIL to immune cells expressing TACI is believed to lead to up-regulation of growth and survival genes and TACI is selectively expressed by Tregs/Bregs, it is believed that APRIL preferentially activates TACI in Tregs/Bregs as opposed to Tcons to selectively up-regulate growth and survival genes in Tregs/Bregs to thereby increase Tregs/Bregs number and/or inhibitory immune activity than Tcons leading to enhanced inhibitory immune function. Thus, modulating the APRIL/TACI interaction on Tregs/Bregs is believed to allow for the selective modification (e.g., enhanced or decreased) Tregs/Bregs number and/or inhibitory immune activity based on the quality of the APRIL/TACI interaction modulation (e.g., enhancing or decreasing, respectively).

Accordingly, the present invention relates, in part, to methods of selectively modifying the number and/or inhibitory immune activity of regulatory T cells (Tregs) and/or regulatory B cells (Bregs) in a subject, comprising administering to the subject a therapeutically effective amount of at least one agent that modulates the interaction of TACI receptor protein expressed by the Tregs and/or Bregs with APRIL ligand such that the number and/or inhibitory immune activity of the Tregs and/or Bregs is selectively modified. In another aspect, the present invention provides methods of selectively modifying the number and/or inhibitory immune activity of Tregs and/or Bregs comprising contacting the Tregs and/or Bregs with at least one agent that modulates the interaction of TACI receptor protein expressed by the Tregs and/or Bregs with APRIL ligand such that the number and/or inhibitory immune activity of the Tregs and/or Bregs is selectively modified. In still another aspect, the present invention provides a cell-based assay for screening for agents that selectively modifies the number and/or inhibitory immune activity of Tregs and/or Bregs comprising contacting Tregs and/or Bregs with a test agent, and determining the ability of the test agent to modulate the interaction of TACI receptor protein expressed by the Tregs and/or Bregs with APRIL ligand, wherein a test agent that modulates the interaction of TACI receptor protein expressed by the Tregs and/or Bregs with APRIL ligand selectively modifies the number and/or inhibitory immune activity of the Tregs and/or Bregs. Numerous other aspects and embodiments of the present invention are described below.

I. Definitions

The articles “a” and “an” are used herein to refer to one or to more than one (i.e. to at least one) of the grammatical object of the article. By way of example, "an element" means one element or more than one element.

The term "administering" is intended to include routes of administration which allow an agent to perform its intended function. Examples of routes of administration for treatment of a body which can be used include injection (subcutaneous, intravenous, parenterally, intraperitoneally, intrathecal, etc.), oral, inhalation, and transdermal routes.

The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal or control level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternatively, the amount of the biomarker in the subject can be considered "significantly" higher or lower than the normal and/or control amount if the amount is at least about two, and preferably at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, two times, three times, four times, five times, or more, or any range in between, such as 5%-100%, higher or lower, respectively, than the normal and/or control amount of the biomarker. Such significant modulation values can be applied to any metric described herein, such as altered level of expression, altered activity, changes in cancer cell hyperproliferative growth, changes in cancer cell death, changes in biomarker inhibition, changes in test agent binding, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subject not having the associated disease) and preferably, the average expression level or copy number of the biomarker in several control samples. The altered level of expression is greater or less than the standard error of the assay employed to assess expression or copy number, and is preferably at least twice, and more preferably three, four, five or ten or more times the expression level or copy number of the biomarker in a control sample (e.g., sample from a healthy subject not having the associated disease) and preferably, the average expression level or copy number of the biomarker in several control samples.

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies, such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

In addition, intrabodies are well-known antigen-binding molecules having the characteristic of antibodies, but that are capable of being expressed within cells in order to bind and/or inhibit intracellular targets of interest (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publs. WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBS Lett.* 508:407-412; Shaki-Loewenstein et al. (2005) *J. Immunol. Meth.* 303:19-39).

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Nat. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Nat. Acad. Sci. U.S.A.* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov et al. (1994) *Mol. Immunol.* 31:1047-1058). Antibody portions, such as Fab and $F(ab')_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized," which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the "predictive score."

The term "biomarker" includes a measurable entity of the present invention that has been determined to be useful for modulating immune responses and/or predictive of immunomodulatory responses. Biomarkers can include, without limitation, nucleic acids and proteins, including those shown in Table 1, the Examples, and the Figures, as well as interactions between such molecules (e.g., APRIL/TACI interactions). In addition, biomarkers can include immune cells that mediate immunomodulatory activities, such as the number and/or immune activity of Tregs, Bregs, and/or Tcons, ratios thereof, and the like, as described further herein. Biomarkers include markers listed herein which are useful in the diagnosis of cancer and/or sensitivity to anti-cancer treatments thereof, e.g., over- or under-activity, emergence, expression, growth, remission, recurrence or resistance of tumors before, during or after therapy are also included. The predictive functions of the marker may be confirmed by, e.g., (1) increased or decreased copy number (e.g., by FISH, FISH plus SKY, single-molecule sequencing, e.g., as described in the art at least at *J. Biotechnol.,* 86:289-301, or qPCR), overexpression or underexpression (e.g., by ISH, Northern Blot, or qPCR), increased or decreased protein level (e.g., by IHC), or increased or decreased activity (determined by, for example, modulation of a pathway in which the marker is involved), e.g., in more than about 5%, 6%, 7%, 8%, 9%, 10%, 11%, 12%, 13%, 14%, 15%, 20%, 25%, or more of human cancers types or cancer samples; (2) its presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its presence or absence in clinical subset of subjects with cancer (e.g., those responding to a particular therapy or those developing resistance). Biomarkers also include "surrogate markers," e.g., markers which are indirect markers of cancer progression. The term "biomarker" also include markers listed herein which are useful in the analysis of the effects of anti-cancer treatments, such as the size of the tumor, the proliferation and/or metastasis rate of cancer cells, the number of cancer cells, the life span of the subject having the cancer, etc. Biomarkers also include markers listed herein in cell signaling pathways, such as the number of Tregs and/or other T cells, the number of Bregs and/or other B cells, the number and/or inhibitory immune activity of either Tregs or Bregs (Tregs/Bregs), the differentiation rate and/or the apoptosis/cytotoxicity rate of various T cells or other immune cells, the expression of various proteins expressed on the cell surface of T cells or other immune cells, the antigen presentation efficacy, the production of various signal proteins (e.g., interferons) and their responsive genes, DNA methylation and transcription efficacy, senescence/proliferation status, etc.

The term "APRIL", also known as proliferation-inducing ligand, tumor necrosis factor ligand superfamily member 13 (TNFSF13), TALL-2, ZTNF2, and CD256, refers to a family of the tumor necrosis factor (TNF) ligand proteins. APRIL is a ligand for TNFRSF17/BCMA and for TNFRSF13B/TACI. APRIL and its receptors are both important for B cell development. In vitro experiments indicate that APRIL may be able to induce apoptosis in the long-term survival of plasma cells in the bone marrow through its interaction with other TNF receptor family proteins such as TNFRSF6/FAS and TNFRSF14/HVEM (Roth et al. (2001) *Cell Death Diff* 8:403-410). Mice deficient in APRIL have normal immune system development (Varfolomeev et al. (2004) *Mol. Cell. Biol.* 24:997-1006). However, APRIL-deficient mice have also been reported to possess a reduced ability to support plasma cell survival (Belnoue et al. (2008) *Blood* 111:2755-2764). APRIL plays a role in the regulation of tumor cell growth and may be involved in monocyte/macrophage-mediated immunological processes. APRIL also interacts with TNFRSF13B (Wu et al. (2000) *J. Biol. Chem.* 275: 35478-35485) and B-cell activating factor (Roschke et al. (2002) *J. Immunol.* 169:4314-4321). APRIL functions in multiple pathways, including, at least, PEDF induced signaling (e.g., MIF mediated glucocorticoid regulation, MIF regulation of innate immune cells, IL-6 pathway, STAT3 pathway, endothelin-1 signaling pathway, cytokine-cytokine receptor interaction, RAR-gamma-RXR-alpha degradation, all-trans-retinoic acid signaling in brain, etc.), ERK signaling (e.g., Rho family GTPases), regulation of activated PAK-2p34 by proteasome mediated degradation (e.g., TNFR2 non-canonical NF-κB pathway, regulation of mRNA stability by proteins that bind AU-rich elements), TNF superfamily pathway (e.g., human ligand-receptor Interactions and their associated functions), AKT signaling (e.g., p38 signaling), etc. APRIL is believed to be a target for autoimmune diseases and B cell malignancies (Ryan and Grewal (2009) Grewal I S, ed. *Therapeutic Targets of the TNF Superfamily. Advances in Experimental Medicine and Biology*. New York: Springer. pp. 52-63). APRIL is suggested to be related to multiple diseases and disorders including, at least, igg4-related disease, brain glioblastoma multiforme, opsoclonus-myoclonus syndrome, cryptococcal meningitis, rheumatoid arthritis, etc. At least one anti-APRIL monoclonal antibody, BION-1301, has been announced to enter phase I clinical trials for multiple myeloma (see Dulos et al. (2017) AACR Annual Meeting 2017 online proceedings, session PO.IM02.10, #2645/4, at World Wide Web address of www.abstractsonline.com/pp8/#!/4292/presentation/6077).

The nucleic acid and amino acid sequences of a representative human APRIL is available to the public at the GenBank database (Gene ID 8741) and is shown in Table 1. Multiple transcript variants and protein isoforms of APRIL include, at least, NM_003808.3 and NP_003799.1, representing the longest transcript variant alpha and the longest isoform alpha, NM_172087.2 and NP_742084.1, representing the transcript variant beta (lacking an alternate in-frame exon in the central coding region, compared to variant alpha) and the encoded isoform beta, NM_172088.2 and NP_742085.1, representing the transcript variant gamma (lacking an alternate segment in the 3' coding region and 3' UTR, compared to variant alpha) and the encoded isoform gamma (having a distinct and shorter C-terminus, compared to isoform alpha), NM_001198622.1 and NP_001185551.1, representing the transcript variant delta (lacking an alternate in-frame segment in the 5' coding region, compared to variant alpha) and the encoded isoform delta, NM_001198623.1 and NP_001185552.1, representing the transcript variant zeta (lacking an alternate in-frame segment in the 5' coding region, compared to variant alpha) and the encoded isoform zeta, and NM_001198624.1 and NP_001185553.1, representing the transcript variant eta (differing in the 5' UTR, using a downstream start codon, and lacking an alternate in-frame segment in the 5' coding region, compared to variant alpha) and the encoded isoform eta. The domain structure of APRIL polypeptide is well-known and accessible in UniProtKB database under the accession number 075888, including a TNF domain comprising, e.g., amino acid positions 117-248 of NP_003799.1.

Nucleic acid and polypeptide sequences of APRIL orthologs in organisms other than humans are well-known and include, for example, chimpanzee (Pan troglodytes) APRIL (NM_001205130.1 and NP_001192059.1), dog APRIL (NM_001205169.1 and NP_001192098.1), mouse APRIL (NM_023517.2 and NP_076006.2, representing the longer transcript variant 1 and the encoded longer isoform 1, and NM_001159505.1 and NP_001152977.1, representing the transcript variant 2 (using an alternate in-frame splice site in the central coding region, compared to variant 1) and the encoded shorter isoform 2 (lacking one internal amino acid, compared to isoform 1)), cattle APRIL (NM_001034647.2 and NP_001029819.1), and Norway rat (*Rattus norvegicus*) APRIL (NM_001009623.1 and NP_001009623.1).

The term "APRIL activity" includes the ability of an APRIL polypeptide (and its fragments, domains, and/or motifs thereof, discussed herein) to bind its substrate and/or biological activity. APRIL activity may also include one or more of functions, such as binding to its receptors and activating downstream signaling pathways, and/or others disclosed herein. For example, APRIL may interact with TNFRSF17/BCMA and/or with TNFRSF13B/TACI for promoting cell growth and survival, such as plasma cell and/or B cell survival. APRIL may also be proteolytically modified, such as being cleaved, ubiquitinated, deubiquitinated, or otherwise disclosed herein, for it functions.

The term "APRIL substrate(s)" refers to binding partners of an APRIL polypeptide (and its fragments, domains, and/or motifs thereof, discussed herein), e.g., the cellular receptors and/or other TNF superfamily members for multiple signal transduction pathways. Furthermore, APRIL substrates may refer to downstream members in the signaling pathways activated by APRIL binding to its receptor(s).

The term "APRIL-regulated signaling pathway(s)" includes signaling pathways in which APRIL (and its fragments, domains, and/or motifs thereof, discussed herein) binds to at least one of its substrates (e.g., its receptors), through which at least one cellular function and/or activity and/or cellular protein profiles is changed. APRIL-regulated signaling pathways include at least those described herein, such as PEDF induced signaling (e.g., MIF mediated glucocorticoid regulation, MIF regulation of innate immune cells, IL-6 pathway, STAT3 pathway, endothelin-1 signaling pathway, cytokine-cytokine receptor interaction, RAR-gamma-RXR-alpha degradation, all-trans-retinoic acid signaling in brain, etc.), ERK signaling (e.g., Rho family GTPases), regulation of activated PAK-2p34 by proteasome mediated degradation (e.g., TNFR2 non-canonical NF-κB pathway, regulation of mRNA stability by proteins that bind AU-rich elements), TNF superfamily pathway (e.g., human ligand-receptor Interactions and their associated functions), AKT signaling (e.g., p38 signaling), etc.

The term "APRIL modulator" includes any natural or non-natural agent prepared, synthesized, manufactured, and/or purified by man that is capable of modulating the ability of APRIL (and its fragments, domains, and/or motifs thereof, discussed herein) to be expressed, function, and/or bind to a binding partner. In one embodiment, the modulator promotes APRIL and representative embodiments, such as APRIL nucleic acids, polypeptides, multimers, activating antibodies that multimerize APRIL, and the like, are described herein. In another embodiment, the modulator inhibits APRIL. In one embodiment, such inhibitors reduce or inhibit the binding/interaction between APRIL and its substrates or other binding partners. In still another embodiment, such inhibitors may increase or promote the turnover rate, reduce or inhibit the expression and/or the stability (e.g., the half-life), and/or change the cellular localization of APRIL, resulting in at least a decrease in APRIL levels and/or activity. Such inhibitors may be any molecule, including but not limited to small molecule compounds, antibodies or intrabodies, RNA interfering (RNAi) agents (including at least siRNAs, shRNAs, microRNAs (miRNAs), piwi, and other well-known agents). Such inhibitors may be specific to APRIL or also inhibit at least one of other TNF superfamily members. For example, a TGFβ2 inhibitor, trabedersen (AP12009), was tested for its inhibition of APRIL (Tse (2013) *Nat. Rev. Drug Dis.* 12:179). Atacicept (TACI-Ig) is a recombinant fusion protein combining the binding site for B-lymphocyte stimulator (BLyS) and A proliferation-inducing ligand (APRIL) with the constant region of immunoglobulin (Hartung et al. (2010) *Ther Adv Neurol Disord.* 3:205-216). Atacicept (TACI-Ig) blocks the binding of BLys and APRIL to TNFSF13B/TACI and thus inhibits B cells and suppresses autoimmune diseases. Atacicept (TACI-Ig) has also being studied for treatment of B-cell malignancies, including multiple myeloma, B-cell chronic lymphocytic leukemia, and non-Hodgkin's lymphoma (Vasiliou (2008) *Drugs Fut.* 33:921). RNA interference for APRIL polypeptides are well-known and commercially available (e.g., human, mouse, or rat shRNA (Cat. #TF300911, TF515490, and TF701276) and siRNA (Cat. #SR406719, SR510783, and SR305759) products and human or mouse gene knockout kit via CRISPR (Cat. #KN203446 and KN317997) from Origene (Rockville, MD), siRNA/shRNA products (Cat. #sc-39822, sc-39823, and sc-141178) and CRISPR products (Cat. #sc-403296, sc-427459, and sc-403150) from Santa Cruz Biotechnology (Dallas, Texas), Ready-to-package AAV shRNA clones from Vigene Biosciences (Rockville, MD), Cat. #SH895874 and SH897133). Methods for detection, purification, and/or inhibition of APRIL (e.g., by anti-APRIL antibodies) are also well-known and commercially available (e.g., multiple anti-APRIL antibodies from Origene (Cat. #TA306069, TA349496, TA351828, etc.), Novus Biologicals (Littleton, CO, Cat. #NBP1-97587, MAB8843, NBP1-76767, etc.), abcam (Cambridge, MA, Cat. #ab64967, ab16088, etc.), and Santa Cruz Biotechnology (Cat. #sc-374673, sc-57035, etc.). Human APRIL knockout cell lines are also well-known and available from Horizon Discovery (Cambridge, UK, Cat. #HZGHC8741). Selective APRIL blockade with monoclonal antibodies was shown to delay systemic lupus erythematosus in mouse (Huard et al. (2012) *PLoS ONE* 7:e31837).

The term "TAC", also known as transmembrane activator and CAML interactor, tumor necrosis factor receptor superfamily member 13B (TNFRSF13B), CD267, and CVID2, refers to a transmembrane protein family member of the TNF receptor superfamily found predominantly on the surface of B cells. TACI binds to B-cell activating factor (BAFF) and APRIL, which induces activation of several transcription factors such as NFAT, AP-1, and NF-κB and modulates cellular activities. Defects in the function of TACI can lead to immune system diseases and has shown to cause fatal autoimmunity in mice (Seshasayee et al. (2003) *Immunity.* 18:279-288). TACI controls T cell-independent B cell antibody responses, isotype switching, and B cell homeostasis. TACI mediates calcineurin-dependent activation of NF-AT, as well as activation of NF-κB and AP-1. TACI is involved in the stimulation of B- and T-cell function and the regulation of humoral immunity. TACI is suggested to bind multiple binding partners including, at least, B-cell activating factor, TRAF6, TRAF5, TNFSF13/APRIL, TRAF2, and CAMLG (Xia et al. (2000) *J. Exp. Med.* 192:137-143). TACI functions in multiple pathways, including, at least, TNF superfamily pathway (human ligand-receptor interactions and their associated functions), AKT signaling (e.g., p38 signaling and Tec kinases signaling), RANK signaling in osteoclasts (e.g., APRIL pathway, BAFF in B-cell signaling, apoptosis and survival, etc.), PEDF induced signaling (e.g., STAT3 pathway and cytokine-cytokine receptor interaction), TRAF pathway, Syndecan-2 or 4-mediated signaling events. TACI is suggested to be related to multiple diseases and disorders including, at least, immunodeficiency, common variable, 2 (CVID2, a.k.a., hypogammaglobulinemia due to TACI deficiency), and immunoglobulin A deficiency 2 (IGAD2).

The nucleic acid and amino acid sequences of a representative human TACI is available to the public at the GenBank database (Gene ID 23495) and is shown in Table 1 (e.g., NM_012452.2 and NP_036584.1). The domain structure of TACI polypeptide is well-known and accessible in UniProtKB database under the accession number Q4ACX1, including three cysteine-rich domains (CRDs) comprising, e.g., amino acid positions 34-86, 89-170, and 172-230 of NP_036584.1, and a transmembrane region comprising, e.g., amino acid positions 166-186 of NP_036584.1.

Nucleic acid and polypeptide sequences of TACI orthologs in organisms other than humans are well-known and include, for example, chimpanzee (Pan troglodytes) TACI (XM_001161361.4 and XP_001161361.3, and XM_016932352.1 and XP_016787841.1), Rhesus monkey TACI (XM_015118722.1 and XP_014974208.1, and XM_015118723.1 and XP_014974209.1), dog TACI (XM_005620177.2 and XP_005620234.1, and XM_005620179.2 and XP_005620236.1), mouse TACI (NM_021349.1 and NP_067324.1), and chicken TACI (NM_001097537.1 and NP_001091006.1 tumor).

The term "TACI activity" includes the ability of a TACI polypeptide (and its fragments, domains, and/or motifs thereof, discussed herein) to bind its substrate and/or biological activity. TACI activity may also include one or more of functions, such as binding to its ligands and activating downstream signaling pathways, and/or others disclosed herein. For example, TACI may interact with APRIL for promoting B cell survival/proliferation. TACI may also be proteolytically modified, such as being cleaved, ubiquitinated, deubiquitinated, or otherwise disclosed herein, for it functions.

The term "TACI substrate(s)" refers to binding partners of a TACI polypeptide (and its fragments, domains, and/or motifs thereof, discussed herein), e.g., the ligands and/or other TNF superfamily members for multiple signal transduction pathways. Furthermore, TACI substrates may refer to downstream members in the signaling pathways activated by TACI binding to its receptor(s).

The term "TACI-regulated signaling pathway(s)" includes signaling pathways in which TACI (and its fragments, domains, and/or motifs thereof, discussed herein) binds to at least one of its substrates (e.g., its ligands), through which at least one cellular function and/or activity and/or cellular protein profiles is changed. TACI-regulated signaling pathways include at least those described herein, such as TNF Superfamily Pathway (human ligand-receptor interactions and their associated functions), AKT signaling (e.g., p38 signaling and Tec kinases signaling), RANK signaling in osteoclasts (e.g., APRIL pathway, BAFF in B-cell signaling, apoptosis and survival, etc.), PEDF induced signaling (e.g., STAT3 pathway and cytokine-cytokine receptor interaction), TRAF pathway, Syndecan-2 or 4-mediated signaling events, etc.

The term "TACI modulator" includes any natural or non-natural agent prepared, synthesized, manufactured, and/or purified by man that is capable of modulating the ability of TACI (and its fragments, domains, and/or motifs thereof, discussed herein) to be expressed, function, and/or bind to a binding partner. In one embodiment, the modulator promotes TACI and representative embodiments, such as TACI nucleic acids, polypeptides, multimers, activating antibodies that multimerize TACI, and the like, are described herein. In another embodiment, the modulator inhibits TAC. In one embodiment, such inhibitors may reduce or inhibit the binding/interaction between TACI and its substrates or other binding partners. In still another embodiment, such inhibitors may increase or promote the turnover rate, reduce or inhibit the expression and/or the stability (e.g., the half-life), and/or change the cellular localization of TACI, resulting in at least a decrease in TACI levels and/or activity. Such inhibitors may be any molecule, including but not limited to small molecule compounds, antibodies or intrabodies, RNA interfering (RNAi) agents (including at least siRNAs, shRNAs, microRNAs (miRNAs), piwi, and other well-known agents). Such inhibitors may be specific to TACI or also inhibit at least one of other TNF superfamily members (such as cellular receptors). RNA interference for TACI polypeptides are well-known and commercially available (e.g., human or mouse shRNA (Cat. #TF308737 and TF503348) and siRNA (Cat. #SR308311 and SR407026) products and human or mouse gene knockout kit via CRISPR (Cat. #KN211856 and KN317977) from Origene (Rockville, MD), siRNA/shRNA products (Cat. #sc-40243 and sc-40244) and CRISPR products (Cat. #sc-406692 and sc-425465) from Santa Cruz Biotechnology (Dallas, Texas), Ready-to-package AAV shRNA clones from Vigene Biosciences (Rockville, MD), Cat. #SH860094). Methods for detection, purification, and/or inhibition of TACI (e.g., by anti-TACI antibodies) are also well-known and commercially available (e.g., multiple anti-TACI antibodies from Origene (Cat. #TA306064, TA352371, AM26557AF-N, etc.), Novus Biologicals (Littleton, CO, Cat. #NBP2-11937, MAB174, NBP1-84596, etc.), abcam (Cambridge, MA, Cat. #ab79023, ab89744, etc.), and Santa Cruz Biotechnology (Cat. #sc-32775, sc-365253, etc.). Human TACI knockout cell lines are also well-known and available from Horizon Discovery (Cambridge, UK, Cat. #HZGHC23495).

The term "BCMA", also known as B-cell maturation antigen, tumor necrosis factor receptor superfamily member 17 (TNFRSF17), BCM, and CD269, refers to a family of transmembrane protein of the TNF receptor superfamily found predominantly on the surface of mature B cells. BCMA is important for B cell development and autoimmune response. This receptor has been shown to specifically bind to the tumor necrosis factor (ligand) superfamily, member 13b (TNFSF13B/TALL-1/BAFF), and to lead to NF-1B and MAPK8/JNK activation. BCMA also binds to various TRAF family members, and thus may transduce signals for cell survival and proliferation. Besides BAFF, APRIL is also a ligand for BCMA. Other BCMA binding partners include, at least, TRAF1, TRAF2, TRAF3, TRAF5, and TRAF6 (Liu et al. (2003) *Nature* 423:49-56). BCMA functions in multiple pathways, including, at least, TNF Superfamily Pathway (human ligand-receptor interactions and their associated functions), AKT signaling (e.g., p38 signaling and Tec kinases signaling), RANK signaling in osteoclasts (e.g., APRIL pathway, BAFF in B-cell signaling, apoptosis and survival, etc.), PEDF induced signaling (e.g., STAT3 pathway and cytokine-cytokine receptor interaction), and TGF-Beta Pathway (e.g., MAPK family pathway, JAK-STAT pathway, JNK pathway, regulation of eIF4 and p70S6K, SOCS pathway, etc.). TACI is suggested to be related to multiple diseases and disorders including, at least, common variable immunodeficiency (e.g., acquired agammaglobulinemia), cryptococcal meningitis, chronic lymphocytic leukemia, blue cone monochoromacy, leukemia, lymphomas, and multiple myeloma). The nucleic acid and amino acid sequences of a representative human BCMA is available to the public at the GenBank database (Gene ID 608) and is shown in Table 1 (e.g., NM_001192.2 and NP_001183.2). The domain structure of BCMA polypeptide is well-known and accessible in UniProtKB database under the accession number Q02223, including a TNFR-Cys domain comprising, e.g., amino acid positions 7-41 of NP_001183.2, and a transmembrane region comprising, e.g., amino acid positions 55-77 of NP_001183.2. Two cysteine-rich domains comprise, e.g., amino acid positions 4-21 and 24-126 of NP_001183.2.

Nucleic acid and polypeptide sequences of BCMA orthologs in organisms other than humans are well-known and include, for example, chimpanzee (Pan troglodytes) BCMA (XM_523298.5 and XP_523298.2), Rhesus monkey BCMA (XM_001106892.3 and XP_001106892.1), dog BCMA (XM_005621530.2 and XP_005621587.1), cattle BCMA (XM_002697966.4 and XP_002698012.2), mouse BCMA (NM_011608.1 and NP_035738.1), and rat TACI (NM_011608.1 and NP_035738.1).

The term "BCMA activity" includes the ability of a BCMA polypeptide (and its fragments, domains, and/or motifs thereof, discussed herein) to bind its substrate and/or biological activity. BCMA activity may also include one or more of functions, such as binding to its ligands and activating downstream signaling pathways, and/or others disclosed herein. For example, BCMA may interact with APRIL for promoting plasma cell survival/proliferation. BCMA may also be proteolytically modified, such as being cleaved, ubiquitinated, deubiquitinated, or otherwise disclosed herein, for it functions.

The term "BCMA substrate(s)" refers to binding partners of a BCMA polypeptide (and its fragments, domains, and/or motifs thereof, discussed herein), e.g., the ligands (such as APRIL and BAFF) and/or other TNF superfamily members for multiple signal transduction pathways. Furthermore, BCMA substrates may refer to downstream members in the signaling pathways activated by BCMA binding to its receptor(s).

The term "BCMA-regulated signaling pathway(s)" includes signaling pathways in which BCMA (and its fragments, domains, and/or motifs thereof, discussed herein) binds to at least one of its substrates (e.g., its ligands), through which at least one cellular function and/or activity and/or cellular protein profiles is changed. BCMA-regulated signaling pathways include at least those described herein, such as TNF Superfamily Pathway (human ligand-receptor interactions and their associated functions), AKT signaling (e.g., p38 signaling and Tec kinases signaling), RANK signaling in osteoclasts (e.g., APRIL pathway, BAFF in B-cell signaling, apoptosis and survival, etc.), PEDF induced signaling (e.g., STAT3 pathway and cytokine-cytokine receptor interaction), and TGF-Beta Pathway (e.g., MAPK family pathway, JAK-STAT pathway, JNK pathway, regulation of eIF4 and p70S6K, SOCS pathway, etc.

The term "BCMA modulator" includes any natural or non-natural agent prepared, synthesized, manufactured, and/or purified by man that is capable of modulating the ability of BCMA (and its fragments, domains, and/or motifs thereof, discussed herein) to be expressed, function, and/or bind to a binding partner. In one embodiment, the modulator promotes BCMA and representative embodiments, such as BCMA nucleic acids, polypeptides, multimers, activating antibodies that multimerize BCMA, and the like, are described herein. In another embodiment, the modulator inhibits BCMA. In one embodiment, such inhibitors may reduce or inhibit the binding/interaction between BCMA and its substrates or other binding partners. In still another embodiment, such inhibitors may increase or promote the turnover rate, reduce or inhibit the expression and/or the stability (e.g., the half-life), and/or change the cellular localization of BCMA, resulting in at least a decrease in BCMA levels and/or activity. Such inhibitors may be any molecule, including but not limited to small molecule compounds, antibodies or intrabodies, RNA interfering (RNAi) agents (including at least siRNAs, shRNAs, microRNAs (miRNAs), piwi, and other well-known agents). Such inhibitors may be specific to BCMA or also inhibit at least one of other TNF superfamily members (such as cell surface receptors). RNA interference for TACI polypeptides are well-known and commercially available (e.g., human or mouse shRNA (Cat. #TL308735, TF514674, and TF704358) and siRNA (Cat. #SR300419, SR404548, and SR502461) products and human or mouse gene knockout kit via CRISPR (Cat. #KN208851 and KN317980) from Origene (Rockville, MD), siRNA/shRNA products (Cat. #sc-40233 and sc-40234) and CRISPR products (Cat. #sc-403058 and sc-423440) from Santa Cruz Biotechnology (Dallas, Texas), Ready-to-package AAV shRNA clones from Vigene Biosciences (Rockville, MD), Cat. #SH873263). Methods for detection, purification, and/or inhibition of BCMA (e.g., by anti-BCMA antibodies) are also well-known and commercially available (e.g., multiple anti-BCMA antibodies from Origene (Cat. #TA306065, AP00250PU-N, TA311846, etc.), Novus Biologicals (Littleton, CO, Cat. #NBP1-97637, AF593, NBP1-76774, etc.), abcam (Cambridge, MA, Cat. #ab5972, ab17323, etc.), and Santa Cruz Biotechnology (Cat. #sc-11746, sc-390147, etc.). Human BCMA knockout cell lines are also well-known and available from Horizon Discovery (Cambridge, UK, Cat. #HZGHC608). Another representative BCMA inhibitor is GSK2857916, which is an antibody-drug conjugate (ADC) consisting of an afucosylated, humanized monoclonal antibody, directed against the B-cell maturation antigen (BCMA), conjugated to the auristatin analogue and microtubule inhibitor monomethyl auristatin phenylalanine (MMAF), with potential antineoplastic activity. The anti-BCMA antibody moiety of anti-BCMA ADC selectively binds to the BCMA on tumor cell surfaces. Upon internalization, the MMAF moiety binds to tubulin and inhibits its polymerization, which results in G2/M phase arrest and induces tumor cell apoptosis. In addition, GSK2857916 induces antibody-dependent cellular cytotoxicity (ADCC). Altogether, this results in the inhibition of cellular proliferation in tumor cells that overexpress BCMA. Afucosylation of the antibody moiety increases ADCC.

Interactions between APRIL, BCMA, and TACI, as well as their functions, are well-known in the art as described above (see, for example, Yu et al. (2000) *Nat. Immunol.* 1:252-256).

In addition, certain immune cells or states thereof can be biomarkers according to the present invention. The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. For example, antigen-reactive T cells are T cells that selectively bind to an antigen of interest and modulate immunological responses based upon the recognition of antigen. Immune cells can be found in the peripheral blood. The term "peripheral blood cell subtypes" refers to cell types normally found in the peripheral blood including, but is not limited to, eosinophils, neutrophils, T cells, monocytes, NK cells, granulocytes, and B cells. Some immune cells are "antigen presenting cells," include professional antigen presenting cells (e.g., B lymphocytes, monocytes, dendritic cells, Langerhans cells), as well as other antigen presenting cells (e.g., keratinocytes, endothelial cells, astrocytes, fibroblasts, and oligodendrocytes). Immune cells according to the present invention can be selected, determined, and/or modified to have properties described herein. For example, Tregs can be selected, determined, and/or modified to demonstrate expression of TACI but not BCMA.

The term "B cell" refers to a type of white blood cell of the lymphocyte subtype that can secrete antibodies when a mature plasma cell, as well as present antigen and secrete cytokines. An "immature B cell" is a cell that can develop into a mature B cell. Generally, pro-B cells (that express, for example, CD45 or B220) undergo immunoglobulin heavy chain rearrangement to become pro B pre B cells, and further undergo immunoglobulin light chain rearrangement to become an immature B cells. Immature B cells include T1 and T2 B cells. Immature B cells can develop into mature B cells, which can produce immunoglobulins (e.g., IgA, IgG or IgM). Mature B cells express characteristic markers, such as CD21 and CD23, but do not express AA41. B cells can be activated by agents such as lipopolysaccharide (LPS) or IL-4 and antibodies to IgM. B cells, their subtypes, and their stage of development, can be determined based on well-known biomarkers in the art. For example, naive B cells are CD19+CD24intCD38int and memory B cells are CD19+ CD24-CD38low/−CD27+.

The term "Bregs" refers to regulatory B cells, which are B cells that suppress resting and/or activated T cells. Bregs are well-known in the art (see, for example, U.S. Pat. Publ. 2016/0375059; U.S. Pat. Publ. 2016/0152951; U.S. Pat. Publ. 2015/0110737; Zhang et al. (2017) *Blood Cancer J.* 7:e547; and Blaire et al. (2010) *Immunity* 32:129-140). In one embodiment, Bregs express $CD19^{+}CD24^{high}CD38^{high}$. Generally, Bregs produce IL-19, which has strong anti-inflammatory effects and inhibits inflammatory reactions mediated by T cells, such as Th1 type immune responses. Bregs can also produce TGF-β, which is another anti-inflammatory cytokine. In some embodiments, Bregs can also produce cell surface molecules like FasL and/or PD-L1 to cause target cell death. In some embodiments, Bregs are can be $CD19+CD24^{high}CD38^{high}$ Bregs as a distinct subset in the bone marrow aspirate of MM patients when compared with this subset in the peripheral blood compartment (Zhang et al. (2017) *Blood Cancer J.* 24:e547). This distinct Breg subset tightly correlates with the load of CD138+ myeloma cells in the bone marrow and peripheral blood compartments of MM patients. The interaction between Breg and myeloma cells plays a critical role for the survival of Bregs. These Bregs are functional since immunoinhibitory cytokine IL-10 is induced when they are stimulated with PMA. Furthermore, these Bregs decrease myeloma cell lysis induced by elotuzumab ex vivo. Thus, this Breg subset is believed to be critical to regulate treatment responses to anti-multiple myeloma therapies, including monoclonal antibody-based immunotherapies like elotuzumab targeting SLAMF7, on multiple myeloma cells.

The term "T cell" includes, e.g., $CD4^{+}$ T cells and $CD8^{+}$ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells), as well as other antigen presenting cells (e.g., keratinocytes, endothelial cells, astrocytes, fibroblasts, and oligodendrocytes).

The term "Tregs" refers to regulatory T cells, which are naturally occurring CD4+CD25+FOXP3+T lymphocytes that comprise ~5-10% of the circulating CD4+ T cell population, act to dominantly suppress autoreactive lymphocytes, and control innate and adaptive immune responses (Piccirillo and Shevach (2004) *Semin. Immunol.* 16:81-88; Fehervari and Sakaguchi (2004) *Curr. Opin. Immunol.* 16:203-208; Azuma et al. (2003) *Cancer Res.* 63:4516-4520; Cederbom et al. (2000) *Eur. J. Immunol.* 30:1538-1543; Maloy et al. (2003) *J. Exp. Med.* 197:111-119; Serra et al. (2003) *Immunity* 19:877-889; Thornton and Shevach (1998) *J. Exp. Med.* 188:287-296; Janssens et al. (2003) *J. Immunol.* 171:4604-4612; Gasteiger et al. (2013) *J. Exp. Med.* 210:1167-1178; Sitrin et al. (2013) *J. Exp. Med.* 210:1153-1165). Tregs also include CD8+CD25+FOXP3+ T lymphocytes that are functionally suppressive (Correale et al. (2010) *Annu. Neurol.* 67:625-638). Tregs achieve this suppressing, at least in part, by inhibiting the proliferation, expansion, and effector activity of conventional T cells (Tcons). They also suppress effector T cells from destroying their (self-)target, either through cell-cell contact by inhibiting T cell help and activation, or through release of immunosuppressive cytokines such as IL-10 or TGF-β. Depletion of Treg cells was shown to enhance IL-2 induced anti-tumor immunity (Imai et al. (2007) *Cancer Sci.* 98:416-23).

Since Tregs and Bregs both inhibit immune responses, any modulation of Tregs described herein applies to Bregs and vice versa unless otherwise indicated.

Conventional T cells, also known as Tcons or Teffs, have effector functions (e.g., cytokine secretion, cytotoxic activity, and the like) to increase immune responses by virtue of their expression of one or more T cell receptors. Tcons are defined as any T cell population that is not a Treg and include, for example, naïve T cells, activated T cells, memory T cells, resting Tcons, or Tcons that have differentiated toward, for example, the Th1 or Th2 lineages. Thus, increasing the number of Tregs, increasing Treg activity, and/or decreasing Treg cell death (e.g., apoptosis) is useful for suppressing unwanted immune reactions associated with a range of immune disorders (e.g., cGVHD). For example, in a murine model a 1:1 mix of CD4+CD25+ Tregs and CD25− effector T cells added to donor bone marrow stem cells suppressed alloimmune activation and GVHD without increasing malignant relapse post-transplant (Edinger et al. (2003) *Nat. Med.* 9:1144-1150). In humans, impaired Treg reconstitution in HSCT recipients occurs with active cGVHD (Zorn et al. (2005) *Blood* 106:2903-2911). In participants with active cGVHD, impaired Tregs reconstitution, low levels of telomerase, and shortened telomeres, are believed to contribute to decreased survival of Tregs (Zorn et al. (2005) *Blood* 106:2903-2911; Matsuoka et al. (2010) *J. Clin. Invest.* 120:1479-1493; Kawano et al. (2011) *Blood* 118:5021-5030). The role of IL-2 in Tregs homeostasis and function is believed to account for its limited efficacy as an anti-immune disorder therapy, and explain in part the finding that in vivo administration of IL-2 plus syngeneic T-cell-depleted donor marrow prevents GVHD after MHC-mismatched murine allo-SCT, without impacting GVL responses (Sykes et al. (1990) *Proc. Nat. Acad. Sci. U.S.A.* 87:5633-5647; Sykes et al. (1990) *J. Exp. Med.* 171:645-658). In murine allo-HSCT models, co-infusion of Treg expanded ex-vivo with IL-2 also resulted in suppression of GVHD, with improved immune reconstitution and preserved GVL responses (Taylor et al. (2002) *Blood* 99:3493-3499; Trenado et al. (2003) *J. Clin. Invest.* 112:1688-1696). Tregs are also important in suppressing inflammation as well. In the context of ongoing inflammation, it is critical that treatments preferentially enhance Tregs without activating conventional T cells (Tcons) or other effectors that may worsen GVHD. Effective augmentation of Tregs in vivo is also directly relevant to other disorders of impaired peripheral tolerance (e.g., autoimmune diseases like SLE, T1D, MS, psoriasis, RA, IBD, vasculitis), where Treg dysfunction is increasingly implicated (Grinberg-Bleyer et al. (2010) *J. Exp. Med.* 207:1871-1878; Buckner (2010) *Nat. Rev. Immunol.* 10:849-859; Humrich et al. (2010) *Proc. Nat. Acad. Sci. U.S.A.* 107:204-209; Carbone et al. (2014) *Nat. Med.* 20:69-74).

"Naïve Tcons" are CD4+ T cells or CD8+ T cells that have differentiated in bone marrow, and successfully underwent a positive and negative processes of central selection in a thymus, but have not yet been activated by exposure to an antigen. Naïve Tcons are commonly characterized by surface expression of L-selectin (CD62L), absence of activation markers, such as CD25, CD44 or CD69, and absence of memory markers, such as CD45RO. Naïve Tcons are therefore believed to be quiescent and non-dividing, requiring interleukin-7 (IL-7) and interleukin-15 (IL-15) for homeostatic survival (see, at least WO 2010/101870). The presence and activity of such cells are undesired in the context of suppressing immune responses.

Unlike Tregs, "effector Tcons" are not anergic and can proliferate in response to antigen-based T cell receptor activation (Lechler et al. (2001) *Philos. Trans. R. Soc. Lond. Biol. Sci.* 356:625-637). Effector Tcons can be CD4+ or CD8+ T cells. They recognize antigens associated with MHC class I or II molecules, respectively, generally express activation markers, such as CD25, CD44 or CD69, but generally do not express memory markers, such as CD45RO. Generally, increasing the number of Tregs, increasing Treg activity, and/or decreasing Treg cell death (e.g., apoptosis) is useful for suppressing unwanted immune reactions associated with a range of immune disorders (e.g., cGVHD). Tregs are also important in suppressing inflammation as well. In the context of ongoing inflammation, treatments can preferentially enhance Tregs without activating Tcons or other effectors that may worsen GVHD. Effective augmentation of Tregs in vivo is also directly relevant to other disorders of impaired peripheral tolerance (e.g., autoimmune diseases like SLE, T1D, MS, psoriasis, RA, IBD, vasculitis), where Treg dysfunction is increasingly implicated (Grinberg-Bleyer et al. (2010) *J. Exp. Med* 207:1871-1878; Buckner (2010) *Nat. Rev. Immunol.* 10:849-859; Humrich et al. (2010) *Proc. Natl. Acad Sci. U.S.A.* 107:204-209; Carbone et al. (2014) *Nat. Med* 20:69-74).

"Memory Tcons" are antigen-experienced T cells (i.e., T cells that have previously been exposed to and responded to an antigen) represented by at least three distinct subpopulations of T cells. Memory Tcons can reproduce quickly and elicit a stronger immune response when re-exposed to the antigen. Memory Tcons subpopulations can be differentiated based on the differential expression of the chemokine receptor, CCR7, and L-selection (CD62L) (Sallusto et al. (2000) *Curr. Top. Microbiol. Immunol.* 251:167-171). For example, stem memory T cells (Tscm), like naïve cells, are CD45RO−, CCR7+, CD45RA+, CD62L+(L-selectin), CD27+, CD28+, and IL-7Rα+, but they also express large amounts of CD95, IL-2Rβ, CXCR3, and LFA-1, and show numerous functional attributes distinctive of memory cells (Gattinoni et al. (2011) *Nat. Med* 17:1290-1297). Central memory cells (Tem) express L-selectin and the CCR7 and secrete IL-2, but not IFNγ or IL-4. Effector memory cells (Tem) do not express L-selectin or CCR7, but produce effector cytokines like IFNγ and IL-4.

"Exhausted Tcons" are T cells that have progressively lost T-cell function. "Exhaustion" or "unresponsiveness" refers to a state of a cell where the cell does not perform its usual function or activity in response to normal input signals, and includes refractivity of immune cells to stimulation, such as stimulation via an activating receptor or a cytokine. Such a function or activity includes, but is not limited to, proliferation or cell division, entrance into the cell cycle, cytokine production, cytotoxicity, trafficking, phagocytotic activity, or any combination thereof. Normal input signals can include, but are not limited to, stimulation via a receptor (e.g., T cell receptor, B cell receptor, co-stimulatory receptor, and the like).

Exhausted immune cells can have a reduction of at least 10%, 15%, 20%, 25%, 30%, 35%, 40%, 45%, 50%, 55%, 60%, 65%, 70%, 75%, 80%, 85%, 90%, 95%, 99% or more in cytotoxic activity, cytokine production, proliferation, trafficking, phagocytotic activity, or any combination thereof, relative to a corresponding control immune cell of the same type. In one embodiment, a cell that is exhausted is a CD8+ T cell (e.g., an effector CD8+ T cell that is antigen-specific). CD8 cells normally proliferate (e.g., clonally expand) in response to T cell receptor and/or co-stimulatory receptor stimulation, as well as in response to cytokines such as IL-2. Thus, an exhausted CD8 T cell is one which does not proliferate and/or produce cytokines in response to normal input signals. It is well known that the exhaustion of effector functions can be delineated according to several stages, which eventually lead to terminal or full exhaustion and, ultimately, deletion (Yi et al. (2010) *Immunol.* 129:474-481; Wherry and Ahmed (2004) *J. Virol.* 78:5535-5545). In the first stage, functional T cells enter a "partial exhaustion I" phase characterized by the loss of a subset of effector functions, including loss of IL-2 production, reduced TNFα production, and reduced capacity for proliferation and/or ex vivo lysis ability. In the second stage, partially exhausted T cells enter a "partial exhaustion II" phase when both IL-2 and TNFα production ceases following antigenic stimulation and IFNγ production is reduced. "Full exhaustion" or "terminal exhaustion" occurs when CD8+ T cells lose all effector functions, including the lack of production of IL-2, TNFα, and IFNγ and loss of ex vivo lytic ability and proliferative potential, following antigenic stimulation. A fully exhausted CD8+ T cell is one which does not proliferate, does not lyse target cells (cytotoxicity), and/or does not produce appropriate cytokines, such as IL-2, TNFα, or IFNγ, in response to normal input signals. Such lack of effector functions can occur when the antigen load is high and/or CD4 help is low. This hierarchical loss of function is also associated with the expression of co-inhibitor immune receptors, such as PD-1, TIM-3, LAG-3, and the like (Day et al. (2006) *Nature* 443:350-4; Trautmann et al. (2006) *Nat. Med.* 12:1198-202; and Urbani et al. (2006) *J. Virol.* 80:1398-1403). Other molecular markers distinguish the hierarchical stages of immune cell exhaustion, such as high eomesodermin (EOMES) and low TBET expression as a marker of terminally exhausted T cells (Paley et al. (2012) *Science* 338:1220-1225). Additional markers of exhausted T cells, such as the reduction of Bcl-b and the increased production of BLIMP-1 (Pdrm1).

Immune cells can be obtained from a single source or a plurality of sources (e.g., a single subject or a plurality of subjects). A plurality refers to at least two (e.g., more than one). In still another embodiment, the non-human mammal is a mouse. The animals from which cell types of interest are obtained may be adult, newborn (e.g., less than 48 hours old), immature, or in utero. Cell types of interest may be primary cells, stem cells, established cancer cell lines, immortalized primary cells, and the like.

Thus, decreasing the number of Tregs/Bregs, decreasing Treg/Breg activity, and/or increasing Treg/Breg cell death (e.g., apoptosis) is generally useful for increasing immune reactions associated with a range of immune disorders (e.g., cancer, infection, and the like). The inverse is also applicable for decreasing immune reactions by upregulating the numbers and/or inhibitory immune activity of Tregs/Bregs. For example, effective augmentation of Tregs in vivo is also directly relevant to other disorders of impaired peripheral tolerance (e.g., autoimmune diseases like SLE, T1D, MS, psoriasis, RA, IBD, vasculitis), where Treg/Breg dysfunction is increasingly implicated (Grinberg-Bleyer et al. (2010) *J. Exp. Med.* 207:1871-1878; Buckner (2010) *Nat. Rev. Immunol.* 10:849-859; Humrich et al. (2010) *Proc. Natl. Acad. Sci. U.S.A.* 107:204-209; Carbone et al. (2014) *Nat. Med.* 20:69-74).

Modulation of Tregs/Bregs numbers/activity, Tcons activity, Tregs:Tcons interactions, and Bregs:Bcons interactions, can be determined according to well-known methods in the art and as exemplified in the Examples. For example, Tregs/Bregs and/or Tcons proliferation, activity, apoptosis, cytokine production repertoire, Tregs/Bregs activity, Tregs/Bregs apoptosis, cell biomarker expression (e.g., CD4, CD19, CD24, CD25, CD38, CD25, FOXP3, etc. expression), and the like can be analyzed. Moreover, phenotypic analyses of lymphocyte subsets, functional assays of immunomodulation leading to reduced immune responses, plasma cytokines, and the like can be analyzed as described further herein.

Such well-known immune cell characteristics can also be used to purify, enrich, and/or isolate Tregs/Bregs, or alternatively, modulate (e.g., reduce) or determine modulation (e.g., confirm reduction) of Tregs/Bregs. For example, the term "enriched Tregs/Bregs" refer to a composition comprising Tregs/Bregs in addition to other T cells in a proportion where the composition has at least a 1:2, 1:1.9, 1:1.8, 1:1.7, 1:1.6, 1:1.5, 1:1.4, 1:1.3, 1:1.2, 1:1.1, 1:1, 1:0.9, 1:0.8, 1:0.7, 1:0.6, 1:0.5, 1:0.4, 1:0.3, 1:0.2, 1:0.1, or more, or any range in between or any value in between, ratio of Tregs/Bregs to Tcons (i.e., Tregs to Tcons or Bregs to Tcons), CD3+ cells, or to another cellular benchmark. Such ratios can be achieved by purifying a composition comprising T/B cells with various methodologies, such as CD8+ and CD19+ co-depletion in combination with positive selection for CD25+ cells. Such enriched Tregs/Bregs can further be defined in terms of cell markers and/or viability. For example, an enriched Tregs/Bregs cell composition can have greater than 40%, 45%, 50%, 55%, 60%, 65%, 70%, 75%, 80%, 85%, 90%, 95%, 99%, or more, or any range in between or any value in between, total cell viability. It can comprise greater than 40%, 45%, 50%, 55%, 60%, 65%, 70%, 75%, 80%, 85%, 90%, 95%, 99%, or more, or any range in between or any value in between, cells having a particular expression of biomarkers. For example, it can comprise greater than 40%, 45%, 50%, 55%, 60%, 65%, 70%, 75%, 80%, 85%, 90%, 95%, 99%, or more, or any range in between or any value in between, FoxP3+ T cells. Similarly, the term "reduced Tregs/Bregs refers to a reduction in Tregs/Bregs and can be quantified and qualified according to the inverse of the description provided above for enriched Tregs/Bregs. The term "increased Tregs/Bregs" refers to the opposite of reduced Tregs/Bregs.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, and vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. In some embodiments, such cells exhibit such characteristics in part or in full due to the expression and activity of oncogenes or the defective expression and/or activity of tumor suppressor genes, such as retinoblastoma protein (Rb). Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In certain embodiments, the cancer is multiple myeloma. Multiple myeloma, also known as plasma cell myeloma or Kahler's disease, is a cancer of plasma cells, a type of white blood cell normally responsible for producing antibodies. In multiple myeloma, collections of abnormal plasma cells accumulate in the bone marrow, where they interfere with the production of normal blood cells. Most cases of myeloma also feature the production of a paraprotein, an abnormal antibody that can cause kidney problems. Bone lesions and hypercalcemia (high blood calcium levels) are also often encountered. Results of any single test are generally not enough to diagnose multiple myeloma. Diagnosis is based on a combination of factors, including the patient's description of symptoms, the doctor's physical examination of the patient, and the results of blood tests and optional x-rays. The diagnosis of multiple myeloma in a subject may occur through any established diagnostic procedure known in the art. Generally, multiple myeloma is diagnosed when a plasma cell tumor is established by biopsy, or when at least 10% of the cells in the bone marrow are plasma cells in combination with the finding that either blood or urine levels of M protein are over a certain level (e.g., 3 g/dL and 1 g/dL, respectively) or holes in bones due to tumor growth or weak bones (osteoporosis) are found on imaging studies. In addition to cancer therapies described herein, multiple myeloma and other cancers can, in some embodiments, respond to a therapeutically effective amount of a proteasome inhibitor, such as bortezomib. Bortezomib reversibly blocks the function of the proteasome of the cell, affecting numerous biologic pathways, including those related to growth and survival of cancer cells. Numerous other effective proteasome inhibitors are known in the art and include, for example, carfilzomib, MLN9708, delanzomib, oprozomib, AM-114, marizomib, TMC-95A, curcusone-D and PI-1840 (see, for example, U.S. Pat. Publ. 2017/0101684). Bortezomib, currently has been approved for use in patients with multiple myeloma, who have already received at least one prior treatment, whose disease has worsened since their last treatment, and who have already undergone, or are unsuitable for, bone marrow transplantation. Bortezomib has significant activity in patients with relapsed multiple myeloma and MM patients that suffer from renal insufficiency. The efficacy of proteasome inhibitors like bortezomib are known to increase when used in combination with dexamethasone and in combination with other cancer drugs, such as doxorubicin.

Thus, proteasome inhibitors may, therefore, be used in the disclosure, either alone or in combination with other therapies described herein, such as melphalan, prednisone, doxorubicin, dexamethasone, immunomodulating drugs, monoclonal antibody drugs, including drugs based on antibody fragments, kinesin spindle protein (KSP) inhibitors, tyrosine kinase inhibitors, HDAC inhibitors, BCL2 inhibitors, cyclin-dependent kinase inhibitors, mTOR inhibitors, heat-shock protein inhibitors, Bruton's kinase inhibitors, insulin-like growth factor inhibitors, RAS inhibitors, PARP-inhibitors and B-RAF inhibitors.

The term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control patient (can be stored sample or previous sample measurement) with a known outcome; normal tissue or cells isolated from a subject, such as a normal patient or the patient having a condition of interest (cancer is used below as a representative condition), cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid, or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide immunomodulatory therapy (e.g., APRIL/TACI interaction modulator therapy). Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "expression signature" or "signature" refers to a group of two or more coordinately expressed biomarkers. For example, the genes, proteins, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The terms "high," "low," "intermediate," and "negative" in connection with cellular biomarker expression refers to the amount of the biomarker expressed relative to the cellular expression of the biomarker by one or more reference cells. Biomarker expression can be determined according to any method described herein including, without limitation, an analysis of the cellular level, activity, structure, and the like, of one or more biomarker genomic nucleic acids, ribonucleic acids, and/or polypeptides. In one embodiment, the terms refer to a defined percentage of a population of cells expressing the biomarker at the highest, intermediate, or lowest levels, respectively. Such percentages can be defined as the top 0.1%, 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 11%, 12%, 13%, 14%, 15% or more, or any range in between, inclusive, of a population of cells that either highly express or weakly express the biomarker. The term "low" excludes cells that do not detectably express the biomarker, since such cells are "negative" for biomarker expression. The term "intermediate" includes cells that express the biomarker, but at levels lower than the population expressing it at the "high" level. In another embodiment, the terms can also refer to, or in the alternative refer to, cell populations of biomarker expression identified by qualitative or statistical plot regions. For example, cell populations sorted using flow cytometry can be discriminated on the basis of biomarker expression level by identifying distinct plots based on detectable moiety analysis, such as based on mean fluorescence intensities and the like, according to well-known methods in the art. Such plot regions can be refined according to number, shape, overlap, and the like based on well-known methods in the art for the biomarker of interest. In still another embodiment, the terms can also be determined according to the presence or absence of expression for additional biomarkers.

The term "homologous" refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "STING" or "stimulator of interferon genes", also known as transmembrane protein 173 (TMEM173), refers to a five transmembrane protein that functions as a major regulator of the innate immune response to viral and bacterial infections. STING is a cytosolic receptor that senses both exogenous and endogenous cytosolic cyclic dinucleotides (CDNs), activating TBK1/IRF3 (interferon regulatory factor 3), NF-κB (nuclear factor KB), and STAT6 (signal transducer and activator of transcription 6) signaling pathways to induce robust type I interferon and proinflammatory cytokine responses. The term "STING" is intended to include fragments, variants (e.g., allelic variants) and derivatives thereof. Representative human STING cDNA and human STING protein sequences are well-known in the art and are publicly available from the National Center for Biotechnology Information (NCBI). Human STING isoforms include the longer isoform 1 (NM_198282.3 and NP_938023.1), and the shorter isoform 2 (NM_001301738.1 and NP_001288667.1; which has a shorter 5' UTR and lacks an exon in the 3' coding region which results in a shorter and distinct C-terminus compared to variant 1). Nucleic acid and polypeptide sequences of STING orthologs in organisms other than humans are well-known and include, for example, chimpanzee CDH1 (XM_016953921.1 and XP_016809410.1; XM_009449784.2 and XP_009448059.1; XM_001135484.3 and XP_001135484.1), monkey CDH1 (XM_015141010.1 and XP_014996496.1), dog CDH1 (XM_022408269.1 and XP_022263977.1; XM_005617260.3 and XP_005617317.1; XM_022408249.1 and XP_022263957.1; XM_005617262.3 and XP_005617319.1; XM_005617258.3 and XP_005617315.1; XM_022408253.1 and XP_022263961.1; XM_005617257.3 and XP_005617314.1; XM_022408240.1 and XP_022263948.1; XM_005617259.3 and XP_005617316.1; XM_022408259.1 and XP_022263967.1; XM_022408265.1 and XP_022263973.1), cattle CDH1 (NM_001046357.2 and NP_001039822.1), mouse CDH1 (NM_001289591.1 and NP_001276520.1; NM_001289592.1 and NP_001276521.1; NM_028261.1 and NP_082537.1), and rat CDH1 (NM_001109122.1 and NP_001102592.1).

STING agonists have been shown as useful therapies to treat cancer. Agonists of STING well-known in the art and include, for example, MK-1454, STING agonist-1 (MedChem Express Cat No. HY-19711), cyclic dinucleotides (CDNs) such as cyclic di-AMP (c-di-AMP), cyclic-di-GMP (c-di-GMP), cGMP-AMP (2'3'cGAMP or 3'3'cGAMP), or 10-carboxymethyl-9-acridanone (CMA) (Ohkuri et al., Oncoimmunology. 2015; 4(4):e999523), rationally designed synthetic CDN derivative molecules (Fu et al., Sci Transl Med. 2015: 7(283):283ra52. doi: 10.1126/scitranslmed.aaa4306), and 5,6-dimethyl-xanthenone-4-acetic acid (DMXAA) (Corrales et al., Cell Rep. 2015; 11(7):1018-1030). These agonists bind to and activate STING, leading to a potent type I IFN response. On the other hand, targeting the cGAS-STING pathway with small molecule inhibitors would benefit for the treatment of severe debilitating diseases such as inflammatory and autoimmune diseases associated with excessive type I IFNs production due to aberrant DNA sensing and signaling. STING inhibitors are also known and include, for example, CCCP (MedChem Express, Cat No. HY-100941) and 2-bromopalmitate (Tao, et al., IUBMB Life. 2016; 68(11):858-870). It is to be noted that the term can further be used to refer to any combination of features described herein regarding STING molecules. For example, any combination of sequence composition, percentage identify, sequence length, domain structure, functional activity, etc. can be used to describe a STING molecule of the present invention.

The term "STING pathway" or "cGAS-STING pathway" refers to a STING-regulated innate immune pathway, which mediates cytosolic DNA-induced signalling events. Cytosolic DNA binds to and activates cGAS, which catalyzes the synthesis of 2'3'-cGAMP from ATP and GTP. 2'3'-cGAMP binds to the ER adaptor STING, which traffics to the ER-Golgi intermediate compartment (ERGIC) and the Golgi apparatus. STING then activates IKK and TBK1. TBK1 phosphorylates STING, which in turn recruits IRF3 for phosphorylation by TBK1. Phosphorylated IRF3 dimerizes and then enters the nucleus, where it functions with NF-kB to turn on the expression of type I interferons and other immunomodulatory molecules. The cGAS-STING pathway not only mediates protective immune defense against infection by a large variety of DNA-containing pathogens but also detects tumor-derived DNA and generates intrinsic antitumor immunity. However, aberrant activation of the cGAS-STING pathway by self DNA can also lead to autoimmune and inflammatory disease.

The term "immunotherapy" refers to a form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in immunomodulatory therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer. As described above, immunotherapy against immune checkpoint targets, such as PD-1, PD-L1, PD-L2, CTLA-4, and the like are useful.

The term "immune checkpoint" refers to a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, TLT-2, ILT-4, TIGIT, IDO1, IDO2, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein.

Immune checkpoints and their sequences are well-known in the art and representative embodiments are described below. For example, the term "PD-1" refers to a member of the immunoglobulin gene superfamily that functions as a coinhibitory receptor having PD-L1 and PD-L2 as known ligands. PD-1 was previously identified using a subtraction cloning based approach to select for genes upregulated during TCR-induced activated T cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) *Int. Immunol.* 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

The term "IDO" refers to indoleamine 2,3-dioxygenase, which is a monomeric heme-containing cytosolic enzyme that catalyzes the first and rate-limiting step of tryptophan catabolism in the kynurenine pathway. IDO is encoded by the "IDO1" gene and can act on multiple tryptophan substrates including, for example, D-tryptophan, L-tryptophan, 5-hydroxy-tryptophan, tryptamine, and serotonin. The term is intended to include fragments, variants (e.g., allelic variants) and derivatives thereof. Representative human IDO1 cDNA and human IDO protein sequences are well-known in the art and are publicly available from the National Center for Biotechnology Information (NCBI) under accession numbers NM_002164.5 and NP_002155.1, respectively. Nucleic acid and polypeptide sequences of IDO1/IDO orthologs in organisms other than humans are well known and include, for example, mouse IDO1/IDO (NM_008324.1 and NP_032350.1), chimpanzee IDO1/IDO (XM_001137531.2 and XP_0011373531.1), monkey IDO1/IDO (NM_001077483.1 and NP_001070951.1), dog IDO1/IDO (XM_532793.4 and XP_532793.1), cow IDO1/IDO (NM001101866.2 and NP_001095336.1), and rat IDO1/IDO (NM_023973.1 and NP_076463.1). Anti-IDO antibodies are well-known in the art and include, for example, LS-C123833 (Lifespan Biosciences), AG-20A-0035 (Adipogen), MCA5433Z (AbD Serotec), HPA023149 (Atlas Antibodies), OAAB01406 (Aviva Systems Biology), and 210-301-E58 (Rockland). In addition, other inhibitors of IDO (e.g., small molecules) are known and include, for example, NSC-721782 (1-methyl-[D]-tryptophan; Muller et al. (2005) *Nat. Med.* 11:312-319), INCB024360 (Liu et al. (2010) *Blood* 115:3520-3530), and others (see, for example, Muller et al. (2005) *Exp. Opin. Ther. Targ.* 9:831-849). It is to be noted that the term can further be used to refer to any combination of features described herein regarding IDO1/IDO molecules. For example, any combination of sequence composition, percentage identify, sequence length, domain structure, functional activity, etc. can be used to describe a IDO1/IDO molecule of the present invention.

IDO is also encoded by the "IDO2" gene, which encodes a protein, like IDO1, that can similarly act on multiple tryptophan substrates including, for example, D-tryptophan, L-tryptophan, 5-hydroxy-tryptophan, tryptamine, and serotonin (Ball et al. (2007) *Gene* 396:203-213). Thus, references to the term "IDO" encompass both IDO and IDO2 proteins since they have the same enzymatic activity as desired according to the embodiments described herein unless each protein is specifically defined as either IDO or IDO2. The term is intended to include fragments, variants (e.g., allelic variants) and derivatives thereof. Representative human IDO2 cDNA and human IDO2 protein sequences are well-known in the art and are publicly available from the National Center for Biotechnology Information (NCBI) under accession numbers NM_194294.2 and NP_919270.2, respectively. Nucleic acid and polypeptide sequences of IDO2/IDO2 orthologs in organisms other than humans are well known and include, for example, mouse IDO2/IDO2 (NM_145949.2 and NP_666061.3), chimpanzee IDO2/IDO2 (XM_528116.4 and XP_528116.4), monkey IDO2/IDO2 (XM_001095833.2 and XP_001095833.2), dog IDO2/IDO2 (XM_005629824.1, XP_005629881.1, XM_005629827.1, XP_005629884.1, XM_005629826.1, XP_05629883.1, XM 005629825.1, XP_005629882.1, XM_005629828.1, and XP_005629885.1), and rat IDO2/IDO2 (XM_001061228.2, XP_001061228.2, XM_003752920.1, and XP_003752968.1). Anti-IDO2 antibodies are well-known in the art and include, for example, LS-C165098 (Lifespan Biosciences), 600-401-C69 and 210-301-E59 (Rockland), OAAB08672 and OAEBB02067 (Aviva Systems Biology), TA501378 (Origene), EB09548 (Everest Biotech), PA5-19180 (Thermo Fisher Scientific, Inc.), orb20285 and orb30411 (Biorbyt), and AP09441PU-N (Acris Antibodies). In addition, other inhibitors of IDO2 (e.g., small molecules) are known and include, for example, tenatoprazole (Bakmiwewa et al. (2012) *Bioorg. Med. Chem. Lett.* 22:7641-7646), 1-D-methyltryptophan (D-1MT) (Yuasa et al. (2010) Comp. *Biochem. Phsiol. B Biochem. Mol. Biol.* 157:10-15), and others. It is to be noted that the term can further be used to refer to any combination of features described herein regarding IDO2/IDO2 molecules. For example, any combination of sequence composition, percentage identify, sequence length, domain structure, functional activity, etc. can be used to describe a IDO2/IDO2 molecule of the present invention.

"Anti-immune checkpoint" or "immune checkpoint inhibitor or "immune checkpoint blockade" therapy refers to the use of agents that inhibit immune checkpoint nucleic acids and/or proteins. Immune checkpoints share the common function of providing inhibitory signals that suppress immune response and inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can bind to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy). Numerous immune checkpoint inhibitors are known and publicly available including, for example, Keytruda® (pembrolizumab; anti-PD-1 antibody), Opdivo® (nivolumab; anti-PD-1 antibody), Tecentriq® (atezolizumab; anti-PD-L1 antibody), durvalumab (anti-PD-L1 antibody), and the like.

The term "immune disorders" refers to conditions characterized by an unwanted immune response. In some embodiments, the immune disorder is such that a desired anti-immune disorder response suppresses immune responses. Such conditions in which downregulation of an immune response is desired are well-known in the art and include, without limitation, situations of tissue, skin and organ transplantation, in graft-versus-host disease (GVHD), inflammation, or in autoimmune diseases, such as systemic lupus erythematosus, multiple sclerosis, allergy, hypersensitivity response, and a disorder requiring increased regulatory T cell production or function, as described further herein. In other embodiments, the immune disorder is such that a desired response is an increased immune response. Such conditions in which upregulation of an immune response is desired are well-known in the art and include, without limitation, disorders requiring increased CD4+ effector T cell production or function such as combating cancer, infections (e.g., parasitic, bacterial, helminthic, or viral infections), a disorder requiring improved vaccination efficiency, and the like).

The term "immune response" includes T cell mediated and/or B cell mediated immune responses. Exemplary immune responses include T cell responses, e.g., cytokine production and cellular cytotoxicity. In addition, the term immune response includes immune responses that are indirectly affected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" or "downregulate" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. Similarly, a biological function, such as the function of a protein, is inhibited if it is decreased as compared to a reference state, such as a control like a wild-type state. For example, binding of APRIL to TACI is inhibited by an agent if the agent reduces the physical interaction of interest between APRIL and TACI, such as TACI expressed by a Treg and/R Breg. Such inhibition or deficiency can be induced, such as by application of agent at a particular time and/or place, or can be constitutive, such as by a heritable mutation. Such inhibition or deficiency can also be partial or complete (e.g., essentially no measurable activity in comparison to a reference state, such as a control like a wild-type state). Essentially complete inhibition or deficiency is referred to as blocked. The term "promote" or "upregulate" has the opposite meaning.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy.

The "normal" level of expression of a biomarker is the level of expression of the biomarker in cells of a subject, e.g., a human patient, not afflicted with a condition, such as cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

Such "significance" levels can also be applied to any other measured parameter described herein, such as for expression, inhibition, cytotoxicity, cell growth, and the like.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as one or more APRIL/TACI interaction modulator alone or in combination with one or more immunotherapies, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., cell ratios or serum biomarker normalized to the expression of housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to immunomodulatory therapy, such as APRIL/TACI interaction modulator therapy (e.g., APRIL/TACI interaction modulator either alone or in combination with a modulator of the STING pathway and/or an immunotherapy, such as an immune checkpoint inhibition therapy). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC) and/or biomarker target, or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples;

(2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular immunomodulatory therapy (e.g., APRIL/TACI interaction modulators either alone or in combination with a modulator of the STING pathway and/or an immunotherapy) or those developing resistance thereto).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as lung cancer, melanoma, and renal cell carcinoma), development of one or more clinical factors, development of intestinal cancer, or recovery from the disease.

The term "response to therapy" (e.g., APRL/TACI interaction modulator either alone or in combination with a modulator of the STING pathway and/or an immunotherapy, such as an immune checkpoint inhibition therapy) relates to any response to therapy (e.g., APRIL/TACI interaction modulator either alone or in combination with a modulator of the STING pathway and/or an immunotherapy, such as an immune checkpoint inhibition therapy), and, for cancer, preferably to a change in cancer cell numbers, tumor mass, and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any immunomodulatory therapy. The outcome measurement may be pathologic response to therapy given in the neoadjuvant setting. Alternatively, outcome measures, such as overall survival and disease-free survival can be monitored over a period of time for subjects following immunomodulatory therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months.

The term "resistance" refers to an acquired or natural resistance of a cancer sample or a mammal to an immunomodulatory therapy (i.e., being nonresponsive to or having reduced or limited response to the therapeutic treatment), such as having a reduced response to a therapeutic treatment by 5% or more, for example, 10%, 15%, 20%, 25%, 30%, 35%, 40%, 45%, 50%, 55%, 60%, 65%, 70%, 75%, 80%, 85%, 90%, 95%, 100%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to response to therapy. For example, an anti-cancer response includes reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi).

"RNA interference (RNAi)" is an evolutionally conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs, shRNAs, or other RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

In addition to RNAi, genome editing can be used to modulate the copy number or genetic sequence of a biomarker of interest, such as constitutive or induced knockout or mutation of a biomarker of interest, such as APRIL and/or TAC. For example, the CRISPR-Cas system can be used for precise editing of genomic nucleic acids (e.g., for creating non-functional or null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well-known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326:1509-1512; Moscou and Bogdanove (2009) *Science* 326:1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47). Such genetic strategies can use constitutive expression systems or inducible expression systems according to well-known methods in the art.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) *Science* 282:63), and natural product extract libraries. In another embodiment, the compounds are small, organic non-peptidic compounds. In a further embodiment, a small molecule is not biosynthetic.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "selective modulator" or "selectively modulate" as applied to a biologically active agent refers to the agent's ability to modulate the target, such as a cell population, signaling activity, etc. as compared to off-target cell population, signaling activity, etc. via direct or interact interaction with the target. For example, an agent that selectively inhibits the APRIL/TACI interaction over another interaction between APRIL and another receptor, such as BCMA, and/or an APRIL/TACI interaction on a cell population of interest (e.g., soluble may have an activity against the APRIL/TACI interaction that is at least 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 2× (times) or more than the agent's activity against at least one other APRIL receptor (e.g., at least about 3×, 4×, 5×, 6×, 7×, 8×, 9×, 10×, 15×, 20×, 25×, 30×, 35×, 40×, 45×, 50×, 55×, 60×, 65×, 70×, 75×, 80×, 85×, 90×, 95×, 100×, 105×, 110×, 120×, 125×, 150×, 200×, 250×, 300×, 350×, 400×, 450×, 500×, 600×, 700×, 800×, 900×, 1000×, 1500×, 2000×, 2500×, 3000×, 3500×, 4000×, 4500×, 5000×, 5500×, 6000×, 6500×, 7000×, 7500×, 8000×, 8500×, 9000×, 9500×, 10000×, or greater, or any range in between, inclusive). Such metrics are typically expressed in terms of relative amounts of agent required to reduce the interaction/activity by half.

More generally, the term "selective" refers to a preferential action or function. The term "selective" can be quantified in terms of the preferential effect in a particular target of interest relative to other targets. For example, a measured variable (e.g., modulation of Tregs/Bregs versus other cells, such as other immune cells like Tcons) can be 10%, 20%, 25%, 30%, 35%, 40%, 45%, 50%, 55%, 60%, 65%, 70%, 75%, 80%, 85%, 90%, 95%, 1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 45-fold, 50-fold, 55-fold, 60-fold, 70-fold, 80-fold, 90-fold, 100-fold, or greater or any range in between inclusive (e.g., 50% to 16-fold), different in a target of interest versus unintended or undesired targets. The same fold analysis can be used to confirm the magnitude of an effect in a given tissue, cell population, measured variable, measured effect, and the like, such as the Tregs:Tcons ratio, Bregs:Tcons ratio, hyperproliferative cell growth rate or volume, Tregs/Bregs proliferation rate or number, and the like.

By contrast, the term "specific" refers to an exclusionary action or function. For example, specific modulation of the APRIL/TACI interaction refers to the exclusive modulation of the APRIL/TACI interaction and not modulation of APRIL with another receptor such as BCMA. In another example, specific binding of an antibody to a predetermined antigen refers to the ability of the antibody to bind to the antigen of interest without binding to other antigens. Typically, the antibody binds with an affinity ($K_D$) of approximately less than $1\times10^{-7}$ M, such as approximately less than $10^{-8}$ M, $10^{-9}$ M, $10^{-10}$ M, $10^{-11}$ M, or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. In addition, $K_D$ is the inverse of $K_A$. The phrases "an antibody recognizing an antigen" and "an antibody specific for an antigen" are used interchangeably herein with the term "an antibody which binds specifically to an antigen."

The term "sensitize" means to alter cells, such as cancer cells or tumor cells, in a way that allows for more effective treatment with a therapy (e.g., APRIL/TACI interaction modulator either alone or in combination with a modulator of the STING pathway and/or an immunotherapy, such as an immune checkpoint inhibition therapy). In some embodiments, normal cells are not affected to an extent that causes the normal cells to be unduly injured by the therapy (e.g., APRL/TACI interaction modulator either alone or in combination with a modulator of the STING pathway and/or an immunotherapy, such as an immune checkpoint inhibition therapy). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 months for human and 4-6 weeks for mouse. A composition or a method sensitizes response to a therapeutic treatment if the increase in treatment sensitivity or the reduction in resistance is 5% or more, for example, 10%, 15%, 20%, 25%, 30%, 35%, 40%, 45%, 50%, 55%, 60%, 65%, 70%, 75%, 80%, 85%, 90%, 95%, 100%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of an immunomodulatory can be equally applied to methods for sensitizing hyperproliferative or otherwise cancerous cells (e.g., resistant cells) to the therapy.

The term "synergistic effect" refers to the combined effect of two or more therapeutic agents, such as two or more APRIL/TACI interaction modulators, a APRIL/TACI interaction modulator and an immunotherapy, APRIL/TACI interaction modulators either alone or in combination with a modulator of the STING pathway and/or an immunotherapy, such as an immune checkpoint inhibition therapy, and the like, can be greater than the sum of the separate effects of the anticancer agents alone.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "subject" refers to any healthy animal, mammal or human, or any animal, mammal or human afflicted with a cancer, e.g., multiple myeloma, lung, ovarian, pancreatic, liver, breast, prostate, melanoma, and colon carcinomas. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. Cancer cell death can be promoted by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in cancer cell numbers and/or a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

Genetic Code

| | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention and related biomarkers (e.g., biomarkers listed in Table 1) are well-known in the art and readily available on publicly available databases, such as the National Center for Biotechnology Information (NCBI). For example, exemplary nucleic acid and amino acid sequences derived from publicly available sequence databases are provided below.

Representative sequences of the biomarkers described above are presented below in Table 1. It is to be noted that the terms described above can further be used to refer to any combination of features described herein regarding the biomarkers. For example, any combination of sequence composition, percentage identify, sequence length, domain structure, functional activity, etc. can be used to describe a biomarker of the present invention.

TABLE 1

```
SEQ ID NO: 1 Human APRIL Transcript Variant alpha cDNA Sequence
(NM_003808.3, CDS region from position 749-1501)
   1 ccggaaccct gtgtgctggg gaggaatccc gcagtggccg gggggcttga ggccgctgct
  61 ttgtctcttc gtccagagcc ttatgtaaga gcttttctcg ggaaacagga agtcctgctt
 121 gccaatttca gcacagggag tagtgcaggc cttattccaa cacacccggc ccagccttaa
 181 ccccagaact cagccagttt cttgcttccg tgcccctggt tctcctcccc atcgagccca
 241 cccctccttt cccaccttca gtcaccccta gtgaactgcc ccagcgatct ctgctgtgct
 301 tgaccccgag ggtcttccac cctcgccctg accctggaca ctgcccagct tggcccccca
 361 tcctgctcct ggcacaatgc cctctagcca gccaaccttc cctcccccaa ccctggggcc
 421 gccccagggt tcctgcgcac tgcctgttcc tcctgggtgt cactggcagc cctgtccttc
 481 ctagagggac tggaacctaa ttctcctgag gctgagggag ggtggagggt ctcaaggcaa
 541 cgctggcccc acgacggagt gccaggagca ctaacagtac ccttagcttg ctttcctcct
 601 ccctcctttt tattttcaag ttccttttta tttctccttg cgtaacaacc ttcttccctt
 661 ctgcaccact gcccgtaccc ttacccgccc cgccacctcc ttgctacccc actcttgaaa
 721 ccacagctgt tggcagggtc cccagctcat gccagcctca tctcctttct tgctagcccc
 781 caaagggcct ccaggcaaca tgggggcccc agtcagagag ccggcactct cagttgccct
 841 ctggttgagt tgggggcag ctctgggggc cgtggcttgt gccatggctc tgctgaccca
 901 acaaacagag ctgcagagcc tcaggagaga ggtgagccgg ctgcagggga caggaggccc
 961 ctcccagaat ggggaagggt atccctggca gagtctcccg gagcagagtt ccgatgccct
1021 ggaagcctgg gagaatgggg agagatcccg gaaaaggaga gcagtgctca cccaaaaaca
1081 gaagaagcag cactctgtcc tgcacctggt tcccattaac gccacctcca aggatgactc
1141 cgatgtgaca gaggtgatgt ggcaaccagc tcttaggcgt gggagaggcc tacaggccca
1201 aggatatggt gtccgaatcc aggatgctgg agtttatctg ctgtatagcc aggtcctgtt
1261 tcaagacgtg actttcacca tgggtcaggt ggtgtctcga gaaggccaag gaaggcagga
1321 gactctattc cgatgtataa gaagtatgcc ctcccacccg gaccgggcct acaacagctg
1381 ctatagcgca ggtgtcttcc atttacacca aggggatatt ctgagtgtca taattccccg
1441 ggcaagggcg aaacttaacc tctctccaca tggaaccttc ctggggtttg tgaaactgtg
1501 attgtgttat aaaaagtggc tcccagcttg gaagaccagg gtgggtacat actggagaca
1561 gccaagagct gagtatataa aggagaggga atgtgcagga acagaggcgt cttcctgggt
1621 ttggctcccc gttcctcact tttccctttt cattcccacc ccctagactt tgattttacg
1681 gatatcttgc ttctgttccc catggagctc cgaattcttg cgtgtgtgta gatgaggggc
1741 gggggacggg cgccaggcat tgtccagacc tggtcggggc ccactggaag catccagaac
1801 agcaccacca tctagcggcc gctcgaggga agcacccgcc ggttggccga agtccacgaa
1861 gccgccctct gctagggaaa accccctggtt ctccatgcca cacctctctc caggtgccct
1921 ctgcctcttc accccacaag aagccttatc ctacgtcctt ctctccatct atcggacccc
1981 agtttccatc actatctcca gagatgtagc tattatgcgc ccgtctacag gggtgcccg
2041 acgatgacgg tgccttcgca gtcaaattac tcttcgggtc ccaaggtttg gctttcacgc
2101 gctccattgc cccggcgtgg caggccattc caagcccttc cgggctggaa ctggtgtcgg
2161 aggagcctcg ggtgtatcgt acgccctggt gttggtgttg cctcactcct ctgagctctt
2221 ctttctgatc aagccctgct taaagttaaa taaaatagaa tgaatgatac cccggcaaaa
2281 aaaaaaaaaa aaa3

SEQ ID NO: 2 Human APRIL Isoform alpha Amino Acid Sequence
(NP_003799.1)
   1 mpasspflla pkgppgnmgg pvrepalsva lwlswgaalg avacamallt qqtelqslrr
  61 evsrlqgtgg psqngegypw qslpeqssda leawengers rkrravltqk qkkqhsvlhl
 121 vpinatskdd sdvtevmwqp alrrgrglqa qgygvriqda gvyllysqvl fqdvtftmgq
 181 vvsregqgrq etlfrcirsm pshpdrayns cysagvfhlh qgdilsvilp raraklnlsp
 241 hgtflgfvkl

SEQ ID NO: 3 Human APRIL Transcript Variant beta cDNA Sequence
(NM_172087.2, CDS region from position 749-1453)
   1 ccggaaccct gtgtgctggg gaggaatccc gcagtggccg gggggcttga ggccgctgct
  61 ttgtctcttc gtccagagcc ttatgtaaga gcttttctcg ggaaacagga agtcctgctt
```

TABLE 1-continued

```
 121 gccaatttca gcacagggag tagtgcaggc cttattccaa cacacccggc ccagccttaa
 181 ccccagaact cagccagttt cttgcttccg tgcccctggt tctcctcccc atcgagccca
 241 cccctccttt cccaccttca gtcaccccta gtgaactgcc ccagcgatct ctgctgtgct
 301 tgaccccgag ggtcttccac cctcgccctg accctggaca ctgcccagct tggcccccca
 361 tcctgctcct ggcacaatgc cctctagcca gccaaccttc cctcccccaa ccctggggcc
 421 gccccagggt tcctgcgcac tgcctgttcc tcctgggtgt cactggcagc cctgtccttc
 481 ctagagggac tggaacctaa ttctcctgag gctgagggag ggtggagggt ctcaaggcaa
 541 cgctggcccc acgacggagt gccaggagca ctaacagtac ccttagcttg ctttcctcct
 601 ccctcctttt tattttcaag ttccttttta tttctccttg cgtaacaacc ttcttccctt
 661 ctgcaccact gcccgtaccc ttacccgccc cgccacctcc ttgctacccc actcttgaaa
 721 ccacagctgt tggcagggtc cccagctcat gccagcctca tctcctttct tgctagcccc
 781 caaagggcct ccaggcaaca tgggggcccc agtcagagag ccggcactct cagttgccct
 841 ctggttgagt tgggggcag ctctggggc cgtggcttgt gccatggctc tgctgaccca
 901 acaaacagag ctgcagagcc tcaggagaga ggtgagccgg ctgcagggga caggaggccc
 961 ctcccagaat ggggaagggt atccctggca gagtctcccg gagcagagtt ccgatgccct
1021 ggaagcctgg gagaatgggg agagatcccg gaaaaggaga gcagtgctca cccaaaaaca
1081 gaagaatgac tccgatgtga cagaggtgat gtggcaacca gctcttaggc gtgggagagg
1141 cctacaggcc caaggatatg gtgtccgaat ccaggatgct ggagtttatc tgctgtatag
1201 ccaggtcctg tttcaagacg tgactttcac catgggtcag gtggtgtctc gagaaggcca
1261 aggaaggcag gagactctat tccgatgtat aagaagtatg ccctcccacc cggaccgggc
1321 ctacaacagc tgctatagcg caggtgtctt ccatttacac caaggggata ttctgagtgt
1381 cataattccc cgggcaaggg cgaaacttaa cctctctcca catggaacct tcctggggtt
1441 tgtgaaactg tgattgtgtt ataaaaagtg gctcccagct tggaagacca gggtgggtac
1501 atactggaga cagccaagag ctgagtatat aaaggagagg gaatgtgcag gaacagaggc
1561 gtcttcctgg gtttggctcc ccgttcctca cttttccctt ttcattccca cccccctagac
1621 tttgatttta cggatatctt gcttctgttc cccatggagc tccgaattct tgcgtgtgtg
1681 tagatgaggg gcgggggacg ggcgccaggc attgtccaga cctggtcggg gcccactgga
1741 agcatccaga acagcaccac catctagcgg ccgctcgagg gaagcacccg ccggttggcc
1801 gaagtccacg aagccgccct ctgctaggga aaacccctgg ttctccatgc cacacctctc
1861 tccaggtgcc ctctgcctct tcaccccaca agaagcctta tcctacgtcc ttctctccat
1921 ctatcggacc ccagtttcca tcactatctc cagagatgta gctattatgc gcccgtctac
1981 agggggtgcc cgacgatgac ggtgccttcg cagtcaaatt actcttcggg tcccaaggtt
2041 tggctttcac gcgctccatt gccccggcgt ggcaggccat tccaagccct tccgggctgg
2101 aactggtgtc ggaggagcct cgggtgtatc gtacgccctg gtgttggtgt tgcctcactc
2161 ctctgagctc ttctttctga tcaagccctg cttaaagtta aataaaatag aatgaatgat
2221 accccggcaa aaaaaaaaaa aaaaa
```

SEQ ID NO: 4 Human APRIL Isoform beta Amino Acid Sequence (NP_742084.1)

```
  1 mpasspflla pkgppgnmgg pvrepalsva lwlswgaalg avacamallt qqtelqslrr
 61 evsrlqgtgg psqngegypw gslpeqssda leawengers rkrravltqk qkndsdvtev
121 mwqpalrrgr glqaqgygvr iqdagvylly sqvlfqdvtf tmgqvvsreg qgrqetlfrc
181 irsmpshpdr aynscysagv fhlhqgdils vilprarakl nlsphgtflg fvkl
```

SEQ ID NO: 5 Human APRIL Transcript Variant gamma cDNA Sequence (NM_172088.2, CDS region from position 749-1492)

```
   1 ccggaaccct gtgtgctggg gaggaatccc gcagtggccg gggggcttga ggccgctgct
  61 ttgtctcttc gtccagagcc ttatgtaaga gcttttctcg ggaaacagga agtcctgctt
 121 gccaatttca gcacagggag tagtgcaggc cttattccaa cacacccggc ccagccttaa
 181 ccccagaact cagccagttt cttgcttccg tgcccctggt tctcctcccc atcgagccca
 241 cccctccttt cccaccttca gtcaccccta gtgaactgcc ccagcgatct ctgctgtgct
 301 tgaccccgag ggtcttccac cctcgccctg accctggaca ctgcccagct tggcccccca
 361 tcctgctcct ggcacaatgc cctctagcca gccaaccttc cctcccccaa ccctggggcc
 421 gccccagggt tcctgcgcac tgcctgttcc tcctgggtgt cactggcagc cctgtccttc
 481 ctagagggac tggaacctaa ttctcctgag gctgagggag ggtggagggt ctcaaggcaa
 541 cgctggcccc acgacggagt gccaggagca ctaacagtac ccttagcttg ctttcctcct
 601 ccctcctttt tattttcaag ttccttttta tttctccttg cgtaacaacc ttcttccctt
 661 ctgcaccact gcccgtaccc ttacccgccc cgccacctcc ttgctacccc actcttgaaa
 721 ccacagctgt tggcagggtc cccagctcat gccagcctca tctcctttct tgctagcccc
 781 caaagggcct ccaggcaaca tgggggcccc agtcagagag ccggcactct cagttgccct
 841 ctggttgagt tgggggcag ctctggggc cgtggcttgt gccatggctc tgctgaccca
 901 acaaacagag ctgcagagcc tcaggagaga ggtgagccgg ctgcagggga caggaggccc
 961 ctcccagaat ggggaagggt atccctggca gagtctcccg gagcagagtt ccgatgccct
1021 ggaagcctgg gagaatgggg agagatcccg gaaaaggaga gcagtgctca cccaaaaaca
1081 gaagaagcag cactctgtcc tgcacctggt tcccattaac gccacctcca aggatgactc
1141 cgatgtgaca gaggtgatgt ggcaaccagc tcttaggcgt gggagaggcc tacaggccca
1201 aggatatggt gtccgaatcc aggatgctgg agtttatctg ctgtatagcc aggtcctgtt
1261 tcaagacgtg actttcacca tgggtcaggt ggtgtctcga gaaggccaag gaaggcagga
1321 gactctattc cgatgtataa gaagtatgcc ctcccacccg gaccgggcct acaacagctg
1381 ctatagcgca ggtgtcttcc atttacacca aggggatatt ctgagtgtca taattccccg
1441 ggcaagggcg aaacttaacc tctctccaca tggaaccttc ctgggacttt gattttacgg
1501 atatcttgct tctgttcccc atggagctcc gaattcttgc gtgtgtgtag atgaggggcg
1561 ggggacgggc gccaggcatt gtccagacct ggtcggggcc cactggaagc atccagaaca
1621 gcaccaccat ctagcggccg ctcgagggaa gcacccgccg gttggccgaa gtccacgaag
1681 ccgccctctg ctagggaaaa cccctggttc tccatgccac acctctctcc aggtgccctc
1741 tgcctcttca ccccacaaga agccttatcc tacgtccttc tctccatcta tcggacccca
1801 gtttccatca ctatctccag agatgtagct attatgcgcc cgtctacagg gggtgcccga
1861 cgatgacggt gccttcgcag tcaaattact cttcgggtcc caaggtttgg ctttcacgcg
1921 ctccattgcc ccggcgtggc aggccattcc aagcccttcc gggctggaac tggtgtcgga
1981 ggagcctcgg gtgtatcgta cgccctggtg ttggtgttgc ctcactcctc tgagctcttc
```

TABLE 1-continued

```
2041 tttctgatca agccctgctt aaagttaaat aaaatagaat gaatgatacc ccggcaaaaa
2101 aaaaaaaaaa aa

SEQ ID NO: 6 Human APRIL Isoform gamma Amino Acid Sequence
(NP_742085.1)
   1 mpasspflla pkgppgnmgg pvrepalsva lwlswgaalg avacamallt qqtelqslrr
  61 evsrlqgtgg psqngegypw qslpeqssda leawengers rkrravltqk qkkghsvlhl
 121 vpinatskdd sdvtevmwqp alrrgrglqa qgygvriqda gvyllysqvl fqdvtftmgq
 181 vvsregqgrq etlfrcirsm pshpdrayns cysagvfhlh qgdilsviip raraklnlsp
 241 hgtflgl

SEQ ID NO: 7 Human APRIL Transcript Variant delta cDNA Sequence
(NM_001198622.1, CDS region from position 749-1420)
   1 ccggaaccct gtgtgctggg gaggaatccc gcagtggccg gggggcttga ggccgctgct
  61 ttgtctcttc gtccagagcc ttatgtaaga gcttttctcg ggaaacagga agtcctgctt
 121 gccaatttca gcacagggag tagtgcaggc cttattccaa cacacccggc ccagccttaa
 181 ccccagaact cagccagttt cttgcttccg tgcccctggt tctcctcccc atcgagccca
 241 cccctccttt cccaccttca gtcaccccta gtgaactgcc ccagcgatct ctgctgtgct
 301 tgaccccgag ggtcttccac cctcgccctg accctggaca ctgcccagct tggccccccca
 361 tcctgctcct ggcacaatgc cctctagcca gccaaccttc cctcccccaa ccctggggcc
 421 gccccagggt tcctgcgcac tgcctgttcc tcctgggtgt cactggcagc cctgtccttc
 481 ctagagggac tggaacctaa ttctcctgag gctgagggag ggtggagggt ctcaaggcaa
 541 cgctggcccc acgacggagt gccaggagca ctaacagtac ccttagcttg ctttcctcct
 601 ccctcctttt tattttcaag ttccttttta tttctccttg cgtaacaacc ttcttccctt
 661 ctgcaccact gcccgtaccc ttacccgccc cgccacctcc ttgctacccc actcttgaaa
 721 ccacagctgt tggcagggtc cccagctcat gccagcctca tctcctttct tgctagcccc
 781 caaagggcct ccaggcaaca tgggggggccc agtcagagag ccggcactct cagttgccct
 841 ctggttgagt tggggggcag ctctgggggc cgtggcttgt gccatggctc tgctgaccca
 901 acaaacagag ctgcagagcc tcaggagaga ggtgagccgg ctgcagggga caggaggccc
 961 ctcccagaat ggggaagggt atccctggca gagtctcccg gagcagcagc actctgtcct
1021 gcacctggtt cccattaacg ccacctccaa ggatgactcc gatgtgacag aggtgatgtg
1081 gcaaccagct cttaggcgtg ggagaggcct acaggcccaa ggatatggtg tccgaatcca
1141 ggatgctgga gtttatctgc tgtatagcca ggtcctgttt caagacgtga ctttcaccat
1201 gggtcaggtg gtgtctcgag aaggccaagg aaggcaggag actctattcc gatgtataag
1261 aagtatgccc tcccacccgg accgggccta caacagctgc tatagcgcag gtgtcttcca
1321 tttacaccaa ggggatattc tgagtgtcat aattccccgg gcaagggcga aacttaacct
1381 ctctccacat ggaaccttcc tggggtttgt gaaactgtga ttgtgttata aaaagtggct
1441 cccagcttgg aagaccaggg tgggtacata ctggagacag ccaagagctg agtatataaa
1501 ggagagggaa tgtgcaggaa cagaggcgtc ttcctgggtt tggctccccg ttcctcactt
1561 ttccctttc attcccaccc cctagacttt gattttacgg atatcttgct tctgttcccc
1621 atggagctcc gaattcttgc gtgtgtgtag atgaggggcg gggacgggc gccaggcatt
1681 gtccagacct ggtcggggcc cactggaagc atccagaaca gcaccaccat ctagcggccg
1741 ctcgagggaa gcacccgccg gttggccgaa gtccacgaag ccgccctctg ctagggaaaa
1801 cccctggttc tccatgccac acctctctcc aggtgccctc tgcctcttca ccccacaaga
1861 agccttatcc tacgtccttc tctccatcta tcggacccca gtttccatca ctatctccag
1921 agatgtagct attatgcgcc cgtctacagg gggtgcccga cgatgacggt gccttcgcag
1981 tcaaattact cttcgggtcc caaggtttgg ctttcacgcg ctccattgcc ccggcgtggc
2041 aggccattcc aagcccttcc gggctggaac tggtgtcgga ggagcctcgg gtgtatcgta
2101 cgccctggtg ttggtgttgc ctcactcctc tgagctcttc tttctgatca agccctgctt
2161 aaagttaaat aaaatagaat gaatgatacc ccggcaaaaa aaaaaaaaaa aa

SEQ ID NO: 8 Human APRIL Isoform delta Amino Acid Sequence
(NP_001185551.1)
   1 mpasspflla pkgppgnmgg pvrepalsva lwlswgaalg avacamallt qqtelqslrr
  61 evsrlqgtgg psqngegypw qslpeqqhsv lhlvpinats kddsdvtevm wqpalrrgrg
 121 lqaqgygvri qdagvyllys qvlfqdvtft mgqvvsregq grqetlfrci rsmpshpdra
 181 ynscysagvf hlhqgdilsv liprarakln lsphgtflgf vkl

SEQ ID NO: 9 Human APRIL Transcript Variant zeta cDNA Sequence
(NM_001198623.1, CDS region from position 749-1417)
   1 ccggaaccct gtgtgctggg gaggaatccc gcagtggccg gggggcttga ggccgctgct
  61 ttgtctcttc gtccagagcc ttatgtaaga gcttttctcg ggaaacagga agtcctgctt
 121 gccaatttca gcacagggag tagtgcaggc cttattccaa cacacccggc ccagccttaa
 181 ccccagaact cagccagttt cttgcttccg tgcccctggt tctcctcccc atcgagccca
 241 cccctccttt cccaccttca gtcaccccta gtgaactgcc ccagcgatct ctgctgtgct
 301 tgaccccgag ggtcttccac cctcgccctg accctggaca ctgcccagct tggccccccca
 361 tcctgctcct ggcacaatgc cctctagcca gccaaccttc cctcccccaa ccctggggcc
 421 gccccagggt tcctgcgcac tgcctgttcc tcctgggtgt cactggcagc cctgtccttc
 481 ctagagggac tggaacctaa ttctcctgag gctgagggag ggtggagggt ctcaaggcaa
 541 cgctggcccc acgacggagt gccaggagca ctaacagtac ccttagcttg ctttcctcct
 601 ccctcctttt tattttcaag ttccttttta tttctccttg cgtaacaacc ttcttccctt
 661 ctgcaccact gcccgtaccc ttacccgccc cgccacctcc ttgctacccc actcttgaaa
 721 ccacagctgt tggcagggtc cccagctcat gccagcctca tctcctttct tgctagcccc
 781 caaagggcct ccaggcaaca tgggggggccc agtcagagag ccggcactct cagttgccct
 841 ctggttgagt tggggggcag ctctgggggc cgtggcttgt gccatggctc tgctgaccca
 901 acaaacagag ctgcagagcc tcaggagaga ggtgagccgg ctgcagggga caggaggccc
 961 ctcccagaat ggggaagggt atccctggca gagtctcccg gagcagcact ctgtcctgca
1021 cctggttccc attaacgcca cctccaagga tgactccgat gtgacagagg tgatgtggca
1081 accagctctt aggcgtggga gaggcctaca ggcccaagga tatggtgtcc gaatccagga
1141 tgctggagtt tatctgctgt atagccaggt cctgtttcaa gacgtgactt tcaccatggg
```

TABLE 1-continued

```
1201 tcaggtggtg tctcgagaag gccaaggaag gcaggagact ctattccgat gtataagaag
1261 tatgccctcc cacccggacc gggcctacaa cagctgctat agcgcaggtg tcttccattt
1321 acaccaaggg gatattctga gtgtcataat tccccgggca agggcgaaac ttaacctctc
1381 tccacatgga accttcctgg ggtttgtgaa actgtgattg tgttataaaa agtggctccc
1441 agcttggaag accagggtgg gtacatactg gagacagcca agagctgagt atataaagga
1501 gagggaatgt gcaggaacag aggcgtcttc ctgggtttgg ctccccgttc ctcacttttc
1561 ccttttcatt cccacccccct agactttgat tttacggata tcttgcttct gttccccatg
1621 gagctccgaa ttcttgcgtg tgtgtagatg aggggcgggg gacgggcgcc aggcattgtc
1681 cagacctggt cggggcccac tggaagcatc cagaacagca ccaccatcta gcggccgctc
1741 gagggaagca cccgccggtt ggccgaagtc cacgaagccg ccctctgcta gggaaaaccc
1801 ctggttctcc atgccacacc tctctccagg tgccctctgc ctcttcaccc cacaagaagc
1861 cttatcctac gtccttctct ccatctatcg gaccccagtt tccatcacta tctccagaga
1921 tgtagctatt atgcgcccgt ctacaggggg tgcccgacga tgacggtgcc ttcgcagtca
1981 aattactctt cgggtcccaa ggtttggctt tcacgcgctc cattgccccg gcgtggcagg
2041 ccattccaag cccttccggg ctggaactgg tgtcggagga gcctcgggtg tatcgtacgc
2101 cctggtgttg gtgttgcctc actcctctga gctcttcttt ctgatcaagc cctgcttaaa
2161 gttaaataaa atagaatgaa tgataccccg gcaaaaaaaa aaaaaaaaa
```

SEQ ID NO: 10 Human APRIL Isoform zeta Amino Acid Sequence
(NP_001185552.1)

```
  1 mpasspflla pkgppgnmgg pvrepalsva lwlswgaalg avacamallt qqtelqslrr
 61 evsrlqgtgg psqngegypw qslpeqhsvl hlvpinatsk ddsdvtevmw qpalrrgrgl
121 qaqgygvriq dagvyllysq vlfqdvtftm gqvvsregqg rqetlfrcir smpshpdray
181 nscysagvfh lhqgdilsvi iprarakl nl sphgtflgfv kl
```

SEQ ID NO: 11 Human APRIL Transcript Variant eta cDNA Sequence
(NM_001198624.1, CDS region from position 108-725)

```
   1 ccggaaccct gtgtgctggg gaggaatccc gcagtggccg gggggcttga ggccgctgct
  61 ttgtctcttc gtccagagcc ttatccccca aagggcctcc aggcaacatg gggggcccag
 121 tcagagagcc ggcactctca gttgccctct ggttgagttg gggggcagct ctgggggccg
 181 tggcttgtgc catggctctg ctgacccaac aaacagagct gcagagcctc aggagagagg
 241 tgagccggct gcaggggaca ggaggcccct cccagaatgg ggaagggtat ccctggcaga
 301 gtctcccgga gcagcactct gtcctgcacc tggttcccat taacgccacc tccaaggatg
 361 actccgatgt gacagaggtg atgtggcaac cagctcttag gcgtgggaga ggcctacagg
 421 cccaaggata tggtgtccga atccaggatg ctggagttta tctgctgtat agccaggtcc
 481 tgtttcaaga cgtgactttc accatgggtc aggtggtgtc tcgagaaggc caaggaaggc
 541 aggagactct attccgatgt ataagaagta tgccctccca cccggaccgg gcctacaaca
 601 gctgctatag cgcaggtgtc ttccatttac accaagggga tattctgagt gtcataattc
 661 cccgggcaag ggcgaaactt aacctctctc cacatggaac cttcctgggg tttgtgaaac
 721 tgtgattgtg ttataaaaag tggctcccag cttggaagac cagggtgggt acatactgga
 781 gacagccaag agctgagtat ataaaggaga gggaatgtgc aggaacagag gcgtcttcct
 841 gggtttggct ccccgttcct cacttttccc ttttcattcc cacccccctag actttgattt
 901 tacggatatc ttgcttctgt tccccatgga gctccgaatt cttgcgtgtg tgtagatgag
 961 gggcgggggga cgggcgccag gcattgtcca gacctggtcg gggcccactg gaagcatcca
1021 gaacagcacc accatctagc ggccgctcga gggaagcacc cgccggttgg ccgaagtcca
1081 cgaagccgcc ctctgctagg gaaaacccct ggttctccat gccacacctc tctccaggtg
1141 ccctctgcct cttcacccca caagaagcct tatcctacgt ccttctctcc atctatcgga
1201 ccccagtttc catcactatc tccagagatg tagctattat gcgcccgtct acagggggtg
1261 cccgacgatg acggtgcctt cgcagtcaaa ttactcttcg ggtcccaagg tttggctttc
1321 acgcgctcca ttgccccggc gtggcaggcc attccaagcc cttccgggct ggaactggtg
1381 tcggaggagc ctcgggtgta tcgtacgccc tggtgttggt gttgcctcac tcctctgagc
1441 tcttctttct gatcaagccc tgcttaaagt taaataaaat agaatgaatg ataccccggc
1501 aaaaaaaaaa aaaaaaa
```

SEQ ID NO: 12 Human APRIL Isoform eta Amino Acid Sequence
(NP_001185553.1)

```
  1 mggpvrepal svalwlswga algavacama lltqqtelqs lrrevsrlqg tggpsqngeg
 61 ypwqslpeqh svlhlvpina tskddsdvte vmwqpalrrg rglqaqgygv riqdagvyll
121 ysqvlfqdvt ftmgqvvsre gqgrqetlfr cirsmpshpd raynscysag vfhlhqgdil
181 sviiprarak lnlsphgtfl gfvkl8
```

SEQ ID NO: 13 Mouse APRIL Transcript Variant 1 cDNA Sequence
(NM_023517.2, CDS region from position 296-1021)

```
  1 gaaggctggc cgctccttct gggtgtcacg gctgccctgt ccttcctaga taatggcacc
 61 aaattctcct gaggctaggg gggaaggagt gtcagagtgt cactagctcg accctgggga
121 caagggggac taatagtacc ctagcttgat ttcttcctat tctcaagttc ctttttattt
181 ctcccttgcg taacccgctc ttcccttctg tgcctttgcc tgtattccca ccctccctgc
241 tacctcttgg ccacctcact tctgagacca cagctgttgg cagggtccct agctcatgcc
301 agcctcatct ccaggccaca tggggggctc agtcagagag ccagcccttt cggttgctct
361 ttggttgagt tggggggcag ttctggggc tgtgacttgt gctgtcgcac tactgatcca
421 acagacagag ctgcaaagcc taaggcggga ggtgagccgg ctgcagcgga gtggagggcc
481 ttcccagaag cagggagagc gcccatggca gagcctctgg gagcagagtc ctgatgtcct
541 ggaagcctgg aaggatgggg cgaaatctcg gagaaggaga gcagtactca cccagaagca
601 caagaagaag cactcagtcc tgcatcttgt tccagttaac attacctcca aggcagactc
661 tgacgtgaca gaggtgatgt ggcaaccagt acttaggcgt gggagaggcc tggaggccca
721 gggagacatt gtacgagtct gggacactgg aatttatctg ctctatagtc aggtcctgtt
781 tcatgatgtg actttcacaa tgggtcaggt ggtatctcgg gaaggacaag ggagaagaga
841 aactctattc cgatgtatca gaagtatgcc ttctgatcct gaccgtgcct acaatagctg
901 ctacagtgca ggtgtctttc atttacatca aggggatatt atcactgtca aaattccacg
961 ggcaaacgca aaacttagcc tttctccgca tggaacattc ctggggtttg tgaaactatg
```

TABLE 1-continued

```
1021 attgttataa agggggtggg gatttcccat tccaaaaact ggctagacaa aggacaagga
1081 acggtcaaga acagctctcc atggctttgc cttgactgtt gttcctccct ttgcctttcc
1141 cgctcccact atctgggctt tgactccatg gatattaaaa aagtagaata ttttgtgttt
1201 atctcccaca cagccccaaa ttcttttgtt gtgtgtgcga agggggtttt gcgcactgtg
1261 ccaagccttg tccactggaa tgcatccaga acagcagcac catctagcgg caggttgagg
1321 aaagactatg gtctctgcta gggaaaacct tatccaactc ttcaagtacc ctctgcttca
1381 attaacaaga agcccggctt tcagtatttc acctattgcg tccaaattct tgttactatc
1441 tagaaaaaga tatatgttag gtgcctcgat atgcatgcca ttcatcctcc ccattctcct
1501 atacacttcc gagctgggca ctgagcttta cgccttaaat cacagtactc gggaggcaga
1561 tctcgatgag ttcgaggcca acttggtcta aatagtgagt tccaggccac ccaggggtta
1621 caatggtgag accctgtctc aaacaaacta acaaacaaat aaacgaaagg ctctccacg
```

SEQ ID NO: 14 Mouse APRIL Isoform 1 Amino Acid Sequence (NP_076006.2)

```
  1 mpasspghmg gsvrepalsv alwlswgavl gavtcavall iqqtelqslr revsrlqrsg
 61 gpsqkqgerp wqslweqspd vleawkdgak srrrravltq khkkkhsvlh lvpvnitska
121 dsdvtevmwq pvlrrgrgle aqgdivrvwd tglyllysqv lfhdvtftmg qvvsregqgr
181 retlfrcirs mpsdpdrayn scysagvfhl hqgdiltvki pranaklsls phgtflgfvk
241 l
```

SEQ ID NO: 15 Mouse APRIL Transcript Variant 2 cDNA Sequence (NM_001159505.1, CDS region from position 296-1018)

```
   1 gaaggctggc cgctccttct gggtgtcacg gctgccctgt ccttcctaga taatggcacc
  61 aaattctcct gaggctaggg gggaaggagt gtcagagtgt cactagctcg accctgggga
 121 caaggggac taatagtacc ctagcttgat ttcttcctat tctcaagttc ctttttattt
 181 ctcccttgcg taacccgctc ttcccttctg tgcctttgcc tgtattccca ccctccctgc
 241 tacctcttgg ccacctcact tctgagacca cagctgttgg cagggtccct agctcatgcc
 301 agcctcatct ccaggccaca tggggggctc agtcagagag ccagcccttt cggttgctct
 361 ttggttgagt tggggggcag ttctggggc tgtgacttgt gctgtcgcac tactgatcca
 421 acagacagag ctgcaaagcc taaggcggga ggtgagccgg ctgcagcgga gtggagggcc
 481 ttcccagaag cagggagagc gcccatggca gagcctctgg gagcagagtc ctgatgtcct
 541 ggaagcctgg aaggatgggg cgaaatctcg gagaaggaga gcagtactca cccagaagca
 601 caagaagaag cactcagtcc tgcatcttgt tccagttaac attacctcca aggactctga
 661 cgtgacagag gtgatgtggc aaccagtact taggcgtggg agaggcctgg aggcccaggg
 721 agacattgta cgagtctggg acactggaat ttatctgctc tatagtcagg tcctgtttca
 781 tgatgtgact ttcacaatgg gtcaggtggt atctcgggaa ggacaaggga gaagagaaac
 841 tctattccga tgtatcagaa gtatgccttc tgatcctgac cgtgcctaca atagctgcta
 901 cagtgcaggt gtctttcatt tacatcaagg ggatattatc actgtcaaaa ttccacgggc
 961 aaacgcaaaa cttagccttt ctccgcatgg aacattcctg ggtttgtga aactatgatt
1021 gttataaagg gggtggggat ttcccattcc aaaaactggc tagacaaagg acaaggaacg
1081 gtcaagaaca gctctccatg gctttgcctt gactgttgtt cctccctttg cctttcccgc
1141 tcccactatc tgggctttga ctccatggat attaaaaaag tagaatattt tgtgtttatc
1201 tcccacacag ccccaaattc ttttgttgtg tgtgcgaagg gggttttgcg cactgtgcca
1261 agccttgtcc actggaatgc atccagaaca gcagcaccat ctagcggcag gttgaggaaa
1321 gactatggtc tctgctaggg aaaaccttat ccaactcttc aagtaccctc tgcttcaatt
1381 aacaagaagc ccggctttca gtatttcacc tattgcgtcc aaattcttgt tactatctag
1441 aaaaagatat atgttaggtg cctcgatatg catgccattc atcctcccca ttctcctata
1501 cacttccgag ctgggcactg agctttacgc cttaaatcac agtactcggg aggcagatct
1561 cgatgagttc gaggccaact tggtctaaat agtgagttcc aggccaccca ggggttacaa
1621 tggtgagacc ctgtctcaaa caaactaaca aacaaataaa cgaaaggctc tccacg
```

SEQ ID NO: 16 Mouse APRIL Isoform 2 Amino Acid Sequence (NP_001152977.1)

```
  1 mpasspghmg gsvrepalsv alwlswgavl gavtcavall iqqtelqslr revsrlqrsg
 61 gpsqkqgerp wqslwegspd vleawkdgak srrrravltq khkkkhsvlh lvpvnitskd
121 sdvtevmwqp vlrrgrglea qgdivrvwdt glyllysqvl fhdvtftmqq vvsregqgrr
181 etlfrcirsm psdpdrayns cysagvfhlh qgdiltvkip ranaklslsp hgtflgfvkl
```

SEQ ID NO: 17 Human TACI cDNA Sequence (NM_012452.2, CDS region from position 14-895)

```
   1 agcatcctga gtaatgagtg gcctgggccg gagcaggcga ggtggccgga gccgtgtgga
  61 ccaggaggag cgctttccac agggcctgtg gacgggggtg gctatgagat cctgccccga
 121 agagcagtac tgggatcctc tgctgggtac ctgcatgtcc tgcaaaacca tttgcaacca
 181 tcagagccag cgcacctgtg cagccttctg caggtcactc agctgccgca aggagcaagg
 241 caagttctat gaccatctcc tgagggactg catcagctgt gcctccatct gtggacagca
 301 ccctaagcaa tgtgcatact tctgtgagaa caagctcagg agcccagtga accttccacc
 361 agagctcagg agacagcgga gtggagaagt tgaaaacaat tcagacaact cgggaaggta
 421 ccaaggattg gagcacagag gctcagaagc aagtccagct ctcccggggc tgaagctgag
 481 tgcagatcag gtggccctgg tctacagcac gctggggctc tgcctgtgtg ccgtcctctg
 541 ctgcttcctg gtggcggtgg cctgcttcct caagaagagg ggggatccct gctcctgcca
 601 gccccgctca aggccccgtc aaagtccggc caagtcttcc caggatcacg cgatggaagc
 661 cggcagccct gtgagcacat cccccgagcc agtggagacc tgcagcttct gcttccctga
 721 gtgcagggcg cccacgcagg agagcgcagt cacgcctggg acccccgacc ccacttgtgc
 781 tggaaggtgg gggtgccaca ccaggaccac agtcctgcag ccttgcccac acatcccaga
 841 cagtggcctt ggcattgtgt gtgtgcctgc ccaggagggg ggcccaggtg cataaatggg
 901 ggtcagggag ggaaaggagg agggagagag atggagagga ggggagagag aaagagaggt
 961 ggggagaggg gagagagata tgaggagaga gagacagagg aggcagagag ggagagaaac
1021 agaggagaca gagagggaga gagagacaga gggagagaga gacagagggg aagagaggca
1081 gagagggaaa gaggcagaga aggaaagaga caggcagaga aggagagagg cagagaggga
1141 gagaggcaga gagggagaga ggcagagaga cagagaggga gagagggaca gagagagata
1201 gagcaggagg tcggggcact ctgagtccca gttcccagtg cagctgtagg tcgtcatcac
```

TABLE 1-continued

```
1261 ctaaccacac gtgcaataaa gtcctcgtgc ctgctgctca cagcccccga gagcccctcc
1321 tcctggagaa taaaaccttt ggcagctgcc cttcctcaaa aaaaaaaaaa aaaaaaa
```

SEQ ID NO: 18 Human TACI Amino Acid Sequence (NP_036584.1)

```
  1 msglgrsrrg grsrvdqeer fpqglwtgva mrscpeeqyw dpllgtcmsc kticnhqsqr
 61 tcaafcrsls crkeqgkfyd hllrdcisca sicgqhpkqc ayfcenklrs pvnlppelrr
121 qrsgevenns dnsgryqgle hrgseaspal pglklsadqv alvystlglc lcavlccflv
181 avacflkkrg dpcscqprsr prqspakssq dhameagspv stspepvetc sfcfpecrap
241 tqesavtpgt pdptcagrwg chtrttvlqp cphipdsglg ivcvpaqegg pga
```

SEQ ID NO: 19 Mouse TACI cDNA Sequence (NM_021349.1, CDS region from position 1-750)

```
  1 atggctatgg cattctgccc caaagatcag tactgggact cctcaaggaa atcctgtgtc
 61 tcctgtgcac tgacctgcag ccagaggagc cagcgcacct gtacagactt ctgcaaattc
121 atcaattgcc gaaaagagca aggcaggtac tacgaccatc tcctgggggc ctgcgtcagc
181 tgtgactcca cctgcacaca gcaccctcag cagtgtgccc acttctgtga gaaaaggccc
241 agaagccagg cgaacctcca gcccgagctc gggagaccac aggccgggga ggtggaagtc
301 aggtcagaca actcaggaag gcaccaggga tctgagcatg gtccaggatt gaggctaagt
361 agcgaccagc tgactctcta ctgcacactg gggtctgcc tctgcgccat cttctgctgt
421 ttcttggtgg ccttggcctc cttcctcagg cgtagaggag agccactacc cagccagcct
481 gccgggccac gtgggtcaca agcaaactct ccccacgccc accgccccgt gacagaggct
541 tgcgacgagg tgaccgcgtc accccagcct gtggaaacgt gtagcttctg cttcccggag
601 cgcagttctc ccactcagga gagcgcgccg cgttcgctcg ggatacacgg cttcgcgggc
661 actgccgccc cgcagccctg tatgcgtgca acagtaggcg gcctgggtgt cctgcgcgca
721 tccactgggg acgctcgtcc ggcaacttga
```

SEQ ID NO: 20 Mouse TACI Amino Acid Sequence (NP_067324.1)

```
  1 mamafcpkdq ywdssrkscv scaltcsqrs qrtctdfckf incrkeqgry ydhllgacvs
 61 cdstctqhpq qcahfcekrp rsqanlqpel grpqagevev rsdnsgrhqg sehgpglrls
121 sdqltlyctl gvclcaifcc flvalasflr rrgeplpsqp agprgsqans phahrpvtea
181 cdevtaspqp vetcsfcfpe rssptqesap rslgihgfag taapqpcmra tvgglgvlra
241 stgdarpat
```

SEQ ID NO: 21 Human BCMA cDNA Sequence (NM_001192.2, CDS region from position 219-773)

```
  1 aagactcaaa cttagaaact tgaattagat gtggtattca aatccttagc tgccgcgaag
 61 acacagacag cccccgtaag aacccacgaa gcaggcgaag ttcattgttc tcaacattct
121 agctgctctt gctgcatttg ctctggaatt cttgtagaga tattacttgt ccttccaggc
181 tgttctttct gtagctccct tgttttcttt ttgtgatcat gttgcagatg gctgggcagt
241 gctcccaaaa tgaatatttt gacagtttgt tgcatgcttg catacettgt caacttcgat
301 gttcttctaa tactcctcct ctaacatgtc agcgttattg taatgcaagt gtgaccaatt
361 cagtgaaagg aacgaatgcg attctctgga cctgtttggg actgagctta ataatttctt
421 tggcagtttt cgtgctaatg tttttgctaa ggaagataaa ctctgaacca ttaaaggacg
481 agtttaaaaa cacaggatca ggtctcctgg gcatggctaa cattgacctg gaaaagagca
541 ggactggtga tgaaattatt cttccgagag gcctcgagta cacggtggaa gaatgcacct
601 gtgaagactg catcaagagc aaaccgaagg tcgactctga ccattgcttt ccactcccag
661 ctatggagga aggcgcaacc attcttgtca ccacgaaaac gaatgactat tgcaagagcc
721 tgccagctgc tttgagtgct acggagatag agaaatcaat ttctgctagg taattaacca
781 tttcgactcg agcagtgcca ctttaaaaat cttttgtcag aatagatgat gtgtcagatc
841 tctttaggat gactgtattt ttcagttgcc gatacagctt tttgtcctct aactgtggaa
901 actctttatg ttagatatat ttctctaggt tactgttggg agcttaatgg tagaaacttc
961 cttggtttca tgattaaact cttttttttc ctga
```

SEQ ID NO: 22 Human BCMA Amino Acid Sequence (NP_001183.2)

```
  1 mlqmagqcsq neyfdsllha cipcqlrcss ntppltcqry cnasvtnsvk gtnailwtcl
 61 glsliislav fvlmfllrki nseplkdefk ntgsgllgma nidleksrtg deillprgle
121 ytveectced cikskpkvds dhcfplpame egatilvttk tndyckslpa alsateleks
181 isar
```

SEQ ID NO: 23 Mouse BCMA cDNA Sequence (NM_011608.1, CDS region from position 145-702)

```
  1 cacaatacct gtggccctct taagagcagc agggtctttc tttccgcctg acttcctgtc
 61 cacagggaac tcccacagag aatctgctgt tcttcctcga ttttctgtcc actcttcccg
121 tttctttcag tgatccagtc cctcatggcg caacagtgtt tccacagtga atattttgac
181 agtctgctgc atgcttgcaa accgtgtcac ttgcgatgtt ccaaccctcc tgcaacctgt
241 cagccttact gtgatccaag cgtgaccagt tcagtgaaag ggacgtacac ggtgctctgg
301 atcttcttgg ggctgacctt ggtcctctct ttggcacttt tcacaatctc attcttgctg
361 aggaagatga accccgaggc cctgaaggac gagcctcaaa gcccaggtca gcttgacgga
421 tcggctcagc tggacaaggc cgacaccgag ctgactagga tcagggctgg tgacgacagg
481 atctttcccc gaagcctgga gtatacagtg gaagagtgca cctgtgagga ctgtgtcaag
541 agcaaaccca agggggattc tgaccatttc ttcccgcttc cagccatgga ggagggggca
601 accattcttg tcaccacaaa aacgggtgac tacggcaagt caagtgtgcc aactgcttg
661 caaagtgtca tggggatgga gaagccaact cacactagat aatgagcttc ctaactggtg
721 tgaagctgct ttgagaacct tctgtcagga gagctggtgt tttagatgtc gttaggatga
781 ccgtttacca accaagaata cagtttttg to
```

SEQ ID NO: 24 Mouse BCMA Amino Acid Sequence (NP_035738.1)

```
  1 maqqcfhsey fdsllhackp chlrcsnppa tcqpycdpsv tssvkgtytv lwiflgltlv
 61 lslalftisf llrkmnpeal kdepgspgql dgsaqldkad teltriragd drifprsley
```

TABLE 1-continued

```
121 tveectcedc vkskpkgdsd hffplpamee gatilvttkt gdygkssvpt alqsvmgmek
181 pthtr
```

Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.

Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

Included in Table 1 are interactions between APRIL and its receptor TACI; between APRIL and its receptor BCMA; and between APRIL and its receptors, TACI and BCMA, as well as any known APRIL, TACI, and BCMA nucleic acid and polypeptide sequences and variants thereof as described herein.

II. Subjects

In one embodiment, the subject has a condition that would benefit from upregulation or downregulation of an immune response. The subject can be treated with at least one APRIL/TACI interaction modulator, either alone or in combination with a modulator of the STING pathway and/or an immunotherapy, such as an immune checkpoint inhibition therapy. The subject can be a mammal (e.g., mouse, rat, primate, non-human mammal, domestic animal such as dog, cat, cow, horse), and is preferably a human. The term "subject" refers to any healthy animal, mammal or human, or any animal, mammal or human afflicted with an immune disorder. The term "subject" is interchangeable with "patient."

In another embodiment of the methods of the present invention, the subject has not undergone treatment, such as chemotherapy, radiation therapy, targeted therapy, and/or immunomodulatory therapy (e.g., at least one APRIL/TACI interaction modulator, either alone or in combination with a modulator of the STING pathway and/or an immunotherapy therapy, such as an immune checkpoint inhibition therapy). In still another embodiment, the subject has undergone treatment, such as chemotherapy, radiation therapy, targeted therapy, and/or immunomodulatory therapy (e.g., at least one APRIL/TACI interaction modulator, either alone or in combination with a modulator of the STING pathway and/or an immunotherapy, such as an immune checkpoint inhibition therapy). In yet another embodiment, the subject is immunocompetent or immune-incompetent. "Immunocompetent" subjects are those subjects comprising immune cells and immune function required to establish a normal or desired immune response following exposure to an antigen. "Immuno-incompetent" subjects are those subjects lacking one or more immune cell types or lacking an immune function thereof to establish a normal or desired level of at least one immune response following exposure to an antigen. Immuno-incompetent subjects are more susceptible to opportunistic infections, for example viral, fungal, protozoal, or bacterial infections, prion diseases, and certain neoplasms. "Immunodeficient" subjects are subjects in which no native host immune response may be mounted, such as is the case with severe combined immunodeficiency (SCID) mice. "Immunocompromised" subjects have at least one substantially reduced immunological function relative to immunocompetent subjects. In either case, reduction in or absence of immunological function and/or cell types can arise from many different and well-known manners. For example, hematopoietic stem cells (HSCs) that give rise to all immune cells are any project thereof can be negatively affected in development, function, differentiation, survival, and the like. Immuno-incompetent subjects can be generated in many different ways well-known in the art. They can result from modulating the function and/or number of various parameters in numerous combinations. For example, immune cell populations can be targeted for modulation that are resting, mitotic, terminally differentiated, post-mitotic, unactivated, activated, and the like, in order to effect a desired immune-incompetency. "Resting" cells refer to a non-cycling cell in a non-replicative state. Although resting cells may have the ability to replicate and divide upon activation, they are quiescent since they are non-cycling. Thus, "resting" cells are not simply manipulated immune cells that have been stimulated to divide and then engineered to revert to a quiescent, non-dividing phase. Resting cells can be "naïve," which means that they are immune cells that have differentiated in bone marrow, successfully undergone positive and negative selection in the thymus, and are mature, but have not been activated and are not memory cells. Naïve T cells are commonly characterized by the surface expression of L-selectin (CD62L); the absence of the activation markers, CD25, CD44, or CD69; and the absence of memory CD45RO isoform. They also express functional IL-7 receptors, consisting of subunits IL-7 receptor-α, CD127, and common-γ chain, CD132. In the naive state, T cells are thought to be quiescent and non-dividing, requiring the common-gamma chain cytokines IL-7 and IL-15 for homeostatic survival mechanisms. By contrast, activated T cells express or up-regulate expression of surface markers, CD25, CD44, $CD62L^{low}$, and CD69 and may further differentiate into memory T cells. Naïve B cells have not been exposed to antigen since they would either become a memory B cell or a plasma cell that secretes antibodies. In one embodiment, a resting cell becomes "activated" when it is triggered to enter into a state of reproduction or doubling and may include a cell entering the cell cycle, cell division, or mitosis. In another embodiment, a resting cell may also become "activated" when it encounters an external signal, such as an antigen or a cytokine, that initiates the activity of terminally differentiated, mature immunological cells to generate an immune response (e.g., T cell or B cell function).

In some embodiments, the subject is in need of an upregulated immune response, such as by reducing Tregs/Bregs number and/or inhibitory immune activity to remove inhibition of immune responses. In some embodiments, the subject is in need of a downregulated immune response, such as by increasing Tregs/Bregs number and/or inhibitory immune activity to promote inhibition of immune responses. Methods for upregulating and downregulating immune responses according to the present invention are described below.

The methods of the present invention can be used to determine the responsiveness to therapy (e.g., at least one APRIL/TACI interaction modulator, either alone or in combination with a modulator of the STING pathway and/or an immunotherapy, such as an immune checkpoint inhibition therapy) of many different disorders in subjects such as those described above.

The subjects and characteristics thereof useful according to the present invention also apply to cells used according to the present invention, such as cells obtained from said subject and/or cells having properties of those from a subject, such as cancer cells, contacted with at least one APRIL/TACI interaction modulator.

III. Sample Collection, Preparation and Separation

In some embodiments, biomarker presence, absence, amount, and/or activity measurement(s) in a sample from a subject, such as baseline Treg/Breg numbers, Treg ratios, Breg ratios, biomarker expression level, cytokine expression, and the like, is compared to a pre-determined control (standard) sample. The sample from the subject is typically from a diseased tissue, such as cancer cells or tissues, but can be any tissue of interest, such as serum or other bodily sample described herein. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples, such as the normal copy number, amount, or activity of a biomarker in the cell or tissue type of a member of the same species as from which the test sample was obtained or a non-diseased cell or tissue from the subject from which the test samples was obtained. As described herein, a "pre-determined" biomarker amount and/or activity measurement(s) may be a biomarker amount and/or activity measurement(s) used to, by way of example only, evaluate a subject that may be selected for treatment, evaluate a response to an immunomodulatory therapy (e.g., at least one APRIL/TACI interaction modulator, either alone or in combination with a modulator of the STING pathway and/or an immunotherapy, such as an immune checkpoint inhibition therapy), and/or evaluate a response to a combination immunomodulatory therapy (e.g., at least one APRIL/TACI interaction modulator, either alone or in combination with a modulator of the STING pathway and/or an immunotherapy, such as an immune checkpoint inhibition therapy). A pre-determined biomarker amount and/or activity measurement(s) may be determined in populations of patients with or without a condition of interest, such as cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., biomarker expression normalized to the expression of a housekeeping gene, or gene expression at various time points).

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.5 fold, about 1.0 fold, about 1.5 fold, about 2.0 fold, about 2.5 fold, about 3.0 fold, about 3.5 fold, about 4.0 fold, about 4.5 fold, or about 5.0 fold or greater. In some embodiments, the fold change is less than about 1, less than about 5, less than about 10, less than about 20, less than about 30, less than about 40, or less than about 50. In other embodiments, the fold change in biomarker amount and/or activity measurement(s) compared to a predetermined level is more than about 1, more than about 5, more than about 10, more than about 20, more than about 30, more than about 40, or more than about 50.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.).

Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids that encode a biomarker polypeptide or a portion of such a polypeptide, such as APRIL, TACI, BCMA, cytokines like IL-10, and the like. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, NY, 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically, the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the present invention, e.g., complementary to the coding strand of a double-stranded cDNA molecule corresponding to a marker of the present invention or complementary to an mRNA sequence corresponding to a marker of the present invention. Accordingly, an antisense nucleic acid molecule of the present invention can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the present invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the present invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the present invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Nat. Acad. Sci. USA* 86:6553-6556; Lemaitre et al., 1987, *Proc. Nat. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly, such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Nat. Acad. Sci. USA* 87:2264-2268, modified as in Karlin and Altschul (1993) *Proc. Nat. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See the National Center for Biotechnology Information (NCBI) website at ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

Useful fusion proteins include GST fusion proteins or Fc domain fusion protein in which a polypeptide corresponding to a marker of the present invention is fused to the carboxyl terminus of GST sequences, or an Fc domain, respectively. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the present invention (Arkin and Yourvan, 1992, *Proc. Nat. Acad. Sci. USA* 89:7811-7815; Delgrave et al., 1993, *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, CA (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, MA) and pRIT5 (Pharmacia, Piscataway, NJ) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, *In Gene Expression Technology: Methods in Enzymology* vol. 185, Academic Press, San Diego, CA, 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, *In Gene Expression Technology: Methods in Enzymology* vol. 185, Academic Press, San Diego, CA, 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the present invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, CA), and pPicZ (Invitrogen Corp, San Diego, CA).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids, Polypeptides, and Cells

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number and/or Genomic Nucleic Acid Mutations

Methods of evaluating the copy number and/or genomic nucleic acid status (e.g., mutations) of a biomarker nucleic acid are well-known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid.

Alternatively, other methods well-known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well-known in the art (see, e.g., U.S. Pat. Nos. 6,335,167; 6,197,501; 5,830,645; and 5,665,549 and Albertson (1984) *EMBO J* 3: 1227-1234; Pinkel (1988) *Proc. Nat. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR)). In a quantitative amplification, the amount of amplification product will be proportional to the amount of template in the original sample. Comparison to appropriate controls, e.g. healthy tissue, provides a measure of the copy number.

Methods of "quantitative" amplification are well-known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Biomarker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, NY).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well-known in the art (see, e.g., U.S. Pat. Nos. 6,186,796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{15}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well-known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to an immunomodulatory therapy (e.g., APRIL/TACI interaction modulator therapy). Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$ M, $10^{-9}$ M, $10^{-10}$ M, $10^{-11}$ M, or $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify sequences or agents that affect translation of iron-sulfur cluster biosynthesis-related genes.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Nat. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Nat. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Nat. Acad. Sci USA* 88:189). In such cases, ligation will occur only if there is a perfect match at the 3' end of the 5' sequence making it possible to detect the presence of a known mutation at a specific site by looking for the presence or absence of amplification.

e, Methods for Detection of Cell Biomarkers

Cells can be analyzed according to well-known methods in the art. For example, in one embodiment, fluorescence activated cell sorting (FACS), also referred to as flow cytometry, is used to sort and analyze the different cell populations. Cells having a cellular marker or other specific marker of interest are tagged with an antibody, or typically a mixture of antibodies, that bind the cellular markers. Each antibody directed to a different marker is conjugated to a detectable molecule, particularly a fluorescent dye that may be distinguished from other fluorescent dyes coupled to other antibodies. A stream of tagged or "stained" cells is passed through a light source that excites the fluorochrome and the emission spectrum from the cells detected to determine the presence of a particular labeled antibody. By concurrent detection of different fluorochromes, also referred to in the art as multicolor fluorescence cell sorting, cells displaying different sets of cell markers may be identified and isolated from other cells in the population. Other FACS parameters, including, by way of example and not limitation, side scatter (SSC), forward scatter (FSC), and vital dye staining (e.g., with propidium iodide) allow selection of cells based on size and viability. FACS sorting and analysis of HSC and related lineage cells is well-known in the art and described in, for example, U.S. Pat. Nos. 5,137,809; 5,750,397; 5,840,580; 6,465,249; Manz et al. (202) *Proc. Natl. Acad. Sci. U.S.A.* 99:11872-11877; and Akashi et al. (200) *Nature* 404:193-197. General guidance on fluorescence activated cell sorting is described in, for example, Shapiro (2003) *Practical Flow Cytometry,* 4th Ed., Wiley-Liss (2003) and Ormerod (2000) *Flow Cytometry: A Practical Approach,* 3rd Ed., Oxford University Press.

Another method of isolating useful cell populations involves a solid or insoluble substrate to which is bound antibodies or ligands that interact with specific cell surface markers. In immunoadsorption techniques, cells are contacted with the substrate (e.g., column of beads, flasks, magnetic particles, etc.) containing the antibodies and any unbound cells removed. Immunoadsorption techniques may be scaled up to deal directly with the large numbers of cells in a clinical harvest. Suitable substrates include, by way of example and not limitation, plastic, cellulose, dextran, polyacrylamide, agarose, and others known in the art (e.g., Pharmacia Sepharose 6 MB macrobeads). When a solid substrate comprising magnetic or paramagnetic beads is used, cells bound to the beads may be readily isolated by a magnetic separator (see, e.g., Kato and Radbruch (1993) *Cytometry* 14:384-92). Affinity chromatographic cell separations typically involve passing a suspension of cells over a support bearing a selective ligand immobilized to its surface. The ligand interacts with its specific target molecule on the cell and is captured on the matrix. The bound cell is released by the addition of an elution agent to the running buffer of the column and the free cell is washed through the column and harvested as a homogeneous population. As apparent to the skilled artisan, adsorption techniques are not limited to those employing specific antibodies, and may use nonspecific adsorption. For example, adsorption to silica is a simple procedure for removing phagocytes from cell preparations.

FACS and most batch wise immunoadsorption techniques may be adapted to both positive and negative selection procedures (see, e.g., U.S. Pat. No. 5,877,299). In positive selection, the desired cells are labeled with antibodies and removed away from the remaining unlabeled/unwanted cells. In negative selection, the unwanted cells are labeled and removed. Another type of negative selection that may be employed is use of antibody/complement treatment or immunotoxins to remove unwanted cells.

It is to be understood that the purification or isolation of cells also includes combinations of the methods described above. A typical combination may comprise an initial procedure that is effective in removing the bulk of unwanted cells and cellular material, for example leukopheresis. A second step may include isolation of cells expressing a marker common to one or more of the progenitor cell populations by immunoadsorption on antibodies bound to a substrate. An additional step providing higher resolution of different cell types, such as FACS sorting with antibodies to a set of specific cellular markers, may be used to obtain substantially pure populations of the desired cells.

3. Immunomodulatory Therapies

Immunomodulatory therapies, (e.g., at least one APRL/TACI interaction modulator, either alone or in combination with a modulator of the STING pathway and/or an immunotherapy, such as an immune checkpoint inhibition therapy) for use in vitro, ex vivo, and/or in vivo in a subject are provided herein. In one embodiment, such therapy (e.g., at least one APRIL/TACI interaction modulator, either alone or in combination with a modulator of the STING pathway and/or an immunotherapy, such as an immune checkpoint inhibition therapy) or combinations of therapies (e.g., further comprising a vaccine, chemotherapy, radiation, epigenetic modifiers, targeted therapy, and the like) can be administered to a desired subject or once a subject is indicated as being a likely responder to therapy. In another embodiment, such therapy or therapies can be avoided once a subject is indicated as not being a likely responder to the therapy or therapies and an alternative treatment regimen can be administered.

As described further below, immune responses can be upregulated in vitro, ex vivo, and/or in vivo. An exemplary ex vivo approach, for instance, involves removing immune cells from the patient, contacting immune cells in vitro with an agent described herein, and reintroducing the in vitro modulated immune cells into the patient.

In some embodiments, particular combination therapies are also contemplated and can comprise, for example, one or more chemotherapeutic agents and radiation, one or more chemotherapeutic agents and a modulator of the STING pathway and/or immunotherapy, or one or more chemotherapeutic agents, radiation and chemotherapy, each combination of which can be with or a therapy described herein (e.g., at least one APRIL/TACI interaction modulator, either alone or in combination with a modulator of the STING pathway and/or an immunotherapy, such as an immune checkpoint inhibition therapy). For example, it may be desirable to further administer other agents that upregulate immune responses, for example, forms of other B7 family members that transduce signals via costimulatory receptors, in order to further augment the immune response. Such additional agents and therapies are described further below. In addition, it is to be understood that a combination having more than one agent can be administered as a combined single composition or administered separately (simultaneously and/or sequentially). For example, at least one agent can be preadministered to achieve a certain effect (e.g., increasing MHC expression, reducing Tregs, etc.) before subsequent administration of a combination of the at least one agent and one or more additional agents or therapies that upregulates an immune response.

Agents that upregulate an immune response can be used prophylactically in vaccines against various polypeptides (e.g., polypeptides derived from pathogens). Immunity against a pathogen (e.g., a virus) can be induced by vaccinating with a viral protein along with an agent that upregulates an immune response, in an appropriate adjuvant.

In another embodiment, upregulation or enhancement of an immune response function, as described herein, is useful in the induction of tumor immunity.

In another embodiment, the immune response can be stimulated by the methods described herein, such that preexisting tolerance, clonal deletion, and/or exhaustion (e.g., T cell exhaustion) is overcome. For example, immune responses against antigens to which a subject cannot mount a significant immune response, e.g., to an autologous antigen, such as a tumor specific antigens can be induced by administering appropriate agents described herein that upregulate the immune response. In one embodiment, an autologous antigen, such as a tumor-specific antigen, can be coadministered. In another embodiment, the subject agents can be used as adjuvants to boost responses to foreign antigens in the process of active immunization.

In one embodiment, immune cells are obtained from a subject and cultured ex vivo in the presence of an agent as described herein, to expand the population of immune cells and/or to enhance immune cell activation. In a further embodiment the immune cells are then administered to a subject. Immune cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

In still another embodiment, agents described herein useful for upregulating immune responses can further be linked, or operatively attached, to toxins using techniques that are known in the art, e.g., crosslinking or via recombinant DNA techniques. Such agents can result in cellular destruction of desired cells. In one embodiment, a toxin can be conjugated to an antibody, such as a bispecific antibody. Such antibodies are useful for targeting a specific cell population, e.g., using a marker found only on a certain type of cell. The preparation of immunotoxins is, in general, well-known in the art (see, e.g., U.S. Pat. No. 4,340,535, and EP 44167). Numerous types of disulfide-bond containing linkers are known which can successfully be employed to conjugate the toxin moiety with a polypeptide. In one embodiment, linkers that contain a disulfide bond that is sterically "hindered" are preferred, due to their greater stability in vivo, thus preventing release of the toxin moiety prior to binding at the site of action. A wide variety of toxins are known that may be conjugated to polypeptides or antibodies of the present invention. Examples include: numerous useful plant-, fungus- or even bacteria-derived toxins, which, by way of example, include various A chain toxins, particularly ricin A chain, ribosome inactivating proteins such as saporin or gelonin, α-sarcin, aspergillin, restrictocin, ribonucleases, such as placental ribonuclease, angiogenic, diphtheria toxin, and *Pseudomonas* exotoxin, etc. A preferred toxin moiety for use in connection with the present invention is toxin A chain which has been treated to modify or remove carbohydrate residues, deglycosylated A chain. (U.S. Pat. No. 5,776,427). Infusion of one or a combination of such cytotoxic agents, (e.g., ricin fusions) into a patient may result in the death of immune cells.

In particular, APRIL/TACI interaction modulators and exemplary agents useful for inhibiting the APRIL/TACI interaction, or other biomarkers described herein, have been described above.

Other immunomodulatory therapies useful according to the methods of the present invention are also well-known in the art.

The term "targeted therapy" refers to administration of agents that selectively interact with a chosen biomolecule to thereby treat cancer, such as an immunotherapy. For example, bevacizumab (Avastin®) is a humanized monoclonal antibody that targets vascular endothelial growth factor (see, for example, U.S. Pat. Publ. 2013/0121999, WO 2013/083499, and Presta et al. (1997) *Cancer Res.* 57:4593-4599) to inhibit angiogenesis accompanying tumor growth. In some cases, targeted therapy can be a form of immunotherapy depending on whether the target regulates immunomodulatory function. In another example, targeted therapy regarding the inhibition of immune checkpoint inhibitor is useful in combination with the methods of the present invention. The term "immune checkpoint inhibitor" means a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, LT-2, ILT-4, TIGIT, IDO1, IDO2, and A2aR (see, for example, WO 2012/177624). Inhibition of one or more immune checkpoint inhibitors can block or otherwise neutralize inhibitory signaling to thereby upregulate an immune response in order to more efficaciously treat cancer.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

Moreover, certain immunotherapies can be used to promote immune responses. Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation and/or progression of activities that promote immune responses to thereby inhibit immune responses. For example, such agents can be used to counteract that immune promoting responses described above and in the sections below.

In one embodiment, immunotherapy comprises adoptive cell-based immunotherapies. Well-known adoptive cell-based immunotherapeutic modalities, including, without limitation, irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, such as expressing cytokines like GM-CSF, and/or to express tumor-associated antigen (TAA) antigens, such as Mage-1, gp-100, patient-specific neoantigen vaccines, and the like.

In another embodiment, immunotherapy comprises non-cell-based immunotherapies. In one embodiment, compositions comprising antigens with or without vaccine-enhancing adjuvants are used. Such compositions exist in many well-known forms, such as peptide compositions, oncolytic viruses, recombinant antigen comprising fusion proteins, and the like. In still another embodiment, immunomodulatory interleukins, such as IL-2, IL-6, IL-7, IL-12, IL-17, IL-23, and the like, as well as modulators thereof (e.g., blocking antibodies or more potent or longer lasting forms) are used. In yet another embodiment, immunomodulatory cytokines, such as interferons, G-CSF, imiquimod, TNFalpha, and the like, as well as modulators thereof (e.g., blocking antibodies or more potent or longer lasting forms) are used. In another embodiment, immunomodulatory chemokines, such as CCL3, CCL26, and CXCL7, and the like, as well as modulators thereof (e.g., blocking antibodies or more potent or longer lasting forms) are used. In another embodiment, immunomodulatory molecules targeting immunosuppression, such as STAT3 signaling modulators, NFkappaB signaling modulators, and immune checkpoint modulators, are used. The terms "immune checkpoint" and "anti-immune checkpoint therapy" are described above.

The term "untargeted therapy" refers to administration of agents that do not selectively interact with a chosen biomolecule yet treat cancer. Representative examples of untargeted therapies include, without limitation, chemotherapy, gene therapy, and radiation therapy.

For example, nutritional supplements that enhance immune responses, such as vitamin A, vitamin E, vitamin C, and the like, are well-known in the art (see, for example, U.S. Pat. Nos. 4,981,844 and 5,230,902 and PCT Publ. No. WO 2004/004483) can be used in the methods described herein.

Similarly, agents and therapies other than immunotherapy or in combination thereof can be used to stimulate an immune response to thereby treat a condition that would benefit therefrom. For example, chemotherapy, radiation, epigenetic modifiers (e.g., histone deacetylase (HDAC) modifiers, methylation modifiers, phosphorylation modifiers, and the like), and the like are well-known in the art.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiment, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of beta-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Verteporfin (BPD-MA), phthalocyanine, photosensitizer Pc4, demethoxy-hypocrellin A; and 2BA-2-DMHA.

In still another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin (cyclosporin), pimecrolimus, abetimus, gusperimus, ridaforolimus, everolimus, temsirolimus, zotarolimus, etc.), hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an IMPDH inhibitor, mycophenolic acid, myriocin, fingolimod, an NF-xB inhibitor, raloxifene, drotrecogin alfa, denosumab, an NF-xB signaling cascade inhibitor, disulfiram, olmesartan, dithiocarbamate, a proteasome inhibitor, bortezomib, MG132, Prol, NPI-0052, curcumin, genistein, resveratrol, parthenolide, thalidomide, lenalidomide, flavopiridol, non-steroidal anti-inflammatory drugs (NSAIDs), arsenic trioxide, dehydroxymethylepoxyquinomycin (DHMEQ), I3C (indole-3-carbinol)/DIM (di-iodomethane) (13C/DIM), Bay 11-7082, luteolin, cell permeable peptide SN-50, IKBa.-super repressor overexpression, NFKB decoy oligodeoxynucleotide (ODN), or a derivative or analog of any thereof, are used. In yet another embodiment, immunomodulatory antibodies or protein are used. For example, antibodies that bind to CD40, Toll-like receptor (TLR), OX-40, GITR, CD27, or to 4-1BB, T-cell bispecific antibodies, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CD11 a antibody, efalizumab, an anti-CD18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA-4-Ig fusion protein, abatacept, belatacept, an anti-CTLA-4 antibody, ipilimumab, tremelimumab, an anti-eotaxin 1 antibody, bertilimumab, an anti-a4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an IL-1 receptor antagonist, anakinra, an anti-IL-5 antibody, mepolizumab, an IgE inhibitor, omalizumab, talizumab, an IL12 inhibitor, an IL23 inhibitor, ustekinumab, and the like.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium: yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with immunomodulatory therapy (e.g., at least one APRIL/TACI interaction modulator, either alone or in combination with a modulator of the STING pathway and/or an immunotherapy, such as an immune checkpoint inhibition therapy) may vary according to the particular APRIL/TACI interaction modulator or combination therapy thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

Any means for the introduction of a polynucleotide into mammals, human or non-human, or cells thereof may be adapted to the practice of this invention for the delivery of the various constructs of the present invention into the intended recipient. In one embodiment of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well-known and any can be selected for a particular application. In one embodiment of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl.

Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

4. Clinical Efficacy

Clinical efficacy can be measured by any method known in the art. For example, the response to a therapy described herein (e.g., at least one APRIL/TACI interaction modulator, either alone or in combination with a modulator of the STING pathway and/or an immunotherapy, such as an immune checkpoint inhibition therapy), relates to an immune response, such as a response of a cancer, e.g., a tumor, to the therapy, preferably to a change in tumor mass and/or volume after initiation of neoadjuvant or adjuvant chemotherapy. For example, tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) Breast (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular CDK4 and/or CDK6 inhibitor therapeutic regimen is at least 25%, 30%, 35%, 40%, 45%, 50%, 55%, 60%, 65%, 70%, 75%, 80%, 85%, or more.

Additional criteria for evaluating a response to therapy (e.g., at least one APRIL/TACI interaction modulator, either alone or in combination with a modulator of the STING pathway and/or an immunotherapy, such as an immune checkpoint inhibition therapy) are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular APRIL/TACI interaction modulator therapeutic regimen can be administered to a population of subjects and the outcome can be correlated to biomarker measurements that were determined prior to administration of any therapy of interest (e.g., at least one APRIL/TACI interaction modulator, either alone or in combination with a modulator of the STING pathway and/or an immunotherapy, such as an immune checkpoint inhibition therapy). The outcome measurement may be pathologic response to therapy given in the neoadjuvant setting. Alternatively, outcome measures, such as overall survival and disease-free survival can be monitored over a period of time for subjects following therapy (e.g., at least one APRIL/TACI interaction modulator, either alone or in combination with a modulator of the STING pathway and/or an immunotherapy, such as an immune checkpoint inhibition therapy) for whom biomarker measurement values are known. In certain embodiments, the same doses of APRIL/TACI interaction modulator agents are administered to each subject. In related embodiments, the doses administered are standard doses known in the art for APRIL/TACI interaction modulator agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of therapy (e.g., at least one APRIL/TACI interaction modulator, either alone or in combination with a modulator of the STING pathway and/or an immunotherapy, such as an immune checkpoint inhibition therapy) can be determined using methods such as those described in the Examples section and description provided herein. For example, therapeutic responses in settings other than cancers, such as in infections, immune disorders, and the like, are provided herein and are useful as measures of therapeutic efficacy.

5. Further Uses and Methods of the Present Invention

The compositions described herein can be used in a variety of diagnostic, prognostic, and therapeutic applications regarding biomarkers described herein, such as those listed in Table 1. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment.

Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

a. Screening Methods

One aspect of the present invention relates to screening assays, including non-cell based assays. In one embodiment, the assays provide a method for identifying whether a disorder, such as cancer, is likely to respond to a therapy (e.g., at least one APRIL/TACI interaction modulator, either alone or in combination with a modulator of the STING pathway and/or an immunotherapy, such as an immune checkpoint inhibition therapy) and/or whether an agent can modulate the disorder, such as inhibit the growth of or kill a cancer cell that is unlikely to respond to the therapy (e.g., at least one APRL/TACI interaction modulator, either alone or in combination with a modulator of the STING pathway and/or an immunotherapy, such as an immune checkpoint inhibition therapy).

In one embodiment, the present invention relates to assays for screening test agents which bind to, or modulate the biological activity of, a biomarker described herein, such as at least one biomarker listed in Table 1. In one embodiment, a method for identifying such an agent entails determining the ability of the agent to modulate, e.g. inhibit, the biomarker described herein, such as at least one biomarker listed in Table 1.

In one embodiment, an assay is a cell-free or cell-based assay, comprising contacting a biomarker described herein, such as at least one biomarker listed in Table 1, with a test agent, and determining the ability of the test agent to modulate (e.g. inhibit) the enzymatic activity of the biomarker, such as by measuring direct binding of substrates or by measuring indirect parameters as described below.

In another embodiment, an assay is a cell-free or cell-based assay, comprising contacting a biomarker described herein, such as at least one biomarker listed in Table 1, with a test agent, and determining the ability of the test agent to modulate the ability of the biomarker to regulate APRIL/TACI INTERACTIONS and/or immune checkpoints, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies of the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and its natural binding partner can be accomplished by determining the ability of the test agent to modulate the activity of a polypeptide or other product that functions downstream or upstream of its position within the APRIL/TACI interaction pathway.

The present invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the presence, absence, amount, and/or activity level of a biomarker described herein, such as those listed in Table 1, in the context of a biological sample (e.g., blood, serum, cells, or tissue) to thereby determine whether an individual afflicted with a cancer is likely to respond to a therapy (e.g., at least one APRIL/TACI interaction modulator, either alone or in combination with a modulator of the STING pathway and/or an immunotherapy, such as an immune checkpoint inhibition therapy), such as in an original or recurrent cancer. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those listed in Table 1.

Another aspect of the present invention pertains to monitoring the influence of agents (e.g., drugs, compounds, and small nucleic acid-based molecules) on the expression or activity of a biomarker listed in Table 1. These and other agents are described in further detail in the following sections.

The ordinarily skilled artisan will also appreciate that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to a therapy (e.g., at least one APRIL/TACI interaction modulator, either alone or in combination with a modulator of the STING pathway and/or an immunotherapy, such as an immune checkpoint inhibition therapy). In some embodiments, the present invention is useful for classifying a sample (e.g., from a subject) as associated with or at risk for responding to or not responding to a therapy (e.g., at least one APRIL/TACI interaction modulator, either alone or in combination with a modulator of the STING pathway and/or an immunotherapy, such as an immune checkpoint inhibition therapy) using a statistical algorithm and/or empirical data (e.g., the amount or activity of a biomarker described herein, such as at least one biomarker listed in Table 1).

An exemplary method for detecting the amount or activity of a biomarker listed in Table 1, and thus useful for classifying whether a sample is likely or unlikely to respond to a therapy (e.g., at least one APRIL/TACI interaction modulator, either alone or in combination with a modulator of the STING pathway and/or an immunotherapy, such as an immune checkpoint inhibition therapy) involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. For example, the expression of TACI protein on Tregs/Bregs and/or the presence of APRIL ligand indicates that an APRIL/TACI interaction modulator would be likely to have a useful effect. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely immunomodulatory therapy (e.g., at least one APRIL/TACI interaction modulator, either alone or in combination with a modulator of the STING pathway and/or an immunotherapy, such as an immune checkpoint inhibition therapy) responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C & RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to a therapy (e.g., at least one APRL/TACI interaction modulator, either alone or in combination with a modulator of the STING pathway and/or an immunotherapy, such as an immune checkpoint inhibition therapy), a biological sample from the subject during remission, or a biological sample from the subject during treatment for developing a cancer progressing despite therapy (e.g., at least one APRIL/TACI interaction modulator, either alone or in combination with a modulator of the STING pathway and/or an immunotherapy, such as an immune checkpoint inhibition therapy).

d. Prognostic Assays

The diagnostic methods described herein can furthermore be utilized to identify subjects having or at risk of developing a disorder, such as cancer, that is likely or unlikely to be responsive to a therapy (e.g., at least one APRL/TACI interaction modulator, either alone or in combination with a modulator of the STING pathway and/or an immunotherapy, such as an immune checkpoint inhibition therapy). The assays described herein, such as the preceding diagnostic assays or the following assays, can be utilized to identify a subject having or at risk of developing a disorder associated with a misregulation of the amount or activity of at least one biomarker, such as those described in Table 1, such as in cancer. Alternatively, the prognostic assays can be utilized to identify a subject having or at risk for developing a disorder associated with a misregulation of the at least one biomarker, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

Another aspect of the present invention pertains to methods of modulating the expression or activity of one or more biomarkers described herein (e.g., those listed in Table 1, and the Examples, or fragments thereof) for therapeutic purposes. The biomarkers of the present invention have been demonstrated to be useful for identifying immunomodulatory interventions. Accordingly, the activity and/or expression of the biomarker, as well as the interaction between one or more biomarkers or a fragment thereof and its natural binding partner(s) or a fragment(s) thereof, can be modulated in order to modulate immune responses, such as in cancer.

Modulatory methods of the present invention involve contacting a cell with one or more modulators of biomarkers of the present invention, including one or more biomarkers of the present invention, including one or more biomarkers listed in Table 1, and the Examples, or a fragment thereof or agent, that modulates one or more of the activities of biomarker activity associated with the cell. An agent that modulates biomarker activity can be an agent as described herein, such as a nucleic acid or a polypeptide, a naturally-occurring binding partner of the biomarker (e.g., a soluble form), an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the present invention, including one or more biomarkers of the present invention, including one or more biomarkers listed in Table 1, and the Examples, or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 μg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers of the present invention, including one or more biomarkers listed in Table 1 and the Examples or a fragment thereof. Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan), as well as other forms, such as multivalent ligands, activating antibodies, and the like that promote the APRIL/TACI interaction. In another embodiment, the agent inhibits one or more biomarker activities. In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers of the present invention listed in Table 1 and the Examples or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well-known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular melanoma, being treated, the extent of the disease and other factors familiar to the physician of skill in the art and can be determined by the physician.

In some embodiments, the methods of the present invention can be used to increase Tregs/Bregs numbers and/or inhibitor immune activities and treat immune disorders. The functions of activated immune cells can be inhibited by down-regulating immune cell responses, by inducing specific anergy in immune cells, or both. For example, the methods of the present invention can be used to induce tolerance against specific antigens by co-administering an antigen with the therapeutic compositions of such methods. Tolerance can be induced to specific proteins. In one embodiment, immune responses to allergens (e.g., food allergens), or to foreign proteins to which an immune response is undesirable, can be inhibited. For example, patients that receive Factor VIII frequently generate antibodies against this clotting factor. Co-administration of recombinant factor VIII (or by physically linked to Factor VIII, e.g., by cross-linking) in the methods of the present invention can result in downmodulation of immune responses. In similar manners, reduced clonal deletion and/or increased exhaustion (e.g., T cell exhaustion) can be induced.

Downregulating immune responses is useful for treating a number of other "immune disorders" according to the present invention including, without limitation, situations of tissue, skin and other solid organ transplantation (e.g., kidney, liver, heart, and vascularized composite allotransplantation transplants), in hematopoietic stem cell transplantation rejection (e.g., graft-versus-host disease (GVHD)), in autoimmune diseases such as systemic lupus erythematosus, multiple sclerosis, allergy, a transplant, hypersensitivity response, in a disorder requiring increased CD4+ T cell production or function, in a disorder requiring improved vaccination efficiency, and in a disorder requiring increased regulatory T cell production or function. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of an agent described herein prior to or at the time of transplantation can promote the generation of an inhibitory signal. Moreover, inhibition may also be sufficient to energize the immune cells, thereby inducing tolerance in a subject. Induction of long-term tolerance avoids the necessity of repeated administration of these blocking reagents.

Downmodulation of immune responses are also useful in treating autoimmune disease, such as type 1 diabetes (T1D) and multiple sclerosis. Many autoimmune disorders are the result of inappropriate activation of immune cells that are reactive against self-tissue and which promote the production of cytokines and autoantibodies involved in the pathology of the diseases. Preventing the activation of autoreactive immune cells may reduce or eliminate disease symptoms. Administration of agents described herein are useful for preventing the generating of autoantibodies or cytokines which may be involved in the disease process. Additionally, the methods of the present invention can induce antigen-specific tolerance of autoreactive immune cells, which could lead to long-term relief from the disease. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see, e.g., Paul ed., *Fundamental Immunology*, Raven Press, New York, Third Edition 1993, chapter 30).

Inhibition of immune cell activation is also useful therapeutically in the treatment of allergy and allergic reactions, e.g., by inhibiting IgE production. Allergic reactions can be systemic or local in nature, depending on the route of entry of the allergen and the pattern of deposition of IgE on mast cells or basophils. Thus, inhibition of immune cell mediated allergic responses (e.g., to food) locally or systemically according to the methods of the present invention. In one embodiment, the allergy is allergic asthma.

Inhibition of immune cell activation may also be important therapeutically in parasitic and viral infections of immune cells. For example, in the acquired immune deficiency syndrome (AIDS), viral replication is stimulated by immune cell activation. Modulation of these interactions may result in inhibition of viral replication and thereby ameliorate the course of AIDS. Modulation of these interactions may also be useful in promoting the maintenance of pregnancy. Females at risk for spontaneous abortion (e.g., those who have previously had a spontaneous abortion or those who have had difficulty conceiving) because of immunologic rejection of the embryo or fetus can be treated with agents that modulate these interactions.

Downregulation of an immune response according to the methods of the present invention may also be useful in treating an autoimmune attack of autologous tissues. It is therefore within the scope of the present invention to modulate conditions exacerbated by autoimmune attack, such as autoimmune disorders, as well as conditions such as heart disease, myocardial infarction, and atherosclerosis.

In a preferred embodiment, the immune disorder is graft-versus-host-disease (e.g., chronic GVHD). For many patients with hematologic malignancies, allogeneic hematopoietic stem cell transplant (HSCT) offers the only opportunity for cure. Unfortunately, significant obstacles remain, most notably disease recurrence and GVHD. Over 40% of patients undergoing HSCT relapse while more than 50% will develop cGVHD, a debilitating condition with multi-system immune manifestations associated with a considerable morbidity and mortality (Kahl et al. (2007) *Blood* 110:2744-2748; Perez-Simon et al. (2008) *Biol. Blood Marrow Transplant.* 14:1163-1171). Although the incidence in the pediatric population is lower, cGVHD remains a leading cause of non-relapse morbidity and mortality following allogeneic HSCT for malignant disease, occurring in 20 to 50% of children surviving greater than 100 days post-HSCT (Baird et al. (2010) *Pediatr. Clin. North Am.* 57:297-322). Donor cell-mediated immune responses are responsible for GVL and GVHD reactions. Inadequate recognition and destruction of residual tumor cells by a newly engrafted donor immune system permits recurrence of a patient's malignancy, while uncontrolled reactions against host antigens lead to GVHD (Antin (1993) *Blood* 82:2273-2277; Ferrara et al. (2009) *Lancet* 373:1550-1561). Chronic GVHD pathogenesis involves inflammatory T- and B-cell responses to allogeneic (donor/recipient polymorphic) and autologous (donor/recipient non-polymorphic) antigens and it remains a common problem and major therapeutic challenge after allogeneic HSCT, and long-term survivors often experience impaired quality of life and increased late mortality (Subramaniam et al. (2007) *Leukemia* 21:853-859). The increasing use of mobilized peripheral blood progenitor cells rather than bone marrow as a source of stem cells for HCT has resulted in a clear increase in the incidence of cGVHD (Cutler et al. (2001) *J. Clin. Oncol.* 19:3685-3691; Lee et al. (2007) *Blood* 110:4576-4583). The incidence of cGVHD in pediatric patients is expected to rise as allogeneic HSCT is increasingly being performed for non-malignant indications such as sickle cell anemia, immunodeficiency and congenital metabolic diseases. In both adults and children, the inflammatory or fibrotic changes associated with cGVHD most commonly involve the skin, eyes, mouth, liver and respiratory tract. PD-1 expression and/or inhibition can be downregulated in advance of any adoptive cell therapy, such as stem cell therapy, organ transplantation, and the like.

By contrast, the present invention also provides methods for decreasing Tregs/Bregs numbers and/or inhibitor immune activities to upregulate immune responses, as described further above. Agents that upregulate immune responses can be in the form of enhancing an existing immune response or eliciting an initial immune response. Thus, enhancing an immune response using the subject compositions and methods is useful for treating cancer, but can also be useful for treating an infectious disease (e.g., bacteria, viruses, or parasites), asthma associated with impaired airway tolerance, a parasitic infection, and an immunosuppressive disease.

Exemplary infectious disorders include infection with a virus including, but not limited to, human immunodeficiency viruses (HIV), hepatitis C viruses (HCV), T-cell leukemia viruses, Epstein-Barr virus, cytomegalovirus, herpesviruses, varicella-zoster virus, measles, papovaviruses, hepatitis viruses, adenoviruses, parvoviruses, papillomaviruses, prions, and the like, as well as viral skin diseases, such as herpes or shingles, in which case such an agent can be delivered topically to the skin. Non-limiting examples of chronic conditions resulting from infection include hepatitis B (caused by hepatitis B virus (HBV)) and hepatitis C (caused by hepatitis C virus (HCV)) adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyoma virus BK, polyoma virus JC, measles virus, rubella virus, human immunodeficiency virus (HIV), human T cell leukemia virus I, and human T cell leukemia virus II. Parasitic persistent infections can arise as a result of infection by, for example, *Leishmania, Toxoplasma, Trypanosoma, Plasmodium, Schistosoma*, and *Encephalitozoon*. In addition, systemic viral diseases, such as influenza, the common cold, and encephalitis can be treated, such as by using by respiration-based administration, such as intranasal, pulmonary inhalation, lung deposition, and related routes well-known in the art. In certain embodiments, the subject has had surgery to remove cancerous or precancerous tissue, such as by blood compartment purification. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

Immune responses can also be enhanced in an infected patient through an ex vivo approach, for instance, by removing immune cells from the patient, contacting immune cells in vitro with an agent described herein and reintroducing the in vitro stimulated immune cells into the patient.

6. Pharmaceutical Compositions

In another aspect, the present invention provides pharmaceutically acceptable compositions which comprise a therapeutically-effective amount of an agent that modulates (e.g., increases or decreases) biomarker expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well-known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

Other embodiments of the present invention are described in the following Examples. The present invention is further illustrated by the following examples which should not be construed as further limiting.

EXAMPLES

Example 1: Materials and Methods for Examples 2-10 a. T cell purification and isolation

Human T Cell Enrichment Cocktail (RosetteSep™, STEMCELL) was used to purify T cells from PB of donors and MM patients. T cells were further separated into conventional T cells (Tcon, CD4+CD25−) and T regulatory cells (Treg, CD4+CD25+) by anti-CD25 microbeads (Miltenyi Biotec) and FACS sorting on CD25high population. The anergic and suppressive features of CD4+CD25+ regulatory T cells were further confirmed by their inhibition on Tcon proliferation stimulated with CD3/CD28 microbeads. Tregs were cultured in RPMI-1640 with 10% FBS and 5 ng/ml IL-2 (Sigma) unless otherwise mentioned.

b. Cell Lines and Primary Cells

All human MM cell lines were grown in RPMI-1640 with 10% FBS, 100 U/ml penicillin and 100 μg/ml streptomycin. Healthy donor and MM patient samples were obtained after informed consent was provided. Written informed consent was obtained in all cases according to the Declaration of Helsinki. Mononuclear cells (MC) were isolated from peripheral blood (PB) and bone marrow (BM) via density gradient centrifugation using Ficoll-Hypaque (GE Healthcare). CD14+ cells were purified from PBMCs using anti-CD14 microbeads (Miltenyi Biotec). Then the cells were stimulated with GM-CSF (20 ng/mL; R&D)/IL-4 (20 ng/mL; R&D) for DC differentiation or with M-CSF (25 ng/mL; Miltenyi Biotec)/RANKL (50 ng/mL; Miltenyi Biotec) for OC differentiation.

Primary CD138+ plasma cells were purified from BM aspirates using anti-CD138 microbeads (Miltenyi Biotec). Residual CD138− cells were cultured in RPMI-1640 with 10% FBS to generate BM stromal cells.

c. Real-Time Quantitative RT-PCR (qRT-PCR)

RNAs from indicated samples were extracted using RNeasy® Mini Kit or RNeasy® Micro Kit (Qiagen, Valencia, CA) and subject to SuperScript VILO cDNA Synthesis Kit (Thermo Fisher Scientific) to generate first strand cDNA. Gene expression was investigated by real-time qRT-PCR using TaqMan gene expression assay primer sets from Applied Biosystems (Thermo Fisher Scientific) and the Applied Biosystems 7300 Real-Time PCR System, with analysis using 7300 System SDS v1.4 Software. Gene expression was normalized using GAPDH and 18S.

d. Flow Cytometric Analysis and Cell Sorting

Immunofluorescence analysis was performed using BD FACSCanto™ II and BD LSRFortessa™ flow cytometer. Data were analyzed using FlowJo Version 8.6.6 (TreeStar Inc) and FACSDiva Version 5.0 acquisition/analysis software (BD Biosciences). Anti-CD3 (APC/Cy7, SK7), anti-CD8 (FITC, SK1), anti-CD8 (APC/Cy7, SK1), anti-FOXP3 (Alexa Fluor 647, 259D/C7), anti-CD15s (FITC, CSLEX1), and anti-CD4 (FITC, RPA-T4) were obtained from BD Biosciences. Anti-CD4 (Brilliant Violet 421, RPA-T4), anti-CD25 (PE, M-A251), anti-TACI (PE, 1A1), anti-TACI (PE/Cy7, 1A1), anti-CD38 (PE/Cy7, 1-1B-7), anti-IL-10 (FITC, JES3-9D7) and anti-IL-10 (PE/Cy7, JES3-9D7), and anti-TGFβ1 (PE, TW4-61-110) were obtained from BioLegend (San Diego, CA). The LIVE/DEAD Fixable Aqua Dead Cell Stain Kit (Invitrogen) was used to identify viable cells.

For Breg analysis, BMMCs from BM samples of NDMM were resuspended (1×106 cells/ml) in RPMI 1640 media containing 10 μg/ml lipopolysaccharides (LPS, *Escherichia coli* serotype 0111: B4; Sigma-Aldrich) for 1 d to assess whether TACI expression was changed on the cell membrane of three B cell subsets.

For intracellular cytokine staining, protein transport inhibitors (brefeldin A/BFA and Monensin) were added for 6 hours at 37° C. with 5% $CO_2$. The cells were then permeabilized, fixed and stained for anti-Foxp3 or -IL-10, -anti-TGFβ1 by following the instructions of the Cytofix/Cytoperm kit (BD).

e. Tcon Suppression Assay

Tcons were stained by CellTrace CFSE or Violet Cell Proliferation Kit (Invitrogen), and Tregs were stained by CellTrace Violet (CTV) Cell Proliferation Kit (Invitrogen). Tcons (50,000 cells/well) were cultured alone or with autologous Tregs in 96-well plates at various ratios in the presence of APRIL-containing media (400 ng/ml) or clones of antagonistic anti-APRIL mAbs. Tcons were then stimulated with anti-CD3/CD28 beads (Miltenyi Biotec) according to the manufacturer's recommendation. Proliferation (CFSE- or CTV-diluted fractions) of indicated cells was measured by FACS analysis.

f. Generation of iTregs in Ex Vivo Co-Cultures

MM cells, pretreated with mitomycin C (Sigma) to prevent their proliferation, were washed twice and then cocultured with CD3 T cells or Tcons (CD4+CD25−) in 96-well culture plates. 12 T cells or Tcons alone were used as controls. Recombinant human APRIL (200 ng/ml, unless specified) and/or antagonistic anti-APRIL mAbs (A1, clone 01A (Tai et al. (2016) *Blood* 127: 3225-3236; Guadagnoli et al. (2011) *Blood* 117: 6856-6865); A2, clone Aprily-1-1, Invitrogen) were added into cocultures for 4 or 7 d. Culture media was replenished on day 4. The cells were collected for FACS analysis to determine the frequency and phenotype of iTregs.

g. Proliferation Assay

Tcons or Tregs were cultured with or without APRIL (400 ng/ml) for 4 or 7 d followed by 18 h [$^3$H]-thymidine incorporation assays and CellTiter Luminescent Cell Viability (Promega) assays according to the manufacturer's recommendation.

h. CFSE-Dilution-Based Proliferation Assay

Tcons or Tregs were pre-stained by CellTrace CFSE or Violet (CTV) Cell Proliferation Kit (Invitrogen), and then plated in the presence or absence of anti-CD3/CD28 beads (Miltenyi Biotec) with or without APRIL and/or anti-APRIL mAbs. After 4 or 7 d, cells were collected and analyzed by FACS analysis.

i. Statistical Analysis

Experiments were done in triplicate and repeated >2 times. A representative experiment (mean+SD) was selected for figures, except when otherwise indicated. Comparisons between 2 groups were performed with Student's t-test. Multiple groups (>3) were analyzed by one-way ANOVA, and paired groups were analyzed by two-way ANOVA or Student t test. All statistical analyses were performed with GraphPad software (Prism Version 7.03, San Diego, CA, USA). A p value <0.05 was considered statistically significant.

Example 2: Modulating Regulatory T and B Cell Numbers and/or Inhibitory Immune Function The role of regulatory T cells (Tregs) in mediating immune responses has been studied in a variety of immunological contexts, such as the relationship between Treg function and CD38 levels (Feng et al. (2017) *Clin. Cancer Res.* 23:4290-4300). However, it has been challenging to identify genes and pathways that are selectively expressed by immune cell populations and modify such genes and pathways in order to selectively modulate immune cell numbers and/or immune activity of subsets of immune cell populations.

Figure 16A:
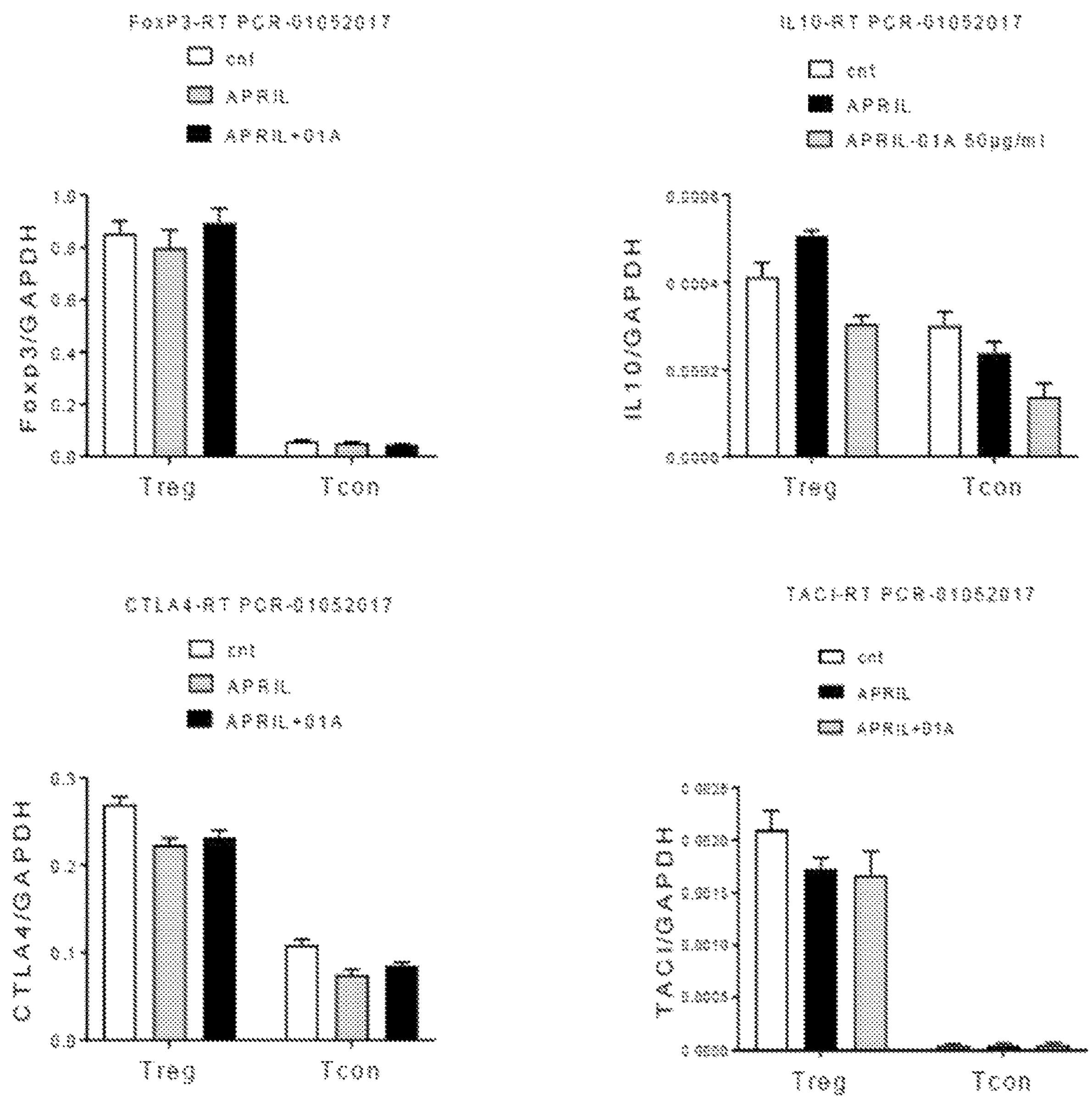
FIG. 16A shows that IL-10 is preferentially induced by APRIL in Tregs vs. Tcons and is associated with higher TACI in Treg vs. Tcons.

It has been determined herein that the interaction between APRIL and one of its receptors, TACI, modulates regulatory T cen B cell numbers and/or inhibitory immune and that modulating the APRIL/TACI interaction can modulate immune responses in a number of contexts (FIGS. 1-34). For example, TACI is significantly expressed on Tregs, such as $CD4^+CD25^{high}FoxP3^{high}$ Tregs, when compared with conventional T cells (Tcons), such as $CD4^+CD25^-$ T cells (FIGS. 13-14, and 33-34). The other APRIL receptor, which is known as BCMA, is not expressed on either subset of T cells. It has been further determined that that APRIL induces the expression of IL10 (FIGS. 15-16, and 20), an immune inhibitory protein (cytokine) that, for example, suppresses inflammatory reactions mediated by T cells, in Tregs but not in Tcons. This result further supports a suppressive role of APRIL on Tcons via Tregs-mediated secretion of immune inhibitory cytokines like IL-10. APRIL significantly induces anti-apoptotic genes BCL2 and Bcl-xL, cell cycle-promoting genes CCND1 and CCND2, as well as PD-L1 gene in TACI-expressing Tregs compared to Tcons (FIGS. 15-16).

Figure 23A:
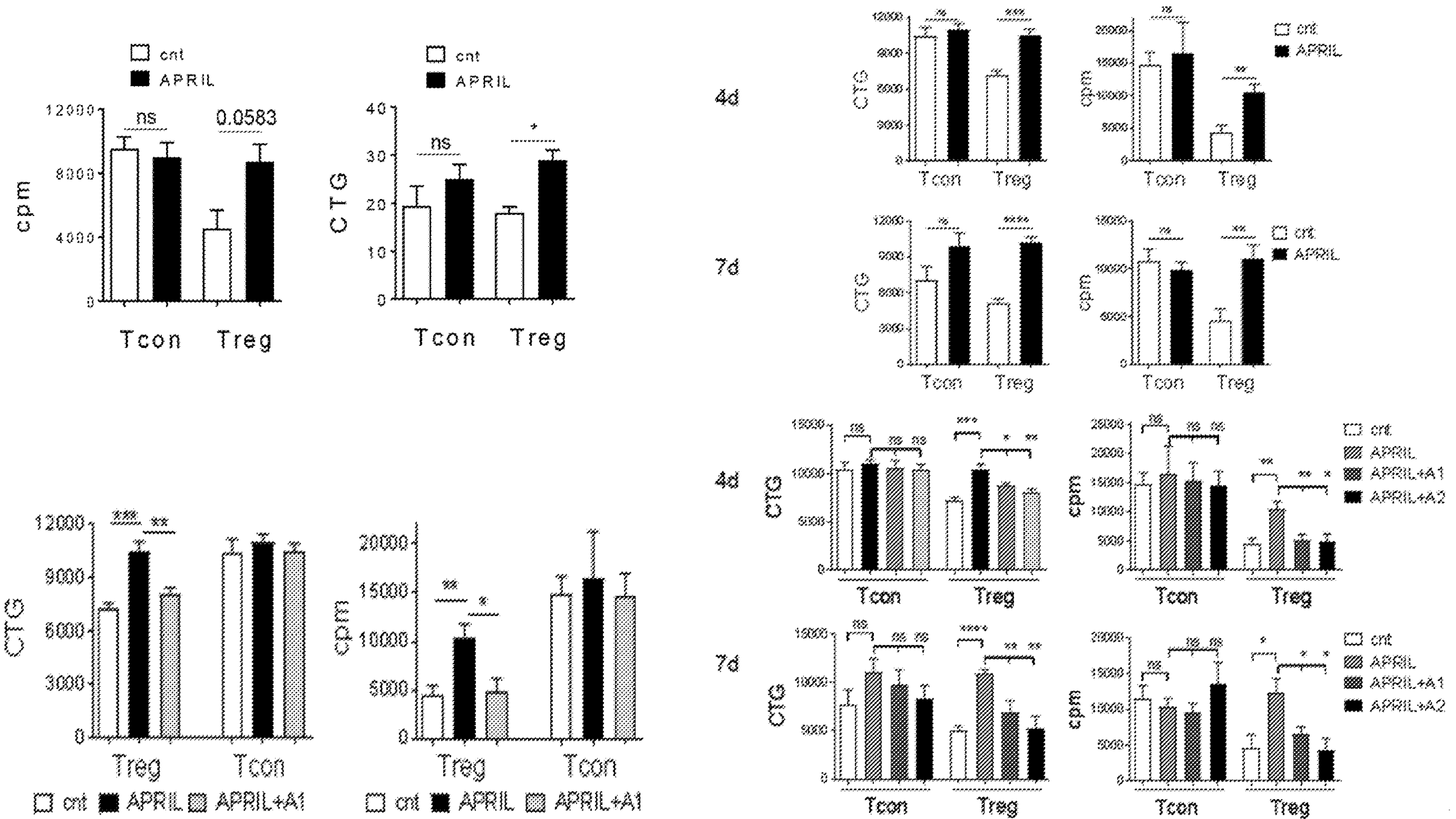
FIG. 23A shows that APRIL, via TACI, significantly protects Tregs vs matched Tcon. APRIL preferentially increases growth and viability of Tregs as compared to Tcons and is associated with higher TACI in Tregs as compared to Tcons, in the same individual. APRIL-dependent increase in growth and viability of Tregs is abrogated by an antagonistic anti-APRIL antibody. Purified Treg and Tcon cells from the same patient were incubated with recombinant human APRIL in media containing low dose IL-2 (5 ng/ml) with or without neutralizing anti-APRIL mAb (A1, clone 01A) followed by luminescence cell viability CellTiter-Glo (CTG) and [$^3$H] thymidine incorporation assays. For the time course analysis (right panels), Tcon and Treg subsets were freshly separated from normal donors. Purified Tregs and paired Tcons were incubated with APRIL (200 ng/ml) of for 4 days and 7 days followed by CTG-based viability and cpm-based proliferation assays. Neutralizing anti-APRIL mAbs (A1, A2) were added. * p<0.02,  p<0.005, * p<0.001, **** p<0.0001.
Figure 23A:
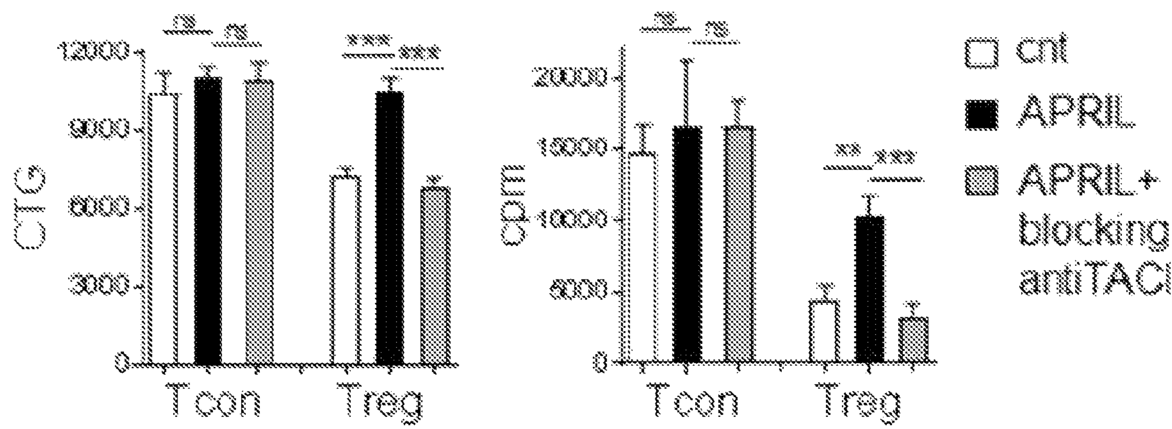
Figure 23B:
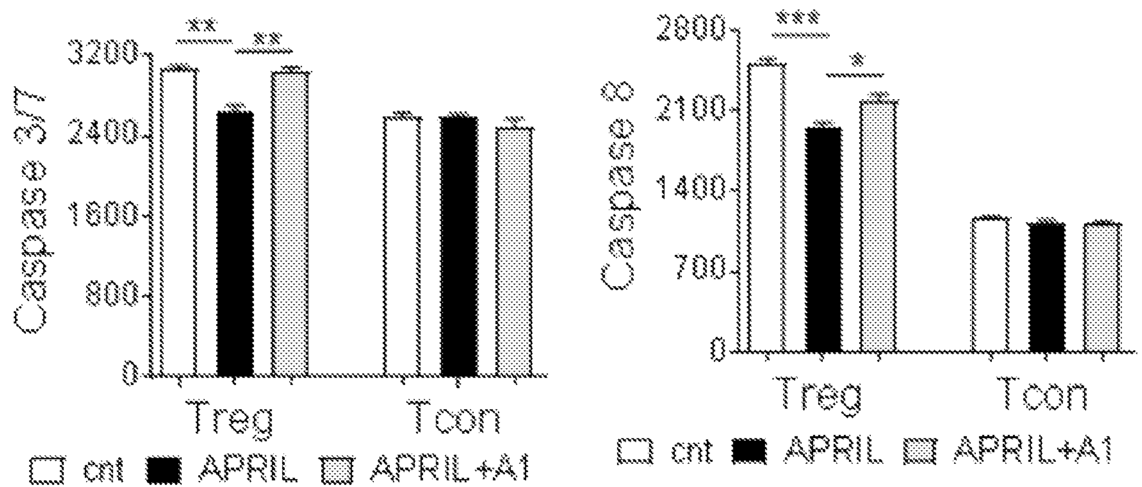
FIG. 23B shows that APRIL inhibits caspase 3/7 and caspase 8 activities in Tregs compared to autologous Tcons of MM patients, and such inhibition is abrogated by an antagonistic anti-APRIL antibody. Purified Treg and Tcon cells from the same patient were incubated with recombinant human APRIL in media containing low dose IL-2 (5 ng/ml) with or without neutralizing anti-APRIL mAb (A1, clone 01A) followed by the CTG-based caspase activity assay. * p<0.02,  p<0.005, *p<0.001, **** p<0.0001.
Figure 24A:
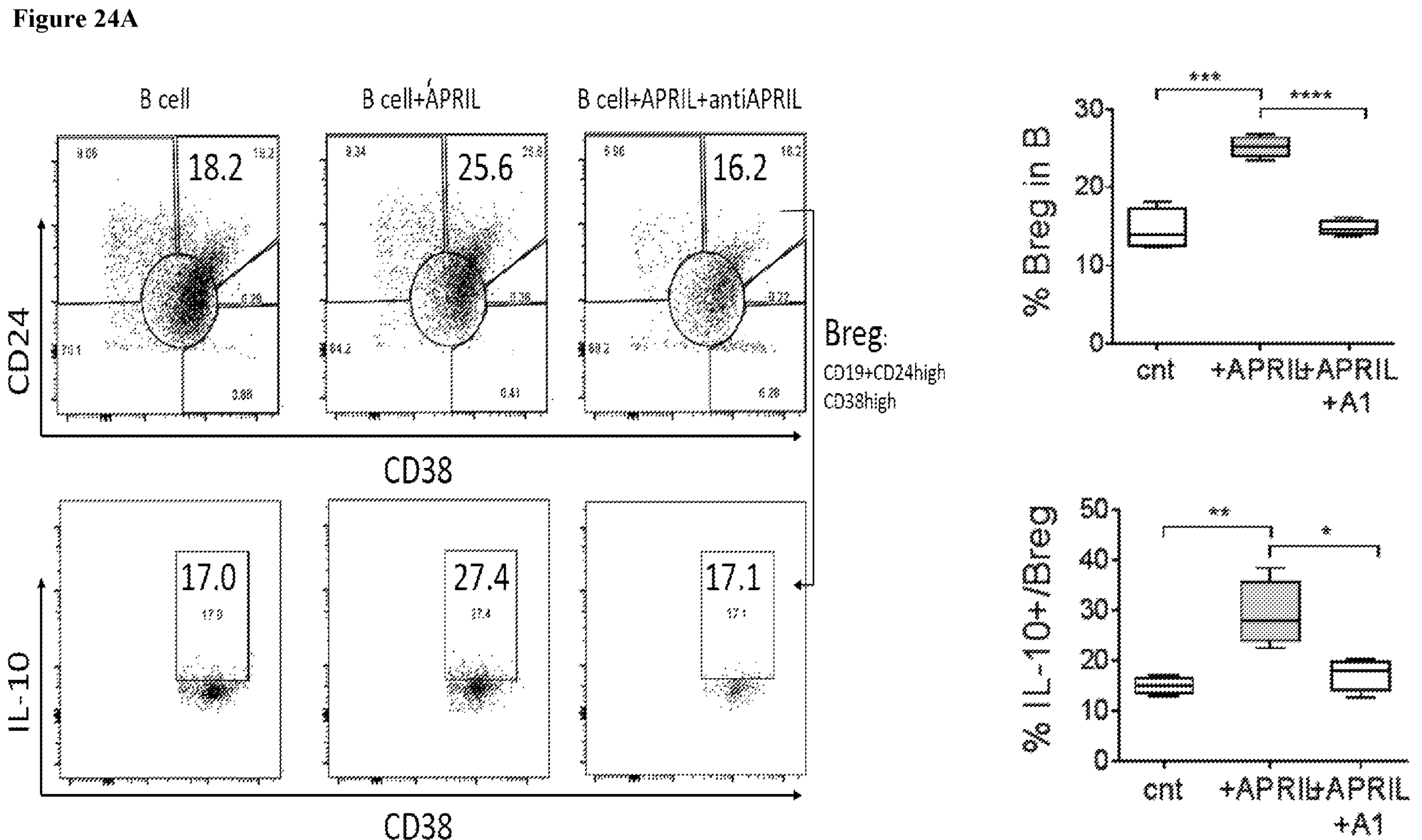
FIG. 24A shows that APRIL increases CD19+ CD24$^{high}$CD38$^{high}$ Bregs to further secret IL-10, which is inhibited by anti-APRIL mAb. MM BM-derived regulatory B cells express TACI to specifically mediate APRIL-induced IL-10 production. Bone marrow mononuclear cells (BMMCs) from MM patients were incubated with APRIL in the presence of anti-APRIL mAb for 7 days. Percentages of Bregs and IL-10+ Bregs (CD19+CD24$^{high}$CD38$^{high}$) were determined using flow cytometry analysis. Left panel shows dot blots of a representative experiment. * p<0.02,  p<0.005, * p<0.0005, **** p<0.0001.
Figure 24B:
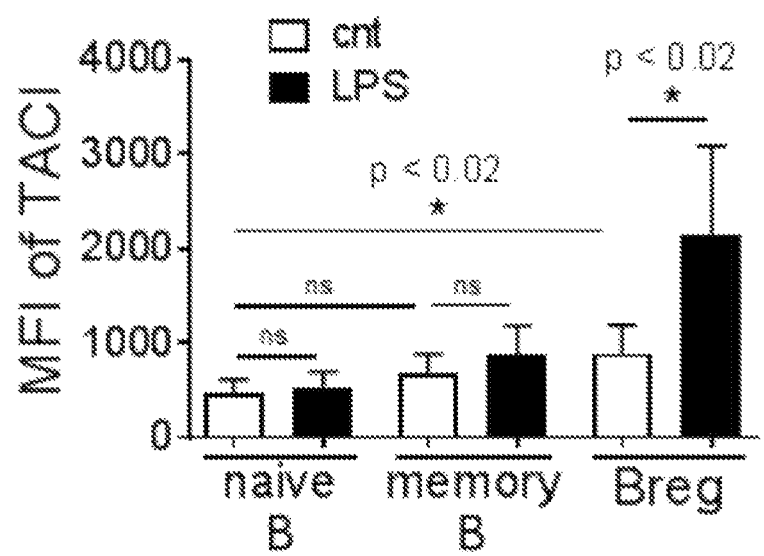
FIG. 24B shows that TACI is highly expressed on the surface of BM-derived Bregs (CD19+CD24$^{high}$CD38$^{high}$) compared to naïve B cells or memory B cells (CD19+ CD24$^{high}$CD38low), and the high expression of TACI on Bregs is further enhanced by treatment of lipopolysaccharides (LPS) that induces IL-10 production from Bregs. BM mononuclear cells isolated from MM patients were treated with LPS and TACI levels were examined in indicated B cell subsets: B regulatory cells (Breg), defined as CD19+ CD24$^{high}$CD38$^{high}$; naïve B cells, defined as CD19+ CD38intCD24int; and memory B cells, defined as CD19+ CD24−CD38low/−. int, intermediate; LPS, lipopolysaccharide. *p<0.02.
Figure 25:
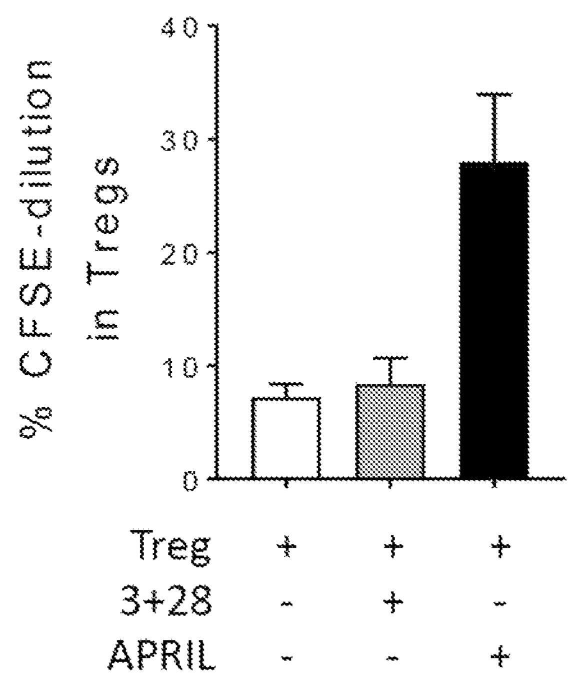
FIG. 25 shows that APRIL directly induces proliferation of Tregs based on an increase in the percentage of CFSE-dilution fraction.
Figure 26:
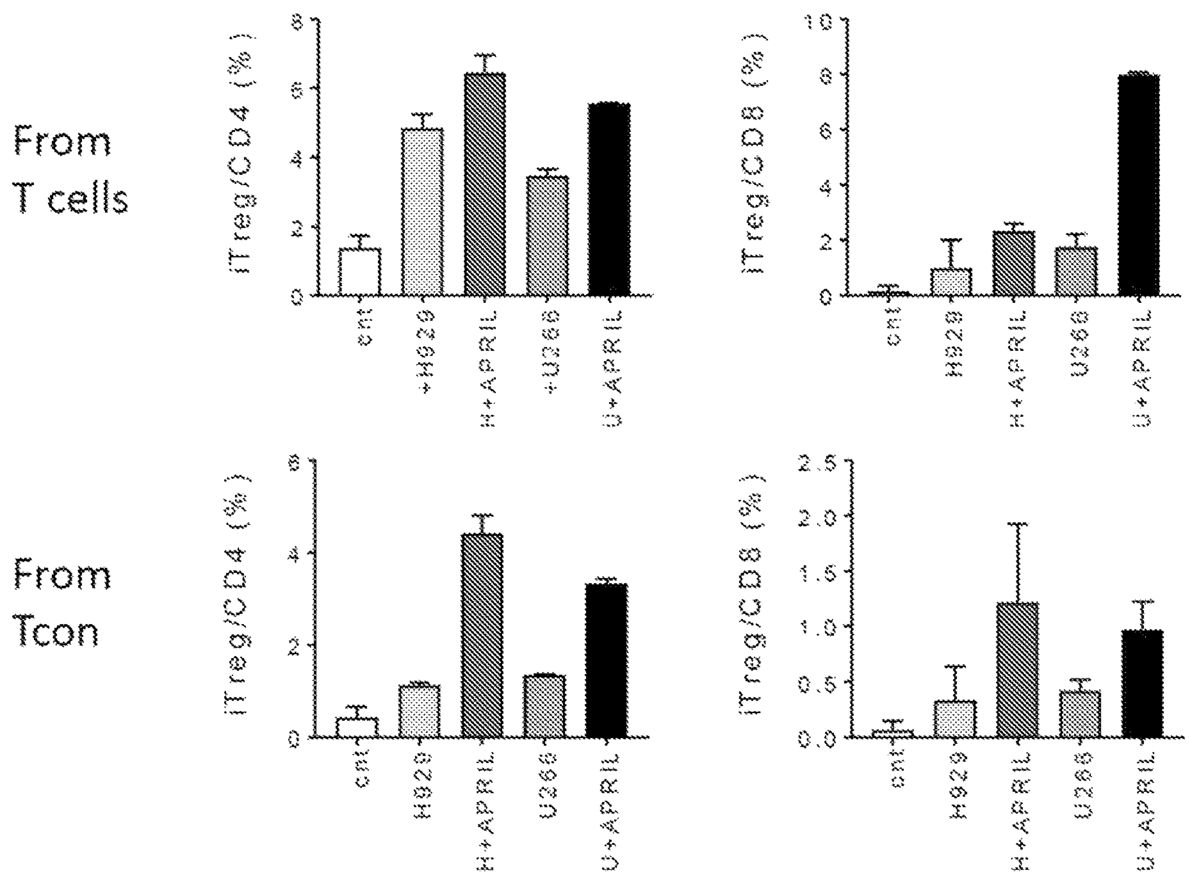
FIG. 26 shows that APRIL induces myeloma cell-induced Tregs (iTreg) in CD4+ and CD4+ T cell subsets in ex vivo co-cultures of MM cells with T cells or Tcons.
Figure 32:
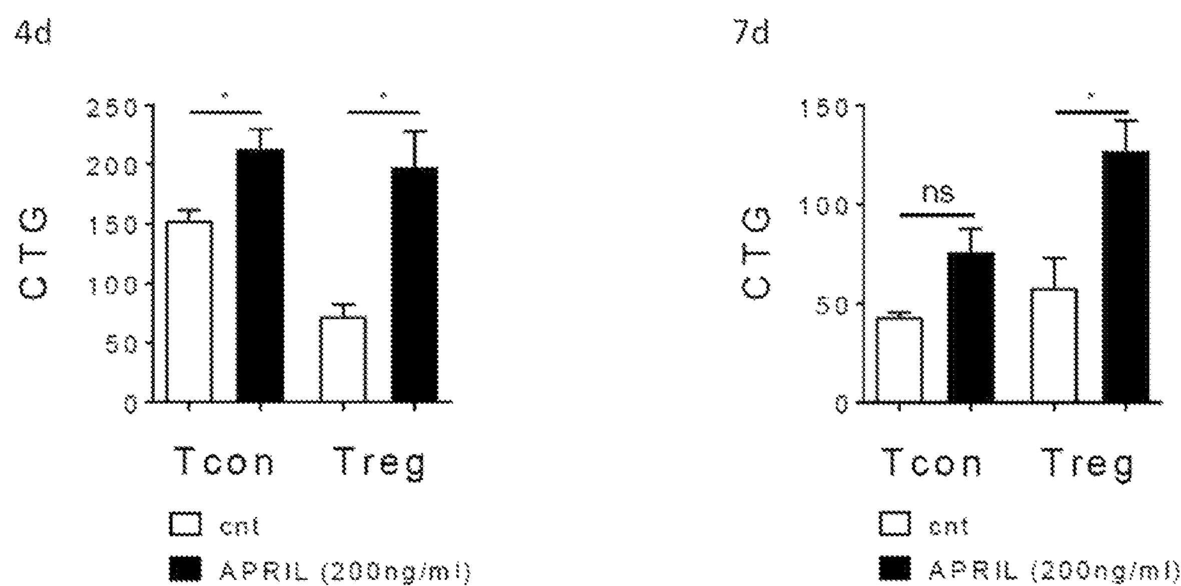
FIG. 32 shows that APRIL further promotes Treg-mediated suppression of Tcon proliferation in a time-dependent manner.

Since APRIL could stimulate growth and survival signaling, such as NFkappaB and ERK1/2, via TACI, it was determined that APRIL significantly increases growth and survival of Tregs vs. Tcon, correlating with elevated TACI levels in Tregs vs. Tcons (FIGS. 23, 25, and 32). Increased proliferation of Tregs was further defined by increased CFSE-dilution fraction, whereas anti-CD3/CD28 beads show negligible effects (FIG. 25). Tregs are increased in MM patients, which is believed to be associated with disease progression. In ex vivo culture, it was determined that APRIL enhances induction of Tregs (iTregs) in CD4+ and CD8+ T cells by multiple myeloma cell lines when co-cultured with T cells or Tcon (FIGS. 17-19, 22, and 26). A neutralizing antiAPRIL monoclonal antibody blocks APRIL-enhanced iTreg in CD4+ and CD8+ T cells, supporting a critical role of APRIL in generation of iTregs. Besides, APRIL by itself cannot convert Tcon into iTreg, confirming a lack of direct impact via the absence of TACI expression in autologous Tcon.

Figure 20A:
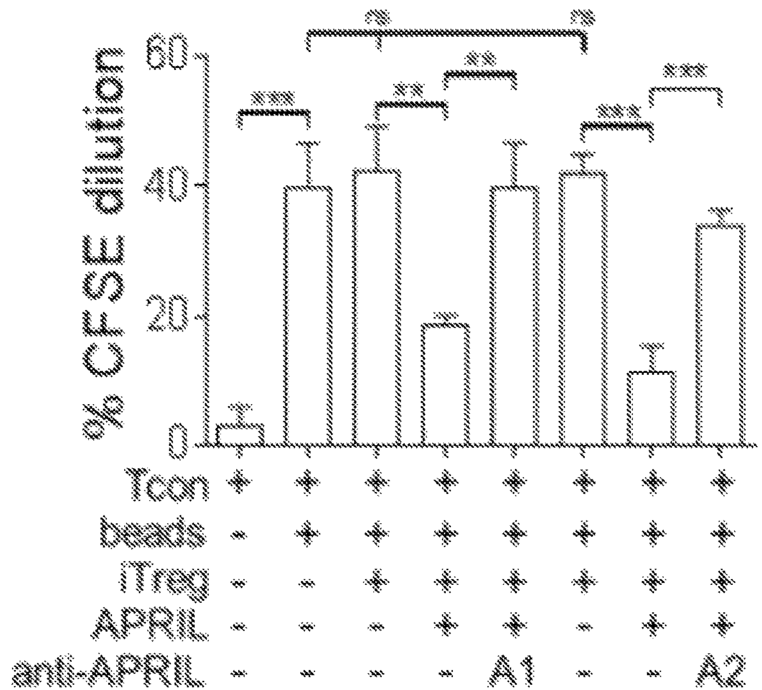
FIG. 20A shows that APRIL further promotes iTreg suppression of Tcon proliferation in ex vivo cocultures, and the suppression of Tcon proliferation is abrogated by an antagonistic anti-APRIL antibody (A1 or A2). MM cell-induced iTreg were purified from the cocultures and subjected to CFSE-dilution assays to determine fractions of autologous Tcon proliferation under indicated conditions. * p<0.05, p<0.01, * p<0.001, ****p<0.0001.
Figure 27:
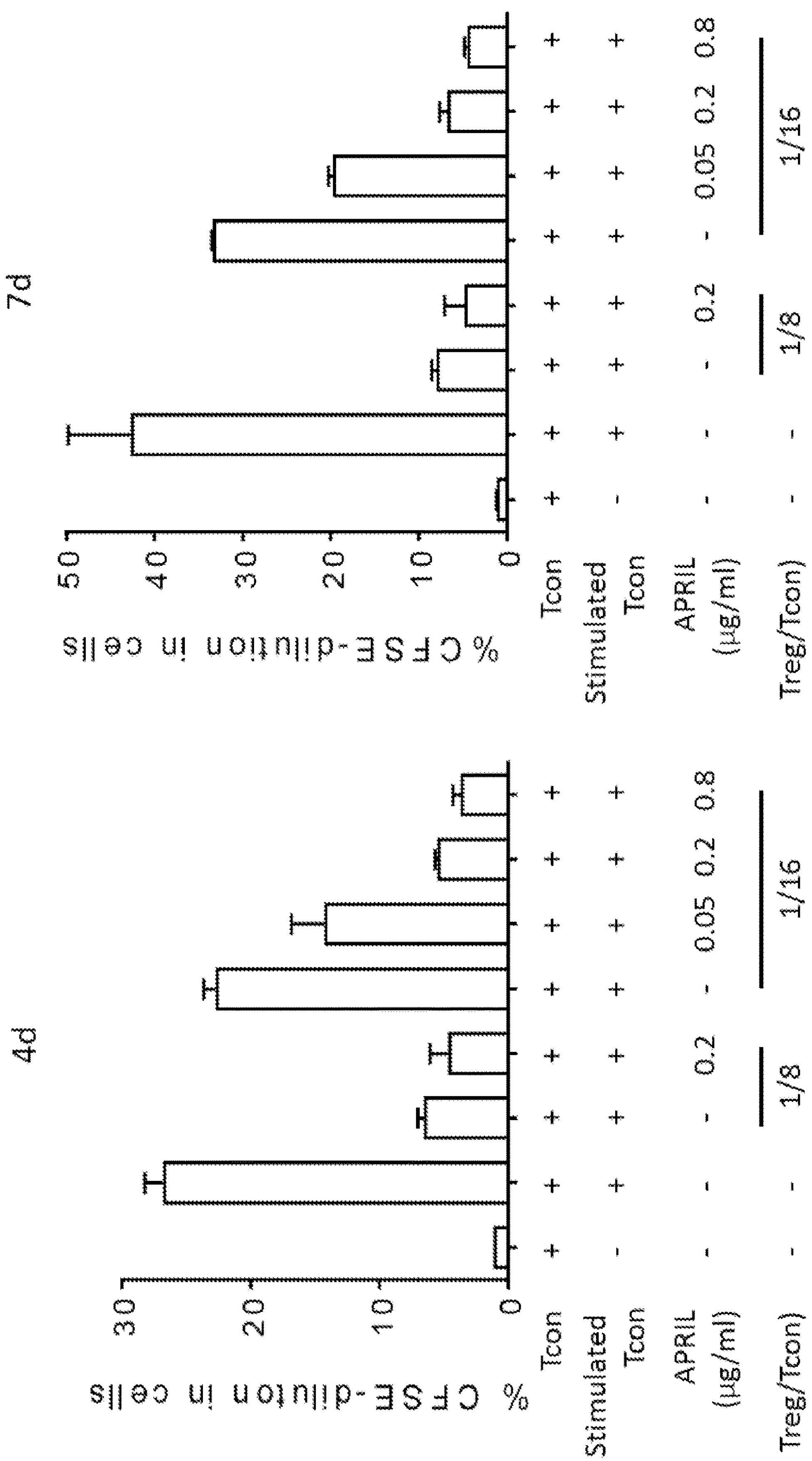
FIG. 27 shows that APRIL further promotes Treg suppression of autologous Tcon proliferation in a Treg/Tcon ratio-, dose, and time-dependent manner, and the suppression of Tcon proliferation is abrogated by an antagonistic anti-APRIL antibody. Purified Tcons were stained with 5 μM CFSE and then stimulated with CD3/CD28 beads (beads) in the presence or absence of autologous Tregs at indicated ratios of Treg/Tcon, with or without APRIL (200 ng/ml). Beads-stimulated Tcons were cocultured with autologous Tregs for 4 days and 7 days at 2 lower ratios of Treg/Tcon in serial dilutions of APRIL (μg/ml). Tcons were cocultured with Tregs at a low Treg/Tcon ratio with APRIL (μg/ml) in the presence or absence of neutralizing anti-APRIL mAb (μg/ml) for 4 days and 7 days. Cl, chimeric homolog of A1 (01A). * $p<0.05$,  $p<0.01$, * $p<0.001$, ****$p<0.0001$.
Figure 27:
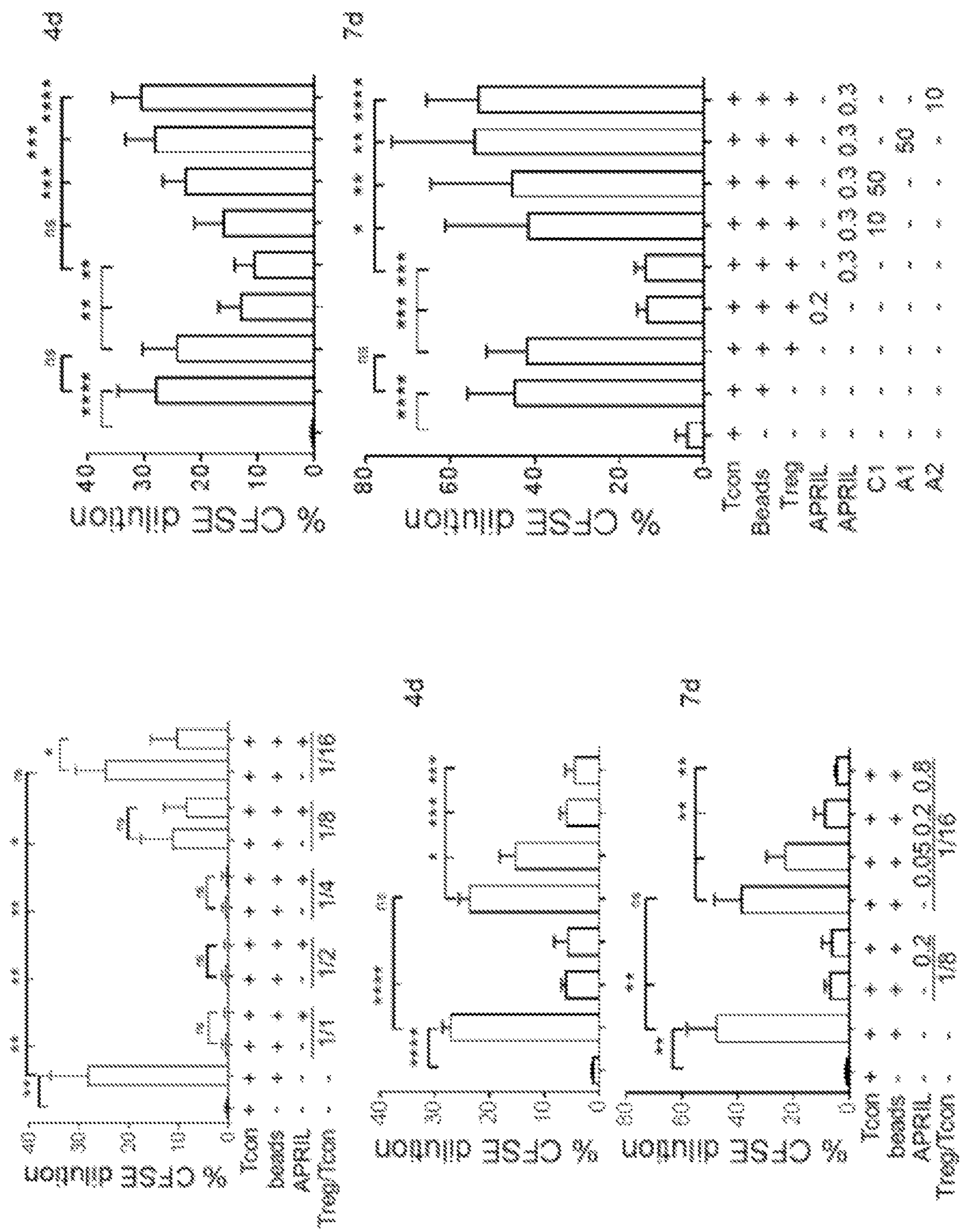
Figure 28:
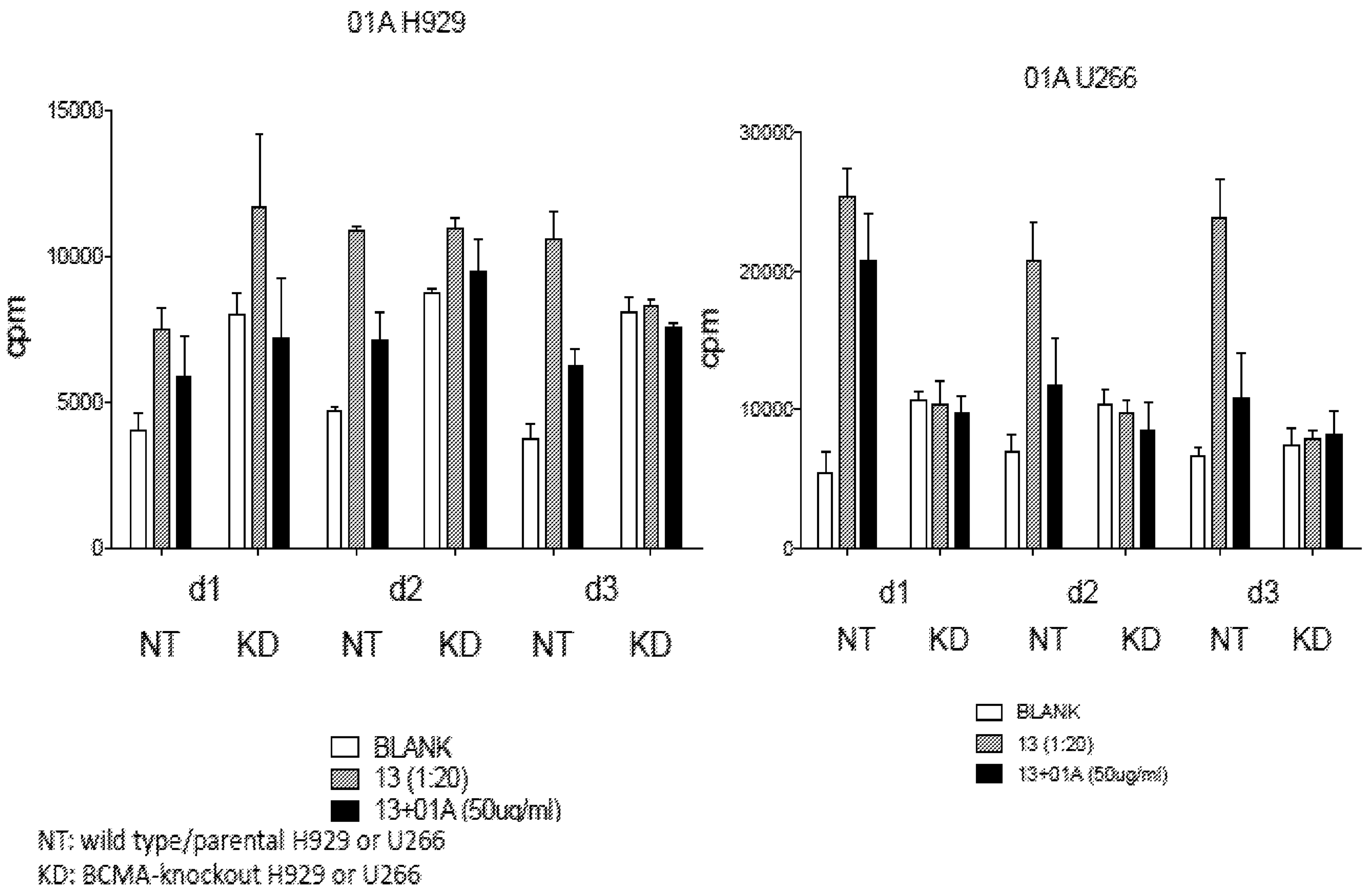
FIG. 28 shows that 01A specifically inhibits APRIL-induced MM cell proliferation via BCMA.
Figure 29:
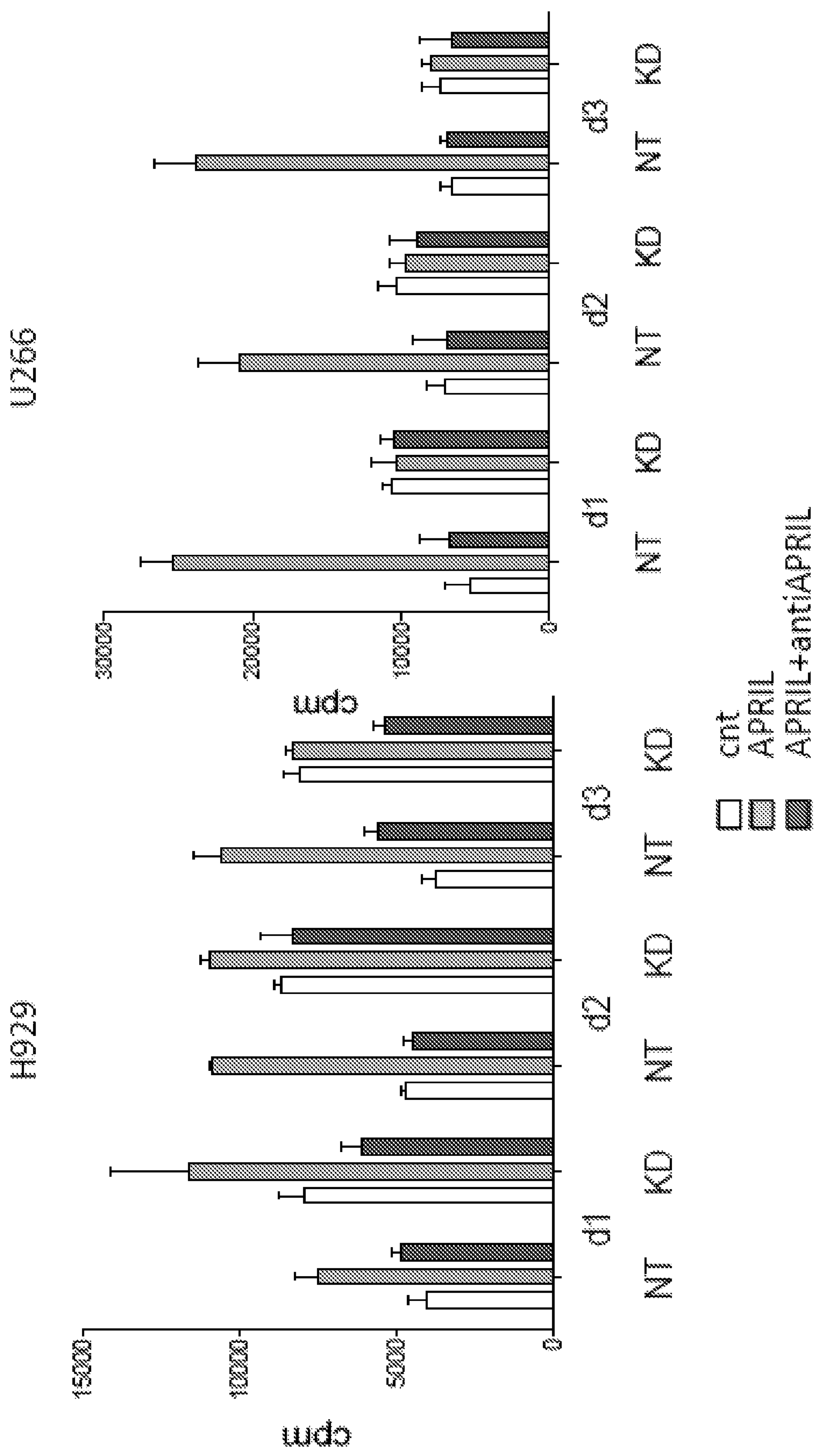
FIG. 29 shows that anti-APRIL mAb selectively blocks APRIL-induced MM cell proliferation.
Figure 30:
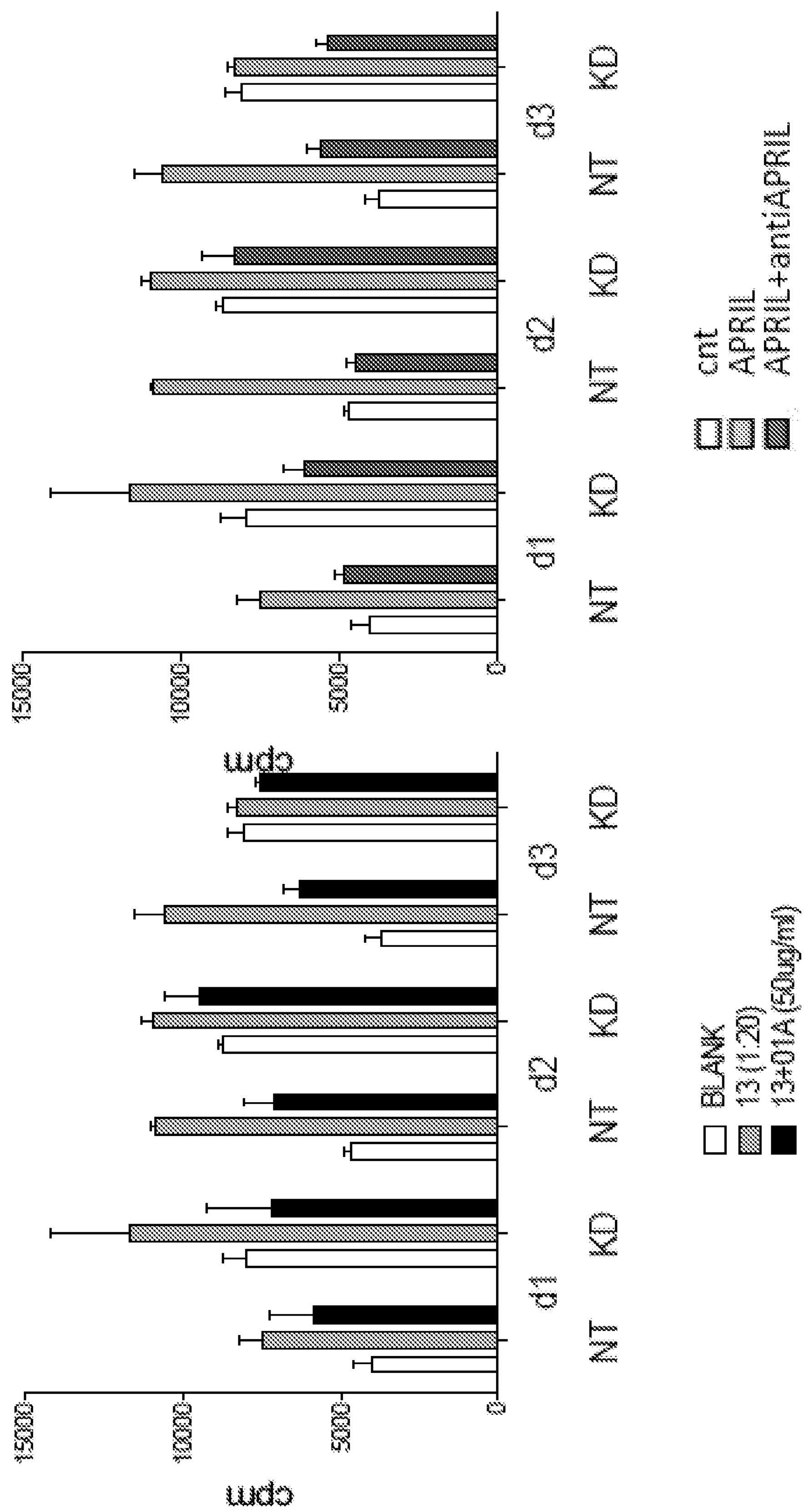
FIG. 30 shows that anti-APRIL mAb and 01A selectively blocks APRIL-induced MM cell proliferation via BCMA.
Figure 31:
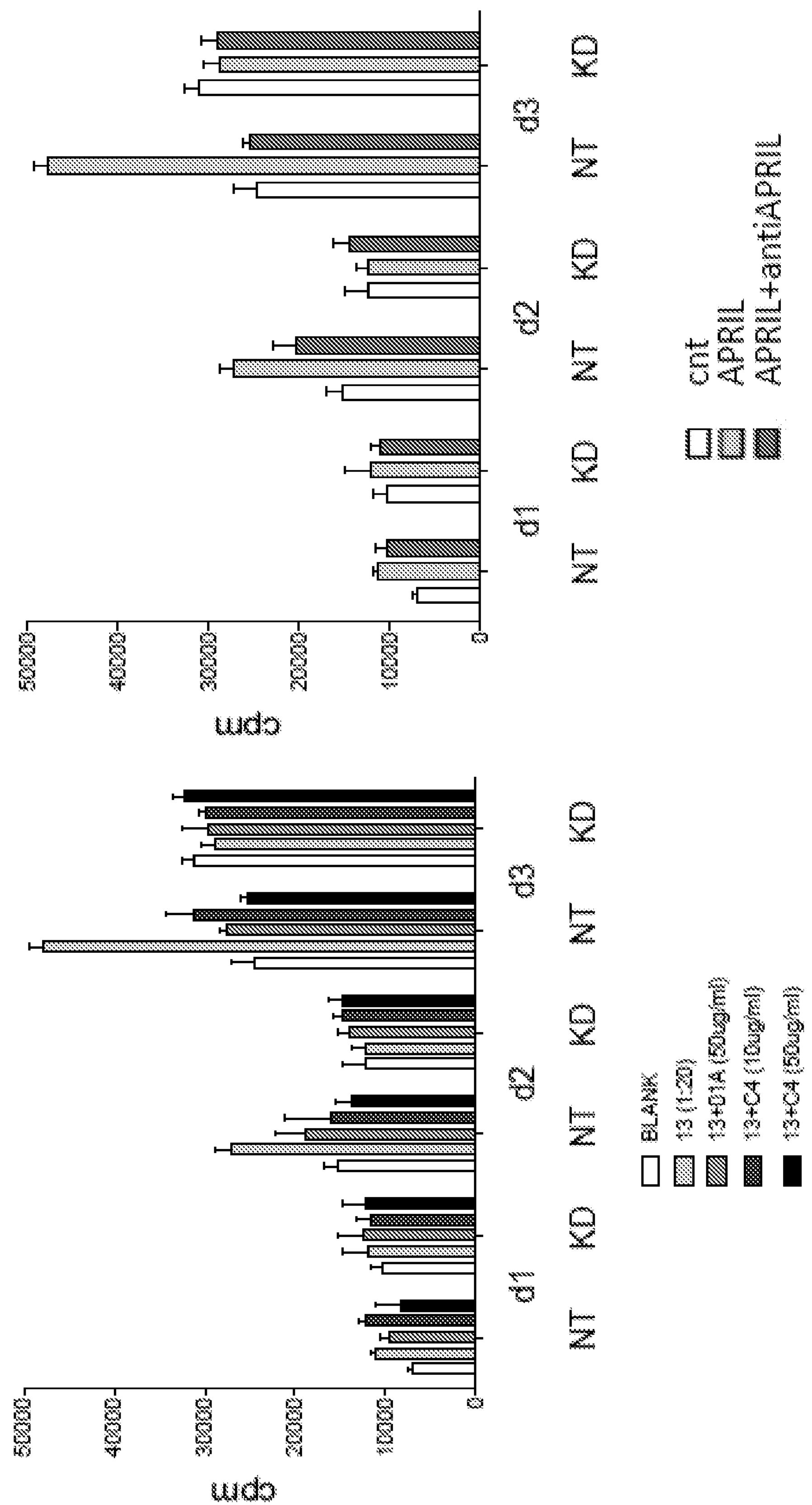
FIG. 31 shows that anti-APRIL mAb and C4/01A selectively block APRIL-induced MM cell proliferation.

Moreover, it has been demonstrated that APRIL further blocked the proliferation of Tcons that were stimulated by anti-CD3/CD28 beads, which is believed to further inhibit the suppressive effects of Tregs on Tcons such as in the ex vivo co-cultures used (FIGS. 20, 27, and 32). Furthermore, APRIL upregulates CD19+CD24$^{high}$CD38$^{high}$ Bregs which further produce IL-10 that can be blocked by blocking APRIL monoclonal antibody. Thus, APRIL can stimulate myeloma cells-promoted Breg number and immunoinhibitory function in ex vivo the co-cultures (FIG. 24).

It is believed that APRIL preferentially activates TACI in Tregs vs. Tcons via up-regulation of potential growth and survival genes, thereby more potently increasing viability of Tregs than Tcons leading to enhanced inhibitory immune function. Thus, modulating the APRIL-TACI interaction is believed to modulate Tregs number and/or inhibitory immune activity. For example, it is believed that an agent that inhibits or blocks the APRIL-TACI interaction, such as a neutralizing anti-APRIL mAb, can revert suppressive function of Tregs on Tcons and further overcome immunosuppression in a bone marrow microenvironment such as in multiple myeloma.

It is further believed that regulatory B cells (Bregs), such as CD19$^{+}$CD24$^{high}$CD38$^{high}$ cells (Zhang et al. (2017) *Blood Cancer* J 7e547) express TACI but not BCMA where APRIL could activate its signaling cascade similarly to that described above regarding Tregs in order to further protect the Bregs. Thus, it is believed that modulating the APRIL-TACI interaction can also modulate Bregs number and/or inhibitory immune activity similarly to that of Tregs described above.

Modulating the APRIL-TACI interaction to modulate Tregs/Bregs number and/or inhibitory immune activity is believed to have a number of uses as described further herein since Tregs and Bregs are involved in many diseases, such as autoimmunity, cancer, and infections, and can be modulated to either upregulate or downregulate immune responses depending on the desired immunomodulation.

For example, cancers, such as multiple myeloma (MM), can benefit from upregulating immune responses. Bregs are significantly associated with active MM disease stage, but not MM samples from patients who have responded to treatment. Since APRIL is mainly produced by non-myeloma tumor cells in the bone marrow microenvironment and one of its receptor, BCMA, is widely expressed on MM cells at high levels, targeting APRIL is believed to block MM cell growth and survival. In addition, due to their expression of TACI but not BCMA and the fact that Tcons have undetected TACI when compared with Tregs from the same individual, APRIL could induce growth and survival of Tregs in a significantly potent manner while minimally affecting autologous Tcons. Furthermore, it is believed that Bregs, which secrete IL-10, can be activated by APRIL via TACI but not BCMA.

Since the majority of MM patients are in a state of immune deficiency, inhibiting the APRIL-TACI interaction, such as using blocking anti-APRIL mAbs or fusion proteins, is believed to relieve the suppressive immune microenvironment by selectively targeting Tregs which express elevated levels of TACI. Since MM patients have severe bone lesions induced by hyperactive osteoclasts which secret significant amount of APRIL, targeting APRIL and/or the APRIL-TACI interaction is also believed to further block osteoclast-inhibited T cell killing on MM cells. This is believed to overcome overall immunosuppressiveness in the bone marrow microenvironment in order to restore anti-MM immunity.

Examples 3-10 described below further confirm these findings.

Example 3: Regulatory T Cells (Tregs) Express Significantly Higher TACI than Paired Conventional T (Tcon)

Figure 33:
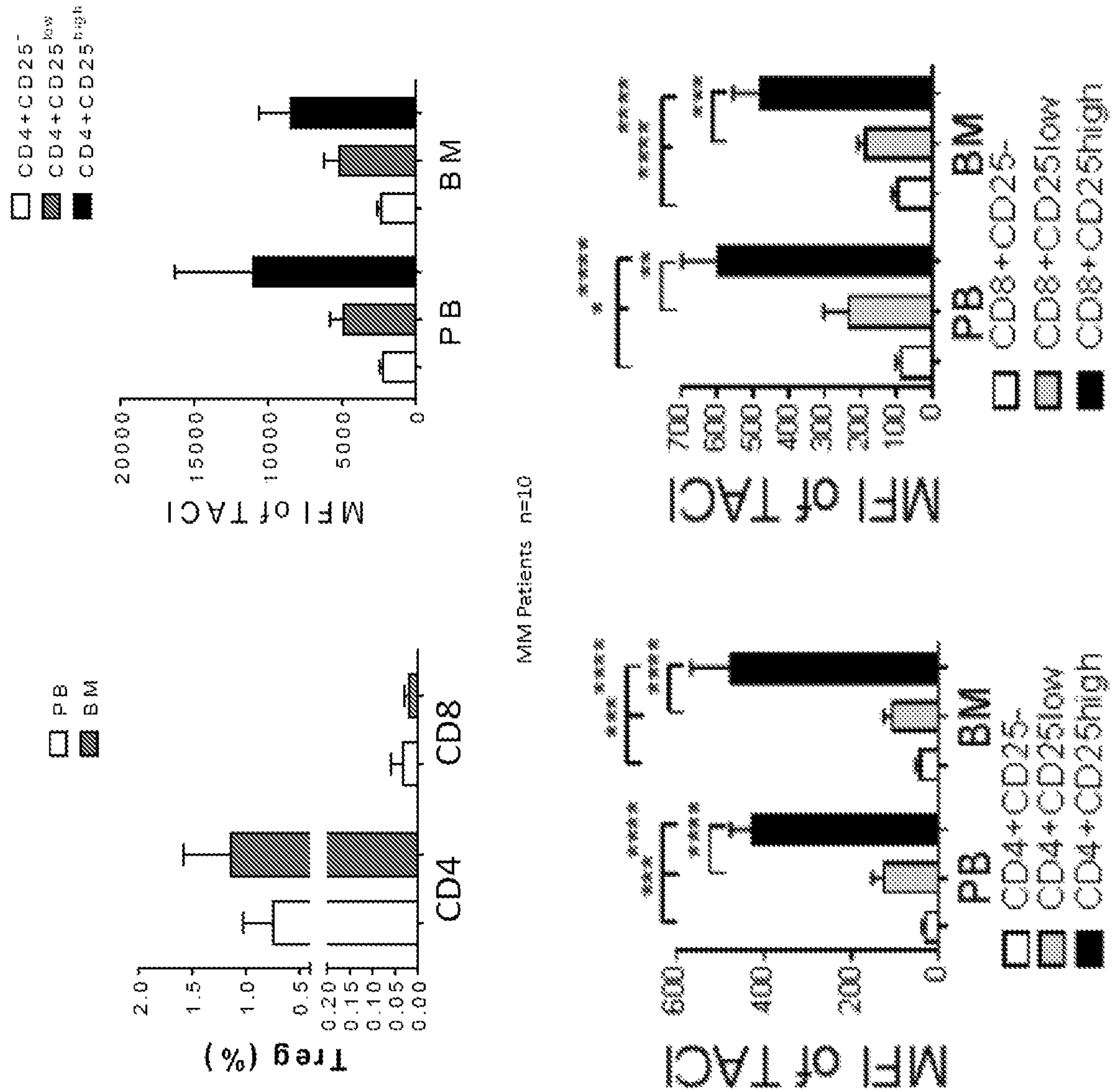
FIG. 33 shows that TACI surface expression is varied among T cell subsets, with highest in CD4+(or CD8+) $CD25^{high}$ followed by CD4+(or CD8+)$CD25^{low}$ and CD4+ (or CD8+)$CD25^{-/negative}$ cells of MM patient samples. Using flow cytometry analysis, TACI protein levels were measured in indicated subsets in CD4+ and CD8+ T cells of PB and BM compartments from MM patients (n=47). * $p<0.05$,  $p<0.01$, * $p<0.001$, **** $p<0.0001$.
Figure 34A:
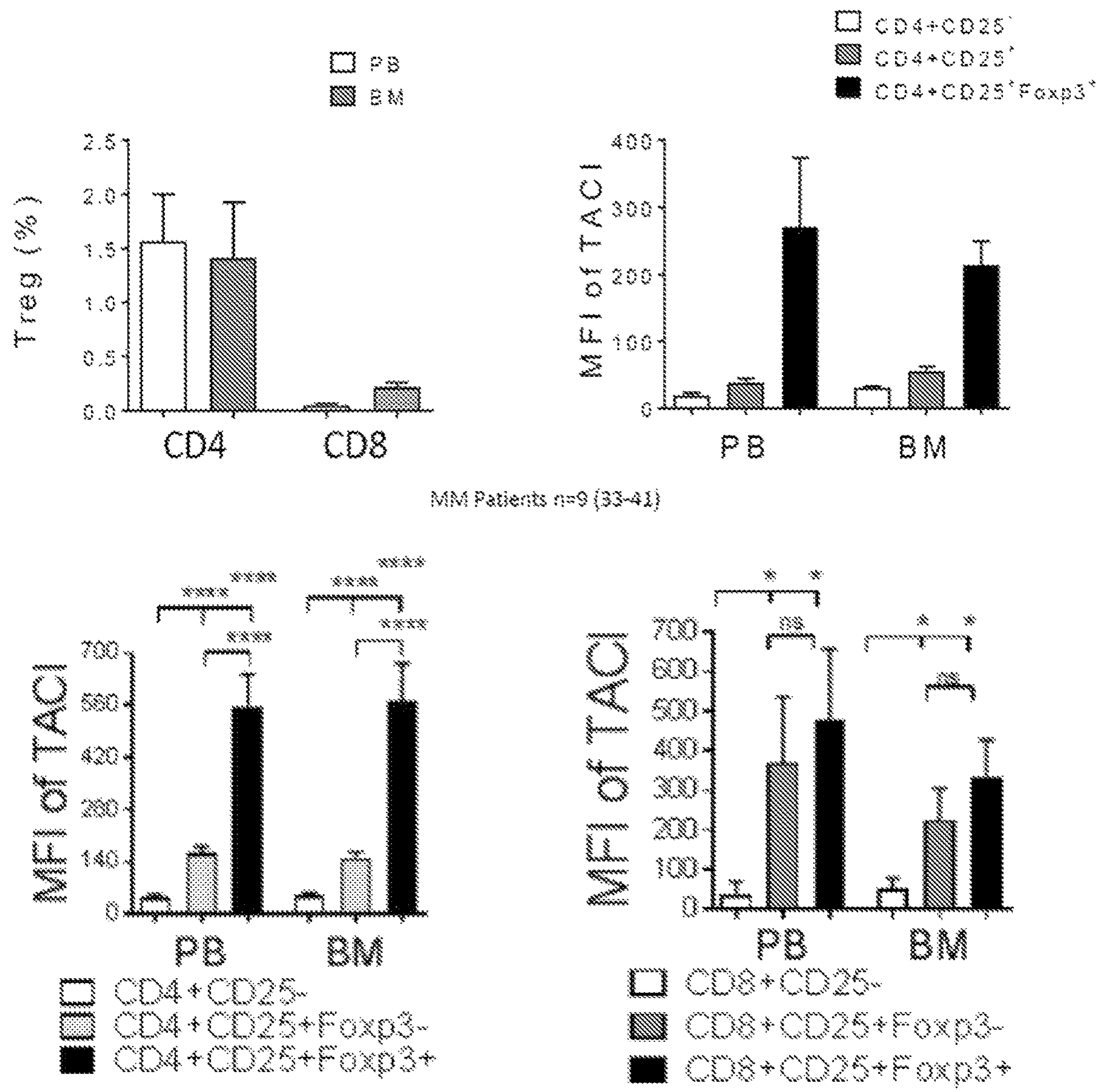
FIG. 34A shows that TACI protein levels are significantly elevated in CD4+(or CD8+)$CD25^{high}$FoxP3+ Tregs of MM patients, when compared with CD4+(or CD8+)CD25− Tcons. Using flow cytometry analysis, median fluorescence intensity (MFI) of TACI was determined in indicated subsets of CD4+ T cells of PB and BM compartments from MM patients (n=47). TACI protein levels are highest on regulatory T subset (Treg, CD4+CD25+Foxp3+) followed by CD4+CD25+Foxp3− subset. TACI MFIs in conventional T cells (Tcon, CD4+CD25-) are similar as isotype control Ab. *$p<0.05$,  $p<0.01$, *$p<0.001$, ****$p<0.0001$.
Figure 34B:
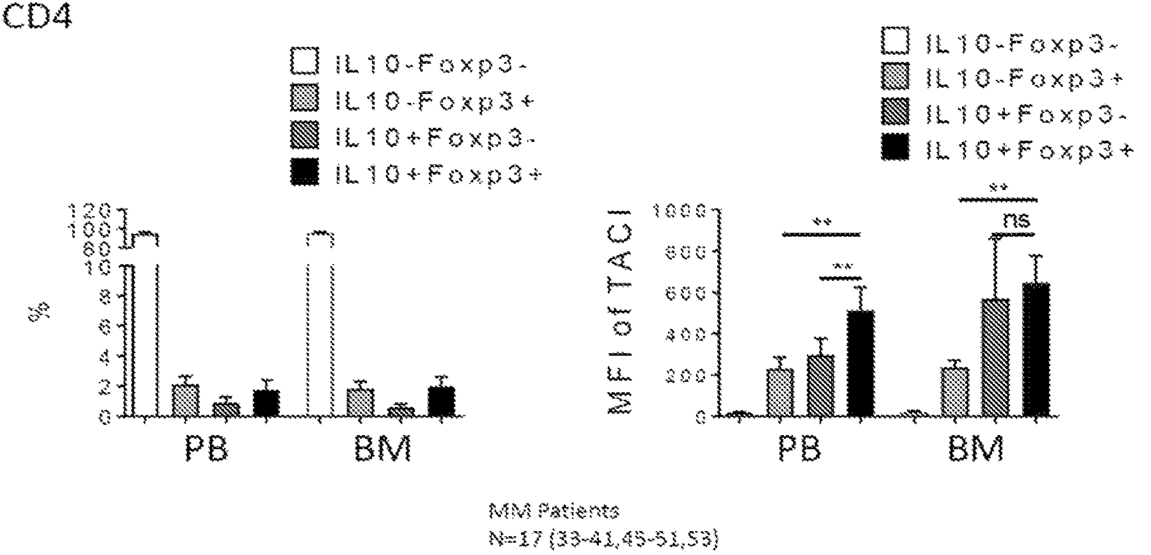
FIG. 34B shows that TACI levels are significantly higher in CD4+FoxP3+IL10+ T cell subsets, when compared with CD4+FoxP3−IL10− cells of paired peripheral blood and bone marrow compartments of MM patients. Using flow cytometry analysis, TACI protein levels were measured in indicated subsets in CD4+ T cells of PB and BM compartments from MM patients (n=47). Percentages and TACI MFI of CD4+T subsets based on levels of IL-10 and Foxp3 were determined. TACI levels are highest in CD4+IL-10+ Foxp3+ subset in PB and BM of MM patients. * $p<0.05$,  $p<0.01$, * $p<0.001$, **** $p<0.0001$.
Figure 34B:
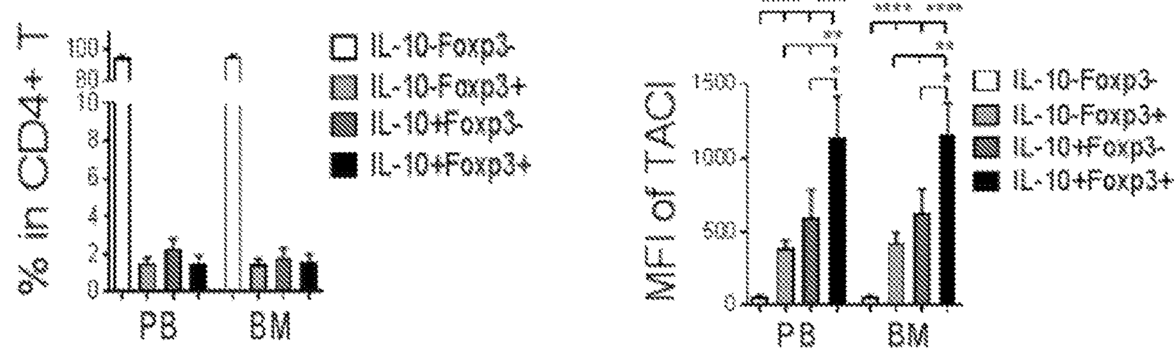
Figure 34C:
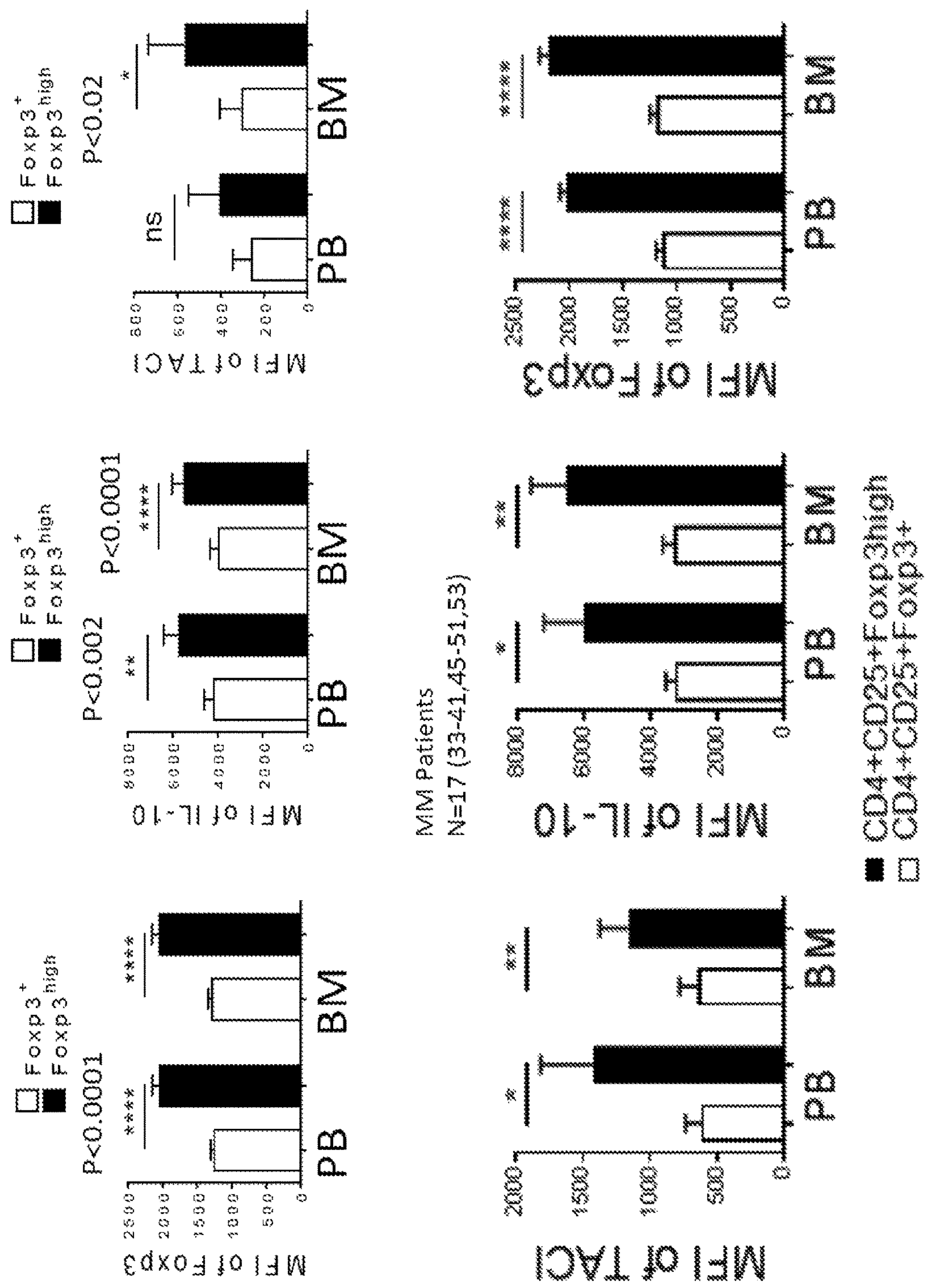
FIG. 34C shows that TACI levels are significantly higher in CD4+$FoxP3^{high}$$IL10^{high}$ T cell subsets, when compared with CD4+FoxP3−IL10− cells of paired peripheral blood and bone marrow compartments of MM patients. Using flow cytometry analysis, the levels of IL-10 and TACI protein were measured in CD4+CD25+$Foxp3^{high}$ subsets within CD4+CD25+Foxp3+ Treg of PB and BM compartments from MM patients (n=47). * $p<0.05$,  $p<0.01$, * $p<0.001$, **** $p<0.0001$.

To define a potential immune regulation of APRIL on T cells which lack BCMA expression, the TACI protein levels, as mean fluorescence intensities (MFIs), were assessed using flow cytometry analysis, on the cell membrane of T cell subsets harvested from MM patients. Among T cells freshly isolated from peripheral blood (PB) or bone marrow (BM) aspirates of MM patients (n=47), CD4+(and CD8+) CD25$^{high}$ T cells have >3-5-fold higher TACI expression than CD4+(and CD8+) CD25low T cells (FIG. 33). Significantly higher TACI levels were also observed on CD4+(and CD8+) CD25low T cells than CD4+(and CD8+) CD25− conventional T (Tcon). TACI is hardly detected on Tcons since MFIs for TACI and isotype control are almost superimposed. In contrast to Tcons (CD4+CD25−), regulatory T cells (Treg, CD4+CD25+Foxp3+) express the highest TACI levels (FIG. 34). CD8 Tregs, CD8+CD25+Foxp3+ cells which are functionally suppressive (Correale et al. (2010) *Annu. Neurol.* 67:625-638) and increased in MM patients (Feyler et al. (2012) *PloS one* 7:e35981), also express higher levels of TACI than CD8+CD25− Tcons (FIG. 34). Next, suppressive cytokine IL-10 was simultaneously measured with TACI and Foxp3 within CD4+CD25+Foxp3+ Tregs. Highest IL-10 levels were found in CD4+CD25+Foxp3$^{high}$ subsets which express highest TACI (FIG. 34C). Furthermore, TACI levels are highest on IL-10+Foxp3+ T cell subsets, despite their low frequencies (<2%) within CD4+ T cells (FIG. 34B, lower left panel). In contrast to IL-10−Foxp3− cells which occupy 95% CD4 T cells and lack TACI expression, IL-10−Foxp3+ and IL-10+Foxp3+ subsets, which account for <24% CD4+ T cells, have 6-8-fold higher TACI expression (FIG. 34B, lower right panel).

Figure 13A:
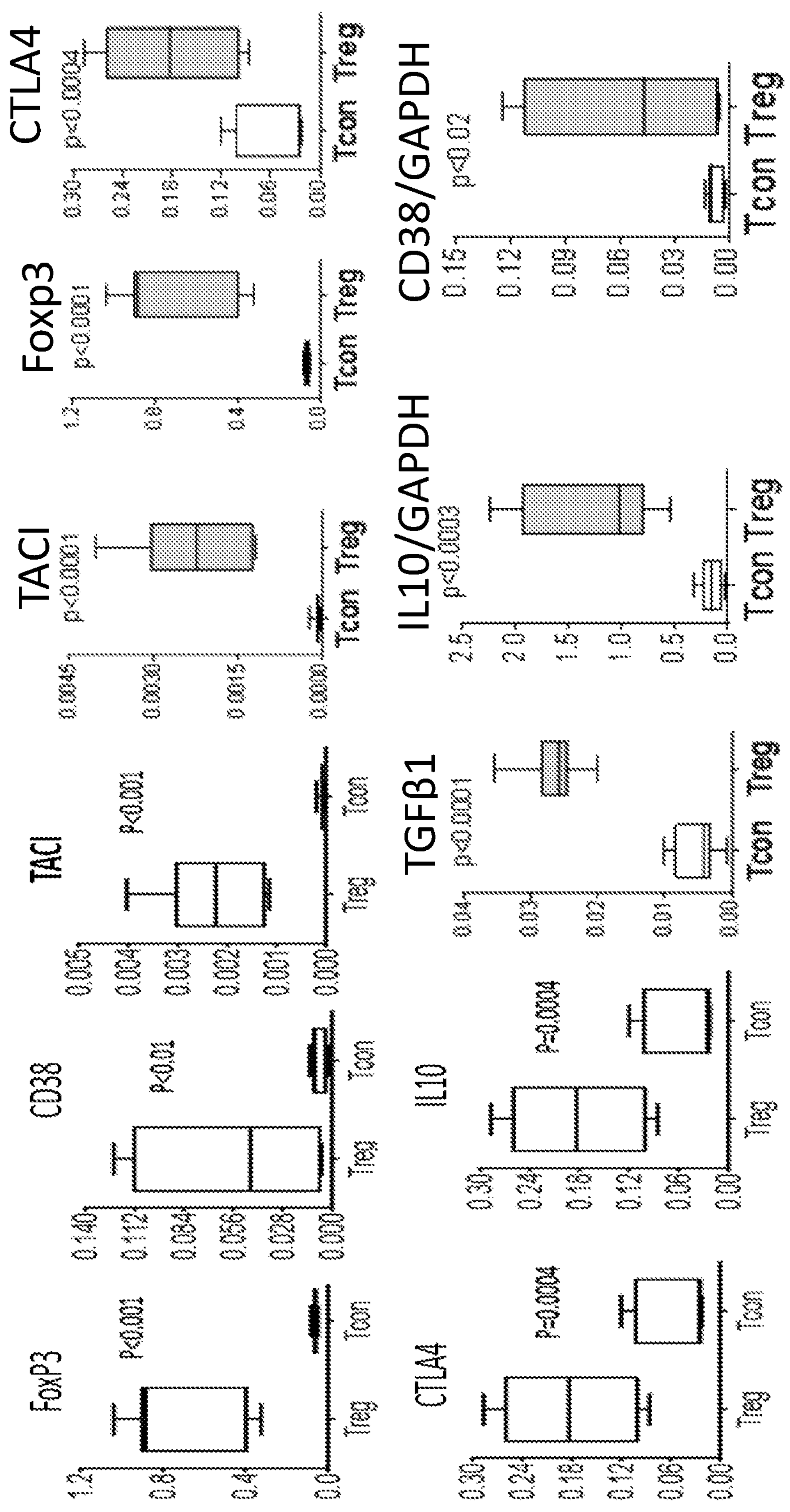
FIG. 13A shows that TACI is differentially expressed in Tregs as compared to autologous Tcons from the same MM patients. For reference, the expression of other genes (IL-10, CD38, Foxp3, CTLA-4, and TGFβ) differentially expressed in Tregs as compared to autologous Tcons are also shown (see also Feng et al. (2017) *Clin. Cancer Res.* 23:4290-4300; Zhang et al. (2017) *Blood Cancer J.* 7:e547). Levels of indicated Treg-related transcripts were examined along with TACI in patient samples.
Figure 13B:
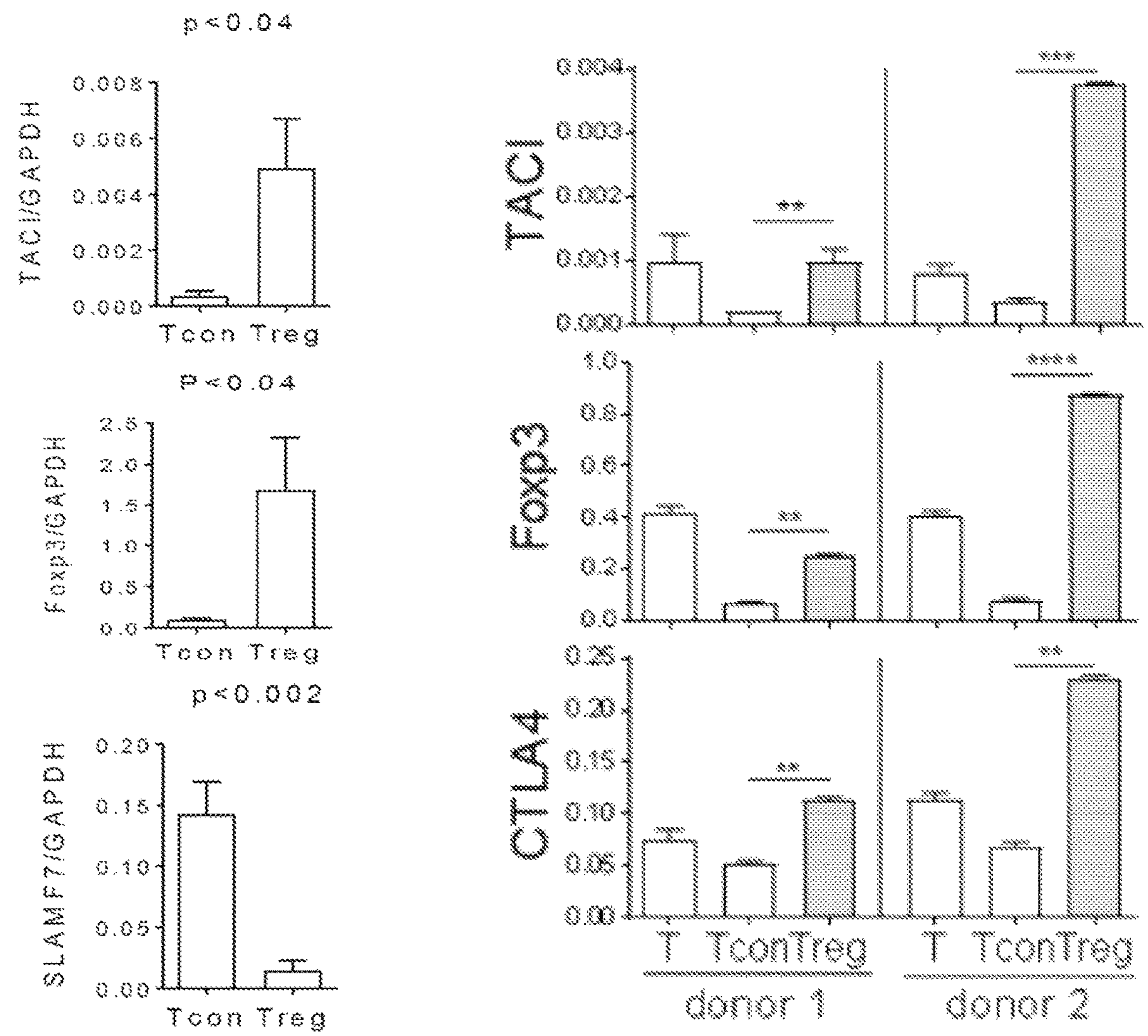
FIG. 13B shows that TACI is differentially expressed in Tregs as compared to autologous Tcons. CD3 T cells (T) from different donors (MM patients) were used to separate Treg from Tcon followed by RNA extraction to quantitate TACI transcripts by qRT-PCR. Foxp3, CTLA-4, and TGFβ serve as control genes to identify Tregs. Expression levels were normalized by internal control GAPDH then shown are relative expression levels in Tregs vs Tcons. SLAMF7 is significantly expressed higher in Tcons vs. Tregs in an autologous setting. * $p<0.05$;  $p<0.01$; * $p<0.001$; **** $p<0.0001$.
Figure 13B:
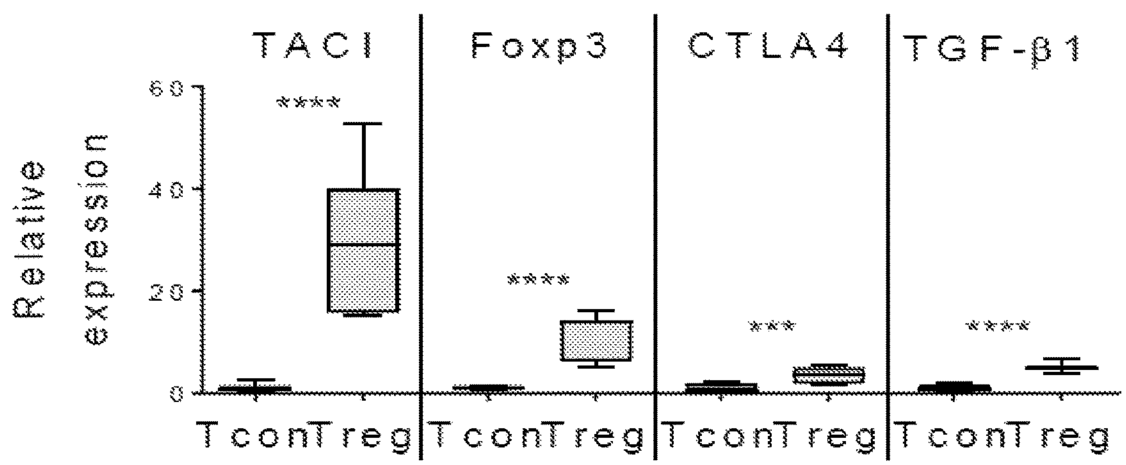
Figure 14:
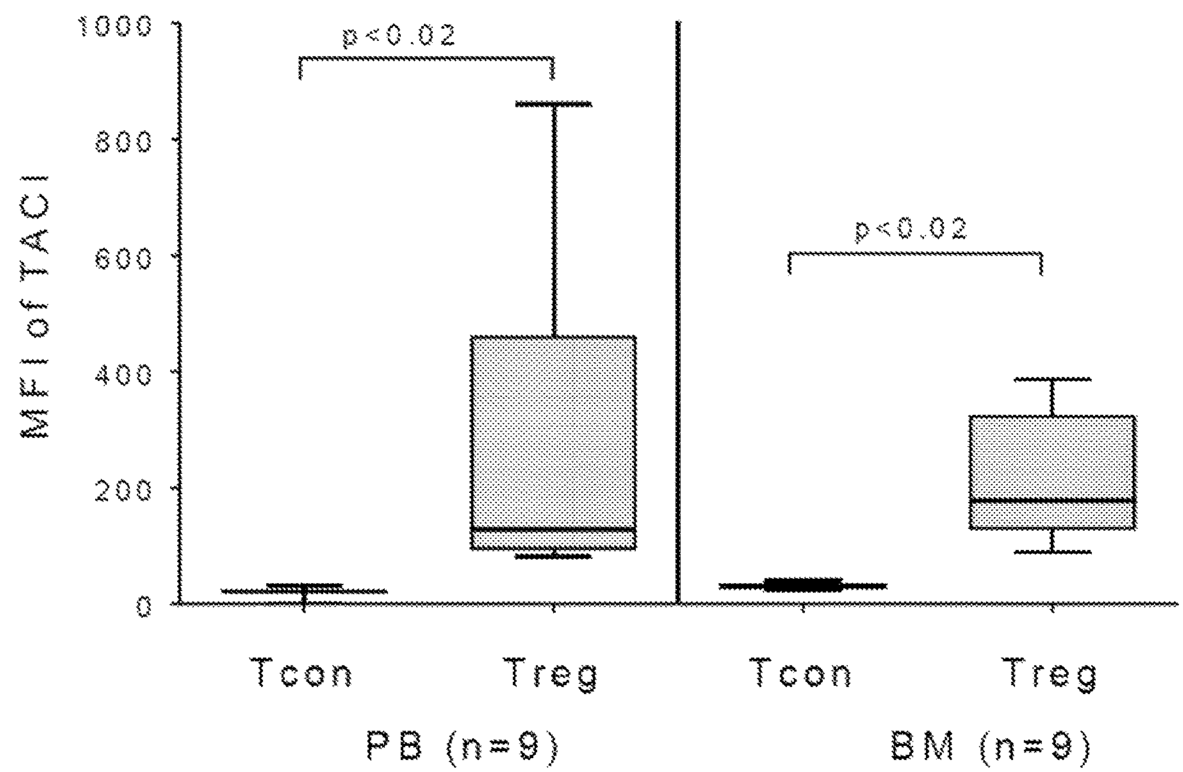
FIG. 14 shows that TACI protein is significantly higher on the surface of Tregs as compared to Tcons of bone marrow and peripheral blood compartments from the same individual patient. TACI MFIs are shown for Treg vs paired Tcon from 9 MM patients.
Figure 15A:
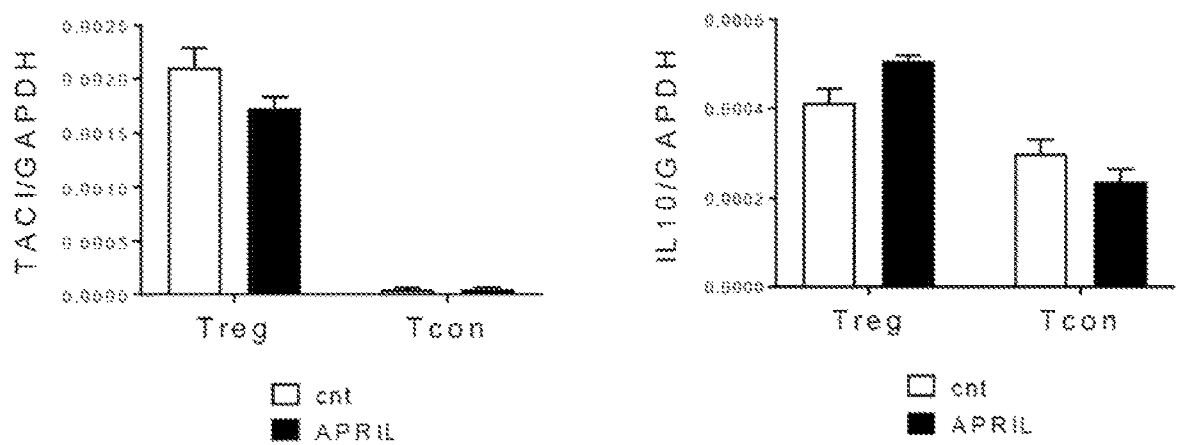
FIG. 15A shows that APRIL induces IL-10 expression in TACI-expressing Tregs vs. Tcons.
Figure 15B:
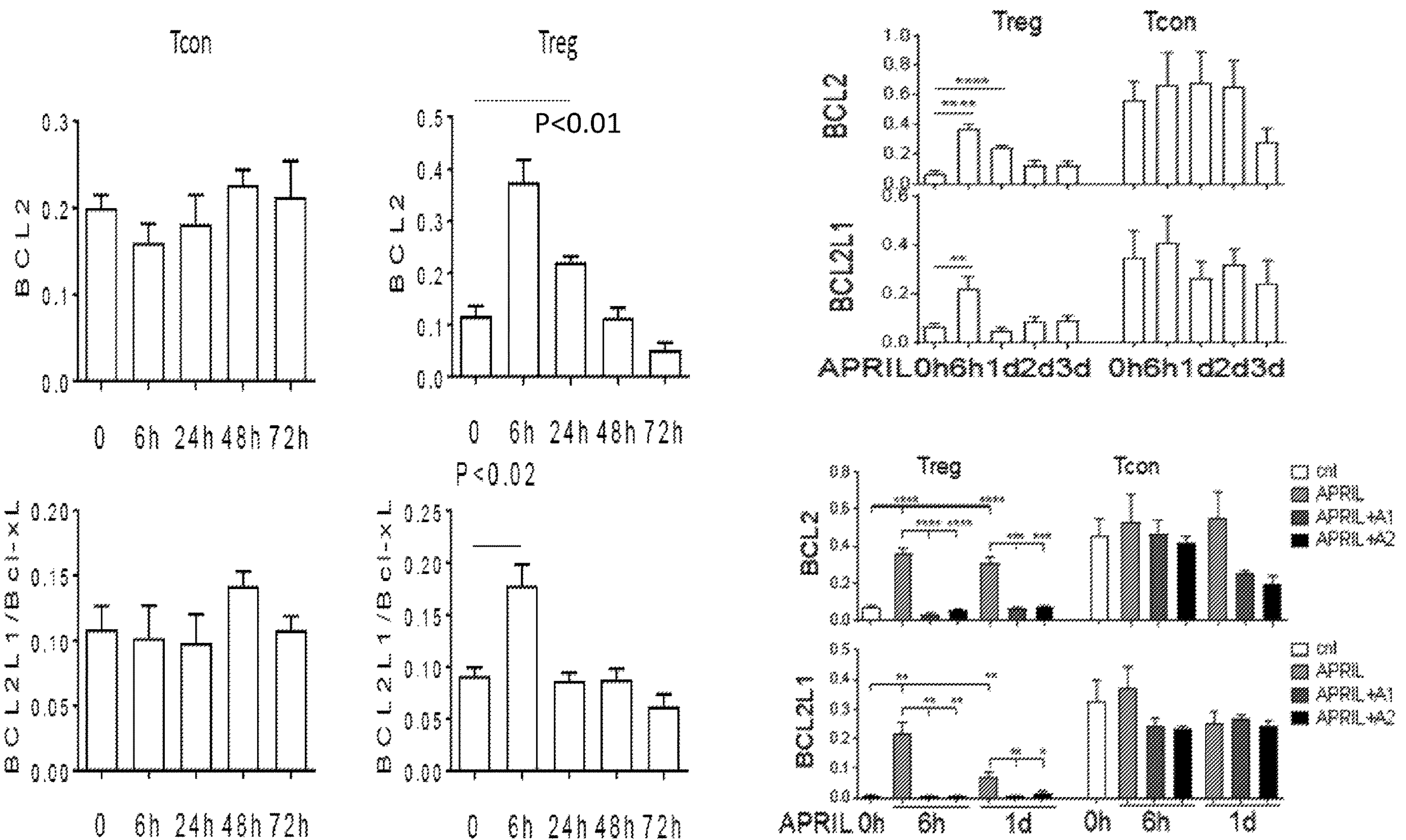
FIG. 15B shows that APRIL induces expression of Bcl2 and Bcl-xL in TACI-expressing Tregs vs. Tcons, and such induction of expression is abrogated by an antagonistic anti-APRIL antibody. Purified Tregs and paired Tcons (n=5) were incubated with APRIL for various time periods. Expression levels of BCL2 and BCL2L1 were then determined using qRT-PCR normalized by internal controls GAPDH. Blocking anti-APRIL mAbs (A1, A2) were added to APRIL-containing media for 6 hours and 1 day. cnt, control media; A2, clone Aprily-1-1. * $p<0.02$;  $p<0.005$; * $p<0.001$; **** $p<0.0001$.
Figure 15C:
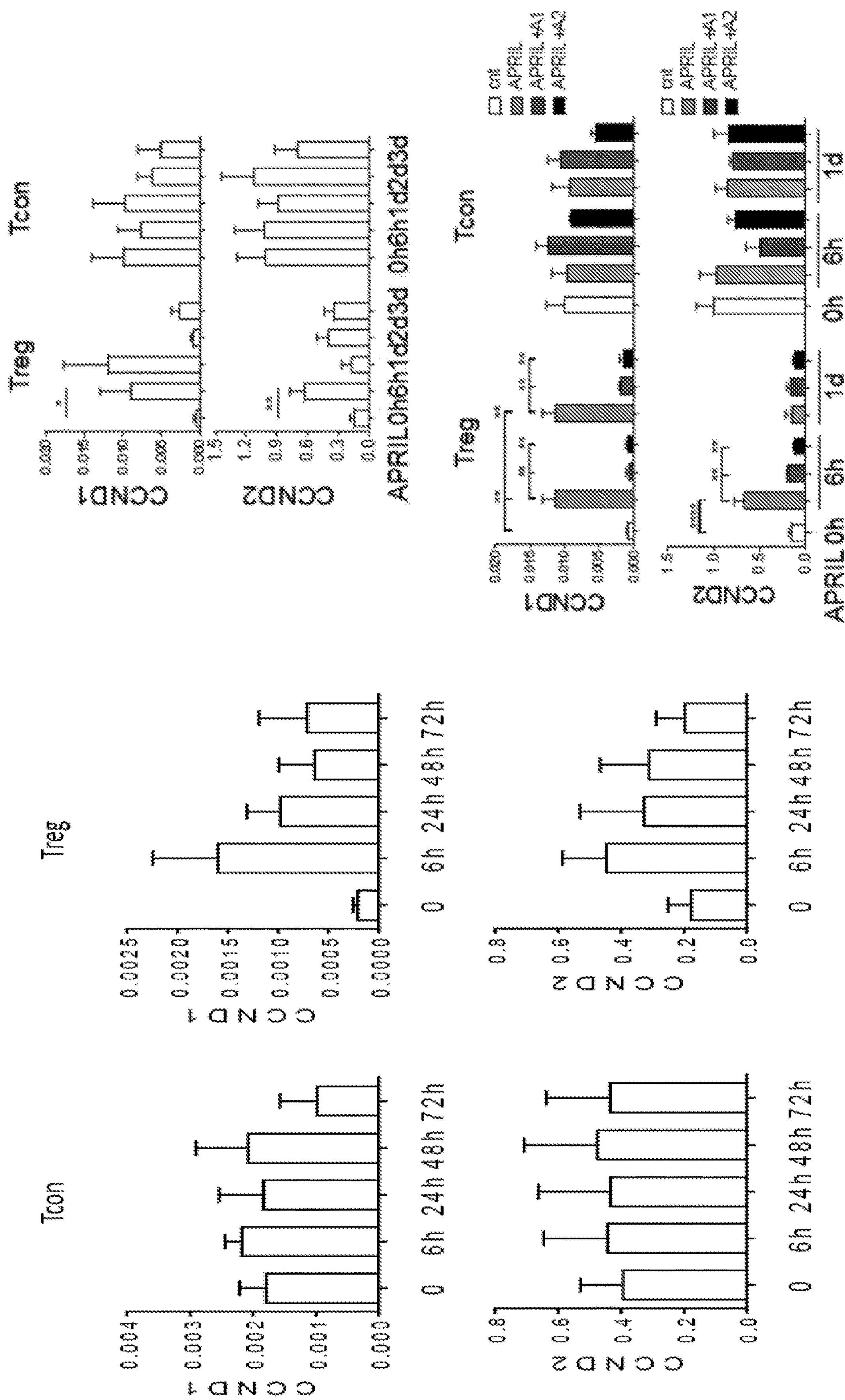
FIG. 15C shows that APRIL induces expression of CCND1 and CCND2 in TACI-expressing Tregs vs. Tcons, and such induction of expression is abrogated by an antagonistic anti-APRIL antibody. Purified Tregs and paired Tcons (n=5) were incubated with APRIL for various time periods. Expression levels of CCND1 and CCND2 were then determined using qRT-PCR normalized by internal controls GAPDH. Blocking anti-APRIL mAbs (A1, A2) were added to APRIL-containing media for 6 hours and 1 day. cnt, control media; A2, clone Aprily-1-1. * $p<0.02$;  $p<0.005$; ** $p<0.0001$.
Figure 15D:
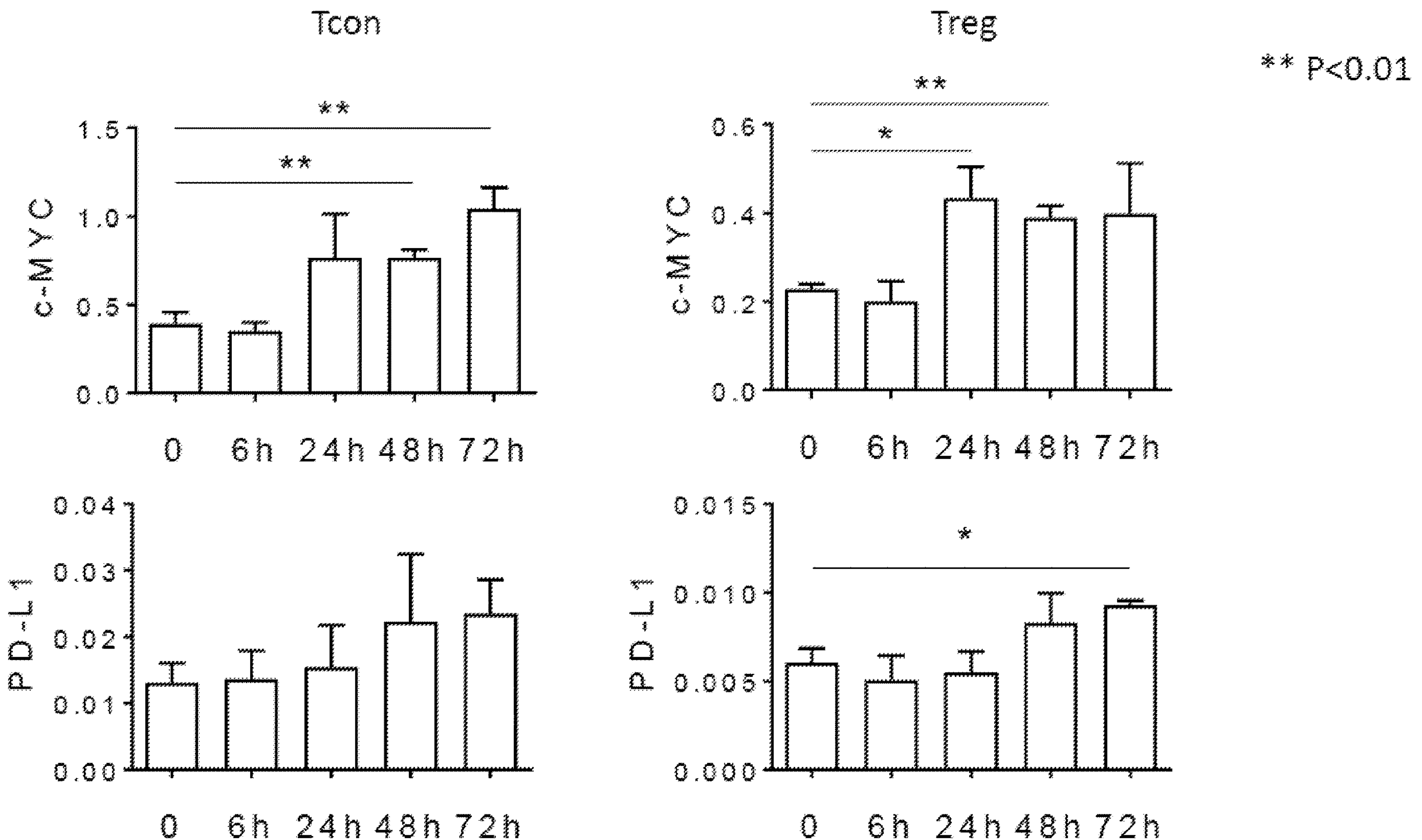
FIG. 15D shows that APRIL induces expression of PD-L1 in TACI-expressing Tregs vs. Tcons.

TACI protein levels are significantly elevated on Tregs when compared with autologous Tcons in both PB and BM compartments from the same MM patient (n=9, p<0.02) (FIG. 14). More than 4-40-fold and 3-15-fold increase in TACI MFIs were seen in Tregs vs. paired Tcons. Significantly, TACI transcripts are higher in Tregs vs. matched Tcons from normal donors (n=2. p<0.01, FIG. 13) and MM patients (n=9, FIGS. 13A and 13B, p<0.0001). Specifically, more than 4-12-fold and >17-52-fold higher levels of TACI transcripts were detected in Tregs than Tcons from normal donors and MM patients, respectively. Elevated levels of Foxp3 (>7-16 fold) and CTLA-4 (>3-9-fold) were confirmed in Tregs vs. paired Tcons. TACI levels are significantly correlated with CTLA-4 (r=0.9715, p<0.0001). Additional negative immune regulators including TGF (p<0.0001, FIG. 13) and IL-10 (p<0.0003, FIG. 34) are significantly increased in Treg vs. paired Tcon of MM patients (FIGS. 13A and 13B). More than 3-34-fold and 2-32-fold higher TGFβ and IL-10 were found in Treg than Tcon, respectively. Thus, mRNA and protein and transcript of TACI are expressed at significantly increased levels in Tregs vs. Tcons from the same individual.

Example 4: APRIL Significantly Supports Viability and Blocks Apoptosis of Tregs, Dependent on TACI-Mediated Induction of Key Growth and Survival Genes To determine whether TACI expression is functional on Tregs, APRIL was added to freshly purified Tregs vs. autologous Tcons, followed by luminescence-based cell viability and [$^3$H] thymidine incorporation assays. Tregs and Tcons were cultured in media containing low IL-2 (5 ng/ml) without CD3/CD28 beads to determine whether APRIL affects Tregs following binding to TACI. APRIL, in a time dependent manner, promoted viability of Tregs vs. Tcons from the same individual (MM patient and normal donors in FIG. 23). Furthermore, APRIL significantly inhibited caspase 3/7 and caspase 8 activity in Treg vs. Tcon from MM patients, indicating that APRIL blocks apoptosis in Tregs (FIG. 23). Conversely, antagonistic anti-APRIL monoclonal antibodies (mAbs) abrogated APRIL-induced growth/proliferation and survival of Tregs. An anti-TACI blocking mAb only significantly neutralized APRIL-induced effects on Tregs but not Tcons (FIG. 23A).

Using quantitative qRT-PCR, key growth and survival genes were next assayed in Tregs compared with Tcons purified from the same individual (n>3) and cultured in low dose IL-2 culture media, with or without APRIL. Following 6 hours of incubation, APRIL significantly induced expression of cell cycle progression genes CCND1 and CCND2, as well as anti-apoptotic genes BCL2 and BCL2L1/BCLxL, in Tregs but not Tcons (FIG. 15). Addition of APRIL every other day further sustained upregulation of these target genes in Tregs vs. Tcons (data not shown). Neutralizing anti-APRIL mAbs completely blocked APRIL-induced expression of these target genes (FIG. 15), confirming specific TACI dependency in Tregs vs. autologous Tcons in response to APRIL stimulation. Furthermore, these results confirmed that freshly isolated Tcons (CD4+CD25−) barely express TACI (FIG. 34).

Figure 16B:
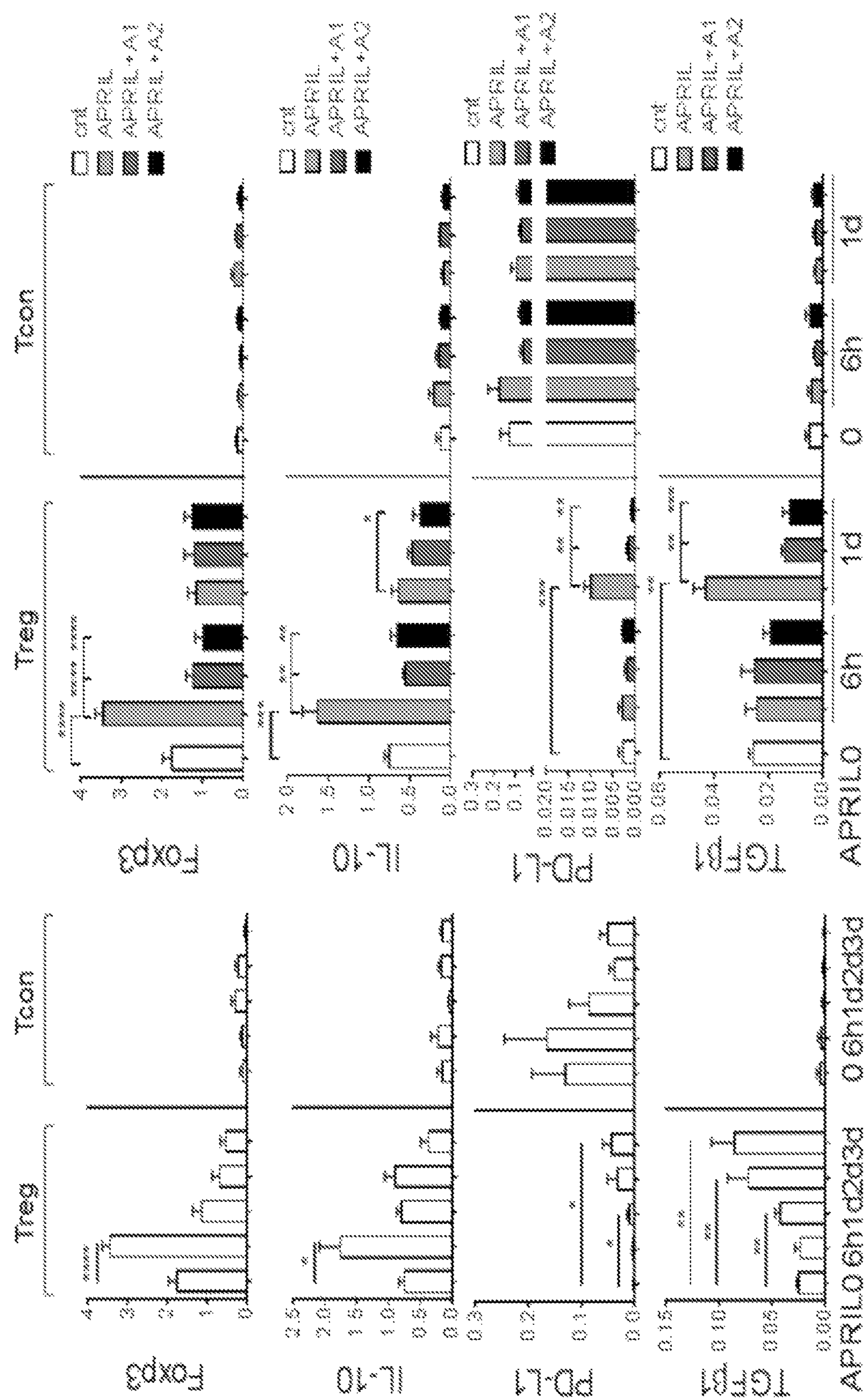
FIG. 16B shows that APRIL selectively induces immune regulatory and suppressive genes in Treg but not paired Tcon. Specifically, APRIL induces expression of Foxp3, IL-10, PD-L1, and TGFβ1, and such induction of expression is abrogated by an antagonistic anti-APRIL antibody. Treg and Tcon cells freshly purified from the same individual (n=5) were incubated with APRIL, alone (left) or in the presence of antagonistic anti-APRIL mAbs (A1, A2; right), for the indicated time periods. cnt, control media. Expression levels of indicated genes by qRT-PCR were normalized by internal controls GAPDH and 18S. *$p<0.05$, $p<0.01$, *$p<0.001$, ****$p<0.0001$.

Example 5: APRIL Signaling Through TACI Significantly Induces Immune Suppressive Genes in Tregs, Thereby Enhancing Inhibitory Effects of Tregs on Autologous Tcons In order to determine whether APRIL modulates immunoregulatory function of Tregs, the changes in the expression of key suppressive molecules in Tregs following APRIL stimulation were examined. More than 11-, 4-, and 5-fold higher mRNA expression of Foxp3, IL-10, and TGFβ were seen in Treg vs. Tcon, respectively (FIG. 16B). Importantly, APRIL enhanced gene expression of Foxp3 and IL-10 at the 6 hour time point in Tregs, whereas APRIL upregulated gene expression of PD-L1 and TGFβ1 from day 1 to day 3 (FIG. 16). In contrast, APRIL did not induce expression of these immune inhibitory cytokines and the checkpoint genes in paired Tcons. In the presence of antagonistic anti-APRIL mAbs, APRIL-triggered increased expression of Foxp3, IL-10, TGFβ1, and PD-L1 are completely blocked at hour 6 and sustained to 1 day after treatments (FIG. 16). Thus, APRIL selectively augments critical immune suppressive cytokine and checkpoint genes in Tregs, but not Tcon. These data further indicate that TACI expression specifically mediates APRIL-induced immune suppressive action of Tregs.

Example 6: APRIL Enhances Treg-Mediated Inhibition of Tcon Proliferation Via TACI Next, the effect of APRIL on Treg-mediated inhibition of T con proliferation was examined. APRIL was added to cocultures of purified Tcons pre-labeled with CFSE and stimulated with CD3/CD28 microbeads at various ratios of autologous Tregs to Tcons. Using flow cytometric analysis to determine percent CFSE-diluted Tcon representing fractions of the proliferative Tcons, the addition of Treg to Tcon (1:1) completely blocked proliferation of Tcons (FIG. 27). With lower ratios of Tregs to Tcons, the inhibition by Treg of Tcon proliferation was proportionally reduced. At the lowest ration of Treg to Tcon (1:16), Tregs did not inhibit proliferative Tcons (FIG. 27). Importantly, APRIL potentiated Treg inhibition of Tcon growth, in a dose- and time-dependent manners (FIG. 27). Conversely, antagonistic anti-APRIL mAbs overcame APRIL-enhanced Treg suppression of Tcon proliferation (FIG. 27). These results further confirm that APRIL action on Tregs (interaction via TACI) further enhances their suppression of paired Tcons.

Figure 17:
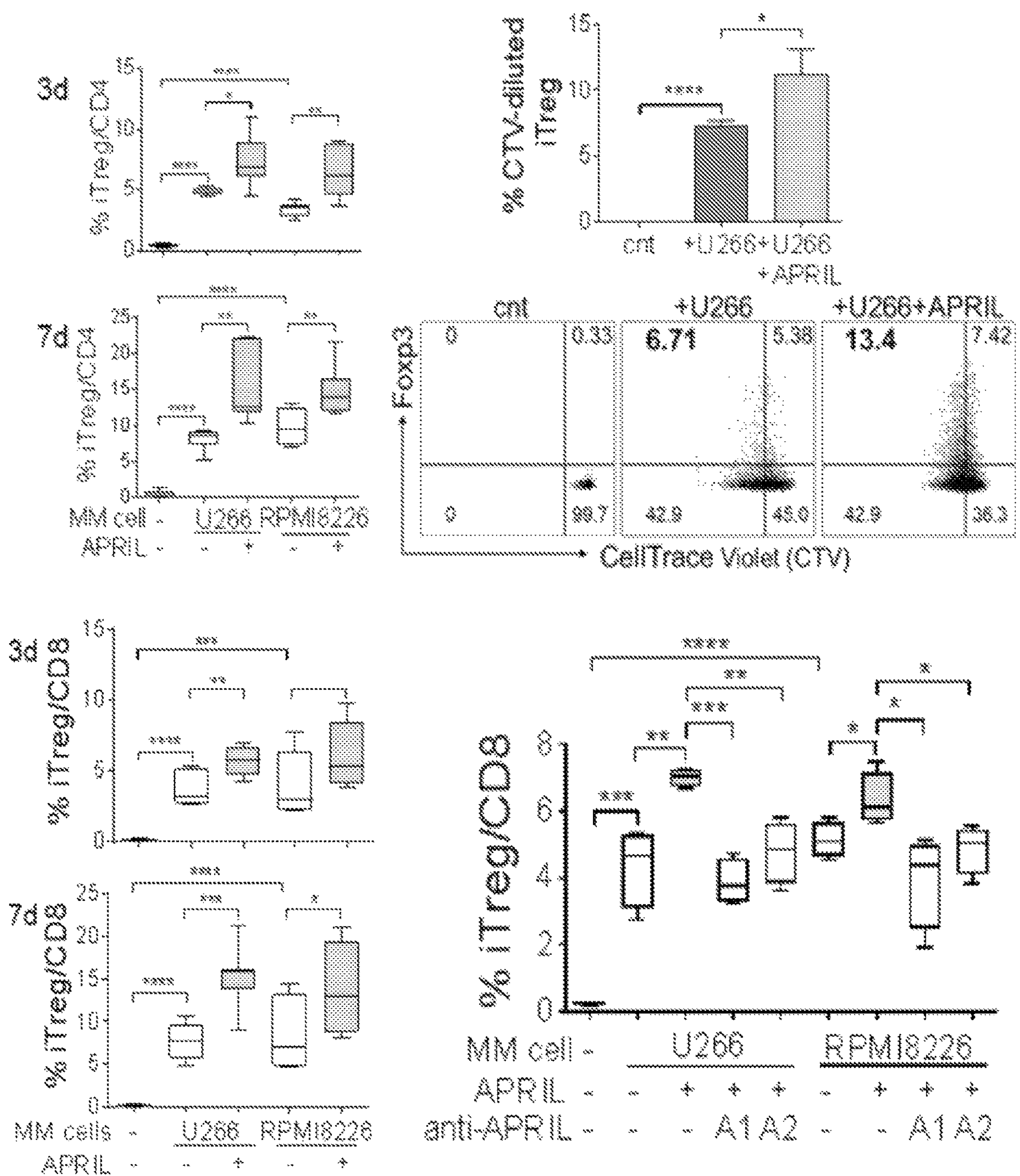
FIG. 17 shows that APRIL selectively enhances MM cell-induced iTregs in CD4+ and CD8+ subsets in ex vivo cocultures, which is blocked by anti-APRIL antibody. Mitomycin C-pre-treated U266 or RPMI8226 MM cells were washed and cocultured with T cells in the presence of APRIL for 3 days and 7 days. Neutralizing anti-APRIL mAbs (A1 or A2) were also added as indicated. Percentages of CD4+CD25+Foxp3+ iTreg gated in CD4 T cells were determined by flow cytometry analysis. Tcons were pre-stained with Cell Trace Violet (CTV) and cocultured with U266 MM cells in APRIL-containing media. Shown are percentages of CTV-diluted iTreg (CTV−Foxp3+) (n=4) and the dot plots of a representative experiment. Percentages of iTreg gated in CD8 T cells were also measured in the same cocultures as above. Dot plots of an additional representative experiment showed the proliferative iTreg (CTV−Foxp3+CD4+) was induced by U266 MM cells from 0 to 4.17%, which was further enhanced by APRIL from 4.17 to 8.02%. Shown are percentages of CTV-diluted iTreg (CTV−Foxp3+). Percentages of resting vs. proliferative iTreg and paired Tcon in CD4+T (n=3) were determined under indicated conditions as above. APRIL selectively increased % CTV− CD4+Foxp3+ iTreg induced by MM cells.* $p<0.05$, $p<0.01$, *$p<0.001$, ****$p<0.0001$.
Figure 17:
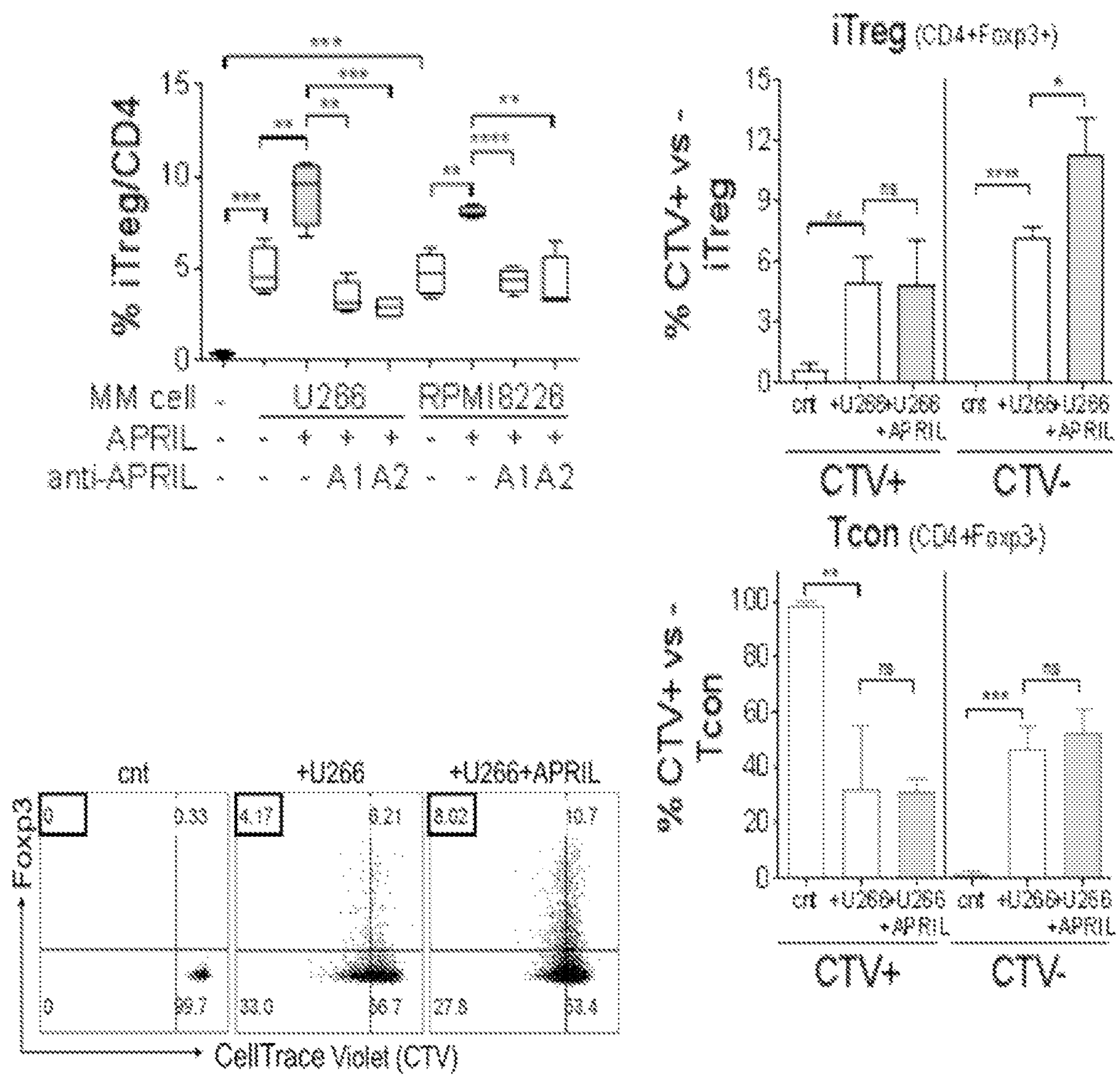
Figure 18:
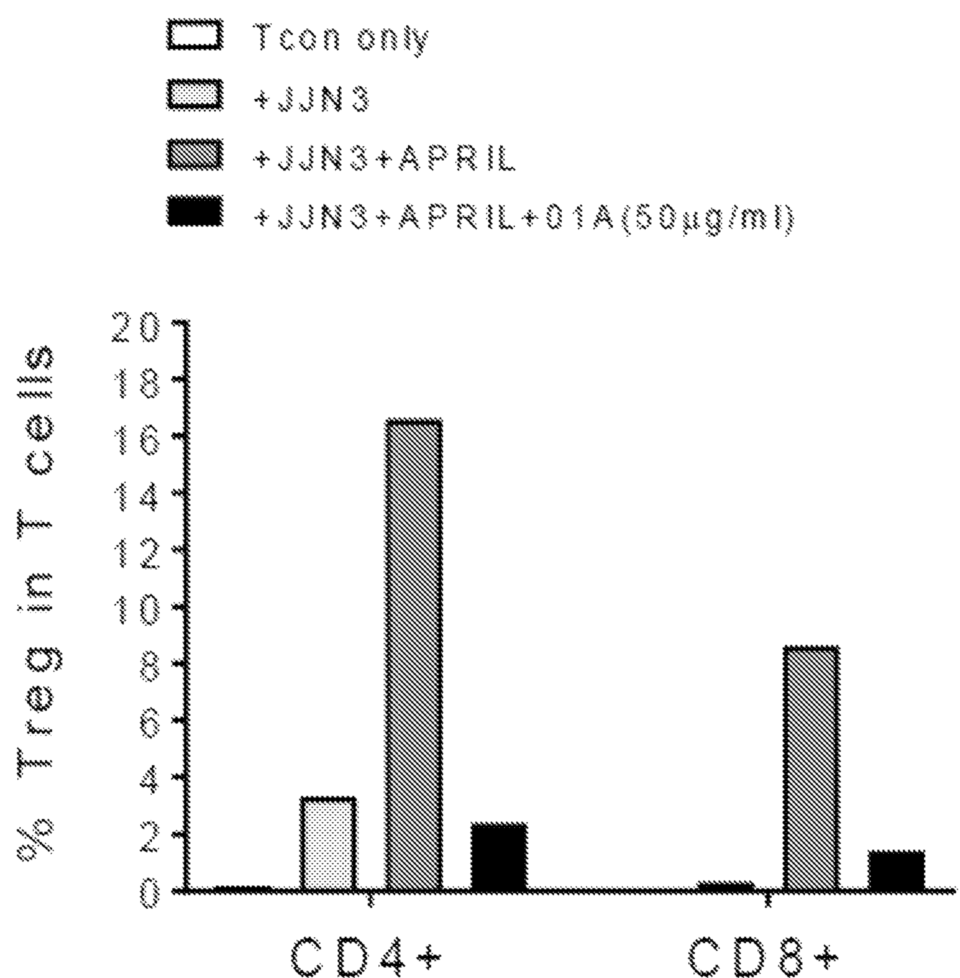
FIG. 18 shows that 01A blocks APRIL-increased iTreg induced by MM cells in CD4+ and CD8+ subsets.
Figure 19:
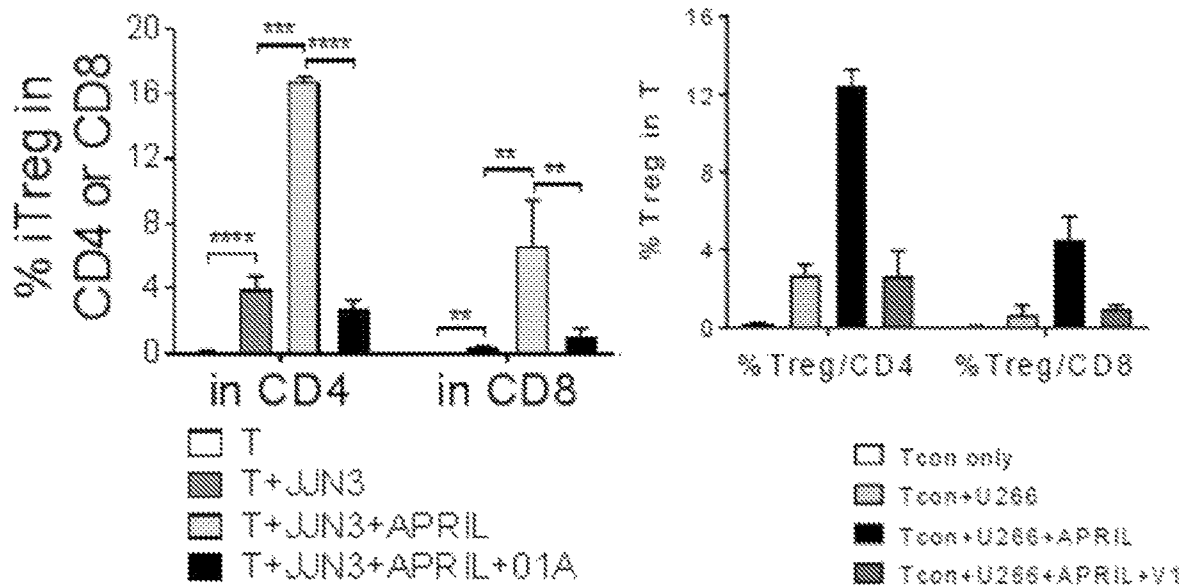
FIG. 19 shows that APRIL upregulates MM cell-induced iTreg, which is blocked by blocking anti-APRIL mAb. JJN3 and U266 MM cells were each cocultured with CD3 T for 4 days. Proportions (%) iTreg within CD4+ and CD8+ T cells were determined. * p<0.05,  p<0.01, * p<0.001, **** p<0.0001.

Example 7: Generation of Functional Treg (iTreg) Induced by MM Cells is Further Augmented by APRIL Dependent on Increased iTreg Proliferation Next, the effect of APRIL on generation of MM-induced iTreg from CD3 T cells, analogous to increased Tregs during disease progression, in ex vivo co-cultures was examined. Following 3 days of cocultures, MM cells (i.e., U266, RPM18226, JJN3), pretreated with mitomycin C to stop their proliferation, significantly induced the percent iTreg (CD25+Foxp3+) to >10-25-fold within CD4+T subset (FIG. 17). The percentages of iTregs continued to rise at day 7 (FIG. 17). Fractions of CD8 iTreg (CD8+CD25+Foxp3+) were also significantly increased to >1−log (FIGS. 17 and 19). APRIL further augmented generation of iTreg within both CD4+ and CD8 T cells at day 3 and continued to day 7 in ex vivo cocultures of MM cells with T cells (FIG. 17). APRIL triggered >1.5-4-fold increases in iTreg in CD4 T cells, compared with control media. Conversely, anti-APRIL m Abs specifically blocked APRIL-enhanced iTreg induced by MM cells.

To further define the mechanisms of APRIL-enhanced MM-induced iTreg, Tcon cells (CD4+CD25−) were pre-labeled with CellTrace Violet (CTV) prior to cocultures with U266 MM cells, with or without APRIL. By quantifying the percent CTV−T cells, MM cells were demonstrated to significantly stimulate the proliferative iTreg cell fraction (FIG. 17). MM cells significantly stimulated proliferative iTreg cell fraction. The percent CTV−Foxp3+CD4+CD25+ was increased from 0% to 7.24±027% (n=3, p 0.0001) following 7 days of cocultures (FIG. 17). A representative dot plot (FIG. 17) showed an increase from 0 to 6.71% and from 0.33 to 538% in percentages of proliferative iTreg and resting iTreg (CTV+Foxp3+CD4+CD25+), respectively. Importantly, APRIL further upregulated percent proliferative iTreg from 6.71 to 13.4% (FIG. 17). Three repeated experiments show that APRIL further increased proliferative iTreg from 7.24±0.27% to 11.28±1.1 (n=3, p<0.02) (FIG. 17). A slight increase in the resting iTreg fraction following APRIL treatment did not reach statistical significance when compared with untreated groups (FIG. 17). In contrast, the proliferative Tcon (CTV−Foxp3−CD4+) fraction remained unchanged or slightly decreased (FIG. 17). Furthermore, TACI MFIs remain highest on iTreg, and APRIL did not further increase TACI on iTreg in ex vivo cocultures (data not shown). Conversely, anti-APRIL mAbs specifically blocked APRIL-enhanced iTreg induced by MM cells (FIG. 17).

Example 8: Upregulation of IL-10 and TGFβ are Critical Mediators of APRIL-Triggered Immune Suppression in MM Cell-Induced iTreg, and APRIL Triggers Immune Suppressive Effects in MM Cell-Induced iTreg in IL-10-Dependent and -Independent Mechanisms To confirm that APRIL enhanced iTreg function, iTreg was purified from ex vivo cocultures and its inhibition on the proliferation of Tcons was assessed. At high ratio of iTreg to Tcon, iTregs significantly blocked the growth of autologous Tcons (data not shown), consistent with previous reports (Feng et al. (2017) *Clin. Cancer Res.* 23:4290-4300; Frassanito et al. (2015) *Eur. J. Haematol.* 95:65-74). While cultures at lower iTreg to Tcon ratios (1:16) did not change growth of Tcon, the addition of APRIL resulted in iTreg-dependent blockade on Tcon proliferation (p<0.005, FIG. 17). Conversely, neutralizing anti-APRIL mAbs overcame APRIL-enhanced suppressive effects of iTreg on Tcon.

Figure 20B:
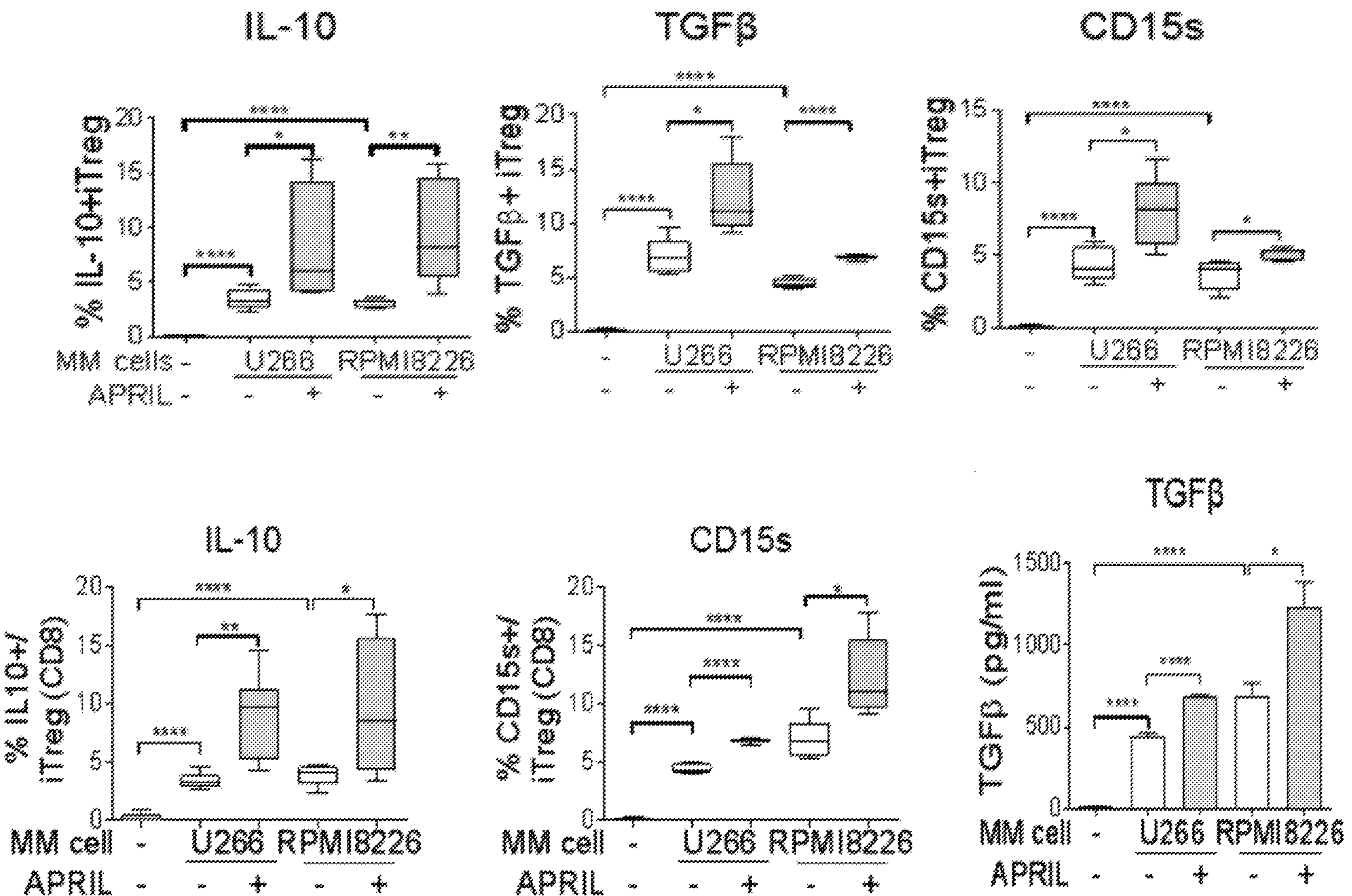
FIG. 20B shows that APRIL selectively induces immunosuppressive markers in MM cell-induced iTreg. Specifically, APRIL induces gene expression of IL-10, TGFβ, and CD15s in MM-induced iTreg (CD4+) and iTreg (CD8+). Three potential Treg suppressive markers were assessed in CD4+ iTregs in the presence or absence of APRIL (upper panel). IL-10 and CD15s were also evaluated in CD8+ iTregs, from the same cultures (lower panel). TGFβ levels were also determined by ELISA in the supernatant of cocultures in the same co-cultures. * p<0.05,  p<0.01, * p<0.001, **** p<0.0001.

Next, the effect of APRIL on the expression of immune inhibitory cytokines in Tregs, which could further enhance the suppression of Tcon, was examined. It was further showed that percentages of IL10+ and TGFβ+ iTreg within CD4 T cells were significantly increased when compared with control T cells in the absence of MM cells (p<0.0001, FIG. 20B). Importantly, APRIL further augmented the percent IL10+ TGFβ+ iTreg (p<0.05, FIG. 20). CD15s (sialyl Lewis x), another highly specific marker of activated and most suppressive effector Treg (Miyara et al. (2015) *Proc. Natl. Acad. Sci. U.S.A.* 112:7225-7230), was also significantly increased in iTregs. Fractions of IL10+ and CD15s+ CD8+ iTreg were similarly increased by APRIL (FIG. 20B). TGFβ secretion was significantly increased by APRIL in ex vivo cocultures (FIG. 20B). These data strongly indicate that IL-10, TGFβ, and CD15s regulate APRIL-enhanced immune suppressive capabilities of MM cell-induced iTreg.

Figure 21A:
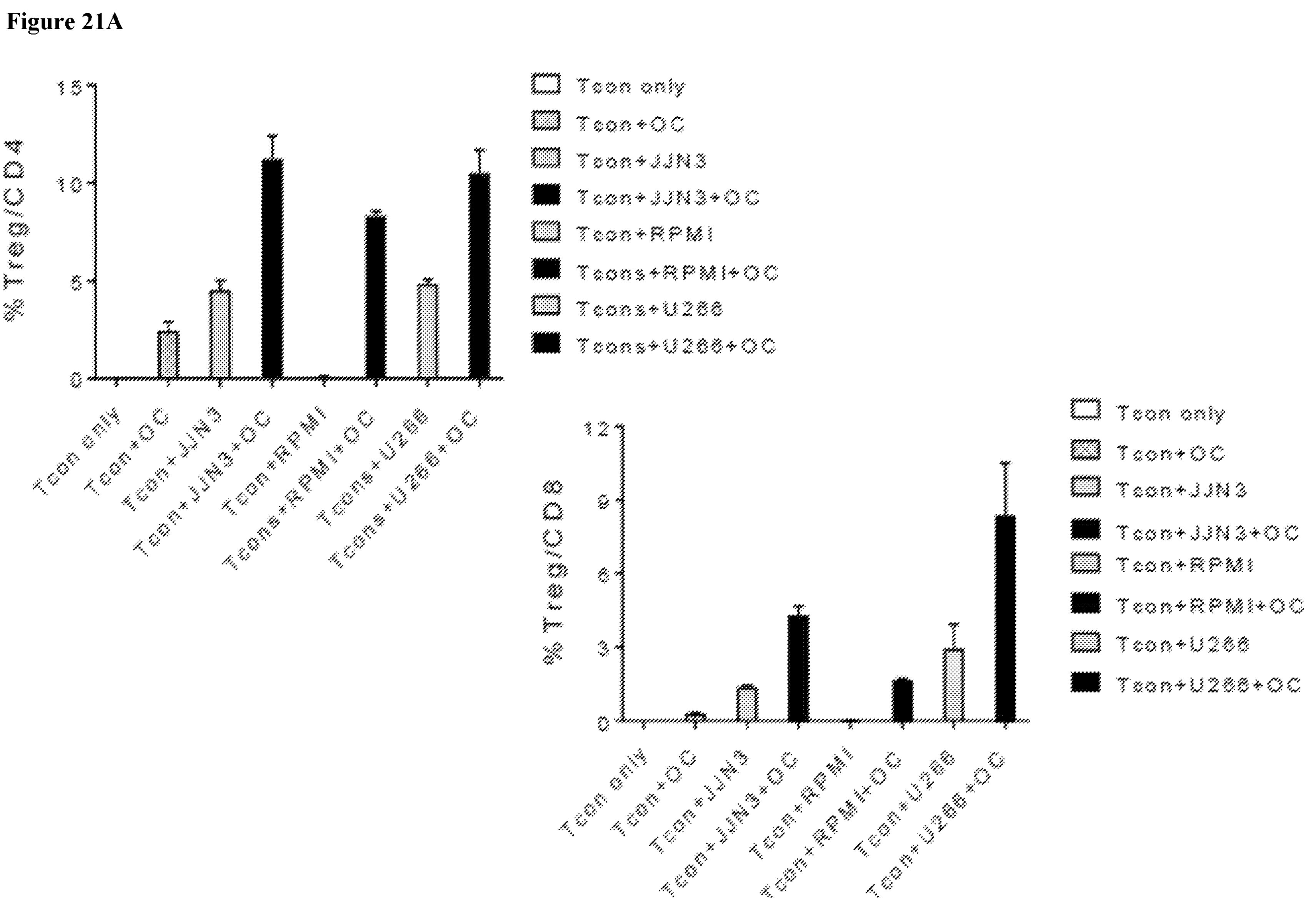
FIG. 21A shows that OC further upregulates iTreg induction by MM cells in the co-cultures.
Figure 21B:
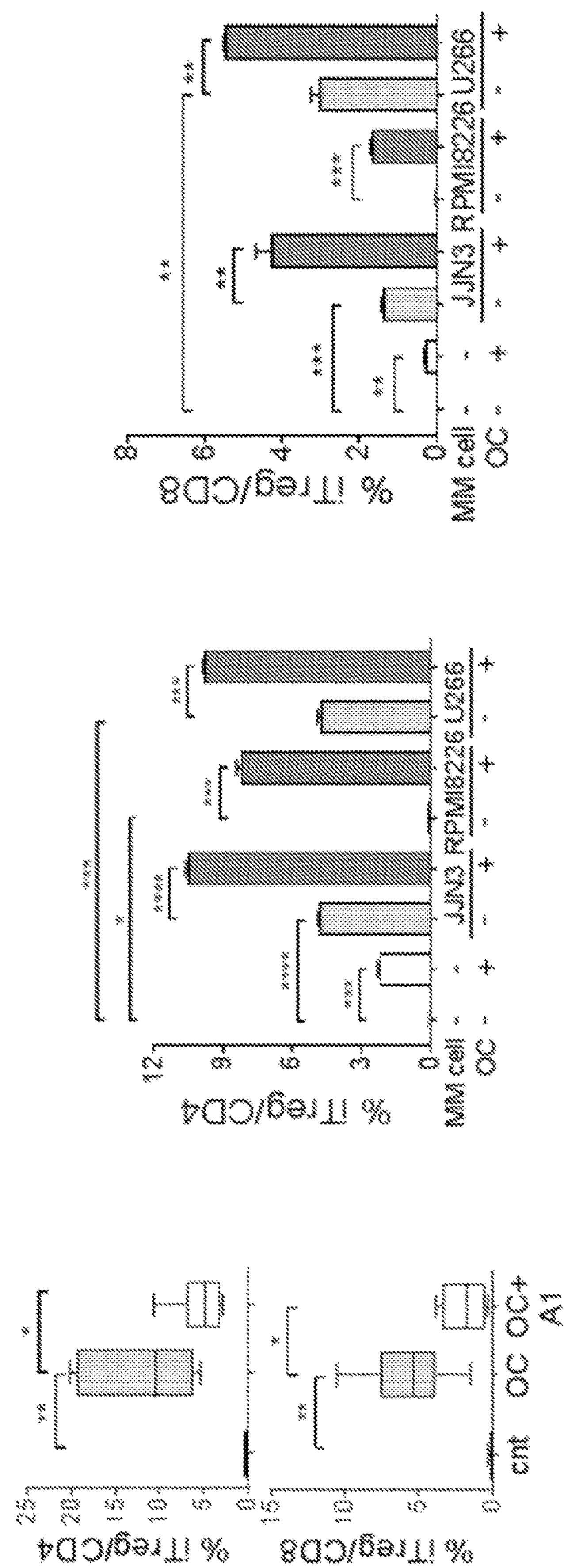
FIG. 21B shows that OC further upregulates iTreg induction by MM cells in the co-cultures via cell-cell contact and APRIL-dependent manners. iTreg induction is abrogated by an antagonistic anti-APRIL antibody. Osteoclasts (OC) were differentiated from CD14+ cells following 3-week stimulation with M-CSF and RANKL and then co-cultured with autologous T cells for 7 days in the presence or absence of anti-APRIL mAbs (A1, 10 g/ml). Generation of iTreg was determined by gating CD25+Foxp3+ in CD4+ and CD8+ T cells. CD3 T cells were cocultured with OCs from the same donors for 7 days. Using flow cytometry analysis, percentages of CD25+Foxp3+ iTreg in CD4+ or CD8+ T cells were also determined in the same cocultures. When noted, A1 (50 μg/ml) was added. *p<0.05, p<0.01, *p<0.001, ****p<0.0001.
Figure 21C:
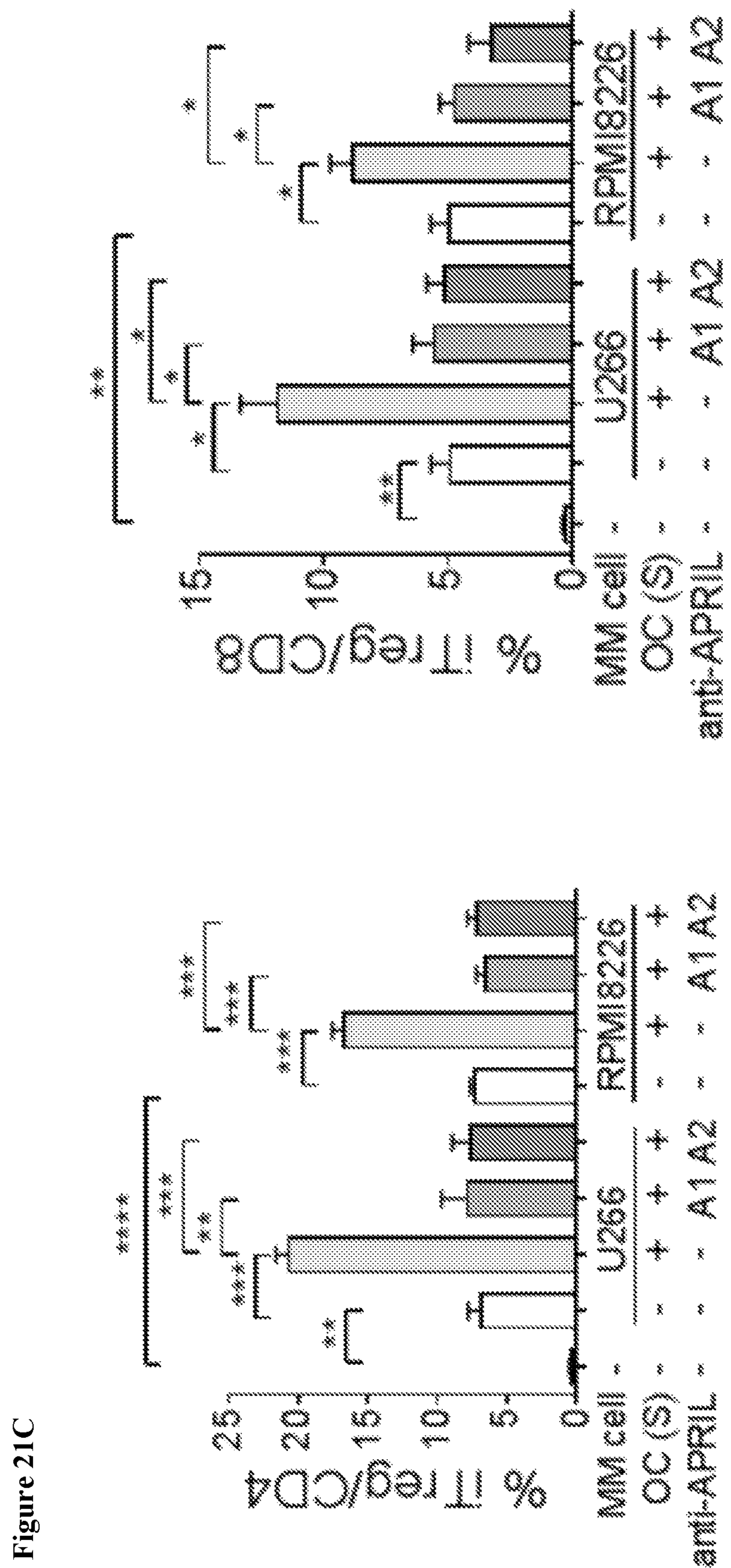
FIG. 21C shows that OC culture supernatant upregulates iTreg induction by MM cells, which is specifically blocked by an antagonistic anti-APRIL antibody. Osteoclasts (OC) were differentiated from CD14+ cells following 3-week stimulation with M-CSF and RANKL and then co-cultured with autologous T cells for 7 d in the presence or absence of anti-APRIL mAbs (A1, 10 g/ml). Generation of iTreg was determined by gating CD25+Foxp3+ in CD4+ and CD8+ T cells. CD3 T cells were cultured in the supernatants (S) from 3-week OC cultures from the same donors for 7 d. Using flow cytometry analysis, percentages of CD25+Foxp3+ iTreg in CD4+ or CD8+T were also determined in the same cocultures. When noted, A1 or A2 (50 μg/ml) was added. * p<0.05, p<0.01, *p<0.001, ****p<0.0001.
Figure 21D:
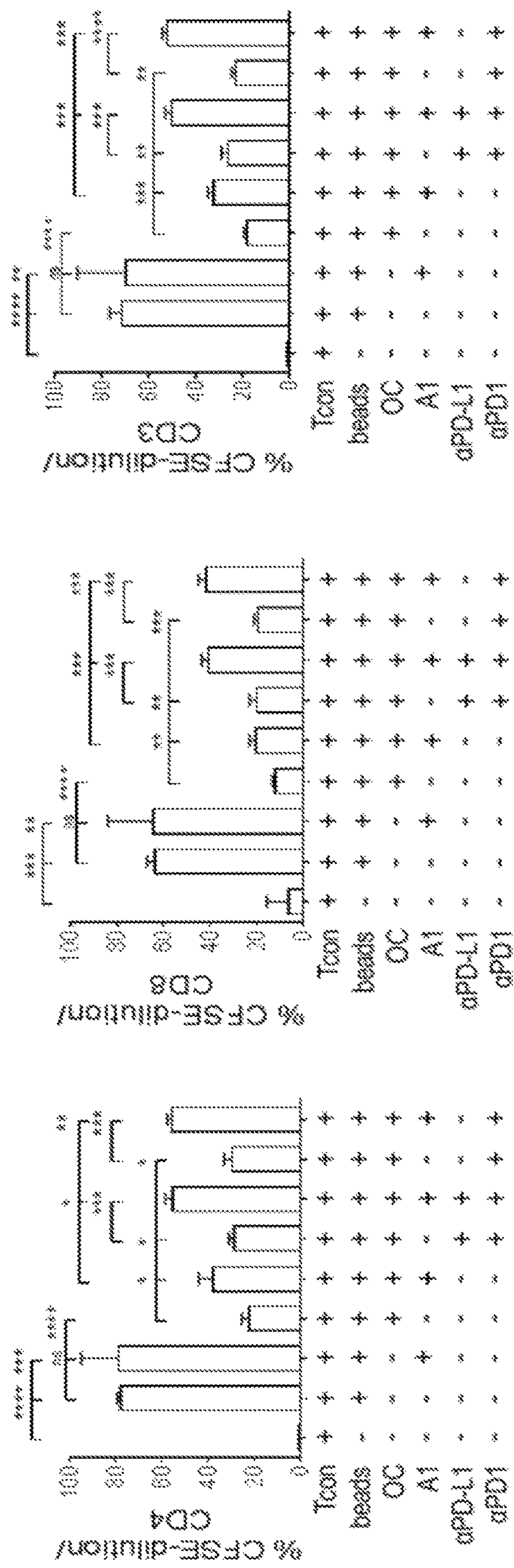
FIG. 21D shows that Tcon proliferation is inhibited by co-culturing with autologous OC. This inhibition is abrogated by an antagonistic anti-APRIL antibody, and to a greater extent by a combination of anti-APRIL antibody, anti-PD1 antibody, and anti-PD-L1 antibody. CD3 T cells, pre-stained with CFSE, were co-cultured with OCs from the same donor under indicated conditions for 7 days followed by flow cytometric analysis to determine fractions of proliferative Tcons. When noted, antagonistic anti-APRIL mAbs A1 or A2 (50 μg/ml) or anti(α)-PD-1 anti(α)-PD-L1 mAbs (10 μg/ml) were added. *p<0.05, p<0.01, *p<0.001, ****p<0.0001.
Figure 22:
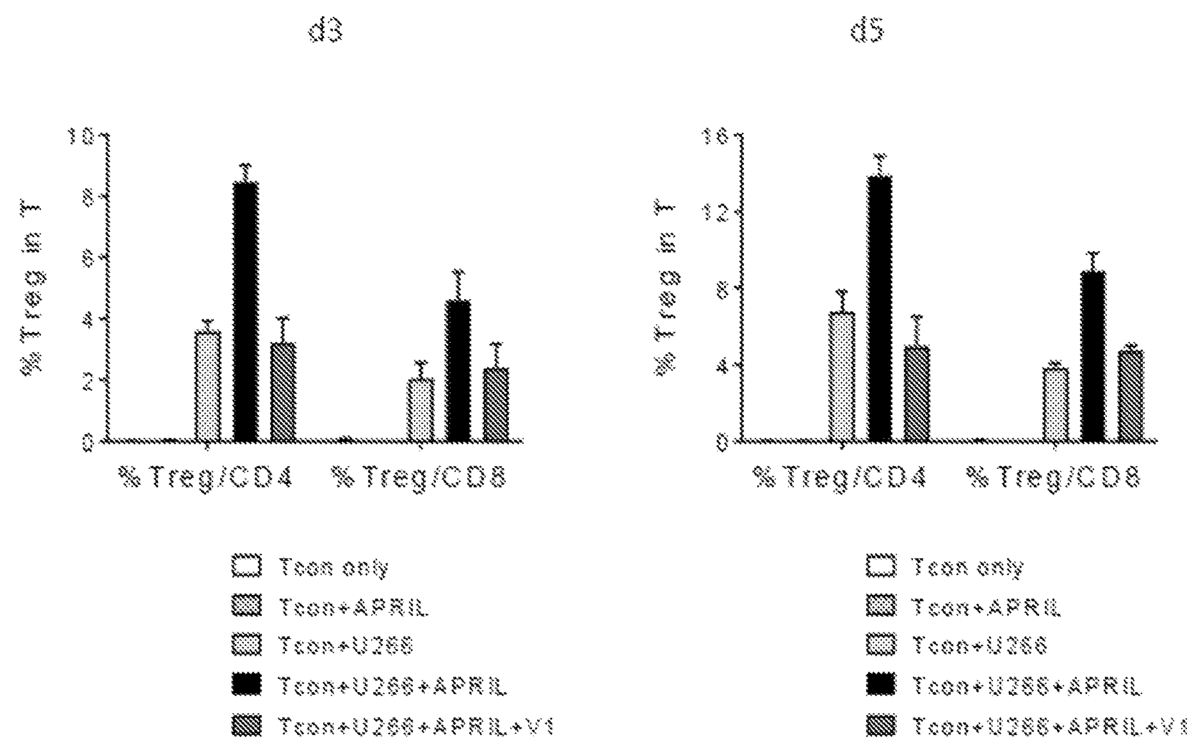
FIG. 22 shows that APRIL increases MM cell-induced iTreg ex vivo, which is blocked by blocking anti-APRIL mAb.

Example 9: Anti-APRIL mAbs Block OC-Induced iTregs, and Tregs Contribute to Osteoclast (OC)-Induced Immune Suppression on Tcons The effect of OCs on iTreg suppression of Tcon was examined. It was examined whether OCs induce iTreg to block Tcons. It was further confirmed whether APRIL and PD-L1, which are produced by OCs (Tai et al. (2016) *Blood* 127: 3225-3236; An et al. (2016) *Blood* 128: 1590-1603), regulate OC suppression on Tcons. OCs significantly induced generation of CD4+ and CD8+ iTreg from T cells following 7 days of cocultures (FIG. 21). Antagonistic anti-APRIL mAb partially reduced OC-induced iTregs. OC culture supernatants further upregulated MM cell-induced CD4+ and CD8+ iTreg cells, which was specifically and significantly blocked in the presence of anti-APRIL mAbs (FIG. 21). Percentages of MM-induced iTreg were further increased when T cells were co-cultured with MM cells and OCs (FIG. 21). Thus, OCs further enhance MM-induced iTreg via APRIL and cell-cell contact. OCs inhibited expansion of Tcons whereas anti-APRIL, or -PD1, or -PD-L1 mAbs partially reverted OC-inhibited Tcon proliferation (FIG. 21D). Furthermore, combined treatments of anti-APRIL with either -PD1 or -PD-L1 further overcame OC suppression on Tcons. These results indicate that OC-downregulated Tcon number is mediated by increased Tregs and soluble factors including APRIL and PD-L1.

Example 10: APRIL Affects Function of BM-Derived MM Bregs Via TACI

Since Bregs can regulate Treg immunobiology and that BM-derived Bregs (CD19+CD24$^{high}$CD38$^{high}$) closely interact with MM cells in the BM microenvironment to mitigate and can abrogate responses to monoclonal antibody (i.e., elotuzumab) treatment (Zhang et al. (2017) *Blood Cancer J.* 7:e547), the expression of TACI on Bregs from MM patients was examined. Bregs, when compared with naïve B cells (CD19+CD24low/− CD38low), showed a significantly elevated TACI levels (p<0.02, FIG. 24B). BCMA is undetectable in Breg, naïve B, and memory B (CD19+CD24highCD38low/−) cells (data not shown). Following treatment with lipopolysaccharides (LPS) which significantly induces IL-10 production from Breg (Zhang et al. (2017) *Blood Cancer J.* 7:e547), TACI levels are significantly increased in Bregs (p<0.02) but not in naïve and or memory B cells.

BM mononuclear cells (BMMCs) from MM patients were further incubated with APRIL in the presence or absence of inhibiting anti-APRIL mAb, followed by flow cytometry analysis to quantitate percent Breg in B cells and percent IL-10 production in Bregs. APRIL significantly upregulated percent Breg in B cells (FIG. 24A) from 14.59±1.36% to 25.2±0.69% (p=0.0004, n=4, FIG. 24). Importantly, APRIL further increased functional Bregs as IL-10 production in Bregs was significantly enhanced from 15.02±0.88% to 29.22±3.33% (p<0.007, FIG. 24). Conversely, an anti-APRIL mAb abolished APRIL-induced increases in Breg number and IL-10 production.

Based on the description provided herein, a new function of APRIL signaling via TACI is identified herein. APRIL signaling via TACI in Tregs and Bregs of MM patients inhibit effector T cells, thereby promoting an immunosuppressive BM microenvironment. APRIL, abundantly secreted from MM-promoting OCs, significantly upregulates pro-survival and proliferative, as well as suppressive, capabilities of Tregs dependent on TACI. APRIL selectively enhances MM cell- and OC-driven iTregs to potentiate their inhibitory effects on Tcons by upregulating immune suppressive molecules including Foxp3, IL-10, TGFβ, PD-L1, CD15s. Conversely, blocking the APRIL-TACI axis using antagonistic anti-APRIL mAbs, alone and with PD1/PD-L1 checkpoint inhibitors, downregulates these immune regulatory cells, thereby alleviating the suppressive BM microenvironment.

First, Tregs (CD4+/CD8+CD25+FOXP3+) were shown to have significantly elevated TACI when compared with matched Tcons (CD4+/CD8+CD25−) freshly harvested from the same individuals. Increased TACI protein and mRNA in Tregs vs. paired Tcons is further confirmed by significantly increased expression of genes critical for Treg identify and function such as Foxp3, CTLA-4, TGFβ, and IL-10. Importantly, TACI levels are highly correlated with CTLA-4 (r=0.9715, p<0.0001), indicating that TACI may directly regulate the immune suppressive function of Tregs. TACI expression is also significantly higher on IL-10+ Foxp3−CD4+ T cells when compared with IL-10-Foxp3−CD4+ T cells (FIG. 34). The IL-10+Foxp3−CD4+ subset is as small as the IL10+Foxp3+CD4+ subset (~<24%) when compared with IL-10−Foxp3−CD4+(>95%) within CD4+ T cells. This small sub-population of T cells (IL-10+Foxp3−) can inhibit the proliferative Tcons (CD4+CD25−) in an IL-10-independent manner and with similar efficiency as CD4+CD25+Foxp3+ Tregs (Vieira et al. (2004) *J. Immunol.* 172:5986-5993). Although TACI is also induced in activated Tcon cells, TACI levels are significantly higher on immunosuppressive Tregs than activated Tcons. Regardless of their origin, these results further indicate that Tregs comprise diverse and heterogeneous subsets with multiple markers. Importantly, the APRIL-dependent mechanisms of Treg immunobiology is delineated herein, which will provide the framework for novel cancer immunotherapies.

APRIL significantly stimulates proliferation and survival of Tregs via TACI-dependent induction of genes including CCND1/2, BCL2, BCL2L1/BCLxL. Importantly, APRIL increased growth and survival in Tregs vs Tcons were inhibited by neutralizing anti-APRIL and -TACI mAbs. APRIL further protects Tregs by inhibiting caspase 3/7 and 8 activities, as well as inducing anti-apoptotic molecules. Most importantly, APRIL augments the production of immune inhibitory factors in Tregs including Foxp3, IL-10, TGFβ, and PD-Li. In contrast, these essential Treg-related genes are expressed only at low levels in Tcons purified from the same individual, and their expression is unaffected by APRIL. As expected, Tregs abrogate the proliferation of autologous Tcons stimulated with CD3/CD28 beads in a Treg to Tcon ratio-dependent manner. APRIL, in a dose- and time-dependent fashion, promotes suppression of Tcons by Tregs even at low Treg to Tcon ratios. Conversely, antagonistic anti-APRIL mAbs block APRIL-enhanced immune suppression induced by Tregs.

The iTregs resulting from MM cell-induced conversion from Tcons in ex vivo cocultures are as highly suppressive as nTreg (Feng et al. (2017) *Clin. Cancer Res.* 23:4290-4300; Frassanito et al. (2015) *Eur. J. Haematol.* 95:65-74; Feyler et al. (2012) *PloS one* 7:e35981; Kawano et al. (2018) *J. Clin. Invest.* DOI:10.1172/JCI88169). Importantly, the results herein demonstrate that APRIL selectively enhances iTreg-mediated inhibition of Tcon proliferation. TACI levels are significantly higher in iTregs than Tcons in cocultures with MM cells. Significantly, in the presence of MM cells, APRIL preferentially upregulates proliferation of iTreg (CD4+CD25+Foxp3+) subsets, but not the remaining Tcon (CD25−Foxp3−) (FIG. 17). It is likely that the elevated TACI protein on iTregs permits APRIL-induced downstream targets to further promote expansion of immunosuppressive iTregs. Importantly, IL-10-dependent and -independent (i.e., TGFβ1, CD15s) mechanisms occur in purified iTregs which block proliferation of Tcon from the same individual, an effect which is further potentiated by APRIL. These results confirm the importance of APRIL signaling via TACI in enhancing the immune suppressive capabilities of Tregs (both iTregs and nTregs) on matched Tcons.

It is demonstrated for the first time herein that APRIL induces Foxp3 in Tregs via TACI. Foxp3, a master transcriptional factor critical for the development, function, and lineage commitment of Tregs, has been widely used as a Treg specific marker. The results herein strongly indicate that APRIL-mediated active immune suppression is dependent on TACI expression. Neutralizing anti-TACI reagents inhibited these APRIL-induced targets. APRIL further increases TGFβ and PD-L1 at later time points, following IL-10 and Foxp3 upregulation in Tregs. Thus, APRIL, via TACI, preferentially induces multiple immune inhibitors and checkpoint molecules in Tregs to further sustain a local suppressive tumor milieu. APRIL also upregulates IL-10+ Bregs derived from MM BM via TACI, not BCMA. Since Bregs can facilitate the conversion of T cells to Tregs and inhibit effector T cells via both IL-10-dependent and -independent mechanisms (Blair et al. (2010) *Immunity* 32:129-140; Mauri et al. (2017) *J. Clin. Invest.* 127:772-779), the results herein indicate that Bregs further upregulate APRIL-induced Tregs in the MM BM milieu, at least in part, mediated by IL-10. Importantly, neutralizing anti-APRIL mAbs abrogate APRIL-induced increased Breg numbers and IL-10 production.

The results herein show that OCs, a key source of APRIL and PD-L1 in the MM BM, stimulate iTregs to suppress Tcon proliferation, establishing Treg as a crucial cellular factor mediating OC-inhibited immune suppression, as has been shown recently (An et al. (2016) *Blood* 128:1590-1603). These results, coupled with immune suppressive molecules induced in MM cells by APRIL (Tai et al. (2016) *Blood* 127:3225-3236), identify positive feedback loops between malignant PCs, Tregs, and Bregs to further exacerbate immune evasion and MM progression. The results herein further confirm an immunosuppressive role of APRIL in tumor progression and drug resistance in multiple human cancers and related animal models (Tai et al. (2016) *Blood* 127:3225-3236; Matthes et al. (2015) *Leukemia* 29:1901-1908; Planelles et al. (2004) *Cancer Cell* 6:399-408; Moreaux et al. (2004) *Blood* 103:3148-3157; Wang et al. (2013) *PloS one* 8:e55298).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web and/or the National Center for Biotechnology Information (NCBI) on the World Wide Web.

EQUIVALENTS

Those skilled in the art will recognize, or be able to ascertain using no more than routine experimentation, many equivalents to the specific embodiments of the present invention described herein. Such equivalents are intended to be encompassed by the following claims.

What is claimed is:

1. An in vitro or ex vivo method of selectively decreasing the number and/or inhibitory immune activity of Tregs and/or Bregs comprising contacting the Tregs and/or Bregs with 1) an immune checkpoint therapy comprising an anti-PD-1 antibody, an anti-PD-L1 antibody, and/or an anti-PD-L2 antibody, and 2) an antibody that blocks the interaction of TACI receptor protein expressed by the Tregs and/or Bregs with APRIL ligand and selectively decreases the number and/or inhibitory immune activity of the Tregs and/or Bregs, wherein the antibody that blocks the interaction of TACI receptor protein expressed by the Tregs and/or Bregs with APRIL ligand is an anti-APRIL antibody or an anti-TACI antibody.

2. The method of claim 1, wherein the antibody that blocks the interaction of TACI receptor protein expressed by the Tregs and/or Bregs with APRIL ligand is an anti-APRIL antibody.

3. The method of claim 1, wherein the antibody that blocks the interaction of TACI receptor protein expressed by the Tregs and/or Bregs with APRIL ligand is an anti-TACI antibody.

4. The method of claim 1, wherein the antibody that blocks the interaction of TACI receptor protein expressed by the Tregs and/or Bregs with APRIL ligand downregulates the interaction between the TACI receptor protein expressed by the Tregs and/or Bregs with APRIL ligand.

5. The method of claim 1, wherein expression of IL10, PD-L1, and/or one or more growth or survival genes selected from the group consisting of MCLA, Bc1-2, Bc1-xL, CCND1, CCND2, and BIRC3, is decreased.

6. The method of claim 1, wherein the anti-PD-1 antibody, anti-PD-L1 antibody, and/or anti-PD-L2 antibody and/or the antibody that blocks the interaction of TACI receptor protein expressed by the Tregs and/or Bregs with APRIL ligand is murine, chimeric, humanized, composite, or human.

7. The method of claim 1, wherein the anti-PD-1 antibody, anti-PD-L1 antibody, and/or anti-PD-L2 antibody and/or the antibody that blocks the interaction of TACI receptor protein expressed by the Tregs and/or Bregs with APRIL ligand is detectably labeled, comprises an Fc domain, and/or is selected from the group consisting of Fv, Fav, F(ab')2, Fab', dsFv, scFv, sc(Fv)2, and diabodies fragments.

8. The method of claim 1, wherein the anti-PD-1 antibody, anti-PD-L1 antibody, and/or anti-PD-L2 antibody and/or the antibody that blocks the interaction of TACI receptor protein expressed by the Tregs and/or Bregs with APRIL ligand is conjugated to a cytotoxic agent.

9. The method of claim 8, wherein the cytotoxic agent is selected from the group consisting of a chemotherapeutic agent, a biologic agent, a toxin, and a radioactive isotope.

10. The method of claim 1, further comprising:

a) contacting the Tregs and/or Bregs with a STING agonist;

b) contacting the Tregs and/or Bregs with an immune checkpoint inhibitor, wherein the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, IDO, IDO2, and A2aR; and/or c) contacting the Tregs and/or Bregs in the presence of cancer cells.

11. The method of claim 10, wherein the antibody that blocks the interaction of TACI receptor protein expressed by the Tregs and/or Bregs with APRIL ligand, either alone or in further combination with A) the STING agonist and/or B) the immune checkpoint inhibitor, contacts the Tregs and/or Bregs in the presence of Tcons and i) does not significantly modulate the number of the Tcons and/or ii) modulates immunomodulatory cytokine production in the Tregs and/or Bregs.

12. The method of claim 10, wherein the antibody that blocks the interaction of TACI receptor protein expressed by the Tregs and/or Bregs with APRIL ligand, either alone or in further combination with the A) the STING agonist and/or B) the immune checkpoint inhibitor, contacts the Tregs and/or Bregs in the presence of Tcons and cancer cells, and the antibody that blocks the interaction of TACI receptor protein expressed by the Tregs and/or Bregs with APRIL ligand, either alone or in further combination with the immune checkpoint inhibitor, reduces i) the number of proliferating cancer cells and/or ii) reduces the volume or size of a tumor comprising the cancer cells.

13. The method of claim 10, wherein the Tregs comprise CD4+CD25+, CD4+FOXP3+, CD4+FoxP3+IL10+, CD4+FoxP3$^{high}$IL10$^{high}$ and/or CD4+CD25$^{high}$FOXP3+Tregs.

14. The method of claim 10, wherein the Bregs comprise CD19+CD24$^{high}$CD38$^{high}$ Bregs.

15. The method of claim 10, wherein the Tcons comprise CD4+CD25−Tcons.

16. The method of claim 10, wherein the Tregs and/or Bregs are in the presence of cancer cells, wherein the cancer cells are multiple myeloma cells.

17. The method of claim 1, wherein a) the Tregs comprise CD4+CD25+, CD4+FOXP3+, CD4+FoxP3+IL10+, CD4+FoxP3$^{high}$IL10$^{high}$ and/or CD4+CD25$^{high}$FOXP3+Tregs;

b) the Bregs comprise CD19+CD24$^{high}$CD38$^{high}$ Bregs; and c) the Tcons comprise CD4+CD25−Tcons.

18. The method of claim 2, wherein a) the Tregs comprise CD4+CD25+, CD4+FOXP3+, CD4+FoxP3+IL10+, CD4+FoxP3$^{high}$IL10$^{high}$ and/or CD4+CD25$^{high}$FOXP3+Tregs;

b) the Bregs comprise CD19+CD24$^{high}$CD38$^{high}$ Bregs; and c) the Tcons comprise CD4+CD25−Tcons.

19. The method of claim 3, wherein a) the Tregs comprise CD4+CD25+, CD4+FOXP3+, CD4+FoxP3+IL10+, CD4+FoxP3$^{high}$IL10$^{high}$ and/or CD4+CD25$^{high}$FOXP3+Tregs;

b) the Bregs comprise CD19+CD24$^{high}$CD38$^{high}$ Bregs; and c) the Tcons comprise CD4+CD25−Tcons.

20. The method of claim 1, wherein the Tregs and/or Bregs are in the presence of cancer cells, wherein the cancer cells are multiple myeloma cells.

* * * * *

SEQUENCE LISTING

<160> NUMBER OF SEQ ID NOS: 24

<210> SEQ ID NO 1
<211> LENGTH: 2293
<212> TYPE: DNA
<213> ORGANISM: Homo sapiens

<400> SEQUENCE: 1
ccggaaccct gtgtgctggg gaggaatccc gcagtggccg gggggcttga ggccgctgct 60
ttgtctcttc gtccagagcc ttatgtaaga gcttttctcg ggaaacagga agtcctgctt 120
gccaatttca gcacagggag tagtgcaggc cttattccaa cacacccggc ccagccttaa 180
ccccagaact cagccagttt cttgcttccg tgcccctggt tctcctcccc atcgagccca 240
cccctccttt cccaccttca gtcaccccta gtgaactgcc ccagcgatct ctgctgtgct 300
tgaccccgag ggtcttccac cctcgccctg accctggaca ctgcccagct tggcccccca 360
tcctgctcct ggcacaatgc cctctagcca gccaaccttc cctcccccaa ccctggggcc 420
gccccagggt tcctgcgcac tgcctgttcc tcctgggtgt cactggcagc cctgtccttc 480
ctagagggac tggaacctaa ttctcctgag gctgagggag ggtggagggt ctcaaggcaa 540
cgctggcccc acgacggagt gccaggagca ctaacagtac ccttagcttg ctttcctcct 600
ccctcctttt tattttcaag ttccttttta tttctccttg cgtaacaacc ttcttccctt 660
ctgcaccact gcccgtaccc ttacccgccc cgccacctcc ttgctacccc actcttgaaa 720
ccacagctgt tggcagggtc cccagctcat gccagcctca tctcctttct tgctagcccc 780
caaagggcct ccaggcaaca tggggggccc agtcagagag ccggcactct cagttgccct 840
ctggttgagt tggggggcag ctctgggggc cgtggcttgt gccatggctc tgctgaccca 900
acaaacagag ctgcagagcc tcaggagaga ggtgagccgg ctgcagggga caggaggccc 960
ctcccagaat ggggaagggt atccctggca gagtctcccg gagcagagtt ccgatgccct 1020
ggaagcctgg gagaatgggg agagatcccg gaaaaggaga gcagtgctca cccaaaaaca 1080
gaagaagcag cactctgtcc tgcacctggt tcccattaac gccacctcca aggatgactc 1140
cgatgtgaca gaggtgatgt ggcaaccagc tcttaggcgt gggagaggcc tacaggccca 1200
aggatatggt gtccgaatcc aggatgctgg agtttatctg ctgtatagcc aggtcctgtt 1260
tcaagacgtg actttcacca tgggtcaggt ggtgtctcga gaaggccaag gaaggcagga 1320
gactctattc cgatgtataa gaagtatgcc ctcccacccg gaccgggcct acaacagctg 1380
ctatagcgca ggtgtcttcc atttacacca aggggatatt ctgagtgtca taattccccg 1440
ggcaagggcg aaacttaacc tctctccaca tggaaccttc ctggggtttg tgaaactgtg 1500
attgtgttat aaaaagtggc tcccagcttg gaagaccagg gtgggtacat actggagaca 1560
gccaagagct gagtatataa aggagaggga atgtgcagga acagaggcgt cttcctgggt 1620
ttggctcccc gttcctcact ttcccttttt cattcccacc ccctagactt tgattttacg 1680
gatatcttgc ttctgttccc catggagctc cgaattcttg cgtgtgtgta gatgaggggc 1740
gggggacggg cgccaggcat tgtccagacc tggtcggggc ccactggaag catccagaac 1800
agcaccacca tctagcggcc gctcgaggga agcacccgcc ggttggccga agtccacgaa 1860
gccgccctct gctagggaaa acccctggtt ctccatgcca cacctctctc caggtgccct 1920
ctgcctcttc accccacaag aagccttatc ctacgtcctt ctctccatct atcggacccc 1980
agtttccatc actatctcca gagatgtagc tattatgcgc ccgtctacag gggtgcccg 2040 acgatgacgg tgccttcgca gtcaaattac tcttcgggtc ccaaggtttg gctttcacgc 2100

```
gctccattgc cccggcgtgg caggccattc caagcccttc cgggctggaa ctggtgtcgg   2160

aggagcctcg ggtgtatcgt acgccctggt gttggtgttg cctcactcct ctgagctctt   2220

ctttctgatc aagccctgct taaagttaaa taaaatagaa tgaatgatac cccggcaaaa   2280

aaaaaaaaaa aaa                                                      2293
```

<210> SEQ ID NO 2
<211> LENGTH: 250
<212> TYPE: PRT
<213> ORGANISM: Homo sapiens

<400> SEQUENCE: 2

```
Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250
```

<210> SEQ ID NO 3
<211> LENGTH: 2245
<212> TYPE: DNA
<213> ORGANISM: Homo sapiens

<400> SEQUENCE: 3

```
ccggaaccct gtgtgctggg gaggaatccc gcagtggccg gggggcttga ggccgctgct     60

ttgtctcttc gtccagagcc ttatgtaaga gcttttctcg ggaaacagga agtcctgctt    120

gccaatttca gcacagggag tagtgcaggc cttattccaa cacacccggc ccagccttaa    180
```

```
ccccagaact cagccagttt cttgcttccg tgcccctggt tctcctcccc atcgagccca    240
cccctccttt cccaccttca gtcacccta gtgaactgcc ccagcgatct ctgctgtgct    300
tgaccccgag ggtcttccac cctcgccctg accctggaca ctgcccagct tggcccccca    360
tcctgctcct ggcacaatgc cctctagcca gccaaccttc cctcccccaa ccctggggcc    420
gccccagggt tcctgcgcac tgcctgttcc tcctgggtgt cactggcagc cctgtccttc    480
ctagagggac tggaacctaa ttctcctgag gctgagggag ggtggagggt ctcaaggcaa    540
cgctggcccc acgacggagt gccaggagca ctaacagtac ccttagcttg ctttcctcct    600
ccctcctttt tattttcaag ttccttttta tttctccttg cgtaacaacc ttcttccctt    660
ctgcaccact gcccgtaccc ttacccgccc cgccacctcc ttgctacccc actcttgaaa    720
ccacagctgt tggcagggtc cccagctcat gccagcctca tctcctttct tgctagcccc    780
caaagggcct ccaggcaaca tggggggccc agtcagagag ccggcactct cagttgccct    840
ctggttgagt tgggggcag ctctgggggc cgtggcttgt gccatggctc tgctgaccca    900
acaaacagag ctgcagagcc tcaggagaga ggtgagccgg ctgcagggga caggaggccc    960
ctcccagaat ggggaagggt atccctggca gagtctcccg gagcagagtt ccgatgccct   1020
ggaagcctgg gagaatgggg agagatcccg gaaaaggaga gcagtgctca cccaaaaaca   1080
gaagaatgac tccgatgtga cagaggtgat gtggcaacca gctcttaggc gtgggagagg   1140
cctacaggcc caaggatatg gtgtccgaat ccaggatgct ggagtttatc tgctgtatag   1200
ccaggtcctg tttcaagacg tgactttcac catgggtcag gtggtgtctc gagaaggcca   1260
aggaaggcag gagactctat tccgatgtat aagaagtatg ccctcccacc cggaccgggc   1320
ctacaacagc tgctatagcg caggtgtctt ccatttacac caaggggata ttctgagtgt   1380
cataattccc cgggcaaggg cgaaacttaa cctctctcca catggaacct tcctggggtt   1440
tgtgaaactg tgattgtgtt ataaaaagtg gctcccagct tggaagacca gggtgggtac   1500
atactggaga cagccaagag ctgagtatat aaaggagagg gaatgtgcag gaacagaggc   1560
gtcttcctgg gtttggctcc ccgttcctca cttttccctt ttcattccca cccccctagac   1620
tttgatttta cggatatctt gcttctgttc cccatggagc tccgaattct tgcgtgtgtg   1680
tagatgaggg gcgggggacg ggcgccaggc attgtccaga cctggtcggg gcccactgga   1740
agcatccaga acagcaccac catctagcgg ccgctcgagg gaagcacccg ccggttggcc   1800
gaagtccacg aagccgccct ctgctaggga aaacccctgg ttctccatgc cacacctctc   1860
tccaggtgcc ctctgcctct tcaccccaca agaagcctta tcctacgtcc ttctctccat   1920
ctatcggacc ccagtttcca tcactatctc cagagatgta gctattatgc gcccgtctac   1980
agggggtgcc cgacgatgac ggtgccttcg cagtcaaatt actcttcggg tcccaaggtt   2040
tggctttcac gcgctccatt gccccggcgt ggcaggccat tccaagccct tccgggctgg   2100
aactggtgtc ggaggagcct cgggtgtatc gtacgccctg gtgttggtgt tgcctcactc   2160
ctctgagctc ttctttctga tcaagccctg cttaaagtta aataaaatag aatgaatgat   2220
accccggcaa aaaaaaaaaa aaaaa                                         2245
```

<210> SEQ ID NO 4
<211> LENGTH: 234
<212> TYPE: PRT
<213> ORGANISM: Homo sapiens

<400> SEQUENCE: 4

Met Pro Ala Ser Ser Pro Phe Leu Leu Ala Pro Lys Gly Pro Pro Gly

```
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Asn Asp Ser Asp Val Thr Glu Val Met Trp Gln Pro Ala Leu Arg Arg
        115                 120                 125

Gly Arg Gly Leu Gln Ala Gln Gly Tyr Gly Val Arg Ile Gln Asp Ala
    130                 135                 140

Gly Val Tyr Leu Leu Tyr Ser Gln Val Leu Phe Gln Asp Val Thr Phe
145                 150                 155                 160

Thr Met Gly Gln Val Val Ser Arg Glu Gly Gln Gly Arg Gln Glu Thr
                165                 170                 175

Leu Phe Arg Cys Ile Arg Ser Met Pro Ser His Pro Asp Arg Ala Tyr
            180                 185                 190

Asn Ser Cys Tyr Ser Ala Gly Val Phe His Leu His Gln Gly Asp Ile
        195                 200                 205

Leu Ser Val Ile Ile Pro Arg Ala Arg Ala Lys Leu Asn Leu Ser Pro
    210                 215                 220

His Gly Thr Phe Leu Gly Phe Val Lys Leu
225                 230
```

<210> SEQ ID NO 5
<211> LENGTH: 2112
<212> TYPE: DNA
<213> ORGANISM: Homo sapiens

<400> SEQUENCE: 5

```
ccggaaccct gtgtgctggg gaggaatccc gcagtggccg gggggcttga ggccgctgct      60

ttgtctcttc gtccagagcc ttatgtaaga gcttttctcg ggaaacagga agtcctgctt     120

gccaatttca gcacagggag tagtgcaggc cttattccaa cacacccggc ccagccttaa     180

ccccagaact cagccagttt cttgcttccg tgcccctggt tctcctcccc atcgagccca     240

cccctccttt cccaccttca gtcaccccta gtgaactgcc ccagcgatct ctgctgtgct     300

tgaccccgag ggtcttccac cctcgccctg accctggaca ctgcccagct tggcccccca     360

tcctgctcct ggcacaatgc cctctagcca gccaaccttc cctcccccaa ccctggggcc     420

gccccagggt tcctgcgcac tgcctgttcc tcctgggtgt cactggcagc cctgtccttc     480

ctagagggac tggaacctaa ttctcctgag gctgagggag ggtggagggt ctcaaggcaa     540

cgctggcccc acgacggagt gccaggagca ctaacagtac ccttagcttg ctttcctcct     600

ccctcctttt tattttcaag ttccttttta tttctccttg cgtaacaacc ttcttccctt     660

ctgcaccact gcccgtaccc ttacccgccc cgccacctcc ttgctacccc actcttgaaa     720

ccacagctgt tggcagggtc cccagctcat gccagcctca tctcctttct tgctagcccc     780

caaagggcct ccaggcaaca tgggggcccc agtcagagag ccggcactct cagttgccct     840
```

```
ctggttgagt tggggggcag ctctgggggc cgtggcttgt gccatggctc tgctgaccca    900

acaaacagag ctgcagagcc tcaggagaga ggtgagccgg ctgcagggga caggaggccc    960

ctcccagaat ggggaagggt atccctggca gagtctcccg gagcagagtt ccgatgccct   1020

ggaagcctgg gagaatgggg agagatcccg gaaaaggaga gcagtgctca cccaaaaaca   1080

gaagaagcag cactctgtcc tgcacctggt tcccattaac gccacctcca aggatgactc   1140

cgatgtgaca gaggtgatgt ggcaaccagc tcttaggcgt gggagaggcc tacaggccca   1200

aggatatggt gtccgaatcc aggatgctgg agtttatctg ctgtatagcc aggtcctgtt   1260

tcaagacgtg actttcacca tgggtcaggt ggtgtctcga gaaggccaag gaaggcagga   1320

gactctattc cgatgtataa gaagtatgcc ctcccacccg gaccgggcct acaacagctg   1380

ctatagcgca ggtgtcttcc atttacacca aggggatatt ctgagtgtca taattccccg   1440

ggcaagggcg aaacttaacc tctctccaca tggaaccttc ctgggacttt gattttacgg   1500

atatcttgct tctgttcccc atggagctcc gaattcttgc gtgtgtgtag atgaggggcg   1560

ggggacgggc gccaggcatt gtccagacct ggtcggggcc cactggaagc atccagaaca   1620

gcaccaccat ctagcggccg ctcgagggaa gcacccgccg gttggccgaa gtccacgaag   1680

ccgccctctg ctagggaaaa cccctggttc tccatgccac acctctctcc aggtgccctc   1740

tgcctcttca ccccacaaga agccttatcc tacgtccttc tctccatcta tcggacccca   1800

gtttccatca ctatctccag agatgtagct attatgcgcc cgtctacagg gggtgcccga   1860

cgatgacggt gccttcgcag tcaaattact cttcgggtcc caaggtttgg ctttcacgcg   1920

ctccattgcc ccggcgtggc aggccattcc aagcccttcc gggctggaac tggtgtcgga   1980

ggagcctcgg gtgtatcgta cgccctggtg ttggtgttgc ctcactcctc tgagctcttc   2040

tttctgatca agccctgctt aaagttaaat aaaatagaat gaatgatacc ccggcaaaaa   2100

aaaaaaaaaa aa                                                      2112
```

<210> SEQ ID NO 6
<211> LENGTH: 247
<212> TYPE: PRT
<213> ORGANISM: Homo sapiens

<400> SEQUENCE: 6

```
Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140
```

```
Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Leu
                245


<210> SEQ ID NO 7
<211> LENGTH: 2212
<212> TYPE: DNA
<213> ORGANISM: Homo sapiens

<400> SEQUENCE: 7

ccggaaccct gtgtgctggg gaggaatccc gcagtggccg gggggcttga ggccgctgct     60

ttgtctcttc gtccagagcc ttatgtaaga gcttttctcg ggaaacagga agtcctgctt    120

gccaatttca gcacagggag tagtgcaggc cttattccaa cacacccggc ccagccttaa    180

ccccagaact cagccagttt cttgcttccg tgcccctggt tctcctcccc atcgagccca    240

cccctccttt cccaccttca gtcaccccta gtgaactgcc ccagcgatct ctgctgtgct    300

tgaccccgag ggtcttccac cctcgccctg accctggaca ctgcccagct tggcccccca    360

tcctgctcct ggcacaatgc cctctagcca gccaaccttc cctcccccaa ccctggggcc    420

gccccagggt tcctgcgcac tgcctgttcc tcctgggtgt cactggcagc cctgtccttc    480

ctagagggac tggaacctaa ttctcctgag gctgagggag ggtggagggt ctcaaggcaa    540

cgctggcccc acgacggagt gccaggagca ctaacagtac ccttagcttg ctttcctcct    600

ccctcctttt tattttcaag ttccttttta tttctccttg cgtaacaacc ttcttccctt    660

ctgcaccact gcccgtaccc ttacccgccc cgccacctcc ttgctacccc actcttgaaa    720

ccacagctgt tggcagggtc cccagctcat gccagcctca tctcctttct tgctagcccc    780

caaagggcct ccaggcaaca tggggggccc agtcagagag ccggcactct cagttgccct    840

ctggttgagt tgggggcag ctctgggggc cgtggcttgt gccatggctc tgctgaccca    900

acaaacagag ctgcagagcc tcaggagaga ggtgagccgg ctgcagggga caggaggccc    960

ctcccagaat ggggaagggt atccctggca gagtctcccg gagcagcagc actctgtcct   1020

gcacctggtt cccattaacg ccacctccaa ggatgactcc gatgtgacag aggtgatgtg   1080

gcaaccagct cttaggcgtg ggagaggcct acaggcccaa ggatatggtg tccgaatcca   1140

ggatgctgga gtttatctgc tgtatagcca ggtcctgttt caagacgtga ctttcaccat   1200

gggtcaggtg gtgtctcgag aaggccaagg aaggcaggag actctattcc gatgtataag   1260

aagtatgccc tcccacccgg accgggccta caacagctgc tatagcgcag gtgtcttcca   1320

tttacaccaa ggggatattc tgagtgtcat aattccccgg gcaagggcga aacttaacct   1380

ctctccacat ggaaccttcc tggggtttgt gaaactgtga ttgtgttata aaaagtggct   1440

cccagcttgg aagaccaggg tgggtacata ctggagacag ccaagagctg agtatataaa   1500
```

ggagagggaa tgtgcaggaa cagaggcgtc ttcctgggtt tggctccccg ttcctcactt 1560 ttccctttc attcccaccc cctagacttt gattttacgg atatcttgct tctgttcccc 1620
atggagctcc gaattcttgc gtgtgtgtag atgaggggcg ggggacgggc gccaggcatt 1680
gtccagacct ggtcggggcc cactggaagc atccagaaca gcaccaccat ctagcggccg 1740
ctcgagggaa gcacccgccg gttggccgaa gtccacgaag ccgccctctg ctagggaaaa 1800
cccctggttc tccatgccac acctctctcc aggtgccctc tgcctcttca ccccacaaga 1860
agccttatcc tacgtccttc tctccatcta tcggacccca gtttccatca ctatctccag 1920
agatgtagct attatgcgcc cgtctacagg gggtgcccga cgatgacggt gccttcgcag 1980
tcaaattact cttcgggtcc caaggtttgg ctttcacgcg ctccattgcc ccggcgtggc 2040
aggccattcc aagcccttcc gggctggaac tggtgtcgga ggagcctcgg gtgtatcgta 2100
cgccctggtg ttggtgttgc ctcactcctc tgagctcttc tttctgatca agccctgctt 2160
aaagttaaat aaaatagaat gaatgatacc ccggcaaaaa aaaaaaaaaa aa 2212

<210> SEQ ID NO 8
<211> LENGTH: 223
<212> TYPE: PRT
<213> ORGANISM: Homo sapiens

<400> SEQUENCE: 8

Met Pro Ala Ser Ser Pro Phe Leu Leu Ala Pro Lys Gly Pro Pro Gly
1 5 10 15

Asn Met Gly Gly Pro Val Arg Glu Pro Ala Leu Ser Val Ala Leu Trp
20 25 30

Leu Ser Trp Gly Ala Ala Leu Gly Ala Val Ala Cys Ala Met Ala Leu
35 40 45

Leu Thr Gln Gln Thr Glu Leu Gln Ser Leu Arg Arg Glu Val Ser Arg
50 55 60

Leu Gln Gly Thr Gly Gly Pro Ser Gln Asn Gly Glu Gly Tyr Pro Trp
65 70 75 80

Gln Ser Leu Pro Glu Gln Gln His Ser Val Leu His Leu Val Pro Ile
85 90 95

Asn Ala Thr Ser Lys Asp Asp Ser Asp Val Thr Glu Val Met Trp Gln
100 105 110

Pro Ala Leu Arg Arg Gly Arg Gly Leu Gln Ala Gln Gly Tyr Gly Val
115 120 125

Arg Ile Gln Asp Ala Gly Val Tyr Leu Leu Tyr Ser Gln Val Leu Phe
130 135 140

Gln Asp Val Thr Phe Thr Met Gly Gln Val Val Ser Arg Glu Gly Gln
145 150 155 160

Gly Arg Gln Glu Thr Leu Phe Arg Cys Ile Arg Ser Met Pro Ser His
165 170 175

Pro Asp Arg Ala Tyr Asn Ser Cys Tyr Ser Ala Gly Val Phe His Leu
180 185 190

His Gln Gly Asp Ile Leu Ser Val Ile Ile Pro Arg Ala Arg Ala Lys
195 200 205

Leu Asn Leu Ser Pro His Gly Thr Phe Leu Gly Phe Val Lys Leu
210 215 220

<210> SEQ ID NO 9
<211> LENGTH: 2209
<212> TYPE: DNA

<213> ORGANISM: Homo sapiens

<400> SEQUENCE: 9

```
ccggaaccct gtgtgctggg gaggaatccc gcagtggccg gggggcttga ggccgctgct     60
ttgtctcttc gtccagagcc ttatgtaaga gcttttctcg ggaaacagga agtcctgctt    120
gccaatttca gcacagggag tagtgcaggc cttattccaa cacacccggc ccagccttaa    180
ccccagaact cagccagttt cttgcttccg tgcccctggt tctcctcccc atcgagccca    240
cccctccttt cccaccttca gtcaccccta gtgaactgcc ccagcgatct ctgctgtgct    300
tgaccccgag ggtcttccac cctcgccctg accctggaca ctgcccagct tggcccccca    360
tcctgctcct ggcacaatgc cctctagcca gccaaccttc cctcccccaa ccctggggcc    420
gccccagggt tcctgcgcac tgcctgttcc tcctgggtgt cactggcagc cctgtccttc    480
ctagagggac tggaacctaa ttctcctgag gctgagggag ggtggagggt ctcaaggcaa    540
cgctggcccc acgacggagt gccaggagca ctaacagtac ccttagcttg ctttcctcct    600
ccctcctttt tattttcaag ttccttttta tttctccttg cgtaacaacc ttcttccctt    660
ctgcaccact gcccgtaccc ttacccgccc cgccacctcc ttgctacccc actcttgaaa    720
ccacagctgt tggcagggtc cccagctcat gccagcctca tctcctttct tgctagcccc    780
caaagggcct ccaggcaaca tggggggccc agtcagagag ccggcactct cagttgccct    840
ctggttgagt tggggggcag ctctgggggc cgtggcttgt gccatggctc tgctgaccca    900
acaaacagag ctgcagagcc tcaggagaga ggtgagccgg ctgcagggga caggaggccc    960
ctcccagaat ggggaagggt atccctggca gagtctcccg gagcagcact ctgtcctgca   1020
cctggttccc attaacgcca cctccaagga tgactccgat gtgacagagg tgatgtggca   1080
accagctctt aggcgtggga gaggcctaca ggcccaagga tatggtgtcc gaatccagga   1140
tgctggagtt tatctgctgt atagccaggt cctgtttcaa gacgtgactt tcaccatggg   1200
tcaggtggtg tctcgagaag gccaaggaag gcaggagact ctattccgat gtataagaag   1260
tatgccctcc cacccggacc gggcctacaa cagctgctat agcgcaggtg tcttccattt   1320
acaccaaggg gatattctga gtgtcataat tccccgggca agggcgaaac ttaacctctc   1380
tccacatgga accttcctgg ggtttgtgaa actgtgattg tgttataaaa agtggctccc   1440
agcttggaag accagggtgg gtacatactg gagacagcca agagctgagt atataaagga   1500
gagggaatgt gcaggaacag aggcgtcttc ctgggtttgg ctccccgttc ctcacttttc   1560
ccttttcatt cccacccccct agactttgat tttacggata tcttgcttct gttccccatg  1620
gagctccgaa ttcttgcgtg tgtgtagatg aggggcgggg gacgggcgcc aggcattgtc   1680
cagacctggt cggggcccac tggaagcatc cagaacagca ccaccatcta gcggccgctc   1740
gagggaagca cccgccggtt ggccgaagtc cacgaagccg ccctctgcta gggaaaaccc   1800
ctggttctcc atgccacacc tctctccagg tgccctctgc ctcttcaccc cacaagaagc   1860
cttatcctac gtccttctct ccatctatcg gaccccagtt tccatcacta tctccagaga   1920
tgtagctatt atgcgcccgt ctacaggggg tgcccgacga tgacggtgcc ttcgcagtca   1980
aattactctt cgggtcccaa ggtttggctt tcacgcgctc cattgccccg gcgtggcagg   2040
ccattccaag cccttccggg ctggaactgg tgtcggagga gcctcgggtg tatcgtacgc   2100
cctggtgttg gtgttgcctc actcctctga gctcttcttt ctgatcaagc cctgcttaaa   2160
gttaaataaa atagaatgaa tgataccccg gcaaaaaaaa aaaaaaaaa               2209
```

<210> SEQ ID NO 10
<211> LENGTH: 222
<212> TYPE: PRT
<213> ORGANISM: Homo sapiens

<400> SEQUENCE: 10

```
Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln His Ser Val Leu His Leu Val Pro Ile Asn
                85                  90                  95

Ala Thr Ser Lys Asp Asp Ser Asp Val Thr Glu Val Met Trp Gln Pro
            100                 105                 110

Ala Leu Arg Arg Gly Arg Gly Leu Gln Ala Gln Gly Tyr Gly Val Arg
        115                 120                 125

Ile Gln Asp Ala Gly Val Tyr Leu Leu Tyr Ser Gln Val Leu Phe Gln
    130                 135                 140

Asp Val Thr Phe Thr Met Gly Gln Val Val Ser Arg Glu Gly Gln Gly
145                 150                 155                 160

Arg Gln Glu Thr Leu Phe Arg Cys Ile Arg Ser Met Pro Ser His Pro
                165                 170                 175

Asp Arg Ala Tyr Asn Ser Cys Tyr Ser Ala Gly Val Phe His Leu His
            180                 185                 190

Gln Gly Asp Ile Leu Ser Val Ile Ile Pro Arg Ala Arg Ala Lys Leu
        195                 200                 205

Asn Leu Ser Pro His Gly Thr Phe Leu Gly Phe Val Lys Leu
    210                 215                 220
```

<210> SEQ ID NO 11
<211> LENGTH: 1517
<212> TYPE: DNA
<213> ORGANISM: Homo sapiens

<400> SEQUENCE: 11

```
ccggaaccct gtgtgctggg gaggaatccc gcagtggccg gggggcttga ggccgctgct      60

ttgtctcttc gtccagagcc ttatccccca aagggcctcc aggcaacatg gggggcccag     120

tcagagagcc ggcactctca gttgccctct ggttgagttg gggggcagct ctgggggccg     180

tggcttgtgc catggctctg ctgacccaac aaacagagct gcagagcctc aggagagagg     240

tgagccggct gcaggggaca ggaggcccct cccagaatgg ggaagggtat ccctggcaga     300

gtctcccgga gcagcactct gtcctgcacc tggttcccat taacgccacc tccaaggatg     360

actccgatgt gacagaggtg atgtggcaac cagctcttag gcgtgggaga ggcctacagg     420

cccaaggata tggtgtccga atccaggatg ctggagttta tctgctgtat agccaggtcc     480

tgtttcaaga cgtgactttc accatgggtc aggtggtgtc tcgagaaggc caaggaaggc     540

aggagactct attccgatgt ataagaagta tgccctccca cccggaccgg gcctacaaca     600

gctgctatag cgcaggtgtc ttccatttac accaagggga tattctgagt gtcataattc     660
```

```
cccgggcaag ggcgaaactt aacctctctc cacatggaac cttcctgggg tttgtgaaac    720

tgtgattgtg ttataaaaag tggctcccag cttggaagac cagggtgggt acatactgga    780

gacagccaag agctgagtat ataaaggaga gggaatgtgc aggaacagag gcgtcttcct    840

gggtttggct ccccgttcct cacttttccc ttttcattcc caccccctag actttgattt    900

tacggatatc ttgcttctgt tccccatgga gctccgaatt cttgcgtgtg tgtagatgag    960

gggcggggga cgggcgccag gcattgtcca gacctggtcg ggcccactg gaagcatcca    1020

gaacagcacc accatctagc ggccgctcga gggaagcacc cgccggttgg ccgaagtcca   1080

cgaagccgcc ctctgctagg gaaaacccct ggttctccat gccacacctc tctccaggtg   1140

ccctctgcct cttcacccca caagaagcct tatcctacgt ccttctctcc atctatcgga   1200

ccccagtttc catcactatc tccagagatg tagctattat gcgcccgtct acagggggtg   1260

cccgacgatg acggtgcctt cgcagtcaaa ttactcttcg ggtcccaagg tttggctttc   1320

acgcgctcca ttgccccggc gtggcaggcc attccaagcc cttccgggct ggaactggtg   1380

tcggaggagc ctcgggtgta tcgtacgccc tggtgttggt gttgcctcac tcctctgagc   1440

tcttctttct gatcaagccc tgcttaaagt taaataaaat agaatgaatg ataccccggc   1500

aaaaaaaaaa aaaaaaa                                                  1517
```

<210> SEQ ID NO 12
<211> LENGTH: 205
<212> TYPE: PRT
<213> ORGANISM: Homo sapiens

<400> SEQUENCE: 12

```
Met Gly Gly Pro Val Arg Glu Pro Ala Leu Ser Val Ala Leu Trp Leu
1               5                   10                  15

Ser Trp Gly Ala Ala Leu Gly Ala Val Ala Cys Ala Met Ala Leu Leu
            20                  25                  30

Thr Gln Gln Thr Glu Leu Gln Ser Leu Arg Arg Glu Val Ser Arg Leu
        35                  40                  45

Gln Gly Thr Gly Gly Pro Ser Gln Asn Gly Glu Gly Tyr Pro Trp Gln
    50                  55                  60

Ser Leu Pro Glu Gln His Ser Val Leu His Leu Val Pro Ile Asn Ala
65                  70                  75                  80

Thr Ser Lys Asp Asp Ser Asp Val Thr Glu Val Met Trp Gln Pro Ala
                85                  90                  95

Leu Arg Arg Gly Arg Gly Leu Gln Ala Gln Gly Tyr Gly Val Arg Ile
            100                 105                 110

Gln Asp Ala Gly Val Tyr Leu Leu Tyr Ser Gln Val Leu Phe Gln Asp
        115                 120                 125

Val Thr Phe Thr Met Gly Gln Val Val Ser Arg Glu Gly Gln Gly Arg
    130                 135                 140

Gln Glu Thr Leu Phe Arg Cys Ile Arg Ser Met Pro Ser His Pro Asp
145                 150                 155                 160

Arg Ala Tyr Asn Ser Cys Tyr Ser Ala Gly Val Phe His Leu His Gln
                165                 170                 175

Gly Asp Ile Leu Ser Val Ile Ile Pro Arg Ala Arg Ala Lys Leu Asn
            180                 185                 190

Leu Ser Pro His Gly Thr Phe Leu Gly Phe Val Lys Leu
        195                 200                 205
```

<210> SEQ ID NO 13

```
<211> LENGTH: 1679
<212> TYPE: DNA
<213> ORGANISM: Mus musculus

<400> SEQUENCE: 13

gaaggctggc cgctccttct gggtgtcacg gctgccctgt ccttcctaga taatggcacc     60

aaattctcct gaggctaggg gggaaggagt gtcagagtgt cactagctcg accctgggga    120

caagggggac taatagtacc ctagcttgat ttcttcctat tctcaagttc ctttttattt    180

ctcccttgcg taacccgctc ttcccttctg tgcctttgcc tgtattccca ccctccctgc    240

tacctcttgg ccacctcact tctgagacca cagctgttgg cagggtccct agctcatgcc    300

agcctcatct ccaggccaca tggggggctc agtcagagag ccagcccttt cggttgctct    360

ttggttgagt tggggggcag ttctgggggc tgtgacttgt gctgtcgcac tactgatcca    420

acagacagag ctgcaaagcc taaggcggga ggtgagccgg ctgcagcgga gtggagggcc    480

ttcccagaag cagggagagc gcccatggca gagcctctgg gagcagagtc ctgatgtcct    540

ggaagcctgg aaggatgggg cgaaatctcg gagaaggaga gcagtactca cccagaagca    600

caagaagaag cactcagtcc tgcatcttgt tccagttaac attacctcca aggcagactc    660

tgacgtgaca gaggtgatgt ggcaaccagt acttaggcgt gggagaggcc tggaggccca    720

gggagacatt gtacgagtct gggacactgg aatttatctg ctctatagtc aggtcctgtt    780

tcatgatgtg actttcacaa tgggtcaggt ggtatctcgg gaaggacaag ggagaagaga    840

aactctattc cgatgtatca gaagtatgcc ttctgatcct gaccgtgcct acaatagctg    900

ctacagtgca ggtgtctttc atttacatca aggggatatt atcactgtca aaattccacg    960

ggcaaacgca aaacttagcc tttctccgca tggaacattc ctggggtttg tgaaactatg   1020

attgttataa agggggtggg gatttcccat tccaaaaact ggctagacaa aggacaagga   1080

acggtcaaga acagctctcc atggctttgc cttgactgtt gttcctccct ttgcctttcc   1140

cgctcccact atctgggctt tgactccatg gatattaaaa aagtagaata ttttgtgttt   1200

atctcccaca cagccccaaa ttcttttgtt gtgtgtgcga agggggtttt gcgcactgtg   1260

ccaagccttg tccactggaa tgcatccaga acagcagcac catctagcgg caggttgagg   1320

aaagactatg gtctctgcta gggaaaacct tatccaactc ttcaagtacc ctctgcttca   1380

attaacaaga agcccggctt tcagtatttc acctattgcg tccaaattct tgttactatc   1440

tagaaaaaga tatatgttag gtgcctcgat atgcatgcca ttcatcctcc ccattctcct   1500

atacacttcc gagctgggca ctgagcttta cgccttaaat cacagtactc gggaggcaga   1560

tctcgatgag ttcgaggcca acttggtcta aatagtgagt tccaggccac ccaggggtta   1620

caatggtgag accctgtctc aaacaaacta acaaacaaat aaacgaaagg ctctccacg    1679


<210> SEQ ID NO 14
<211> LENGTH: 241
<212> TYPE: PRT
<213> ORGANISM: Mus musculus

<400> SEQUENCE: 14

Met Pro Ala Ser Ser Pro Gly His Met Gly Gly Ser Val Arg Glu Pro
1               5                   10                  15

Ala Leu Ser Val Ala Leu Trp Leu Ser Trp Gly Ala Val Leu Gly Ala
            20                  25                  30

Val Thr Cys Ala Val Ala Leu Leu Ile Gln Gln Thr Glu Leu Gln Ser
        35                  40                  45
```

```
Leu Arg Arg Glu Val Ser Arg Leu Gln Arg Ser Gly Gly Pro Ser Gln
    50                  55                  60

Lys Gln Gly Glu Arg Pro Trp Gln Ser Leu Trp Glu Gln Ser Pro Asp
65                  70                  75                  80

Val Leu Glu Ala Trp Lys Asp Gly Ala Lys Ser Arg Arg Arg Arg Ala
                85                  90                  95

Val Leu Thr Gln Lys His Lys Lys Lys His Ser Val Leu His Leu Val
            100                 105                 110

Pro Val Asn Ile Thr Ser Lys Ala Asp Ser Asp Val Thr Glu Val Met
        115                 120                 125

Trp Gln Pro Val Leu Arg Arg Gly Arg Gly Leu Glu Ala Gln Gly Asp
    130                 135                 140

Ile Val Arg Val Trp Asp Thr Gly Ile Tyr Leu Leu Tyr Ser Gln Val
145                 150                 155                 160

Leu Phe His Asp Val Thr Phe Thr Met Gly Gln Val Val Ser Arg Glu
                165                 170                 175

Gly Gln Gly Arg Arg Glu Thr Leu Phe Arg Cys Ile Arg Ser Met Pro
            180                 185                 190

Ser Asp Pro Asp Arg Ala Tyr Asn Ser Cys Tyr Ser Ala Gly Val Phe
        195                 200                 205

His Leu His Gln Gly Asp Ile Ile Thr Val Lys Ile Pro Arg Ala Asn
    210                 215                 220

Ala Lys Leu Ser Leu Ser Pro His Gly Thr Phe Leu Gly Phe Val Lys
225                 230                 235                 240

Leu
```

<210> SEQ ID NO 15
<211> LENGTH: 1676
<212> TYPE: DNA
<213> ORGANISM: Mus musculus

<400> SEQUENCE: 15

```
gaaggctggc cgctccttct gggtgtcacg gctgccctgt ccttcctaga taatggcacc     60

aaattctcct gaggctaggg gggaaggagt gtcagagtgt cactagctcg accctgggga    120

caagggggac taatagtacc ctagcttgat ttcttcctat tctcaagttc ctttttattt    180

ctcccttgcg taacccgctc ttcccttctg tgcctttgcc tgtattccca ccctccctgc    240

tacctcttgg ccacctcact tctgagacca cagctgttgg cagggtccct agctcatgcc    300

agcctcatct ccaggccaca tggggggctc agtcagagag ccagcccttt cggttgctct    360

ttggttgagt tgggggggcag ttctgggggc tgtgacttgt gctgtcgcac tactgatcca    420

acagacagag ctgcaaagcc taaggcggga ggtgagccgg ctgcagcgga gtggagggcc    480

ttcccagaag cagggagagc gcccatggca gagcctctgg gagcagagtc ctgatgtcct    540

ggaagcctgg aaggatgggg cgaaatctcg gagaaggaga gcagtactca cccagaagca    600

caagaagaag cactcagtcc tgcatcttgt tccagttaac attacctcca aggactctga    660

cgtgacagag gtgatgtggc aaccagtact taggcgtggg agaggcctgg aggcccaggg    720

agacattgta cgagtctggg acactggaat ttatctgctc tatagtcagg tcctgtttca    780

tgatgtgact ttcacaatgg gtcaggtggt atctcgggaa ggacaaggga gaagagaaac    840

tctattccga tgtatcagaa gtatgccttc tgatcctgac cgtgcctaca atagctgcta    900

cagtgcaggt gtctttcatt tacatcaagg ggatattatc actgtcaaaa ttccacgggc    960

aaacgcaaaa cttagccttt ctccgcatgg aacattcctg ggtttgtga aactatgatt   1020
```

```
gttataaagg gggtggggat ttcccattcc aaaaactggc tagacaaagg acaaggaacg   1080

gtcaagaaca gctctccatg gctttgcctt gactgttgtt cctccctttg cctttcccgc   1140

tcccactatc tgggctttga ctccatggat attaaaaaag tagaatattt tgtgtttatc   1200

tcccacacag ccccaaattc ttttgttgtg tgtgcgaagg gggttttgcg cactgtgcca   1260

agccttgtcc actggaatgc atccagaaca gcagcaccat ctagcggcag gttgaggaaa   1320

gactatggtc tctgctaggg aaaaccttat ccaactcttc aagtaccctc tgcttcaatt   1380

aacaagaagc ccggctttca gtatttcacc tattgcgtcc aaattcttgt tactatctag   1440

aaaaagatat atgttaggtg cctcgatatg catgccattc atcctcccca ttctcctata   1500

cacttccgag ctgggcactg agctttacgc cttaaatcac agtactcggg aggcagatct   1560

cgatgagttc gaggccaact tggtctaaat agtgagttcc aggccaccca ggggttacaa   1620

tggtgagacc ctgtctcaaa caaactaaca aacaaataaa cgaaaggctc tccacg       1676
```

<210> SEQ ID NO 16
<211> LENGTH: 240
<212> TYPE: PRT
<213> ORGANISM: Mus musculus

<400> SEQUENCE: 16

```
Met Pro Ala Ser Ser Pro Gly His Met Gly Gly Ser Val Arg Glu Pro
1               5                   10                  15

Ala Leu Ser Val Ala Leu Trp Leu Ser Trp Gly Ala Val Leu Gly Ala
            20                  25                  30

Val Thr Cys Ala Val Ala Leu Leu Ile Gln Gln Thr Glu Leu Gln Ser
        35                  40                  45

Leu Arg Arg Glu Val Ser Arg Leu Gln Arg Ser Gly Gly Pro Ser Gln
    50                  55                  60

Lys Gln Gly Glu Arg Pro Trp Gln Ser Leu Trp Glu Gln Ser Pro Asp
65                  70                  75                  80

Val Leu Glu Ala Trp Lys Asp Gly Ala Lys Ser Arg Arg Arg Arg Ala
                85                  90                  95

Val Leu Thr Gln Lys His Lys Lys Lys His Ser Val Leu His Leu Val
            100                 105                 110

Pro Val Asn Ile Thr Ser Lys Asp Ser Asp Val Thr Glu Val Met Trp
        115                 120                 125

Gln Pro Val Leu Arg Arg Gly Arg Gly Leu Glu Ala Gln Gly Asp Ile
    130                 135                 140

Val Arg Val Trp Asp Thr Gly Ile Tyr Leu Leu Tyr Ser Gln Val Leu
145                 150                 155                 160

Phe His Asp Val Thr Phe Thr Met Gly Gln Val Val Ser Arg Glu Gly
                165                 170                 175

Gln Gly Arg Arg Glu Thr Leu Phe Arg Cys Ile Arg Ser Met Pro Ser
            180                 185                 190

Asp Pro Asp Arg Ala Tyr Asn Ser Cys Tyr Ser Ala Gly Val Phe His
        195                 200                 205

Leu His Gln Gly Asp Ile Ile Thr Val Lys Ile Pro Arg Ala Asn Ala
    210                 215                 220

Lys Leu Ser Leu Ser Pro His Gly Thr Phe Leu Gly Phe Val Lys Leu
225                 230                 235                 240
```

<210> SEQ ID NO 17
<211> LENGTH: 1377

<212> TYPE: DNA
<213> ORGANISM: Homo sapiens

<400> SEQUENCE: 17

```
agcatcctga gtaatgagtg gcctgggccg gagcaggcga ggtggccgga gccgtgtgga      60

ccaggaggag cgctttccac agggcctgtg gacgggggtg gctatgagat cctgccccga     120

agagcagtac tgggatcctc tgctgggtac ctgcatgtcc tgcaaaacca tttgcaacca     180

tcagagccag cgcacctgtg cagccttctg caggtcactc agctgccgca aggagcaagg     240

caagttctat gaccatctcc tgagggactg catcagctgt gcctccatct gtggacagca     300

ccctaagcaa tgtgcatact tctgtgagaa caagctcagg agcccagtga accttccacc     360

agagctcagg agacagcgga gtggagaagt tgaaaacaat tcagacaact cgggaaggta     420

ccaaggattg gagcacagag gctcagaagc aagtccagct ctcccggggc tgaagctgag     480

tgcagatcag gtggccctgg tctacagcac gctggggctc tgcctgtgtg ccgtcctctg     540

ctgcttcctg gtggcggtgg cctgcttcct caagaagagg ggggatccct gctcctgcca     600

gccccgctca aggccccgtc aaagtccggc caagtcttcc caggatcacg cgatggaagc     660

cggcagccct gtgagcacat cccccgagcc agtggagacc tgcagcttct gcttccctga     720

gtgcagggcg cccacgcagg agagcgcagt cacgcctggg acccccgacc ccacttgtgc     780

tggaaggtgg gggtgccaca ccaggaccac agtcctgcag ccttgcccac acatcccaga     840

cagtggcctt ggcattgtgt gtgtgcctgc ccaggagggg ggcccaggtg cataaatggg     900

ggtcagggag ggaaaggagg agggagagag atggagagga ggggagagag aaagagaggt     960

ggggagaggg gagagagata tgaggagaga gagacagagg aggcagagag ggagagaaac    1020

agaggagaca gagagggaga gagagacaga gggagagaga gacagagggg aagagaggca    1080

gagagggaaa gaggcagaga aggaaagaga caggcagaga aggagagagg cagagaggga    1140

gagaggcaga gagggagaga ggcagagaga cagagaggga gagagggaca gagagagata    1200

gagcaggagg tcggggcact ctgagtccca gttcccagtg cagctgtagg tcgtcatcac    1260

ctaaccacac gtgcaataaa gtcctcgtgc ctgctgctca cagcccccga gagcccctcc    1320

tcctggagaa taaaaccttt ggcagctgcc cttcctcaaa aaaaaaaaaa aaaaaaa       1377
```

<210> SEQ ID NO 18
<211> LENGTH: 293
<212> TYPE: PRT
<213> ORGANISM: Homo sapiens

<400> SEQUENCE: 18

```
Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110
```

```
Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Glu His Arg Gly Ser
    130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175

Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290
```

<210> SEQ ID NO 19
<211> LENGTH: 750
<212> TYPE: DNA
<213> ORGANISM: Mus musculus

<400> SEQUENCE: 19

```
atggctatgg cattctgccc caaagatcag tactgggact cctcaaggaa atcctgtgtc     60

tcctgtgcac tgacctgcag ccagaggagc cagcgcacct gtacagactt ctgcaaattc    120

atcaattgcc gaaaagagca aggcaggtac tacgaccatc tcctgggggc ctgcgtcagc    180

tgtgactcca cctgcacaca gcaccctcag cagtgtgccc acttctgtga gaaaaggccc    240

agaagccagg cgaacctcca gcccgagctc gggagaccac aggccgggga ggtggaagtc    300

aggtcagaca actcaggaag gcaccaggga tctgagcatg gtccaggatt gaggctaagt    360

agcgaccagc tgactctcta ctgcacactg gggtctgcc tctgcgccat cttctgctgt     420

ttcttggtgg ccttggcctc cttcctcagg cgtagaggag agccactacc cagccagcct    480

gccgggccac gtgggtcaca agcaaactct ccccacgccc accgccccgt gacagaggct    540

tgcgacgagg tgaccgcgtc accccagcct gtggaaacgt gtagcttctg cttcccggag    600

cgcagttctc ccactcagga gagcgcgccg cgttcgctcg ggatacacgg cttcgcgggc    660

actgccgccc cgcagccctg tatgcgtgca acagtaggcg gcctgggtgt cctgcgcgca    720

tccactgggg acgctcgtcc ggcaacttga                                     750
```

<210> SEQ ID NO 20
<211> LENGTH: 249
<212> TYPE: PRT
<213> ORGANISM: Mus musculus

<400> SEQUENCE: 20

```
Met Ala Met Ala Phe Cys Pro Lys Asp Gln Tyr Trp Asp Ser Ser Arg
1               5                   10                  15

Lys Ser Cys Val Ser Cys Ala Leu Thr Cys Ser Gln Arg Ser Gln Arg
            20                  25                  30

Thr Cys Thr Asp Phe Cys Lys Phe Ile Asn Cys Arg Lys Glu Gln Gly
        35                  40                  45

Arg Tyr Tyr Asp His Leu Leu Gly Ala Cys Val Ser Cys Asp Ser Thr
    50                  55                  60

Cys Thr Gln His Pro Gln Gln Cys Ala His Phe Cys Glu Lys Arg Pro
65                  70                  75                  80

Arg Ser Gln Ala Asn Leu Gln Pro Glu Leu Gly Arg Pro Gln Ala Gly
                85                  90                  95

Glu Val Glu Val Arg Ser Asp Asn Ser Gly Arg His Gln Gly Ser Glu
            100                 105                 110

His Gly Pro Gly Leu Arg Leu Ser Ser Asp Gln Leu Thr Leu Tyr Cys
        115                 120                 125

Thr Leu Gly Val Cys Leu Cys Ala Ile Phe Cys Cys Phe Leu Val Ala
    130                 135                 140

Leu Ala Ser Phe Leu Arg Arg Arg Gly Glu Pro Leu Pro Ser Gln Pro
145                 150                 155                 160

Ala Gly Pro Arg Gly Ser Gln Ala Asn Ser Pro His Ala His Arg Pro
                165                 170                 175

Val Thr Glu Ala Cys Asp Glu Val Thr Ala Ser Pro Gln Pro Val Glu
            180                 185                 190

Thr Cys Ser Phe Cys Phe Pro Glu Arg Ser Ser Pro Thr Gln Glu Ser
        195                 200                 205

Ala Pro Arg Ser Leu Gly Ile His Gly Phe Ala Gly Thr Ala Ala Pro
    210                 215                 220

Gln Pro Cys Met Arg Ala Thr Val Gly Gly Leu Gly Val Leu Arg Ala
225                 230                 235                 240

Ser Thr Gly Asp Ala Arg Pro Ala Thr
                245


<210> SEQ ID NO 21
<211> LENGTH: 994
<212> TYPE: DNA
<213> ORGANISM: Homo sapiens

<400> SEQUENCE: 21

aagactcaaa cttagaaact tgaattagat gtggtattca aatccttagc tgccgcgaag      60

acacagacag cccccgtaag aacccacgaa gcaggcgaag ttcattgttc tcaacattct     120

agctgctctt gctgcatttg ctctggaatt cttgtagaga tattacttgt ccttccaggc     180

tgttctttct gtagctccct tgttttcttt ttgtgatcat gttgcagatg gctgggcagt     240

gctcccaaaa tgaatatttt gacagtttgt tgcatgcttg catacccttgt caacttcgat    300

gttcttctaa tactcctcct ctaacatgtc agcgttattg taatgcaagt gtgaccaatt     360

cagtgaaagg aacgaatgcg attctctgga cctgtttggg actgagctta ataatttctt     420

tggcagtttt cgtgctaatg tttttgctaa ggaagataaa ctctgaacca ttaaaggacg     480

agtttaaaaa cacaggatca ggtctcctgg gcatggctaa cattgacctg gaaaagagca     540

ggactggtga tgaaattatt cttccgagag gcctcgagta cacggtggaa gaatgcacct     600

gtgaagactg catcaagagc aaaccgaagg tcgactctga ccattgcttt ccactcccag     660

ctatggagga aggcgcaacc attcttgtca ccacgaaaac gaatgactat tgcaagagcc     720
```

```
tgccagctgc tttgagtgct acggagatag agaaatcaat ttctgctagg taattaacca    780

tttcgactcg agcagtgcca ctttaaaaat cttttgtcag aatagatgat gtgtcagatc    840

tctttaggat gactgtattt ttcagttgcc gatacagctt tttgtcctct aactgtggaa    900

actctttatg ttagatatat ttctctaggt tactgttggg agcttaatgg tagaaacttc    960

cttggtttca tgattaaact cttttttttc ctga                                994


<210> SEQ ID NO 22
<211> LENGTH: 184
<212> TYPE: PRT
<213> ORGANISM: Homo sapiens

<400> SEQUENCE: 22

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180


<210> SEQ ID NO 23
<211> LENGTH: 812
<212> TYPE: DNA
<213> ORGANISM: Mus musculus

<400> SEQUENCE: 23

cacaatacct gtggccctct taagagcagc agggtctttc tttccgcctg acttcctgtc     60

cacagggaac tcccacagag aatctgctgt tcttcctcga ttttctgtcc actcttcccg    120

tttctttcag tgatccagtc cctcatggcg caacagtgtt tccacagtga atattttgac    180

agtctgctgc atgcttgcaa accgtgtcac ttgcgatgtt ccaaccctcc tgcaacctgt    240

cagccttact gtgatccaag cgtgaccagt tcagtgaaag ggacgtacac ggtgctctgg    300

atcttcttgg ggctgacctt ggtcctctct ttggcacttt tcacaatctc attcttgctg    360

aggaagatga accccgaggc cctgaaggac gagcctcaaa gcccaggtca gcttgacgga    420

tcggctcagc tggacaaggc cgacaccgag ctgactagga tcagggctgg tgacgacagg    480
```

-continued

```
atctttcccc gaagcctgga gtatacagtg gaagagtgca cctgtgagga ctgtgtcaag    540

agcaaaccca agggggattc tgaccatttc ttcccgcttc cagccatgga ggagggggca    600

accattcttg tcaccacaaa aacgggtgac tacggcaagt caagtgtgcc aactgctttg    660

caaagtgtca tggggatgga gaagccaact cacactagat aatgagcttc ctaactggtg    720

tgaagctgct ttgagaacct tctgtcagga gagctggtgt tttagatgtc gttaggatga    780

ccgtttacca accaagaata cagttttttg tc                                  812


<210> SEQ ID NO 24
<211> LENGTH: 185
<212> TYPE: PRT
<213> ORGANISM: Mus musculus

<400> SEQUENCE: 24

Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Pro Ala Thr Cys
            20                  25                  30

Gln Pro Tyr Cys Asp Pro Ser Val Thr Ser Ser Val Lys Gly Thr Tyr
        35                  40                  45

Thr Val Leu Trp Ile Phe Leu Gly Leu Thr Leu Val Leu Ser Leu Ala
    50                  55                  60

Leu Phe Thr Ile Ser Phe Leu Leu Arg Lys Met Asn Pro Glu Ala Leu
65                  70                  75                  80

Lys Asp Glu Pro Gln Ser Pro Gly Gln Leu Asp Gly Ser Ala Gln Leu
                85                  90                  95

Asp Lys Ala Asp Thr Glu Leu Thr Arg Ile Arg Ala Gly Asp Asp Arg
            100                 105                 110

Ile Phe Pro Arg Ser Leu Glu Tyr Thr Val Glu Glu Cys Thr Cys Glu
        115                 120                 125

Asp Cys Val Lys Ser Lys Pro Lys Gly Asp Ser Asp His Phe Phe Pro
    130                 135                 140

Leu Pro Ala Met Glu Glu Gly Ala Thr Ile Leu Val Thr Thr Lys Thr
145                 150                 155                 160

Gly Asp Tyr Gly Lys Ser Ser Val Pro Thr Ala Leu Gln Ser Val Met
                165                 170                 175

Gly Met Glu Lys Pro Thr His Thr Arg
            180                 185
```